United States Patent
Song et al.

(10) Patent No.: US 12,098,190 B2
(45) Date of Patent: Sep. 24, 2024

(54) HUMANIZED ANTI-C5 ANTIBODIES AND USES THEREOF

(71) Applicants: THE TRUSTEES OF THE UNIVERSITY OF PENNSYLVANIA, Philadelphia, PA (US); KIRA PHARMACEUTICALS (US) LLC, Arlington, MA (US)

(72) Inventors: Wenchao Song, Bryn Mawr, PA (US); Takashi Miwa, Bala Cynwyd, PA (US); Damodar Gullipalli, Philadelphia, PA (US); Ping Tsui, North Potomac, MD (US); Sayaka Sato, Philadelphia, PA (US)

(73) Assignees: The Trustees of the University of Pennsylvania and, Pennsylvania, PA (US); Kira Pharmaceuticals (US) LLC, Arlington, MA (US)

( * ) Notice: Subject to any disclaimer, the term of this patent is extended or adjusted under 35 U.S.C. 154(b) by 784 days.

(21) Appl. No.: 17/273,753

(22) PCT Filed: Sep. 6, 2019

(86) PCT No.: PCT/US2019/049890
§ 371 (c)(1),
(2) Date: Mar. 5, 2021

(87) PCT Pub. No.: WO2020/051418
PCT Pub. Date: Mar. 12, 2020

(65) Prior Publication Data
US 2022/0177556 A1    Jun. 9, 2022

Related U.S. Application Data

(60) Provisional application No. 62/837,833, filed on Apr. 24, 2019, provisional application No. 62/727,666, filed on Sep. 6, 2018.

(51) Int. Cl.
*C07K 16/18*   (2006.01)
*A61P 37/02*   (2006.01)
*A61K 39/00*   (2006.01)

(52) U.S. Cl.
CPC ............. *C07K 16/18* (2013.01); *A61P 37/02* (2018.01); *A61K 2039/505* (2013.01); *C07K 2317/24* (2013.01); *C07K 2317/94* (2013.01)

(58) Field of Classification Search
None
See application file for complete search history.

(56) References Cited

U.S. PATENT DOCUMENTS

| 4,736,866 | A | 4/1988 | Leder |
| 4,870,009 | A | 9/1989 | Evans |
| 9,079,949 | B1 | 7/2015 | Andrien, Jr. |
| 11,578,137 | B2 * | 2/2023 | Song ............... C07K 16/2896 |
| 2011/0182817 | A1 | 7/2011 | Matsuura |
| 2014/0314772 | A1 | 10/2014 | Guo |
| 2015/0239966 | A1 | 8/2015 | Baciu |
| 2015/0299305 | A1 | 10/2015 | Andrien, Jr. |
| 2016/0068592 | A1 | 3/2016 | Chung |
| 2016/0176954 | A1 | 6/2016 | Ruike |
| 2016/0200805 | A1 | 7/2016 | Fung |
| 2016/0229908 | A1 | 8/2016 | Igawa |
| 2016/0251433 | A1 | 9/2016 | Andrien, Jr. |
| 2016/0355580 | A1 | 12/2016 | Rother |
| 2017/0332611 | A1 | 11/2017 | Hu |
| 2017/0355756 | A1 | 12/2017 | Julien |
| 2018/0002415 | A1 | 1/2018 | Ruike |
| 2019/0071477 | A1 | 3/2019 | Bao |
| 2020/0148754 | A1 | 5/2020 | Song |
| 2022/0204602 | A1 | 6/2022 | Song |

FOREIGN PATENT DOCUMENTS

| CA | 2680760 | 9/2008 |
| CN | 102459335 | 5/2012 |
| CN | 105143261 | 12/2015 |
| CN | 105963694 | 9/2016 |
| CN | 106459189 | 2/2017 |
| CN | 108137702 | 6/2018 |
| CN | 110461879 | 11/2019 |
| CN | 110709101 | 1/2020 |
| CN | 113038967 | 6/2021 |
| JP | 2011529700 | 12/2011 |
| JP | 2016513088 | 5/2016 |
| JP | 2017509312 | 4/2017 |
| JP | 2017512463 | 5/2017 |
| JP | 2017514496 | 6/2017 |
| JP | 2017226655 | 12/2017 |
| JP | 2018520542 | 7/2018 |

(Continued)

OTHER PUBLICATIONS

Crescioli et al., 2016, "IgG4 Characteristics and Functions in Cancer Immunity", Current Allergy and Asthma Reports, 16:1-11.
Eculizumab Heavy Chain—Variable Domain, 2020, PBD: 515K_H.
Eculizumab Light Chain—Variable Domain, 2020, PBD: 515K_L.
Gorsuch WB, Chrysanthou E, Schwaeble WJ, Stahl GL. The complement system in ischemia-reperfusion injuries. Immunobiology. Nov. 2012;217(11):1026-1033.
Guo RF, Ward PA. Role of C5a in inflammatory responses. Annu Rev Immunol. 2005;23:821-852.
Le Quintrec et al., 2015, "Eculizumab for Treatment of Rapidly Progressive C3 Glomerulopathy", Am. J. Kidney Dis., 65:484-489.
Marc MM, Kristan SS, Rozman A, Kern I, Flezar M, Kosnik M, Korosec P. Complement factor C5a in acute exacerbation of Chronic Obstructive Pulmonary Disease. Scand J Immunol. May 2010;71(5):386-391.

(Continued)

*Primary Examiner* — Daniel E Kolker
*Assistant Examiner* — James Ryland Melchior
(74) *Attorney, Agent, or Firm* — Riverside Law LLP

(57) ABSTRACT

This invention relates to inhibition of the complement signaling using an anti-C5 antibody. Specifically, the invention relates to methods of treating a complement-mediated disease or complement-mediated disorder in an individual by contacting the individual with an anti-C5 antibody.

20 Claims, 45 Drawing Sheets
Specification includes a Sequence Listing.

(56) References Cited

FOREIGN PATENT DOCUMENTS

| KR | 20150035354 | 4/2015 |
|---|---|---|
| KR | 20160127038 | 11/2016 |
| RU | 2477137 | 3/2013 |
| WO | 199634096 | 10/1996 |
| WO | 2007103549 | 9/2007 |
| WO | 2011137395 | 11/2011 |
| WO | 2011143637 | 11/2011 |
| WO | 2014110438 | 7/2014 |
| WO | 2014160958 | 10/2014 |
| WO | 2014194213 | 12/2014 |
| WO | 2015127134 | 8/2015 |
| WO | 2015134894 | 9/2015 |
| WO | 2016098356 | 6/2016 |
| WO | 2016160756 | 10/2016 |
| WO | 2017035362 | 3/2017 |
| WO | 2017104479 | 6/2017 |
| WO | 2017104779 | 6/2017 |
| WO | 2017217524 | 12/2017 |
| WO | 2018165062 | 9/2018 |
| WO | 2018175833 | 9/2018 |
| WO | 2020051418 | 3/2020 |
| WO | 2020219922 | 10/2020 |
| WO | 2022134047 | 6/2022 |

OTHER PUBLICATIONS

Mayer CL, Leibowitz CS, Kurosawa S, Stearns-Kurosawa DJ. Shiga toxins and the pathophysiology of hemolytic uremic syndrome in humans and animals. Toxins (Basel). Nov. 8, 2012;4(11):1261-87. doi: 10.3390/toxins4111261.
Morgan et al., 2015, "Complement, a target for therapy in inflammatory and degenerative diseases", Nature Reviews, 14:857.
Pouw et al., 2019, "Potentiation of complement regulator factor H protects human endothelial cells from complement attack in aHUS sera" Blood Advances, 4:621-632.
Risitano et al., 2012, "Platelets and platelet-like particles mediate intercellular RNA transfer", Blood, 119:6307-6316.
Salmon JE, Girardi G. Antiphospholipid antibodies and pregnancy loss: a disorder of inflammation. J Reprod Immunol. Jan. 2008;77(1):51-56.
Wang Yan et al., 2015, "Applications of Eculizumab, a humanized anti-complement factor C5 monoclonal antibody", Chinese Journal of Clinical Pharmacology and Therapeutics, 4:455-459.
Ward PA. Role of C5 activation products in sepsis. ScientificWorldJournal. Dec. 14, 2010;10:2395-402.
Williams AL, Gullipalli D, Ueda Y, Sato S, Zhou L, Miwa T, Tung KS, Song WC. C5 inhibition prevents renal failure in a mouse model of lethal C3 glomerulopathy. Kidney Int. Jun. 2017;91(6):1386-1397.
Yarilin, A., 1999. Fundamental , M.: Medisina, 608, pp. 172-174.
Boerner et al., 1991, "Production of antigen-specific human monoclonal antibodies from in vitro-primed human splenocytes", J. Immunol. , 147:86-95.
Brodeur et al., 1987, "Monoclonal Antibody Production Techniques and Applications", Dekker, Inc., New York, 51-63.
Chen et al., 1995, Enhancement and destruction of antibody function by somatic mutation: unequal occurrence is controlled by V gene combinatorial associations. Embo J., 14:2784-2794.
Fukuzawa et al., 2017, "Long Lasting Neutralization of C5 By SKY59, A Novel Recycling Antibody, is a Potential Therapy for Complement-Mediated Diseases", Scientific Reports, 7:1-12.
Hwang et al, 2005, "Immunogenicity of engineered antibodies", Method, 36:3-10.
Janus Asbjørn Schatz-Jakobsen et al., 2016, "Structural Basis for Eculizumab-Mediated Inhibition of the Complement Terminal Pathway", J Immunol, 197:337-344.
Koenig et al., 2017, Mutational landscape of antibody variable domains reveals a switch modulating the interdomain conformational dynamics and antigen binding. PNAS, 114:E486-E495.
Kozbor D et al., 1984, "A human hybrid myeloma for production of human monoclonal antibodies", J. Immunol., 133:3001-3005.
Kussie, 1994, "A Single Engineered Amino Acid Substitution Changes Antibody Fine Specificity" J immunol, 152:146-152.
Michelfelder et al., 2018, "The MFHR1 fusion protein is a novel synthetic multitarget complement inhibitor with therapeutic potential.", J. Am. Soc. Nephrol., 29:1141-1153.
Myzithras et al., 2016, "Utility of immunodeficient mouse models for characterizing the preclinical pharmacokinetics of immunogenic antibody therapeutics", Mabs, 8:1606-1611.
Paolo et al., 2017, "Targeted Delivery of Neutralizing Anti-C5 Antibody to Renal Endothelium Prevents Complement-Dependent Tissue Damage", Frontiers in Immunology, 8.
Rudikoff et al., 1981, "Single Amino Acid Substitution Altering Antigen-binding Specificity", Proc. Natl. Acad. Sci., 79:1979-1983.
Sheridan et al., 2018, "Design and preclinical characterization of ALXN1210: A novel anti-C5 antibody with extended duration of action", PLoS One, 13:e0195909.
Thomas et al., 1996, "Inhibition of Complement Activity by Humanized anti-C5 Antibody and Single-Chain Fv", Mol Immunol., 33:1389-1401.
Zelek et al., 2018, "Characterizing a pH-switch anti-C5 antibody as a tool for human and mouse complement C5 purification and cross-species inhibition of classical and reactive lysis", 155:396-403.
Zelek et al., 2019, "Development and characterization of novel anti-C5 monoclonal antibodies capable of inhibiting complement in multiple species", Immunology, 157:283-295.

* cited by examiner figure 1

CDR1, CDR2 and CDR3 sequences are bolded and highlighted in gray

Parent mAb (humanized 2G1 comprising VH-11801 and VL-1901)

CDR1, CDR2 and CDR3 sequences are bolded and highlighted in gray
Engineered mAb H1-SL1.9 (humanized 2G1 comprising VH-11001 with N→H mutation in CDR1 and VL-1901 with Y→H mutation in CDR1)

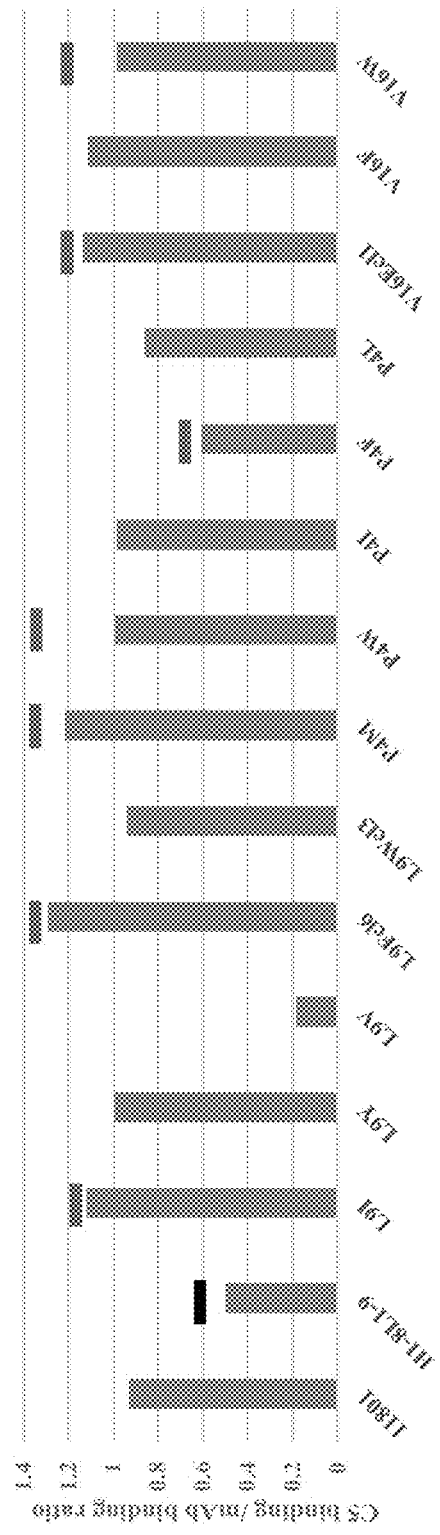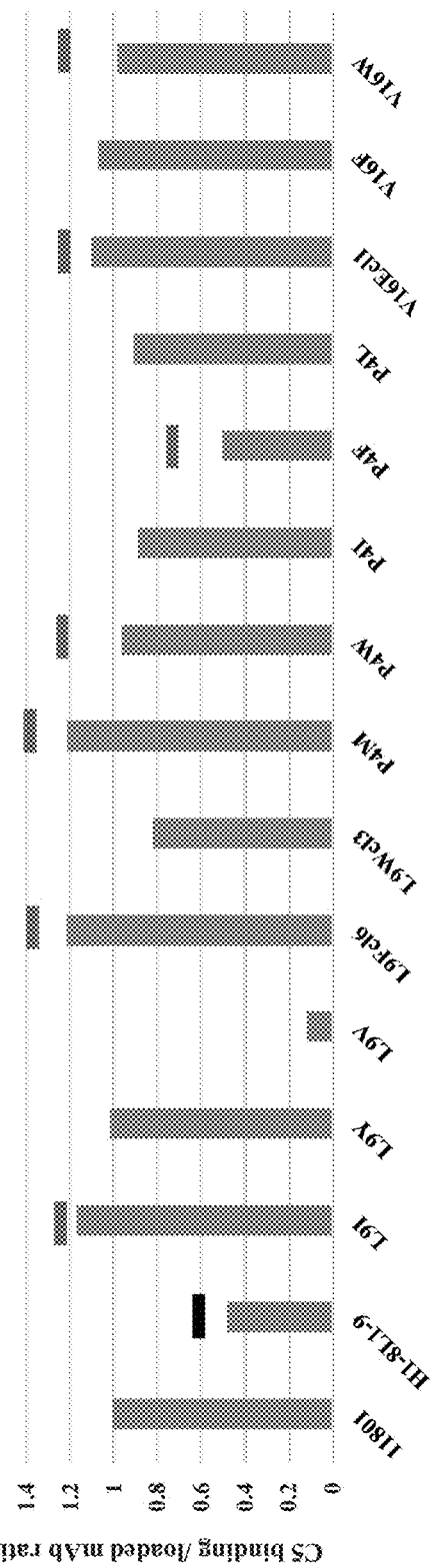
Figure 21

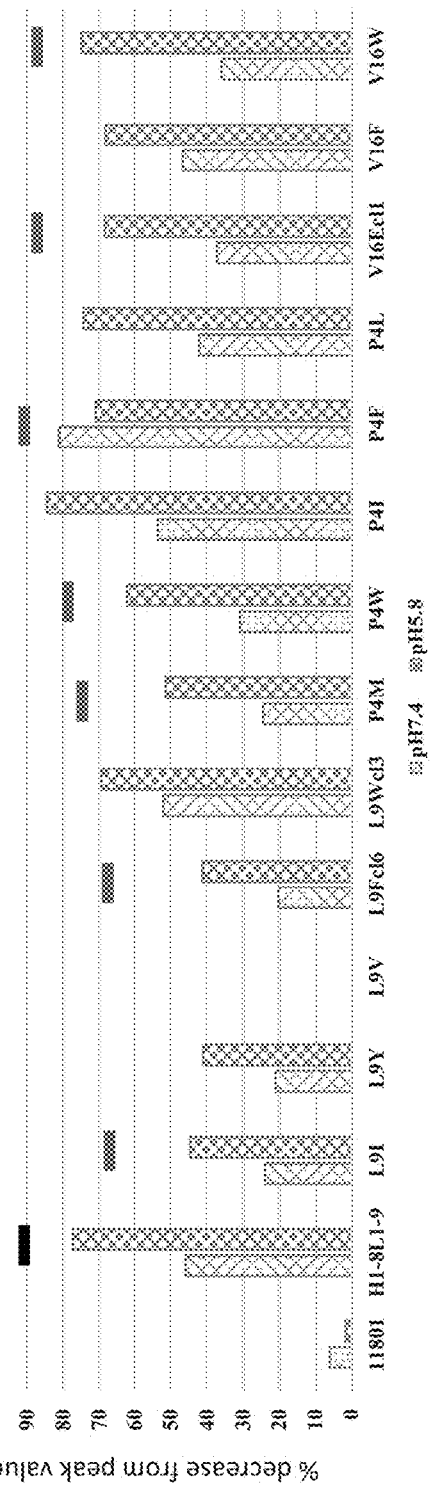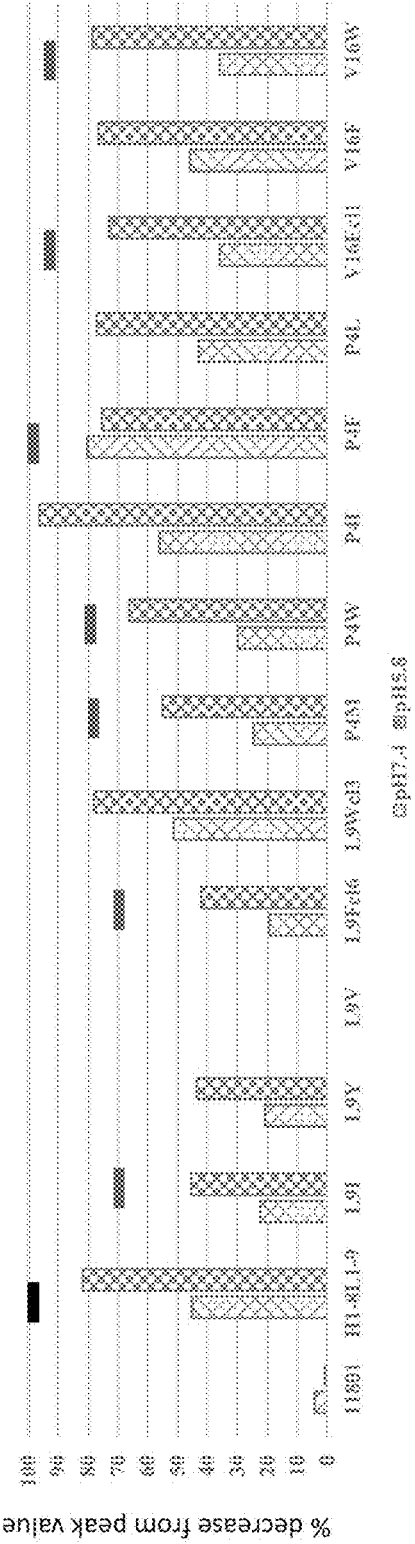
Figure 22

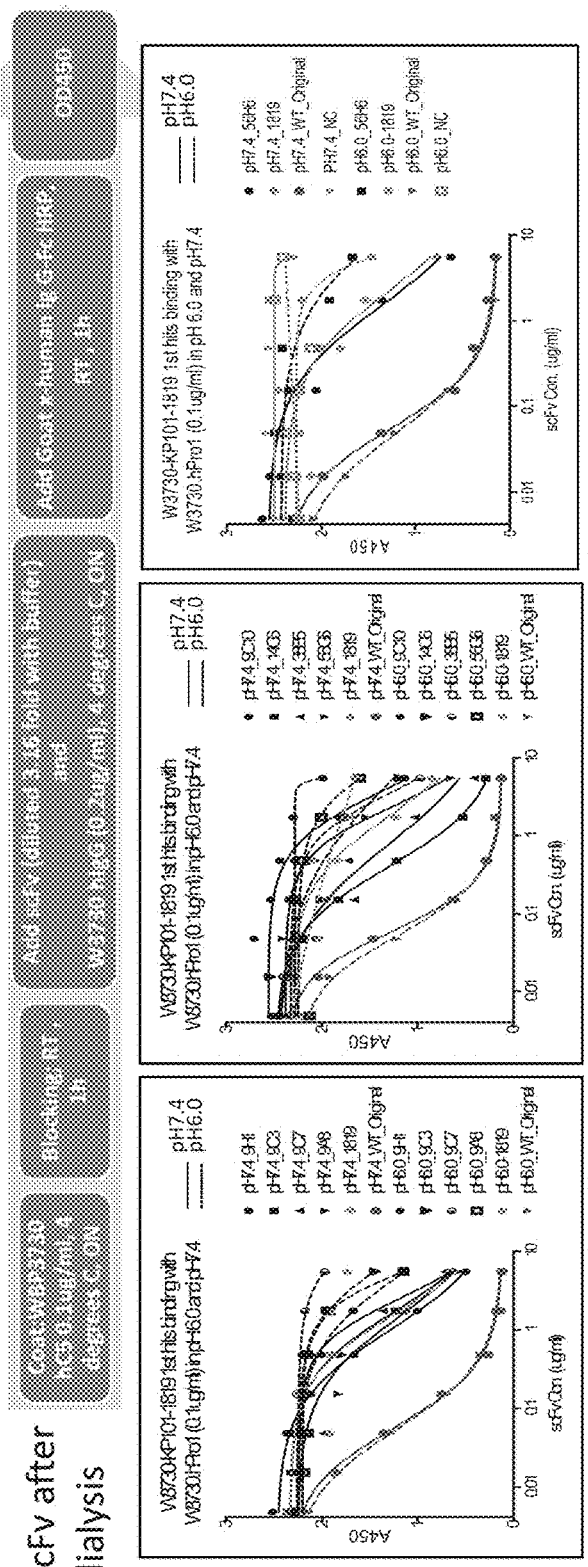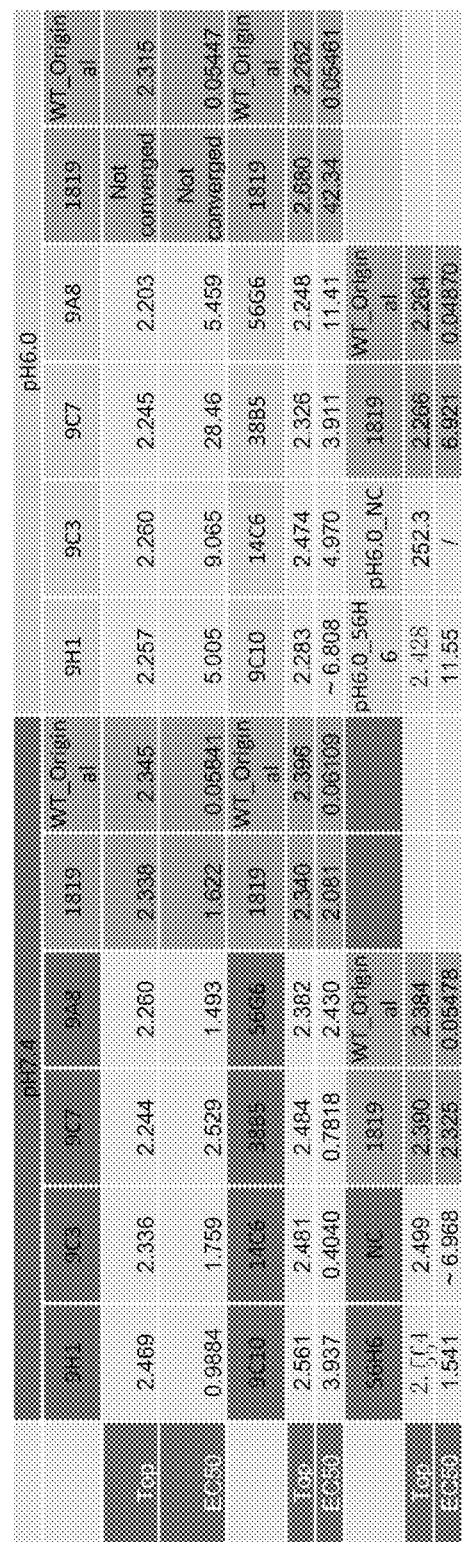
Figure 27

FMEH-VH

```
cagcatgatcagtgtcctcctccaaagtcctgaacatagactctaaccatggactggacc
tgggtcttctcctcctgctgctgtcagtaactgcagtgtgtcactccaggttcagctggtg
 W  V  F  L  L  L  L  S  V  T  A  G  V  H  S  Q  V  Q  L  V
cagtctggagctgaggtgaagaagcctgggtcctcagtgaaggtctcctgcaaggcttct
 Q  S  G  A  E  V  K  K  P  G  S  S  V  K  V  S  C  K  A  S
ggatacacagcattcYTDYNMFgactggtgcgacagccccctggacaagggcctt
 G  Y  T  A  F  T  D  Y  N  M  F  D  W  V  R  Q  A  P  G  Q  G  L
gagtggatggaDINPNYGGTVHactatggttatcatcctacaaccagaaattcaag
 E  W  M  G  D  I  N  P  N  Y  G  G  T  V  Y  Y  N  Q  K  F  K
gacagagtcaccatgaccacagacacatccacgagtacagcctacatggagctgagaagc
 D  R  V  T  M  T  T  D  T  S  T  S  T  A  Y  M  E  L  R  S
ctgagatctgaggacacggccgtgtattactgtgcgagaagggacattgttactccgtt
 L  R  S  E  D  T  A  V  Y  Y  C  A  R  R  D  I  V  T  P  V
aattcctacaaatggtacttcgatgtgtggggccaaggacaatggtcaccgtctcttca
 N  S  Y  K  W  Y  F  D  V  W  G  Q  G  T  M  V  T  V  S  S
```

CDR1, CDR2 and CDR3 sequences are bolded and highlighted in gray
Heavy chain sequence of mAb H1-sL1-9 variant FMEH CDR1  (SEQ ID NO: 47)
CDR2  (SEQ ID NO: 57)
CDR3  (SEQ ID NO: 49)
(SEQ ID NO: 58)
(SEQ ID NO: 59)

HUMANIZED ANTI-C5 ANTIBODIES AND USES THEREOF

CROSS-REFERENCE TO RELATED APPLICATIONS

This application is a national phase application filed under 35 U.S.C. § 371 claiming benefit to PCT International Application PCT/US2019/049890, filed Sep. 6, 2019, which claims priority to U.S. Provisional Application No. 62/727,666, filed Sep. 6, 2018 and U.S. Provisional Application No. 62/837,833, filed Apr. 24, 2019, the disclosures of which are hereby incorporated by reference herein in their entireties.

STATEMENT REGARDING FEDERALLY SPONSORED RESEARCH OR DEVELOPMENT

This invention was made with government support under NIH grant numbers AI085596 and AI117410 awarded by the National Institutes of Health (NIH). The government has certain rights in the invention.

BACKGROUND OF THE INVENTION

The complement system is part of innate immunity that plays a key role in host defense. However, activated complement also has the potential to cause significant tissue injury and destruction and dysregulated complement activity has been found to be associated with a number of rare and common diseases such as paroxysmal nocturnal hemoglobinuria (PNH), atypical hemolytic uremic syndrome, rheumatoid arthritis, age-related macular degeneration etc. Thus, anti-complement therapy is a promising way of treating these human disorders.

Complement C5 is a critical protein in the terminal pathway of complement activation and is the precursor protein for generating the potent pro-inflammatory mediator C5a, as well as the cytolytic membrane attack complex (MAC).

A number of human inflammatory and autoimmune diseases are mediated by C5a and/or MAC, and blocking C5 activation should prevent C5a and MAC generation and be of therapeutic value. A humanized mouse anti-human C5 mAb, eculizumab, has been used to treat two complement-mediated diseases paroxysmal nocturnal hemoglobinuria (PNH) and atypical hemolytic uremic syndrome (aHUS). However, not all PNH patients are responsive to eculizumab treatments and one of the reasons for non-responsiveness is genetic polymorphism of human C5 with loss of epitope binding to eculizumab. Additionally, due to high plasma concentration of C5 and targeted-mediated rapid removal of antibody, eculizumab has to be administered to patients at high doses and frequency.

Thus, there is a need in the art for anti-human C5 mAbs with longer half-life that can inhibit terminal complement activity via different mechanisms and contact sites on C5 and thereby more effectively and more conveniently treat complement-dependent pathologies. The present invention addresses and meets these and other needs.

SUMMARY

In one embodiment, the invention comprises an antibody that specifically binds to C5. In one embodiment, the C5 is human C5. In one embodiment, the antibody is a monoclonal antibody. In one embodiment, the antibody is a humanized antibody. In one embodiment, the antibody is a chimeric antibody. In some embodiments, the antibody is a full-length antibody. In some embodiments, the antibody is an antibody fragment, which includes, but is not limited to, Fab, Fab', F(ab)2, F(ab')2, and scFv. In some embodiments, the antibody is part of a construct, for example a fusion construct comprising the antibody and a targeting moiety or an effector moiety. In some embodiments, the antibody is part of a conjugate construct, such as an antibody drug conjugate construct.

In some embodiments, the anti-C5 antibody exhibits pH-dependent binding to C5. In some embodiments, the pH-dependent anti-C5 antibody binds more strongly to C5 at a more neutral pH (e.g., about pH 7.4; such as that found in the blood) than it does at a more acidic pH (e.g., about pH 5.8; such as that found in the endosome). In some embodiments, the pH-dependent anti-C5 antibody dissociate more quickly from C5 at a more acidic pH (e.g., about pH 5.8; such as that found in the endosome) than it does at neutral pH (e.g., about pH 7.4; such as that found in the blood).

In one embodiment, the pH-dependent antibody specifically binds to human C5, wherein the pH dependent antibody comprises at least one CDR selected from the group consisting of: a VH-CDR1 comprising a variant of SEQ ID NO: 3 having at least one substitution relative to SEQ ID NO: 3; a VH-CDR2 comprising a variant of SEQ ID NO: 4 having at least one substitution relative to SEQ ID NO: 4, a VH-CDR3 comprising a variant of SEQ ID NO: 5 having at least one substitution relative to SEQ ID NO: 5; a VL-CDR1 comprising a variant of SEQ ID NO: 8 having at least one substitution relative to SEQ ID NO: 8; a VL-CDR2 comprising a variant of SEQ ID NO: 9 having at least one substitution relative to SEQ ID NO: 9; and a VL-CDR3 comprising a variant of SEQ ID NO: 10 having at least one substitution relative to SEQ ID NO: 10.

In one embodiment, the antibody comprises at least one of the CDRs selected from the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:11, or a variant or variants thereof. In one embodiment, the antibody comprises the CDRs: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:11, or a variant or variants thereof.

In one embodiment, the antibody comprises a heavy chain comprising the amino acid sequence of SEQ ID NO:2, or a variant thereof. In one embodiment, the antibody comprises a light chain comprising the amino acid sequence of SEQ ID NO:13, or a variant thereof. In one embodiment, the antibody comprises a heavy chain comprising the amino acid sequence of SEQ ID NO:2 and a light chain comprising the amino acid sequence of SEQ ID NO:13, or a variant or variants thereof.

In one embodiment, the antibody comprises at least one of the CDRs selected from the group consisting of: VH-CDR1: SEQ ID NO:3; VH-CDR2: SEQ ID NO:4; VH-CDR3: SEQ ID NO:5; VL-CDR1: SEQ ID NO:14; VL-CDR2: SEQ ID NO:9; and VL-CDR3: SEQ ID NO:10, or a variant or variants thereof. In one embodiment, the antibody comprises the CDRs: VH-CDR1: SEQ ID NO:3; VH-CDR2: SEQ ID NO:4; VH-CDR3: SEQ ID NO:5; VL-CDR1: SEQ ID NO:14; VL-CDR2: SEQ ID NO:9; and VL-CDR3: SEQ ID NO:10, or a variant or variants thereof.

In one embodiment, the antibody comprises a heavy chain comprising the amino acid sequence of SEQ ID NO:2, or a variant thereof. In one embodiment, the antibody comprises a light chain comprising the amino acid sequence of SEQ ID NO:16, or a variant thereof. In one embodiment, the antibody comprises a heavy chain comprising the amino acid sequence of SEQ ID NO:2 and a light chain comprising the amino acid sequence of SEQ ID NO:16, or a variant or variants thereof.

In one embodiment, the antibody comprises at least one of the CDRs selected from the group consisting of: VH-CDR1: SEQ ID NO:17; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In one embodiment, the antibody comprises the CDRs: VH-CDR1: SEQ ID NO:17; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof.

In one embodiment, the antibody comprises a heavy chain comprising the amino acid sequence of SEQ ID NO:19, or a variant thereof. In one embodiment, the antibody comprises a light chain comprising the amino acid sequence of SEQ ID NO:7, or a variant thereof. In one embodiment, the antibody comprises a heavy chain comprising the amino acid sequence of SEQ ID NO:19 and a light chain comprising the amino acid sequence of SEQ ID NO:7, or a variant or variants thereof.

In one embodiment, the antibody comprises at least one of the CDRs selected from the group consisting of: VH-CDR1: SEQ ID NO:20; VH-CDR2: SEQ ID NO:4; VH-CDR3: SEQ ID NO:5; VL-CDR1: SEQ ID NO:23; VL-CDR2: SEQ ID NO:9; and VL-CDR3: SEQ ID NO:10, or a variant or variants thereof. In one embodiment, the antibody comprises the CDRs: VH-CDR1: SEQ ID NO:20; VH-CDR2: SEQ ID NO:4; VH-CDR3: SEQ ID NO:5; VL-CDR1: SEQ ID NO:23; VL-CDR2: SEQ ID NO:9; and VL-CDR3: SEQ ID NO:10, or a variant or variants thereof.

In one embodiment, the antibody comprises a heavy chain comprising the amino acid sequence of SEQ ID NO:22, or a variant thereof. In one embodiment, the antibody comprises a light chain comprising the amino acid sequence of SEQ ID NO:25, or a variant thereof. In one embodiment, the antibody comprises a heavy chain comprising the amino acid sequence of SEQ ID NO:22 and a light chain comprising the amino acid sequence of SEQ ID NO:25, or a variant or variants thereof.

In one embodiment, the antibody comprises at least one of the CDRs selected from the group consisting of: VH-CDR1: SEQ ID NO:3; VH-CDR2: SEQ ID NO:26; VH-CDR3: SEQ ID NO:5; VL-CDR1: SEQ ID NO:8; VL-CDR2: SEQ ID NO:9; and VL-CDR3: SEQ ID NO:29, or a variant or variants thereof. In one embodiment, the antibody comprises the CDRs: VH-CDR1: SEQ ID NO:3; VH-CDR2: SEQ ID NO:26; VH-CDR3: SEQ ID NO:5; VL-CDR1: SEQ ID NO:8; VL-CDR2: SEQ ID NO:9; and VL-CDR3: SEQ ID NO:29, or a variant or variants thereof.

In one embodiment, the antibody comprises a heavy chain comprising the amino acid sequence of SEQ ID NO:28, or a variant thereof. In one embodiment, the antibody comprises a light chain comprising the amino acid sequence of SEQ ID NO:31, or a variant thereof. In one embodiment, the antibody comprises a heavy chain comprising the amino acid sequence of SEQ ID NO:28 and a light chain comprising the amino acid sequence of SEQ ID NO:31, or a variant or variants thereof.

In one embodiment, the antibody comprises at least one of the CDRs selected from the group consisting of: VH-CDR1: SEQ ID NO:3; VH-CDR2: SEQ ID NO:34; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In one embodiment, the antibody comprises the CDRs: VH-CDR1: SEQ ID NO:3; VH-CDR2: SEQ ID NO:34; VH-CDR3: SEQ ID NO:5; VL-CDR1: SEQ ID NO:8; VL-CDR2: SEQ ID NO:9; and VL-CDR3: SEQ ID NO:10, or a variant or variants thereof.

In one embodiment, the antibody comprises a heavy chain comprising the amino acid sequence of SEQ ID NO:36, or a variant thereof. In one embodiment, the antibody comprises a light chain comprising the amino acid sequence of SEQ ID NO:7, or a variant thereof. In one embodiment, the antibody comprises a heavy chain comprising the amino acid sequence of SEQ ID NO:36 and a light chain comprising the amino acid sequence of SEQ ID NO:7, or a variant or variants thereof.

In one embodiment, the antibody comprises at least one of the CDRs selected from the group consisting of: VH-CDR1: SEQ ID NO:37; VH-CDR2: SEQ ID NO:38; VH-CDR3: SEQ ID NO:39; VL-CDR1: SEQ ID NO:23; VL-CDR2: SEQ ID NO:9; and VL-CDR3: SEQ ID NO:10, or a variant or variants thereof. In one embodiment, the antibody comprises the CDRs: VH-CDR1: SEQ ID NO:37; VH-CDR2: SEQ ID NO:38; VH-CDR3: SEQ ID NO:39; VL-CDR1: SEQ ID NO:23; VL-CDR2: SEQ ID NO:9; and VL-CDR3: SEQ ID NO:10, or a variant or variants thereof.

In one embodiment, the antibody comprises a heavy chain comprising the amino acid sequence of SEQ ID NO:41, or a variant thereof. In one embodiment, the antibody comprises a light chain comprising the amino acid sequence of SEQ ID NO:25, or a variant thereof. In one embodiment, the antibody comprises a heavy chain comprising the amino acid sequence of SEQ ID NO:41 and a light chain comprising the amino acid sequence of SEQ ID NO:25, or a variant or variants thereof.

In one embodiment, the antibody comprises at least one of the CDRs selected from the group consisting of: VH-CDR1: SEQ ID NO:42; VH-CDR2: SEQ ID NO:43; VH-CDR3: SEQ ID NO:44; VL-CDR1: SEQ ID NO:23; VL-CDR2: SEQ ID NO:9; and VL-CDR3: SEQ ID NO:10, or a variant or variants thereof. In one embodiment, the antibody comprises the CDRs: VH-CDR1: SEQ ID NO:42; VH-CDR2: SEQ ID NO:43; VH-CDR3: SEQ ID NO:44; VL-CDR1: SEQ ID NO:23; VL-CDR2: SEQ ID NO:9; and VL-CDR3: SEQ ID NO:10, or a variant or variants thereof.

In one embodiment, the antibody comprises a heavy chain comprising the amino acid sequence of SEQ ID NO:46, or a variant thereof. In one embodiment, the antibody comprises a light chain comprising the amino acid sequence of SEQ ID NO:25, or a variant thereof. In one embodiment, the antibody comprises a heavy chain comprising the amino acid sequence of SEQ ID NO:46 and a light chain comprising the amino acid sequence of SEQ ID NO:25, or a variant or variants thereof.

In one embodiment, the antibody comprises at least one of the CDRs selected from the group consisting of: VH-CDR1: SEQ ID NO:47; VH-CDR2: SEQ ID NO:48; VH-CDR3: SEQ ID NO:49; VL-CDR1: SEQ ID NO:23; VL-CDR2: SEQ ID NO:9; and VL-CDR3: SEQ ID NO:10, or a variant or variants thereof. In one embodiment, the antibody comprises the CDRs: VH-CDR1: SEQ ID NO:47; VH-CDR2: SEQ ID NO:48; VH-CDR3: SEQ ID NO:49; VL-CDR1: SEQ ID NO:23; VL-CDR2: SEQ ID NO:9; and VL-CDR3: SEQ ID NO:10, or a variant or variants thereof.

In one embodiment, the antibody comprises a heavy chain comprising the amino acid sequence of SEQ ID NO:51, or a variant thereof. In one embodiment, the antibody comprises a light chain comprising the amino acid sequence of SEQ ID NO:25, or a variant thereof. In one embodiment, the antibody comprises a heavy chain comprising the amino acid sequence of SEQ ID NO:51 and a light chain comprising the amino acid sequence of SEQ ID NO:25, or a variant or variants thereof.

In one embodiment, the antibody comprises at least one of the CDRs selected from the group consisting of VH-CDR1: SEQ ID NO:52; VH-CDR2: SEQ ID NO:53; VH-CDR3: SEQ ID NO:54; VL-CDR1: SEQ ID NO:23; VL-CDR2: SEQ ID NO:9; and VL-CDR3: SEQ ID NO:10, or a variant or variants thereof. In one embodiment, the antibody comprises the CDRs: VH-CDR1: SEQ ID NO:52; VH-CDR2: SEQ ID NO:53; VH-CDR3: SEQ ID NO:54; VL-CDR1: SEQ ID NO:23; VL-CDR2: SEQ ID NO:9; and VL-CDR3: SEQ ID NO:10, or a variant or variants thereof.

In one embodiment, the antibody comprises a heavy chain comprising the amino acid sequence of SEQ ID NO:56, or a variant thereof. In one embodiment, the antibody comprises a light chain comprising the amino acid sequence of SEQ ID NO:25, or a variant thereof. In one embodiment, the antibody comprises a heavy chain comprising the amino acid sequence of SEQ ID NO:56 and a light chain comprising the amino acid sequence of SEQ ID NO:25, or a variant or variants thereof.

In one embodiment, the antibody comprises at least one of the CDRs selected from the group consisting of: VH-CDR1: SEQ ID NO:47; VH-CDR2: SEQ ID NO:57; VH-CDR3: SEQ ID NO:49; VL-CDR1: SEQ ID NO:23; VL-CDR2: SEQ ID NO:9; and VL-CDR3: SEQ ID NO:10, or a variant or variants thereof. In one embodiment, the antibody comprises the CDRs: VH-CDR1: SEQ ID NO:47; VH-CDR2: SEQ ID NO:57; VH-CDR3: SEQ ID NO:49; VL-CDR1: SEQ ID NO:23; VL-CDR2: SEQ ID NO:9; and VL-CDR3: SEQ ID NO:10, or a variant or variants thereof.

In one embodiment, the antibody comprises a heavy chain comprising the amino acid sequence of SEQ ID NO:59, or a variant thereof. In one embodiment, the antibody comprises a light chain comprising the amino acid sequence of SEQ ID NO:25, or a variant thereof. In one embodiment, the antibody comprises a heavy chain comprising the amino acid sequence of SEQ ID NO:59 and a light chain comprising the amino acid sequence of SEQ ID NO:25, or a variant or variants thereof.

In one embodiment, the antibody comprises at least one of the CDRs selected from the group consisting of: VH-CDR1: SEQ ID NO:37; VH-CDR2: SEQ ID NO:62; VH-CDR3: SEQ ID NO:39; VL-CDR1: SEQ ID NO:23; VL-CDR2: SEQ ID NO:9; and VL-CDR3: SEQ ID NO:10, or a variant or variants thereof. In one embodiment, the antibody comprises the CDRs: SEQ ID NO:37; VH-CDR2: SEQ ID NO:62; VH-CDR3: SEQ ID NO:39; VL-CDR1: SEQ ID NO:23; VL-CDR2: SEQ ID NO:9; and VL-CDR3: SEQ ID NO:10, or a variant or variants thereof.

In one embodiment, the antibody comprises a heavy chain comprising the amino acid sequence of SEQ ID NO:64, or a variant thereof. In one embodiment, the antibody comprises a light chain comprising the amino acid sequence of SEQ ID NO:25, or a variant thereof. In one embodiment, the antibody comprises a heavy chain comprising the amino acid sequence of SEQ ID NO:64 and a light chain comprising the amino acid sequence of SEQ ID NO:25, or a variant or variants thereof.

In one embodiment, the antibody comprises at least one of the CDRs selected from the group consisting of VH-CDR1: SEQ ID NO:42; VH-CDR2: SEQ ID NO:65; VH-CDR3: SEQ ID NO:44; VL-CDR1: SEQ ID NO:23; VL-CDR2: SEQ ID NO:9; and VL-CDR3: SEQ ID NO:10, or a variant or variants thereof. In one embodiment, the antibody comprises the CDRs: SEQ ID NO:42; VH-CDR2: SEQ ID NO:65; VH-CDR3: SEQ ID NO:44; VL-CDR1: SEQ ID NO:23; VL-CDR2: SEQ ID NO:9; and VL-CDR3: SEQ ID NO:10, or a variant or variants thereof.

In one embodiment, the antibody comprises a heavy chain comprising the amino acid sequence of SEQ ID NO:67, or a variant thereof. In one embodiment, the antibody comprises a light chain comprising the amino acid sequence of SEQ ID NO:25, or a variant thereof. In one embodiment, the antibody comprises a heavy chain comprising the amino acid sequence of SEQ ID NO:67 and a light chain comprising the amino acid sequence of SEQ ID NO:25, or a variant or variants thereof.

In one embodiment, the antibody comprises at least one of the CDRs selected from the group consisting of: VH-CDR1: SEQ ID NO:52; VH-CDR2: SEQ ID NO:68; VH-CDR3: SEQ ID NO:54; VL-CDR1: SEQ ID NO:23; VL-CDR2: SEQ ID NO:9; and VL-CDR3: SEQ ID NO:10, or a variant or variants thereof. In one embodiment, the antibody comprises the CDRs: SEQ ID NO:52; VH-CDR2: SEQ ID NO:68; VH-CDR3: SEQ ID NO:54; VL-CDR1: SEQ ID NO:23; VL-CDR2: SEQ ID NO:9; and VL-CDR3: SEQ ID NO:10, or a variant or variants thereof.

In one embodiment, the antibody comprises a heavy chain comprising the amino acid sequence of SEQ ID NO:70, or a variant thereof. In one embodiment, the antibody comprises a light chain comprising the amino acid sequence of SEQ ID NO:25, or a variant thereof. In one embodiment, the antibody comprises a heavy chain comprising the amino acid sequence of SEQ ID NO:70 and a light chain comprising the amino acid sequence of SEQ ID NO:25, or a variant or variants thereof.

In various embodiments, any of the antibodies of the invention described herein, having any of the variable regions described herein, may comprise an Fc fragment or Fc domain. For example, in some embodiments, an antibody described herein, comprises an Fc fragment of an immunoglobulin. Exemplary immunoglobulins include, but is not limited to, IgG1, IgG2, IgG3, IgG4, IgM, IgA, IgE, and IgD. In one embodiment, the antibody comprises a human IgG4 Fc. In one embodiment, the antibody comprises a human IgG4 Fc comprising the amino acid sequence of SEQ ID NO: 32. In one embodiment, the antibody comprises a human IgG4 Fc having a S108P mutation relative to SEQ ID NO: 32. In one embodiment, the human IgG4 Fc having an S108P mutation relative to SEQ ID NO: 32 comprises the amino acid sequence of SEQ ID NO: 33. In one embodiment, the antibody comprises a human IgG4 Fc having an S108P mutation, a M308L mutation, and a N314A mutation relative to SEQ ID NO: 32. In one embodiment, the a human IgG4 Fc having an S108P mutation, a M308L mutation, and a N314A mutation relative to SEQ ID NO: 32 comprises the amino acid sequence of SEQ ID NO: 61.

In one embodiment, the antibody is at least one selected from the group consisting of mAbs L3-1, L1-2, H1-4, H1-8/L1-9, and H2-6/L3-5. In one embodiment, antibody is a mAb H1-8/L1-9 variation.

In some embodiments, the anti-C5 antibody or antigen-binding fragment thereof comprises a substitution of the proline residue at position #4 (i.e., P4) in VH CDR2, relative to SEQ ID NO:4. In various embodiments, the substitution at P4 is P4→F4 (i.e., P4F), P4→L4 (i.e., P4L), P4→M4 (i.e., P4M), P4→W4 (i.e., P4W), or P4→I4 (i.e., P4I).

In some embodiments, the anti-C5 antibody or antigen-binding fragment thereof comprises a substitution of the threonine residue at position #9 (i.e., T9) in VH CDR2, relative to SEQ ID NO:4. In various embodiments, the substitution at T9 is T9→H9 (i.e., T9H), T9→F9 (i.e., T9F), T9→L9 (i.e., T9L), T9→M9 (i.e., T9M), T9→W9 (i.e., T9W), or T9→I9 (i.e., T9I).

In some embodiments, the anti-C5 antibody or antigen-binding fragment thereof comprises a substitution of the proline residue at position #4 (i.e., P4) in VH CDR2, relative to SEQ ID NO:4, and a substitution of the threonine residue at position #9 (i.e., T9) in VH CDR2, relative to SEQ ID NO:4. In various embodiments, the substitution at P4 is P4→F4 (i.e., P4F), P4→L4 (i.e., P4L), P4→M4 (i.e., P4M), P4→W4 (i.e., P4W), or P4→I4 (i.e., P4I); and the substitution at T9 is T9→H9 (i.e., T9H), T9→F9 (i.e., T9F), T9→L9 (i.e., T9L), T9→M9 (i.e., T9M), T9→W9 (i.e., T9W), or T9→I9 (i.e., T9I).

In some embodiments, the anti-C5 antibody or antigen-binding fragment thereof comprises a substitution of the valine residue at position #16 (i.e., V16) in VH CDR3, relative to SEQ ID NO:5. In various embodiments, the substitution at V16 is V16→F16 (i.e., V16F), V16→E16 (i.e., V16E) or V16→W16 (i.e., V16W).

In some embodiments, the anti-C5 antibody or antigen-binding fragment thereof comprises a substitution of the leucine residue at position #9 (i.e., L9) in VH CDR1, relative to SEQ ID NO:20. In various embodiments, the substitution at L9 is L9→W9 (i.e., L9W), L9→I9 (i.e., L9I), L9→V9 (i.e., L9V), L9→Y9 (i.e., L9Y), or L9→F9 (i.e., L9F).

In some embodiments, the anti-C5 antibody or antigen-binding fragment thereof comprises a substitution at two or more of the group consisting of proline 4 (i.e., P4) in VH CDR2, relative to SEQ ID NO:4, threonine 9 (i.e., T9) in VH CDR2, relative to SEQ ID NO:4, valine 16 (i.e., V16) in VH CDR3, relative to SEQ ID NO:5, and leucine 9 (i.e., L9) in VH CDR1, relative to SEQ ID NO:20. In various embodiments, the anti-C5 antibody or antigen-binding fragment thereof comprising a substitution at two or more of the group consisting of proline 4 (i.e., P4) in VH CDR2, relative to SEQ ID NO:4, valine 16 (i.e., V16) in VH CDR3, relative to SEQ ID NO:5, and leucine 9 (i.e., L9) in VH CDR1, relative to SEQ ID NO:20 comprises the two or more substitutions selected from the group consisting of L9I/P4M, L9I/P4W, L9I/P4F, L9F/P4M, L9F/P4W, L9F/P4F, L9I/P4M/V16W, L9I/P4W/V16W, L9I/P4F/V16W, L9F/P4M/V16W, L9F/P4W/V16W, L9F/P4F/V16W, L9I/P4M/V16E, L9I/P4W/V16E, L9I/P4F/V16E, L9F/P4M/V16E, L9F/P4W/V16E, L9F/P4F/V16E, L9I/P4M/T9H/V16W, L9I/P4W/T9H/V16W, L9I/P4F/T9H/V16W, L9F/P4M/T9H/V16W, L9F/P4W/T9H/V16W, L9F/P4F, T9H/V16W, L9I/P4M/T9H/V16E, L9I/P4W/T9H/V16E, L9I/P4F/T9H/V16E, L9F/P4M/T9H/V16E, L9F/P4W/T9H/V16E, and L9F/P4F/T9H/V16E.

In one embodiment, the present invention relates to a method of treating a complement pathway-mediated disease or disorder in an individual, comprising the step of administering to said individual the anti-C5 antibody of claim. In one embodiment, the disease or disorder is at least selected from the group consisting of: macular degeneration (MD), age-related macular degeneration (AMD), ischemia reperfusion injury, arthritis, rheumatoid arthritis, asthma, allergic asthma, lupus, ulcerative colitis, stroke, post-surgery systemic inflammatory syndrome, chronic obstructive pulmonary disease (COPD), paroxysmal nocturnal hemoglobinuria (PNH) syndrome, myasthenia gravis, neuromyelitis optica, (NMO), multiple sclerosis, delayed graft function, antibody-mediated rejection, atypical hemolytic uremic syndrome (aHUS), central retinal vein occlusion (CRVO), central retinal artery occlusion (CRAO), epidermolysis bullosa, sepsis, organ transplantation, inflammation (including, but not limited to, inflammation associated with cardiopulmonary bypass surgery and kidney dialysis), C3 glomerulopathy, membranous nephropathy, IgA nephropathy, glomerulonephritis (including, but not limited to, anti-neutrophil cytoplasmic antibody (ANCA)-mediated glomerulonephritis, lupus nephritis, and combinations thereof), ANCA-mediated vasculitis, Shiga toxin induced HUS, and antiphospholipid antibody-induced pregnancy loss, or any combinations thereof. In some embodiments, the AP-mediated disease is C3 glomerulopathy. In some embodiments, the AP-mediated disease is macular degeneration, such as age-related macular degeneration. In one embodiment, administration of the anti-C5 antibody inhibits the generation of a C5a or C5b protein.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:11, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: VH-CDR1: SEQ ID NO:3; VH-CDR2: SEQ ID NO:4; VH-CDR3: SEQ ID NO:5; VL-CDR1: SEQ ID NO:14; VL-CDR2: SEQ ID NO:9; and VL-CDR3: SEQ ID NO:10, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences:

VH-CDR1: SEQ ID NO:17; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: VH-CDR1: SEQ ID NO:20; VH-CDR2: SEQ ID NO:4; VH-CDR3: SEQ ID NO:5; VL-CDR1: SEQ ID NO:23; VL-CDR2: SEQ ID NO:9; and VL-CDR3: SEQ ID NO:10, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: VH-CDR1: SEQ ID NO:3; VH-CDR2: SEQ ID NO:26; VH-CDR3: SEQ ID NO:5; VL-CDR1: SEQ ID NO:8; VL-CDR2: SEQ ID NO:9; and VL-CDR3: SEQ ID NO:29, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: VH-CDR1: SEQ ID NO:37; VH-CDR2: SEQ ID NO:38; VH-CDR3: SEQ ID NO:39; VL-CDR1: SEQ ID NO:23; VL-CDR2: SEQ ID NO:9; and VL-CDR3: SEQ ID NO:10, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: VH-CDR1: SEQ ID NO:42; VH-CDR2: SEQ ID NO:43; VH-CDR3: SEQ ID NO:44; VL-CDR1: SEQ ID NO:23; VL-CDR2: SEQ ID NO:9; and VL-CDR3: SEQ ID NO:10, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: VH-CDR1: SEQ ID NO:47; VH-CDR2: SEQ ID NO:48; VH-CDR3: SEQ ID NO:49; VL-CDR1: SEQ ID NO:23; VL-CDR2: SEQ ID NO:9; and VL-CDR3: SEQ ID NO:10, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: VH-CDR1: SEQ ID NO:52; VH-CDR2: SEQ ID NO:53; VH-CDR3: SEQ ID NO:54; VL-CDR1: SEQ ID NO:23; VL-CDR2: SEQ ID NO:9; and VL-CDR3: SEQ ID NO:10, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: VH-CDR1: SEQ ID NO:47; VH-CDR2: SEQ ID NO:57; VH-CDR3: SEQ ID NO:49; VL-CDR1: SEQ ID NO:23; VL-CDR2: SEQ ID NO:9; and VL-CDR3: SEQ ID NO:10, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: VH-CDR1: SEQ ID NO:37; VH-CDR2: SEQ ID NO:62; VH-CDR3: SEQ ID NO:39; VL-CDR1: SEQ ID NO:23; VL-CDR2: SEQ ID NO:9; and VL-CDR3: SEQ ID NO:10, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: VH-CDR1: SEQ ID NO:42; VH-CDR2: SEQ ID NO:65; VH-CDR3: SEQ ID NO:44; VL-CDR1: SEQ ID NO:23; VL-CDR2: SEQ ID NO:9; and VL-CDR3: SEQ ID NO:10, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: VH-CDR1: SEQ ID NO:52; VH-CDR2: SEQ ID NO:68; VH-CDR3: SEQ ID NO:54; VL-CDR1: SEQ ID NO:23; VL-CDR2: SEQ ID NO:9; and VL-CDR3: SEQ ID NO:10, or a variant or variants thereof. In one embodiment, the antibody is an antibody fragment selected from the group consisting of a Fab, Fab', F(ab)2, F(ab')2, scFv, and combinations thereof.

In some embodiments, the present invention is an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO:2, or a variant thereof. In one embodiment, the antibody is an antibody fragment selected from the group consisting of a Fab, Fab', F(ab)2, F(ab')2, scFv, and combinations thereof.

In some embodiments, the present invention is an antibody against human C5, wherein the antibody has a light chain variable (vL) region that has an amino acid sequence that is more than about 90% (such as more than any of 91%, 92%, 93%, 94%, 95%, 96%, 97%, 98%, or 99%) identical to SEQ ID NO:7, or a variant thereof. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:2, and wherein the vL region has an amino acid sequence that is more than about 90% (such as more than any of 91%, 92%, 93%, 94%, 95%, 96%, 97%, 98%, or 99%) identical to SEQ ID NO:7. In one embodiment, the antibody is an antibody fragment selected from the group consisting of a Fab, Fab', F(ab)2, F(ab')2, scFv, and combinations thereof.

In some embodiments, the present invention is an antibody against human C5, wherein the antibody has a light chain variable (vL) region that has an amino acid sequence that is more than about 90% (such as more than any of 91%, 92%, 93%, 94%, 95%, 96%, 97%, 98%, or 99%) identical to SEQ ID NO:13, or a variant thereof. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:2, and wherein the vL region has an amino acid sequence that is more than about 90% (such as more than any of 91%, 92%, 93%, 94%, 95%, 96%, 97%, 98%, or 99%) identical to SEQ ID NO:13. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a light chain variable (vL) region that has an amino acid sequence that is more than about 90% (such as more than any of 91%, 92%, 93%, 94%, 95%, 96%, 97%, 98%, or 99%) identical to SEQ ID NO:16. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:2, and wherein the vL region has an amino acid sequence that is more than about 90% (such as more than any of 91%, 92%, 93%, 94%, 95%, 96%, 97%, 98%, or 99%) identical to SEQ ID NO:16. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO:19. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a light chain variable (vL) region that has an amino acid sequence that is more than about 90% (such as more than any of 91%, 92%, 93%, 94%, 95%, 96%, 97%, 98%, or 99%) identical to SEQ ID NO:7. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:19, and wherein the vL region has an amino acid sequence that is more than about 90% (such as more than any of 91%, 92%, 93%, 94%, 95%, 96%, 97%, 98%, or 99%) identical to SEQ ID NO:7. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO:22. In one embodiment, the antibody is an antibody fragment selected from the group consisting of a Fab, Fab', F(ab)2, F(ab')2, scFv, and combinations thereof.

In one embodiment, the present invention relates to an antibody against human C5, wherein the antibody has a light chain variable (vL) region that has an amino acid sequence that is more than about 90% (such as more than any of 91%, 92%, 93%, 94%, 95%, 96%, 97%, 98%, or 99%) identical to SEQ ID NO:25. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:22, and wherein the vL region has an amino acid sequence that is more than about 90% (such as more than any of 91%, 92%, 93%, 94%, 95%, 96%, 97%, 98%, or 99%) identical to SEQ ID NO:25. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO:28. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a light chain variable (vL) region that has an amino acid sequence that is more than about 90% (such as more than any of 91%, 92%, 93%, 94%, 95%, 96%, 97%, 98%, or 99%) identical to SEQ ID NO:31. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:28, and wherein the vL region has an amino acid sequence that is more than about 90% (such as more than any of 91%, 92%, 93%, 94%, 95%, 96%, 97%, 98%, or 99%) identical to SEQ ID NO:31. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO:41. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:41, and wherein the vL region has an amino acid sequence that is more than about 90% (such as more than any of 91%, 92%, 93%, 94%, 95%, 96%, 97%, 98%, or 99%) identical to SEQ ID NO:25. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO:46. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:46, and wherein the vL region has an amino acid sequence that is more than about 90% (such as more than any of 91%, 92%, 93%, 94%, 95%, 96%, 97%, 98%, or 99%) identical to SEQ ID NO:25. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO:51. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:51, and wherein the vL region has an amino acid sequence that is more than about 90% (such as more than any of 91%, 92%, 93%, 94%, 95%, 96%, 97%, 98%, or 99%) identical to SEQ ID NO:25. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO:56. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:56, and wherein the vL region has an amino acid sequence that is more than about 90% (such as more than any of 91%, 92%, 93%, 94%, 95%, 96%, 97%, 98%, or 99%) identical to SEQ ID NO:25. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO:59. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:59, and wherein the vL region has an amino acid sequence that is more than about 90% (such as more than any of 91%, 92%, 93%, 94%, 95%, 96%, 97%, 98%, or 99%) identical to SEQ ID NO:25. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO:64. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:64, and wherein the vL region has an amino acid sequence that is more than about 90% (such as more than any of 91%, 92%, 93%, 94%, 95%, 96%, 97%, 98%, or 99%) identical to SEQ ID NO:25. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO:67. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:67, and wherein the vL region has an amino acid sequence that is more than about 90% (such as more than any of 91%, 92%, 93%, 94%, 95%, 96%, 97%, 98%, or 99%) identical to SEQ ID NO:25. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO:70. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO:70, and wherein the vL region has an amino acid sequence that is more than about 90% (such as more than any of 91%, 92%, 93%, 94%, 95%, 96%, 97%, 98%, or 99%) identical to SEQ ID NO:25. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a Fc fragment that has an amino acid sequence that is more than about 90% (such as more than any of 91%, 92%, 93%, 94%, 95%, 96%, 97%, 98%, or 99%) identical to SEQ ID NO:32. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a Fc fragment that has an amino acid sequence that is more than about 90% (such as more than any of 91%, 92%, 93%, 94%, 95%, 96%, 97%, 98%, or 99%) identical to SEQ ID NO:33. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a Fc fragment that has an amino acid sequence that is more than about 90% (such as more than any of 91%, 92%, 93%, 94%, 95%, 96%, 97%, 98%, or 99%) identical to SEQ ID NO:61. In one embodiment, the antibody is an antibody fragment selected from the group consisting of a Fab, Fab', F(ab)2, F(ab')2, scFv, and combinations thereof.

In one embodiment, the present invention relates to a cell comprising at least one of the antibodies described elsewhere herein. In some embodiments, the cell produces the antibody of at least one of the antibodies described elsewhere herein. In one embodiment, the cell is a hybridoma.

In one embodiment, the present invention is a cell line comprising at least one of the antibodies described elsewhere herein. In some embodiments, the cell line produces at least one of the antibodies described elsewhere herein. In some embodiments, the cell line is a hybridoma cell line.

In one embodiment, the present invention relates to a genetically modified non-human animal. In one embodiment, the genetically modified non-human animal expresses human C5. In one embodiment, the genetically modified non-human animal is a rodent. In one embodiment, the genetically modified non-human animal is a mouse. In one embodiment, the genetically modified non-human animal is a NOD/SCID mouse. In one embodiment, the genetically modified non-human animal is a FcRn/SCID mouse.

BRIEF DESCRIPTION OF THE DRAWINGS

The foregoing summary, as well as the following detailed description of exemplary embodiments of the invention, will be better understood when read in conjunction with the appended drawings. It should be understood, however, that the invention is not limited to the precise arrangements and instrumentalities of the embodiments shown in the drawings. In the drawings:

FIG. 1 depicts nucleotide and amino acid sequences of a humanized variable heavy chain (VH) of mAb 2G1 (humanized 2G1 VH-11801) and humanized variable light chain (VL) of mAb 2G1 (humanized 2G1 VL-1901). Humanization was achieved by CDR grating from murine mAb 2G1 VH into a germline encoded human VH frame (11801) and CDR grating from murine mAb 2G1 VL into a germline encoded human VL frame (1901). The amino acid sequences of signal peptides are underlined and that of CDR1, CDR2 and CDR3 is bolded and shaded.

FIG. 2 depicts nucleotide and amino acid sequences of mAb L3-1, humanized VH-11801 and humanized VL-1901 with a Q→H substitution in VL-CDR3.

FIG. 3 depicts nucleotide and amino acid sequences of mAb L1-2, humanized VH-11801 and humanized VL-1901 with a T→H substitution in VL-CDR1.

FIG. 4 depicts nucleotide and amino acid sequences of mAb H1-4, humanized VH-11801 and humanized VL-1901 with a I→H substitution in VH-CDR1.

FIG. 5 depicts nucleotide and amino acid sequences of mAb H1-8/L1-9, humanized VH-11801 and humanized VL-1901 with a N→H substitution in VH-CDR1 and a Y→H substitution in VL-CDR1.

FIG. 6 depicts nucleotide and amino acid sequences of mAb H2-6/L3-5, humanized VH-11801 and humanized VL-1901 with a Y→H substitution in VH-CDR2 and a E→H substitution in VL-CDR3.

FIG. 20 depicts the results of ELISA assay demonstrating improved binding at pH 7.4 to C5 of mAb H1-8/L1-9 ScFV variants having at least one substitution at leucine 9 (i.e., L9) in VH CDR1, relative to SEQ ID NO:20, proline 4 (i.e., P4) in VH CDR2, relative to SEQ ID NO:4, and/or valine 16 (i.e., V16) in VH CDR3, relative to SEQ ID NO:5 (i.e., L9→W9 (i.e., L9W), L9→I9 (i.e., L9I), L9→V9 (i.e., L9), L9→Y9 (i.e., L9Y), L9→F9 (i.e., L9F), P4→F4 (i.e., P4F), P4→L4 (i.e., P4L), P4→M4 (i.e., P4M), P4→W4 (i.e., P4W), P4→I4 (i.e., P4I), V16→F16 (i.e., V16F), V16→E16 (i.e., V16E) and V16→W16 (i.e., V16W)). Binding of mAb H1-8/L1-9 ScFV variants is shown in column 3 (OD450) and 4 (OD450 confirm) and that of the parental mAb H1-8/L1-9 ScFV is shown in column 8 (WT/OD450).

FIG. 21 depicts the results of an Octet assay assessing the relative C5 binding affinity of mAb H1-8/L1-9 variants expressed in Expi-CHO cells as human IgG4. Expi-CHO cells were transfected with H1-8 VH variants as specified and L1-9 VL (SEQ ID No: 23) and cell culture supernatant was assessed 2 days after transfection. For a given cell culture supernatant, the ratio of C5 binding response to that of antibody binding response was calculated and used as a measure of C5 binding affinity. Shown in the figure are calculated ratios from two separate Octet assays of a transfection experiment with mAb H1-8/L1-9 IgG4 variants having at least one substitution at leucine 9 (i.e., L9) in VH CDR1, relative to SEQ ID NO:20, proline 4 (i.e., P4) in VH CDR2, relative to SEQ ID NO:4, and/or valine 16 (i.e., V16) in VH CDR3, relative to SEQ ID NO:5 (i.e., L9→W9 (i.e., L9W), L9→I9 (i.e., L9I), L9→V9 (i.e., L9V), L9→Y9 (i.e., L9Y), L9→F9 (i.e., L9F), P4→F4 (i.e., P4F), P4→L4 (i.e., P4L), P4→M4 (i.e., P4M), P4→W4 (i.e., P4W), P4→I4 (i.e., P4I), V16→F16 (i.e., V16F), V16→E16 (i.e., V16E) and V16→W16 (i.e., V16W)).

FIG. 22 depicts the results of an Octet assay assessing the dissociation rate at pH 7.4 and pH 5.8, respectively, of C5 and mAb H1-8/L1-9 variants. The % decrease for each mAb at pH 7.4 and pH 5.8 from peak C5 binding response after switching from association phase to dissociation phase was calculated. Shown in the figure are calculated % decreases in two separate Octet assays of a transfection experiment with mAb H1-8/L1-9 IgG4 variants having at least one substitution at leucine 9 (i.e., L9) in VH CDR1, relative to SEQ ID NO:20, proline 4 (i.e., P4) in VH CDR2, relative to SEQ ID NO:4, and/or valine 16 (i.e., V16) in VH CDR3, relative to SEQ ID NO:5 (i.e., L9→W9 (i.e., L9W), L9→i9 (i.e., L9I), L9→V9 (i.e., L9V), L9→Y9 (i.e., L9Y), L9→F9 (i.e., L9F), P4→F4 (i.e., P4F), P4→L4 (i.e., P4L), P4→M4 (i.e., P4M), P4→W4 (i.e., P4W), P4→I4 (i.e., P4I), V16→F16 (i.e., V16F), V16→E16 (i.e., V16E) and V16→W16 (i.e., V16W)).

FIG. 23 lists 18 combination substitution variants (i.e., L9I/P4M, L9I/P4W, L9I/P4F, L9F/P4M, L9F/P4W, L9F/P4F, L9I/P4M/V16W, L9I/P4W/V16W, L9I/P4F/V16W, L9F/P4M/V16W, L9F/P4W/V16W, L9F/P4F/V16W, L9I/P4M/V16E, L9I/P4W/V16E, L9T/P4F/V16E, L9F/P4M/V16E, L9F/P4W/V16E, and L9F/P4F/V16E). These combination variants were derived from 7 single variants of mAb H1-8/L1-9 IgG4 (i.e. L9I, L9F, P4M, P4W, P4F, V16E, V16W) that showed improved C5 binding aff

DETAILED DESCRIPTION OF THE INVENTION

Figure 7:
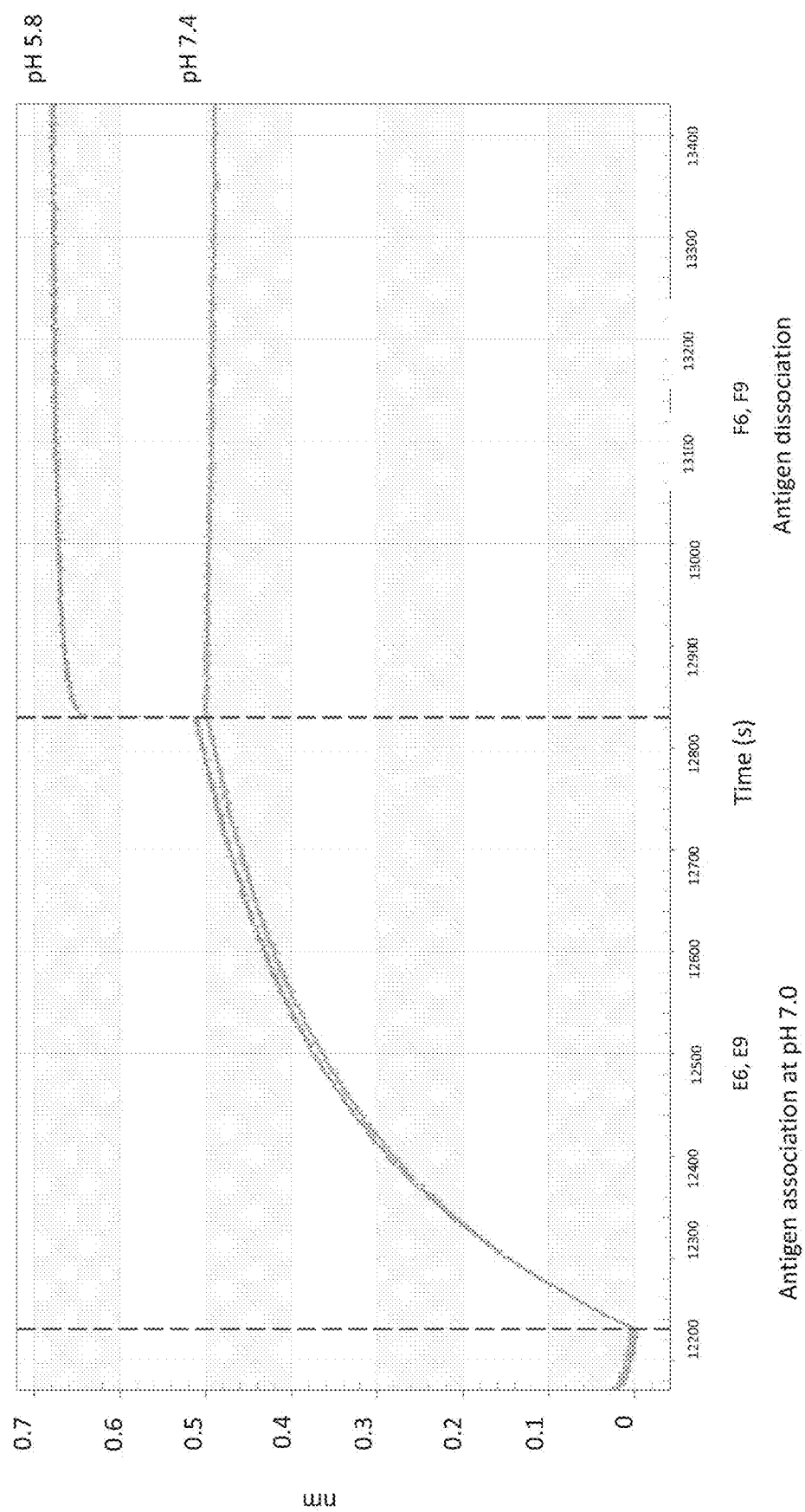
FIG. 7 depicts an Octet tracing of C5 binding and dissociation of the parental humanized mAb 11801 (VH-11801 (SEQ ID NO:2) and VL-1901 (SEQ ID NO:7)) at pH 5.8 and pH 7.4.
Figure 8:
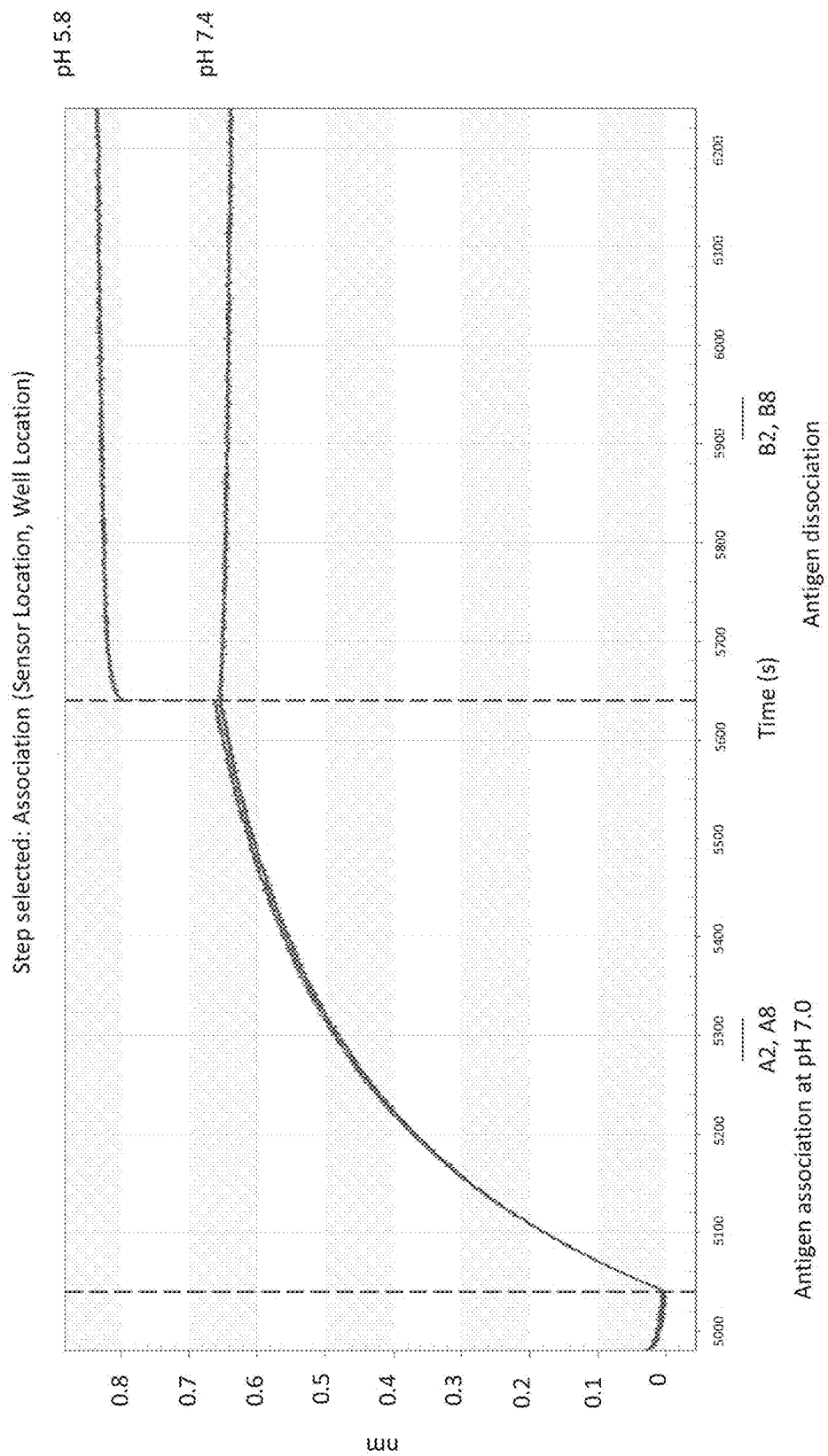
FIG. 8 depicts an Octet tracing of C5 binding and dissociation of the mAb L3-1 at pH 5.8 and pH 7.4.
Figure 9:
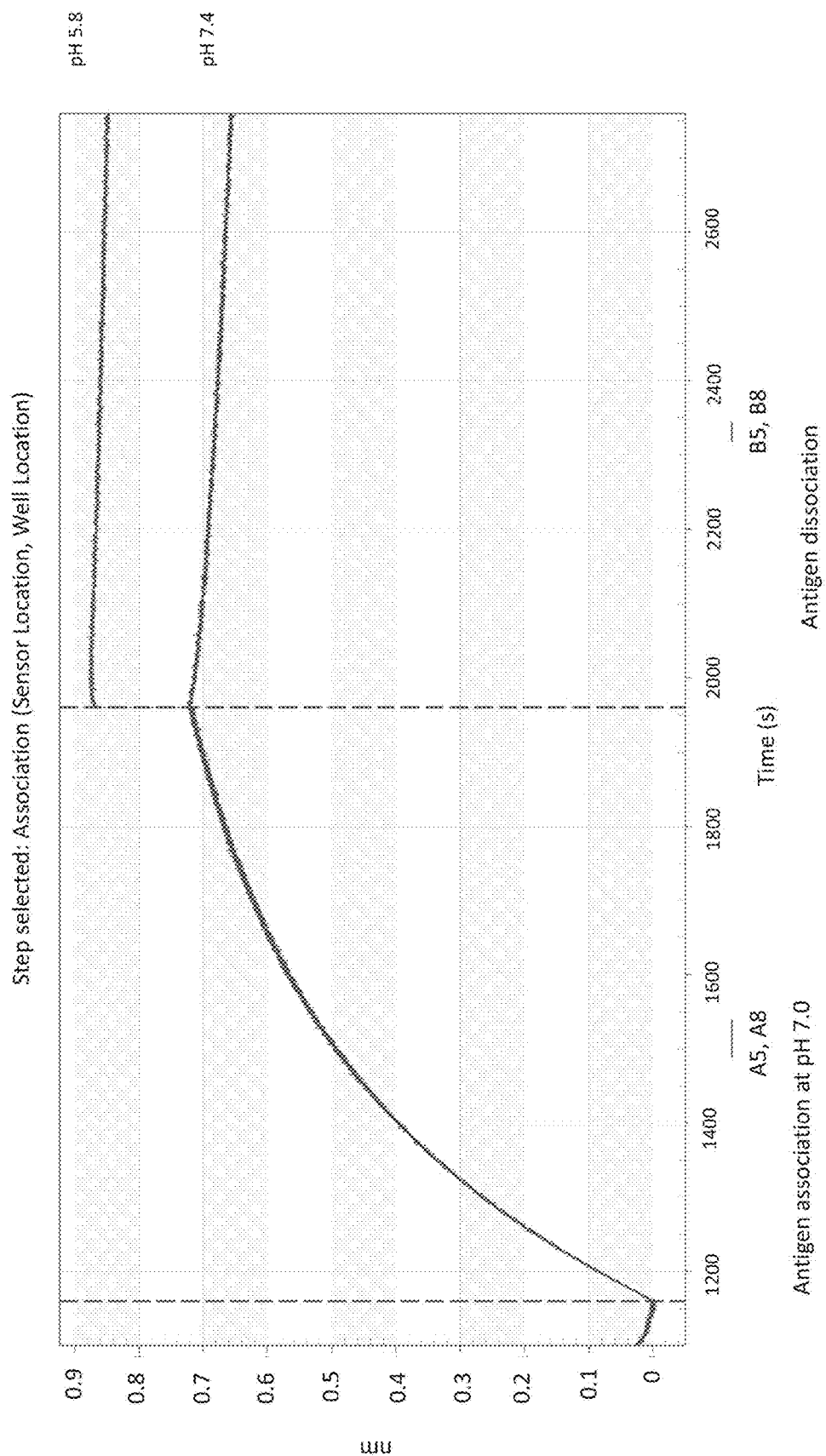
FIG. 9 depicts an Octet tracing of C5 binding and dissociation of the mAb L1-2 at pH 5.8 and pH 7.4.
Figure 10:
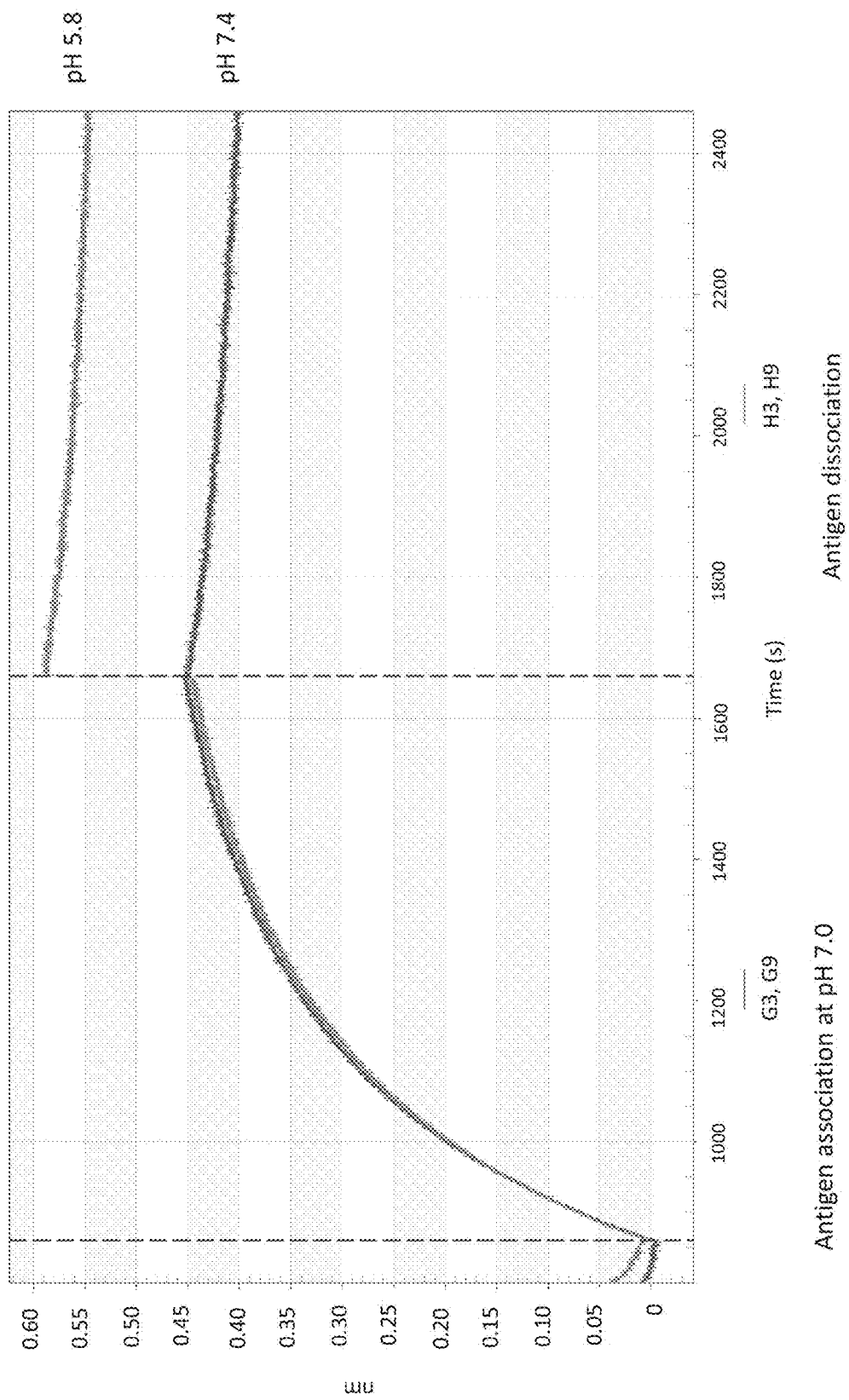
FIG. 10 depicts an Octet tracing of C5 binding and dissociation of the mAb H1-4 at pH 5.8 and pH 7.4.
Figure 11:
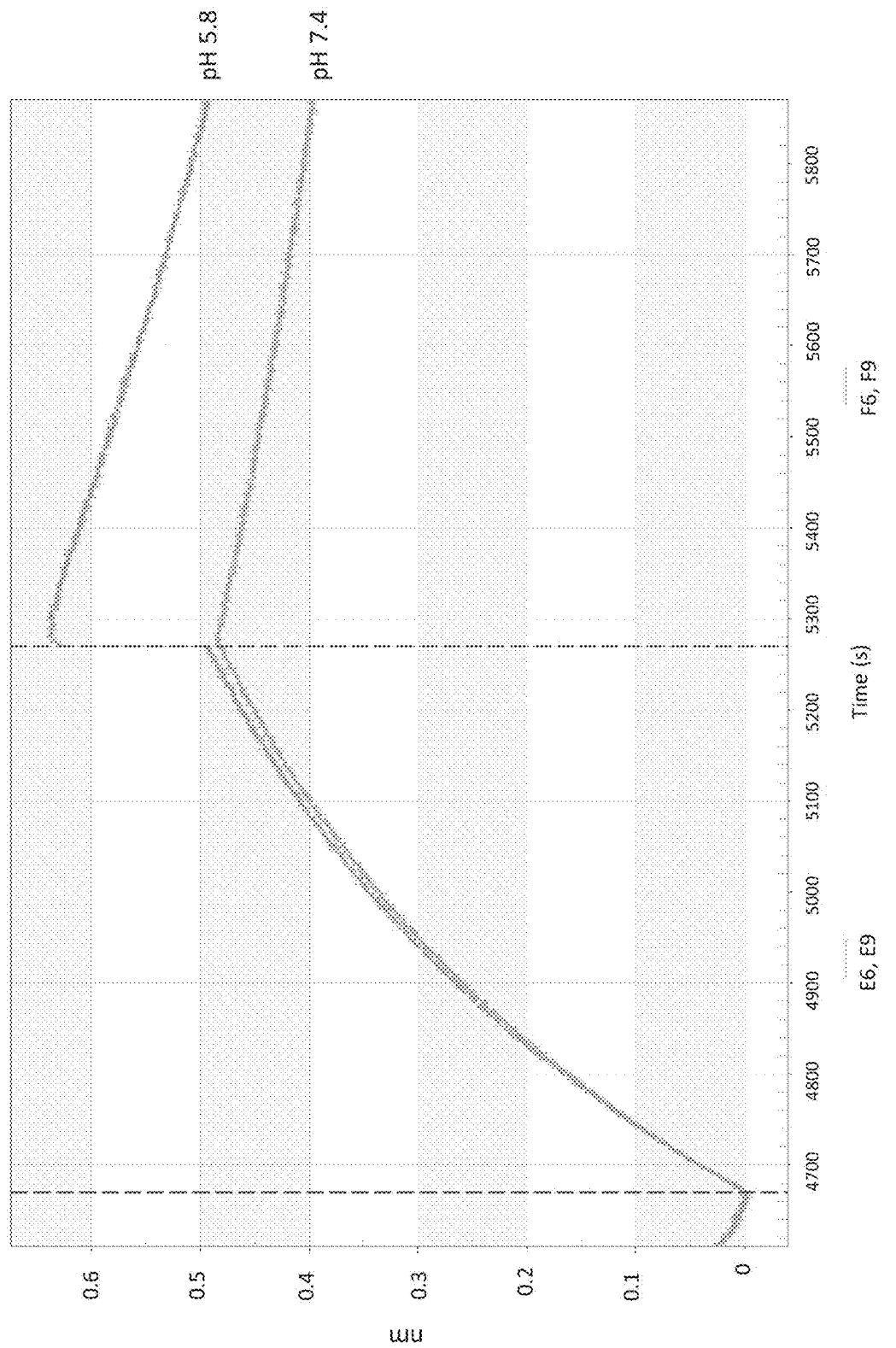
FIG. 11 depicts an Octet tracing of C5 binding and dissociation of the mAb H2-6/L3-5 at pH 5.8 and pH 7.4.
Figure 12:
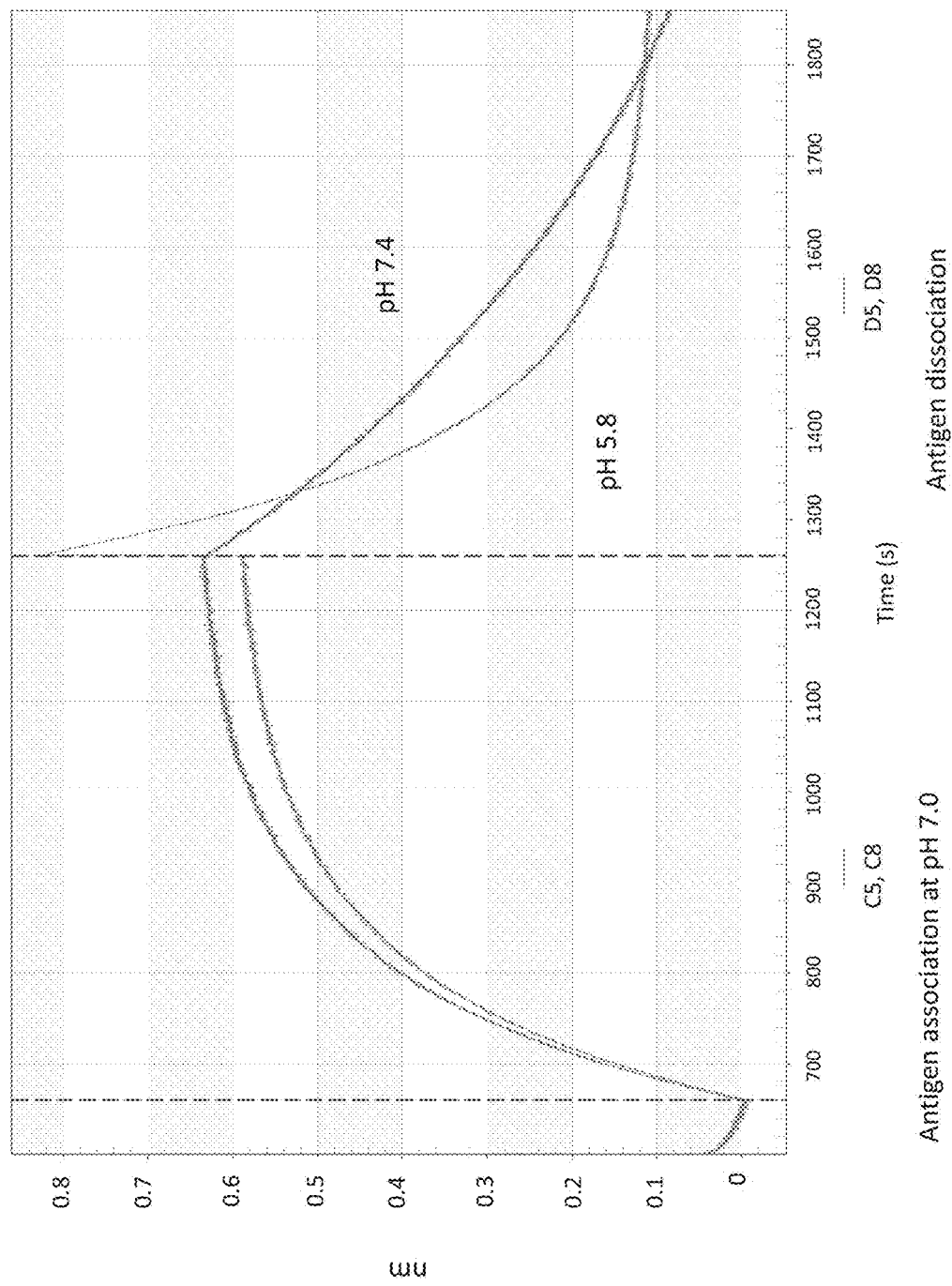
FIG. 12 depicts an Octet tracing of C5 binding and dissociation of the mAb H1-8/L1-9 at pH 5.8 and pH 7.4.

This invention relates to the inhibition of complement signaling using an anti-C5 antibody. In some embodiments, the anti-C5 antibody exhibits pH-dependent binding to C5. In some embodiments, the pH-dependent anti-C5 antibody binds more strongly to C5 at a more neutral pH (e.g., about pH 7.4; such as that found in the blood) than it does at a more acidic pH (e.g., about pH 5.8; such as that found in the endosome). In various embodiments, the invention is directed to compositions and methods for treating a complement-mediated disease or complement-mediated disorder in an individual by contacting the individual with an anti-C5 antibody. The complement-mediated pathologies and conditions that can be treated with the compositions and methods of the invention include, but are not limited to, macular degeneration (MD), age-related macular degeneration (AMD), ischemia reperfusion injury, arthritis, rheumatoid arthritis, lupus, ulcerative colitis, stroke, post-surgery systemic inflammatory syndrome, asthma, allergic asthma, chronic obstructive pulmonary disease (COPD), paroxysmal nocturnal hemoglobinuria (PNH) syndrome, myasthenia gravis, neuromyelitis optica, (NMO), multiple sclerosis, delayed graft function, antibody-mediated rejection, atypical hemolytic uremic (aHUS) syndrome, central retinal vein occlusion (CRVO), central retinal artery occlusion (CRAO), epidermolysis bullosa, sepsis, organ transplantation, inflammation (including, but not limited to, inflammation associated with cardiopulmonary bypass surgery and kidney dialysis), C3 glomerulopathy, membranous nephropathy, IgA nephropathy, glomerulonephritis (including, but not limited to, anti-neutrophil cytoplasmic antibody (ANCA)-mediated glomerulonephritis, lupus nephritis, and combinations thereof), ANCA-mediated vasculitis, Shiga toxin induced HUS, and antiphospholipid antibody-induced pregnancy loss, or any combinations thereof.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The terms "inhibit" and "inhibition," as used herein, means to reduce, suppress, diminish or block an activity or function by at least about 10% relative to a control value. In some embodiments, the activity is suppressed or blocked by at least about 50% compared to a control value. In some embodiments, the activity is suppressed or blocked by at least about 75%. In some embodiments, the activity is suppressed or blocked by at least about 95%.

The terms "effective amount" and "pharmaceutically effective amount" refer to a sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

The terms "patient," "subject," "individual," and the like are used interchangeably herein, and refer to any animal, in some embodiments a mammal, and in some embodiments a human, having a complement system, including a human in need of therapy for, or susceptible to, a condition or its sequelae. The individual may include, for example, dogs, cats, pigs, cows, sheep, goats, horses, rats, monkeys, and mice and humans.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected/homeostatic) respective characteristic. Characteristics which are normal or expected for one cell, tissue type, or subject, might be abnormal for a different cell or tissue type.

A "disease" is a state of health of a subject wherein the subject cannot maintain homeostasis, and wherein if the disease is not ameliorated then the subject's health continues to deteriorate.

In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Operably linked" or "operatively linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "therapeutic treatment" is a treatment administered to a subject who exhibits signs of disease or disorder, for the purpose of diminishing or eliminating those signs.

As used herein, "treating a disease or disorder" means reducing the frequency and/or severity of a sign and/or symptom of the disease or disorder is experienced by a patient.

The phrase "biological sample", "sample" or "specimen" as used herein, is intended to include any sample comprising a cell, a tissue, or a bodily fluid in which expression of a nucleic acid or polypeptide can be detected. The biological sample may contain any biological material suitable for detecting the desired biomarkers, and may comprise cellular and/or non-cellular material obtained from the individual. Examples of such biological samples include but are not limited to blood, lymph, bone marrow, biopsies and smears. Samples that are liquid in nature are referred to herein as "bodily fluids." Biological samples may be obtained from a patient by a variety of techniques including, for example, by scraping or swabbing an area or by using a needle to obtain bodily fluids. Methods for collecting various body samples are well known in the art.

The term "antibody," as used herein, refers to an immunoglobulin molecule which is able to specifically bind to a specific epitope of an antigen. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab, Fab', F(ab)2 and F(ab')2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from a subject with heavy chain disease, or prepared by the cloning and expression of VH (variable heavy chain immunoglobulin) genes from a subject.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes and binds to a specific target molecule, but does not substantially recognize or bind other molecules in a sample. In some instances, the terms "specific binding" or "specifically binding," is used to mean that the recognition and binding is dependent upon the presence of a particular structure (e.g., an antigenic determinant or epitope) on the target molecule. If, for example, an antibody specifically binds to epitope "A," the presence of an unlabelled molecule containing epitope A (or free, unlabeled A) in a reaction containing labeled "A" and the antibody, will reduce the amount of labeled A bound to the antibody.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Differentially decreased expression" or "down regulation" refers to biomarker product levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments therebetween than a control.

"Differentially increased expression" or "up regulation" refers to biomarker product levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween than a control.

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In some embodiments, the first region comprises a first portion and the second region comprises a second portion, whereby, when the first and second portions are arranged in an antiparallel fashion, at least about 50%, and or at least about 75%, or at least about 90%, or at least about 95% of the nucleotide residues of the first portion are capable of base pairing with nucleotide residues in the second portion. In some embodiments, all nucleotide residues of the first portion are capable of base pairing with nucleotide residues in the second portion.

The term "DNA" as used herein is defined as deoxyribonucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Isolated" means altered or removed from the natural state. For example, a nucleic acid or a peptide naturally present in its normal context in a living subject is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

The term "hybridoma," as used herein refers to a cell resulting from the fusion of a B-lymphocyte and a fusion partner such as a myeloma cell. A hybridoma can be cloned and maintained indefinitely in cell culture and is able to produce monoclonal antibodies. A hybridoma can also be considered to be a hybrid cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "progeny" as used herein refers to a descendent or offspring and includes the offspring of a mammal, and also included the differentiated or undifferentiated decedent cell derived from a parent cell. In one usage, the term progeny refers to a descendent cell which is genetically identical to the parent. In another use, the term progeny refers to a descendent cell which is genetically and phenotypically identical to the parent. In yet another usage, the term progeny refers to a descendent cell that has differentiated from the parent cell.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

As used herein, "conjugated" refers to covalent attachment of one molecule to a second molecule.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis. In various embodiments, the variant sequence is at least 99%, at least 98%, at least 97%, at least 96%, at least 95%, at least 94%, at least 93%, at least 92%, at least 91%, at least 90%, at least 89%, at least 88%, at least 87%, at least 86%, at least 85% identical to the reference sequence.

The term "regulating" as used herein can mean any method of altering the level or activity of a substrate. Non-limiting examples of regulating with regard to a protein include affecting expression (including transcription and/or translation), affecting folding, affecting degradation or protein turnover, and affecting localization of a protein. Non-limiting examples of regulating with regard to an enzyme further include affecting the enzymatic activity. "Regulator" refers to a molecule whose activity includes affecting the level or activity of a substrate. A regulator can be direct or indirect. A regulator can function to activate or inhibit or otherwise modulate its substrate.

A "scanning window," as used herein, refers to a segment of a number of contiguous positions in which a sequence may be evaluated independently of any flanking sequence. A scanning window generally is shifted incrementally along the length of a sequence to be evaluated with each new segment being independently evaluated. An incremental shift may be of 1 or more than one position.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

This invention relates to the inhibition of the complement signaling and complement-related disorders using an anti-human C5 antibody. In some embodiments, the anti-C5 antibody exhibits pH-dependent binding to C5. In some embodiments, the pH-dependent anti-C5 antibody binds more strongly to C5 at a more neutral pH (e.g., about pH 7.4; such as that found in the blood) than it does at a more acidic pH (e.g., about pH 5.8; such as that found in the endosome). Such pH-dependent binding provides for greater persistence of administered antibody molecules, because immune complexes (i.e., anti-C5 mAb bound to C5) taken up by cells will dissociate in the acidic environment of the endosome and iallow the freed antibody to be recycled back out of the cell through the neonatal Fc receptor (FcRn) where it is available to bind to a new C5 molecule.

In one embodiment, the invention is directed to inhibiting the complement signaling cascade by specifically targeting complement component C5 protein, or a fragment of the protein C5a or C5b. In one embodiment, the invention is directed to methods of treating and preventing inflammation and autoimmune diseases mediated by unwanted, uncontrolled, excessive complement activation. In one embodiment the invention is directed towards the treatment of complement-mediated disease or complement-mediated disorder in an individual by contacting the individual with an anti-C5 antibody.

In one embodiment, the invention is a method of treating a complement-mediated disease or disorder in an individual, comprising the step of administering to said individual an anti-C5 antibody, thereby inhibiting the generation of a C5a or C5b protein, and formation of MAC. Examples of complement-mediated pathologies that can be treated using the methods of the invention include, but are not limited to macular degeneration (MD), age-related macular degeneration (AMD), ischemia reperfusion injury, arthritis, rheumatoid arthritis, lupus, ulcerative colitis, stroke, post-surgery systemic inflammatory syndrome, asthma, allergic asthma, chronic obstructive pulmonary disease (COPD), paroxysmal nocturnal hemoglobinuria (PNH) syndrome, myasthenia gravis, neuromyelitis optica, (NMO), multiple sclerosis, delayed graft function, antibody-mediated rejection, atypical hemolytic uremic (aHUS) syndrome, central retinal vein occlusion (CRVO), central retinal artery occlusion (CRAO), epidermolysis bullosa, sepsis, organ transplantation, inflammation (including, but not limited to, inflammation associated with cardiopulmonary bypass surgery and kidney dialysis), C3 glomerulopathy, membranous nephropathy, IgA nephropathy, glomerulonephritis (including, but not limited to, anti-neutrophil cytoplasmic antibody (ANCA)-mediated glomerulonephritis, lupus nephritis, and combinations thereof), ANCA-mediated vasculitis, Shiga toxin induced HUS, and antiphospholipid antibody-induced pregnancy loss, or any combinations thereof. In some embodiments, the compositions and methods of the invention are useful for treating subject, including subjects having PNH, who are not responsive to treatment with eculizumab. By way of non-limiting example, some subjects may have a mutation in the alpha chain of C5 that may render them resistant to treatment of eculizumab (see Genetic variants in C5 and poor response to eculizumab. Nishimura J, et al., N Engl J Med. 2014 Feb. 13; 370(7):632-9).

The ability of the immune system to discriminate between "self" and "non-self" antigens is vital to the functioning of the immune system as a specific defense against invading microorganisms. "Non-self" antigens are those antigens on substances entering or present in the body which are detectably different or foreign from the subject's own constituents, whereas "self" antigens are those which, in the healthy subject, are not detectably different or foreign from its own constituents. In various embodiments of the methods, the complement activation that is inhibited is that which was triggered by at least one of the group consisting of a microbial antigen, a non-biological foreign surface, altered self-tissue, or combinations thereof. One example of a non-biological foreign surface is blood tubing such as that used in cardio-pulmonary bypass surgery or kidney dialysis. Examples of altered self-tissues include apoptotic, necrotic and ischemia-stressed tissues and cells, tissues and cells devoid of functional complement regulating proteins, or combinations thereof.

In some embodiments, the anti-C5 antibodies of the invention inhibit the downstream effects of activation of the alternative complement pathway (AP), the classical pathway (CP), or the lectin pathway (LP). Generally, the CP is initiated by antigen-antibody complexes, the LP is activated by binding of lectins to sugar molecules on microbial surfaces, while the AP is constitutively active at a low level but can be quickly amplified on bacterial, viral, and parasitic cell surfaces due to the lack of regulatory proteins. Host cells are usually protected from AP complement activation by regulatory proteins. But in some situations, such as when the regulatory proteins are defective or missing, the AP can also be activated uncontrollably on host cells, leading to complement-mediated disease or disorder. The CP consists of components C1, C2, C4 and converges with the AP at the C3 activation step. The LP consists of mannose-binding lectins (MBLs) and MBL-associated serine proteases (Masps) and shares with the CP the components C4 and C2. The AP consists of components C3 and several factors, such as factor B, factor D, properdin, C5 and the fluid phase regulator factor H. Complement activation consists of three stages: (a) recognition, (b) enzymatic activation, and (c) membrane attack leading to cell death. The first phase of CP complement activation begins with C1. C1 is made up of three distinct proteins: a recognition subunit, C1q, and the serine protease subcomponents, C1r and C1s, which are bound together in a calcium-dependent tetrameric complex, C1r2 s2. An intact C1 complex is necessary for physiological activation of C1 to result. Activation occurs when the intact C1 complex binds to immunoglobulin complexed with antigen. This binding activates C1s which then cleaves both the C4 and C2 proteins to generate C4a and C4b, as well as C2a and C2b. The C4b and C2a fragments combine to form the C3 convertase, C4b2a, which in turn cleaves C3 to form C3a and C3b. Activation of the LP is initiated by MBL binding to certain sugars on the target surface and this triggers the activation of MBL-associated serine proteases (MASPs) which then cleave C4 and C2 in a manner analogous to the activity of C1s of the CP, resulting in the generation of the C3 convertase, C4b2a. Thus, the CP and LP are activated by different mechanisms but they share the same components C4 and C2 and both pathways lead to the generation of the same C3 convertase, C4b2a. The cleavage of C3 by C4b2a into C3b and C3a is a central event of the complement pathway for two reasons. It initiates the AP amplification loop because surface deposited C3b is a central intermediate of the AP. Both C3a and C3b are biologically important. C3a is proinflammatory and together with C5a are referred to as anaphylatoxins. C3b and its further cleavage products also bind to complement receptors present on neutrophils, eosinophils, monocytes and macrophages, thereby facilitating phagocytosis and clearance of C3b-opsonized particles. Finally, C3b can associate with C4b2a to form the C5 convertase of the CP and LP to activate the terminal complement sequence, leading to the production of C5a, a potent proinflammatory mediator, and the assembly of the lytic membrane attack complex (MAC), C5-C9.

In one embodiment, the activity of the complement pathway that is inhibited using a method of the invention is complement pathway activation induced by at least one of the group selected from a lipopolysaccharide (LPS), lipooligosaccharide (LOS), pathogen-associated molecular patterns (PAMPs) and danger-associated molecular patterns (DAMPs). In another embodiment, the activity of complement signaling that is inhibited using a method of invention is the generation of C5a protein. In another embodiment, the activity of complement signaling that is inhibited using a method of invention is the generation of C5b protein. In another embodiment, the activity of complement signaling that is inhibited using a method of the invention is the formation of MAC. In another embodiment, the activity of the complement pathway that is inhibited using a method of the invention is C5 dependent.

In one embodiment, the invention is a method of inhibiting initiation of terminal complement activation in an individual, comprising the step of administering to said individual an anti-C5 antibody, thereby inhibiting initiation of terminal complement activation originating from CP, LP or AP activation in an individual. Examples of these embodiments are PNH patients who suffer from complement-mediated hemolysis and individuals suffering from complement-mediated aHUS, asthma, ischemic/reperfusion injury, rheumatoid arthritis and ANCA-mediated kidney diseases. In various embodiments of the invention, diseases and disorders that can be treated using the compositions and methods of the invention include, but are not limited to, complement-mediated hemolysis, complement-mediated aHUS, C3 glomerulopathy, neuromyelitis optica, myasthenia gravis, asthma, ischemic/reperfusion injury, rheumatoid arthritis and ANCA-mediated kidney diseases or disorders.

In various other embodiments, provided herein are methods of identifying a potential anti-C5 antibody having inhibitory effects on terminal complement activation. One such method is the sheep red blood cell lysis assay as described below. Briefly, sheep RBCs ($1 \times 10^7$ cells per assay sample prepared in PBS, Complement Technology Inc) were incubated at 37° C. for 20 min with 50% normal human serum (NHS, from Complement Technology Inc) in gelatin veronal buffer (GVB2+, Sigma; total assay volume: 100 μl). Before addition to the sheep RBCs, NHS was pre-incubated with anti-C5 mAbs for 1 hr at 4° C. Lysis reaction was stopped by addition of ice-cold 40 mM EDTA in PBS. The incubation mixtures were centrifuged for 5 min at 1500 rpm and the supernatant was collected and measured for OD405 nm. Samples without NHS or with EDTA added were used as negative lysis controls, and a sample of sheep RBCs lysed completely with distilled water was used as a positive control (100% lysis) against which % lysis in other samples was normalized. A separate method that can be used in confirmatory screening of anti-human C5 blocking mAbs includes the steps of: a) coating a plate with lipopolysaccharide (LPS); b) washing the plate to remove unbound LPS; c) adding bovine serum albumin (BSA) in phosphate buffered saline (PBS); d) washing the plate to remove unbound BSA; e) adding a mixture of a candidate anti-C5 antibody compound that has been pre-incubated with serum and is mixed into normal human serum; f) washing the plate; g) adding an HRP-conjugated anti-human C5b-9 or anti-human C6 antibody (anti-human TCC antibody, clone aE11 or biotin-labeled anti-human C6 antibody, both from Quidel); h) washing the plate to remove unbound antibody; i) adding HRP Substrate Reagent; j) adding sulphuric acid to stop the reaction; k) measuring the optical density at 450 nm; l) comparing the optical density of the plate containing the candidate anti-C5 antibody compound to the optical density of a positive comparator control and a negative comparator control; wherein when the optical density is diminished as compared with the positive comparator control, the anti-C5 antibody is identified.

Anti-C5 Antibodies

In some embodiments, the invention includes compositions comprising an antibody that specifically binds to C5. In one embodiment, the anti-C5 antibody is a polyclonal antibody. In another embodiment, the anti-C5 antibody is a monoclonal antibody. In some embodiments, the anti-C5 antibody is a chimeric antibody. In further embodiments, the anti-C5 antibody is a humanized antibody. In some embodiments, the antibody is an antibody fragment. In some embodiments, the C5 is human C5.

In some embodiments, the anti-C5 antibody exhibits pH-dependent binding to C5. In some embodiments, the pH-dependent anti-C5 antibody binds more strongly to C5 at a more neutral pH (e.g., about pH 7.4; such as that found in the blood) than it does at a more acidic pH (e.g., about pH 5.8; such as that found in the endosome).

In some embodiments, binding of the antibody or the fragment of the antibody to human-C5 is associated with a reduction in the generation of C5a or C5b and the formation of MAC in the complement activation pathway in an intact organism. In some embodiments, the invention is a protein or a polypeptide capable of binding to human C5. In some embodiments, the antibody or antibody fragment; the protein or the polypeptide binds to a relevant portion or fraction or epitope of the human-C5; and the binding of the antibody, or the antibody fragment thereof, or the protein or the polypeptide to the relevant portion of the human-C5 is associated with a reduction in the generation of C5a or C5b and the formation of MAC in an intact organism.

In some embodiments, the human-C5 binding antibody or a C5 binding antibody fragment thereof, is further conjugated to a protein, a peptide or another compound. In some embodiments, the human-C5 binding antibody, or an antibody fragment thereof, is conjugated to a protein, a peptide or other compound. In some embodiments, the protein, peptide or other compound to which the human-C5 binding antibody or antibody fragment thereof is conjugated is a targeting moiety (i.e., the targeting moiety specifically binds to a molecule other than human-C5). In some embodiments, the protein, peptide, or other compound to which the human-C5 binding antibody or antibody fragment thereof is conjugated to is an effector molecule (e.g., a cytotoxic molecule).

In various embodiments, any of the antibodies of the invention described herein, having any of the variable regions described herein, may comprise an Fc fragment or Fc domain. For example, in some embodiments, an antibody described herein, comprises an Fc fragment of an immunoglobulin. Exemplary immunoglobulins include, but is not limited to, IgG1, IgG2, IgG3, IgG4, IgM, IgA, IgE, and IgD. In one embodiment, the antibody comprises an Fc of human IgG4. SEQ ID NO:32 is an example amino acid sequence of a human IgG4 Fc fragment. In some embodiments, the antibody of the invention comprises a human IgG4 Fc fragment having an S108P mutation relative to SEQ ID NO:32. SEQ ID NO:33 is an example amino acid sequence of a human IgG4 Fc fragment having an S108P mutation relative to SEQ ID NO: 32. In some embodiments, the antibody of the invention comprises a human IgG4 Fc fragment having one or more of: an S108P mutation, a M308L mutation, and a N314A mutation, relative to SEQ ID NO: 32. In some embodiments, the antibody of the invention comprises a human IgG4 Fc fragment having an S108P mutation, a M308L mutation, and a N314A mutation, relative to SEQ ID NO: 32 (also referred to herein as having an Fc PLA mutation). SEQ ID NO:61 is an example amino acid sequence of a human IgG4 Fc fragment having an S108P mutation, a M308L mutation, and a N314A mutation relative to SEQ ID NO:32.

In one embodiment, the anti-C5 antibody or an antigen-binding fragment thereof comprises at least one of the CDRs selected from the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR1 comprising the amino acid sequence of SEQ ID NO:3 or a variant thereof comprising up to about 3 (such as about any of 1, 2, or 3) amino acid substitutions; and VL-CDR1: SEQ ID NO:8, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:3; and VL-CDR1: SEQ ID NO:8.

In some embodiments, the anti-C5 antibody or antigen-binding fragment thereof comprises: VH-CDR2 comprising the amino acid sequence of SEQ ID NO:4, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:4; and VL-CDR2: SEQ ID NO:9.

In some embodiments, the anti-C5 antibody or antigen-binding fragment thereof comprises: VH-CDR3 comprising the amino acid sequence of SEQ ID NO:5, or a variant thereof comprising up to about 3 (such as about any of 1, 2, or 3) amino acid substitutions; and VL-CDR3: SEQ ID NO:10, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:5; and VL-CDR3: SEQ ID NO:10.

In some embodiments, the anti-C5 antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5, or a variant thereof comprising up to about 3 (such as about any of 1, 2, or 3) amino acid substitutions; VL-CDR1 comprising the amino acid sequence of SEQ ID NO:8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5; VL-CDR1 comprising the amino acid sequence of SEQ ID NO:8, or a variant thereof comprising up to about 3 (such as about any of 1, 2, or 3) amino acid substitutions: VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:3; VH-CDR2 comprising the amino acid sequence of SEQ ID NO:4; VH-CDR3 comprising the amino acid sequence of SEQ ID NO:5; VL-CDR1 comprising the amino acid sequence of SEQ ID NO:8; VL-CDR2 comprising the amino acid sequence of SEQ ID NO:9; and VL-CDR3 comprising the amino acid sequence of SEQ ID NO:10.

In one embodiment, the anti-C5 antibody or an antigen-binding fragment thereof comprises at least one of the CDRs selected from the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:11, or a variant or variants thereof. In another embodiment, the anti-C5 antibody comprises all of the CDRs of the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:11, or a variant or variants thereof.

In some embodiments, the anti-C5 antibody or antigen-binding fragment thereof comprises: VH-CDR1 comprising the amino acid sequence of SEQ ID NO:3 or a variant thereof comprising up to about 3 (such as about any of 1, 2, or 3) amino acid substitutions; and VL-CDR1: SEQ ID NO:8, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:3; and VL-CDR1: SEQ ID NO:8.

In some embodiments, the anti-C5 antibody or antigen-binding fragment thereof comprises: VH-CDR2 comprising the amino acid sequence of SEQ ID NO:4, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:4; and VL-CDR2: SEQ ID NO:9.

In some embodiments, the anti-C5 antibody or antigen-binding fragment thereof comprises: VH-CDR3 comprising the amino acid sequence of SEQ ID NO:5, or a variant thereof comprising up to about 3 (such as about any of 1, 2, or 3) amino acid substitutions; and VL-CDR3: SEQ ID NO:

11, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:5; and VL-CDR3: SEQ ID NO:11.

In some embodiments, the anti-C5 antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5, or a variant thereof comprising up to about 3 (such as about any of 1, 2, or 3) amino acid substitutions; VL-CDR1 comprising the amino acid sequence of SEQ ID NO:8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:11, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5; VL-CDR1 comprising the amino acid sequence of SEQ ID NO:8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:11.

In some embodiments, the anti-C5 antibody or antigen-binding fragment thereof comprises: VH-CDR1 comprising the amino acid sequence of SEQ ID NO:3; VH-CDR2 comprising the amino acid sequence of SEQ ID NO:4; VH-CDR3 comprising the amino acid sequence of SEQ ID NO:5; VL-CDR1 comprising the amino acid sequence of SEQ ID NO:8; VL-CDR2 comprising the amino acid sequence of SEQ ID NO:9; and VL-CDR3 comprising the amino acid sequence of SEQ ID NO:11.

In some embodiments, the anti-C5 antibody or an antigen binding fragment thereof comprises a heavy chain comprising the amino acid sequence of SEQ ID NO:2, or a variant thereof. In other embodiments, the anti-C5 antibody comprises a light chain comprising the amino acid sequence of SEQ ID NO:13, or a variant thereof. In another embodiment, the anti-C5 antibody is mAb L3-1, or a variant thereof. The monoclonal anti-C5 antibody mAb L3-1 comprises a heavy chain comprising the amino acid sequence of SEQ ID NO:2 and a light chain comprising the amino acid sequence of SEQ ID NO:13. In one embodiment, the anti-C5 antibody comprises an Fc fragment. In one embodiment, the anti-C5 antibody comprises a human IgG4 Fc fragment or variant thereof. In one embodiment, the anti-C5 antibody mAb L3-1 comprises a heavy chain comprising the amino acid sequence of SEQ ID NO:2; a light chain comprising the amino acid sequence of SEQ ID NO:13; and a human IgG4 Fc fragment comprising the amino acid sequence of SEQ ID NO: 32. In one embodiment, the anti-C5 antibody comprises a human IgG4 Fc fragment having an S108P mutation relative to SEQ ID NO: 32, or variant thereof. In one embodiment, the anti-C5 antibody mAb L3-1 comprises a heavy chain comprising the amino acid sequence of SEQ ID NO:2; a light chain comprising the amino acid sequence of SEQ ID NO:13; and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody mAb L3-1 comprises a heavy chain comprising the amino acid sequence of SEQ ID NO:2; a light chain comprising the amino acid sequence of SEQ ID NO:13; and a human IgG4 having an S108P mutation, a M308L mutation, and a N314A mutation relative to SEQ ID NO: 32, comprising the amino acid sequence of SEQ ID NO: 61. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:3; VH-CDR2: SEQ ID NO:4; VH-CDR3: SEQ ID NO:5; VL-CDR1: SEQ ID NO:14; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:3; VH-CDR2: SEQ ID NO:4; VH-CDR3: SEQ ID NO:5; VL-CDR1: SEQ ID NO:14; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR1 comprising the amino acid sequence of SEQ ID NO:3 or a variant thereof comprising up to about 3 (such as about any of 1, 2, or 3) amino acid substitutions; and VL-CDR1: SEQ ID NO:14, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:3; and VL-CDR1: SEQ ID NO:14.

In some embodiments, the anti-C5 antibody or antigen-binding fragment thereof comprises: VH-CDR2 comprising the amino acid sequence of SEQ ID NO:4, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:4; and VL-CDR2: SEQ ID NO:9

In some embodiments, the anti-C5 antibody or antigen-binding fragment thereof comprises: VH-CDR3 comprising the amino acid sequence of SEQ ID NO:5, or a variant thereof comprising up to about 3 (such as about any of 1, 2, or 3) amino acid substitutions; and VL-CDR3: SEQ ID NO:10, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:5; and VL-CDR3: SEQ ID NO:10.

In some embodiments, the anti-C5 antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5, or a variant thereof comprising up to about 3 (such as about any of 1, 2, or 3) amino acid substitutions; VL-CDR1 comprising the amino acid sequence of SEQ ID NO:14, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5; VL-CDR1 comprising the amino acid sequence of SEQ ID NO:14, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:3; VH-CDR2 comprising the amino acid sequence of SEQ ID NO:4; VH-CDR3 comprising the amino acid sequence of SEQ ID NO:5; VL-CDR1 comprising the amino acid sequence of SEQ ID NO:14; VL-CDR2 comprising the amino acid sequence of SEQ ID NO:9; and VL-CDR3 comprising the amino acid sequence of SEQ ID NO:10.

In some embodiments, the anti-C5 antibody or an antigen binding fragment thereof comprises a heavy chain comprising the amino acid sequence of SEQ ID NO:2, or a variant thereof. In other embodiments, the anti-C5 antibody comprises a light chain comprising the amino acid sequence of SEQ ID NO:16, or a variant thereof. In another embodiment, the anti-C5 antibody is mAb L1-2, or a variant thereof. The monoclonal anti-C5 antibody mAb L1-2 comprises a heavy chain comprising the amino acid sequence of SEQ ID NO:2 and a light chain comprising the amino acid sequence of SEQ ID NO:16. In one embodiment, the anti-C5 antibody comprises an Fc fragment. In one embodiment, the anti-C5 antibody comprises a human IgG4 Fc fragment or variant thereof. In one embodiment, the anti-C5 antibody mAb L1-2 comprises a heavy chain comprising the amino acid sequence of SEQ ID NO:2; a light chain comprising the amino acid sequence of SEQ ID NO:16; and a human IgG4 Fc fragment comprising the amino acid sequence of SEQ ID NO: 32. In one embodiment, the anti-C5 antibody comprises a human IgG4 Fc fragment having an S108P mutation relative to SEQ ID NO: 32, or variant thereof. In one embodiment, the anti-C5 antibody mAb L1-2 comprises a heavy chain comprising the amino acid sequence of SEQ ID NO:2; a light chain comprising the amino acid sequence of SEQ ID NO:16; and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody mAb L1-2 comprises a heavy chain comprising the amino acid sequence of SEQ ID NO:2; a light chain comprising the amino acid sequence of SEQ ID NO:16; and a human IgG4 Fc fragment having an S108P mutation, a M308L mutation, and a N314A mutation relative to SEQ ID NO: 32, comprising the amino acid sequence of SEQ ID NO: 61. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:17; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:17; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR1 comprising the amino acid sequence of SEQ ID NO:17 or a variant thereof comprising up to about 3 (such as about any of 1, 2, or 3) amino acid substitutions; and VL-CDR1: SEQ ID NO:8, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:17; and VL-CDR1: SEQ ID NO:8.

In some embodiments, the anti-C5 antibody or antigen-binding fragment thereof comprises: VH-CDR2 comprising the amino acid sequence of SEQ ID NO:4, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:4; and VL-CDR2: SEQ ID NO:9

In some embodiments, the anti-C5 antibody or antigen-binding fragment thereof comprises: VH-CDR3 comprising the amino acid sequence of SEQ ID NO:5, or a variant thereof comprising up to about 3 (such as about any of 1, 2, or 3) amino acid substitutions; and VL-CDR3: SEQ ID NO:10, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:5; and VL-CDR3: SEQ ID NO:10.

In some embodiments, the anti-C5 antibody or antigen-binding fragment thereof comprises: VH-CDR1 comprising the amino acid sequence of SEQ ID NO:17, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5, or a variant thereof comprising up to about 3 (such as about any of 1, 2, or 3) amino acid substitutions; VL-CDR1 comprising the amino acid sequence of SEQ ID NO:8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:17, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5; VL-CDR1 comprising the amino acid sequence of SEQ ID NO:8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:17; VH-CDR2 comprising the amino acid sequence of SEQ ID NO:4; VH-CDR3 comprising the amino acid sequence of SEQ ID NO:5; VL-CDR1 comprising the amino acid sequence of SEQ ID NO:8; VL-CDR2 comprising the amino acid sequence of SEQ ID NO:9; and VL-CDR3 comprising the amino acid sequence of SEQ ID NO:10.

In some embodiments, the anti-C5 antibody or an antigen binding fragment thereof comprises a heavy chain comprising the amino acid sequence of SEQ ID NO:19, or a variant thereof. In other embodiments, the anti-C5 antibody comprises a light chain comprising the amino acid sequence of SEQ ID NO:7, or a variant thereof. In another embodiment, the anti-C5 antibody is mAb H1-4, or a variant thereof. The monoclonal anti-C5 antibody mAb H1-4 comprises a heavy chain comprising the amino acid sequence of SEQ ID NO:19 and a light chain comprising the amino acid sequence of SEQ ID NO:7. In one embodiment, the anti-C5 antibody comprises an Fc fragment. In one embodiment, the anti-C5 antibody comprises a human IgG4 Fc fragment or variant thereof. In one embodiment, the anti-C5 antibody mAb H1-4 comprises a heavy chain comprising the amino acid sequence of SEQ ID NO:19; a light chain comprising the amino acid sequence of SEQ ID NO:7; and a human IgG4 Fc fragment comprising the amino acid sequence of SEQ ID NO: 32. In one embodiment, the anti-C5 antibody comprises a human IgG4 Fc fragment having an S108P mutation relative to SEQ ID NO: 32, or variant thereof. In one embodiment, the anti-C5 antibody mAb H1-4 comprises a heavy chain comprising the amino acid sequence of SEQ ID NO:19; a light chain comprising the amino acid sequence of SEQ ID NO:7; and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody mAb H1-4 comprises a heavy chain comprising the amino acid sequence of SEQ ID NO:19; a light chain comprising the amino acid sequence of SEQ ID NO:7; and a human IgG4 Fc fragment having an S108P mutation, a M308L mutation, and a N314A mutation relative to SEQ ID NO: 32, comprising the amino acid sequence of SEQ ID NO: 61. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:20; VH-CDR2: SEQ ID NO:4; VH-CDR3: SEQ ID NO:5; VL-CDR1: SEQ ID NO:23; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:20; VH-CDR2: SEQ ID NO:4; VH-CDR3: SEQ ID NO:5; VL-CDR1: SEQ ID NO:23; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR1 comprising the amino acid sequence of SEQ ID NO:20 or a variant thereof comprising up to about 3 (such as about any of 1, 2, or 3) amino acid substitutions; and VL-CDR1: SEQ ID NO:23, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:20; and VL-CDR1: SEQ ID NO:23.

In some embodiments, the anti-C5 antibody or antigen-binding fragment thereof comprises: VH-CDR2 comprising the amino acid sequence of SEQ ID NO:4, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:4; and VL-CDR2: SEQ ID NO:9

In some embodiments, the anti-C5 antibody or antigen-binding fragment thereof comprises: VH-CDR3 comprising the amino acid sequence of SEQ ID NO:5, or a variant thereof comprising up to about 3 (such as about any of 1, 2, or 3) amino acid substitutions; and VL-CDR3: SEQ ID NO:10, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:5; and VL-CDR3: SEQ ID NO:10.

In some embodiments, the anti-C5 antibody or antigen-binding fragment thereof comprises: VH-CDR1 comprising the amino acid sequence of SEQ ID NO:20, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5, or a variant thereof comprising up to about 3 (such as about any of 1, 2, or 3) amino acid substitutions; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:20, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:20; VH-CDR2 comprising the amino acid sequence of SEQ ID NO:4; VH-CDR3 comprising the amino acid sequence of SEQ ID NO:5; VL-CDR1 comprising the amino acid sequence of SEQ ID NO:23; VL-CDR2 comprising the amino acid sequence of SEQ ID NO:9; and VL-CDR3 comprising the amino acid sequence of SEQ ID NO:10.

In some embodiments, the anti-C5 antibody or an antigen binding fragment thereof comprises a heavy chain comprising the amino acid sequence of SEQ ID NO:22, or a variant thereof. In other embodiments, the anti-C5 antibody comprises a light chain comprising the amino acid sequence of SEQ ID NO:25, or a variant thereof. In another embodiment, the anti-C5 antibody is mAb H1-8/L1-9, or a variant thereof. The monoclonal anti-C5 antibody mAb H1-8/L1-9 comprises a heavy chain comprising the amino acid sequence of SEQ ID NO:22 and a light chain comprising the amino acid sequence of SEQ ID NO:25. In one embodiment, the anti-C5 antibody comprises an Fc fragment. In one embodiment, the anti-C5 antibody comprises a human IgG4 Fc fragment or variant thereof. In one embodiment, the anti-C5 antibody mAb H1-8/L1-9 comprises a heavy chain comprising the amino acid sequence of SEQ ID NO:22; a light chain comprising the amino acid sequence of SEQ ID NO:25; and a human IgG4 Fc fragment comprising the amino acid sequence of SEQ ID NO: 32. In one embodiment, the anti-C5 antibody comprises a human IgG4 Fc fragment having an S108P mutation relative to SEQ ID NO: 32, or variant thereof. In one embodiment, the anti-C5 antibody mAb H1-8/L1-9 comprises a heavy chain comprising the amino acid sequence of SEQ ID NO:22; a light chain comprising the amino acid sequence of SEQ ID NO:25; and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody mAb H1-8/L1-9 comprises a heavy chain comprising the amino acid sequence of SEQ ID NO:22; a light chain comprising the amino acid sequence of SEQ ID NO:25; and a human IgG4 Fc fragment having an S108P mutation, a M308L mutation, and a N314A mutation relative to SEQ ID NO: 32, comprising the amino acid sequence of SEQ ID NO: 61. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:3; VH-CDR2: SEQ ID NO:26; VH-CDR3: SEQ ID NO:5; VL-CDR1: SEQ ID NO:8; VL-CDR2: SEQ ID NO:9; and VL-CDR3: SEQ ID NO:29, or a variant or variants thereof. In another embodiment, the anti-C5 antibody comprises all of the CDRs of the group consisting of: VH-CDR1: SEQ ID NO:3; VH-CDR2: SEQ ID NO:26; VH-CDR3: SEQ ID NO:5; VL-CDR1: SEQ ID NO:8; VL-CDR2: SEQ ID NO:9; and VL-CDR3: SEQ ID NO:29, or a variant or variants thereof.

In some embodiments, the anti-C5 antibody or antigen-binding fragment thereof comprises: VH-CDR1 comprising the amino acid sequence of SEQ ID NO:3 or a variant thereof comprising up to about 3 (such as about any of 1, 2, or 3) amino acid substitutions; and VL-CDR1: SEQ ID NO:8, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:3; and VL-CDR1: SEQ ID NO:8.

In some embodiments, the anti-C5 antibody or antigen-binding fragment thereof comprises: VH-CDR2 comprising the amino acid sequence of SEQ ID NO:26, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:26; and VL-CDR2: SEQ ID NO:9

In some embodiments, the anti-C5 antibody or antigen-binding fragment thereof comprises: VH-CDR3 comprising the amino acid sequence of SEQ ID NO:5, or a variant thereof comprising up to about 3 (such as about any of 1, 2, or 3) amino acid substitutions; and VL-CDR3: SEQ ID NO:29, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:5; and VL-CDR3: SEQ ID NO:29.

In some embodiments, the anti-C5 antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:26, or a variant thereof comprising up to about 3 (such as about any of 1, 2, or 3)

amino acid substitutions; VH-CDR3 comprising the amino acid sequence of SEQ ID NO:5, or a variant thereof comprising up to about 3 (such as about any of 1, 2, or 3) amino acid substitutions; VL-CDR1 comprising the amino acid sequence of SEQ ID NO:8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:29, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:26, or a variant thereof comprising up to about 3 (such as about any of 1, 2, or 3) amino acid substitutions; VH-CDR3 comprising the amino acid sequence of SEQ ID NO:5; VL-CDR1 comprising the amino acid sequence of SEQ ID NO:8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:29.

In some embodiments, the anti-C5 antibody or antigen-binding fragment thereof comprises: VH-CDR1 comprising the amino acid sequence of SEQ ID NO:3; VH-CDR2 comprising the amino acid sequence of SEQ ID NO:26; VH-CDR3 comprising the amino acid sequence of SEQ ID NO:5; VL-CDR1 comprising the amino acid sequence of SEQ ID NO:8; VL-CDR2 comprising the amino acid sequence of SEQ ID NO:9; and VL-CDR3 comprising the amino acid sequence of SEQ ID NO:29.

In some embodiments, the anti-C5 antibody or an antigen binding fragment thereof comprises a heavy chain comprising the amino acid sequence of SEQ ID NO:28, or a variant thereof. In other embodiments, the anti-C5 antibody comprises a light chain comprising the amino acid sequence of SEQ ID NO:31, or a variant thereof. In another embodiment, the anti-C5 antibody is mAb H2-6/L3-5, or a variant thereof. The monoclonal anti-C5 antibody mAb H2-6/L3-5 comprises a heavy chain comprising the amino acid sequence of SEQ ID NO:28 and a light chain comprising the amino acid sequence of SEQ ID NO:31. In one embodiment, the anti-C5 antibody comprises an Fc fragment. In one embodiment, the anti-C5 antibody comprises a human IgG4 Fc fragment or variant thereof. In one embodiment, the anti-C5 antibody mAb H2-5/L3-5 comprises a heavy chain comprising the amino acid sequence of SEQ ID NO:28; a light chain comprising the amino acid sequence of SEQ ID NO:31; and a human IgG4 Fc fragment comprising the amino acid sequence of SEQ ID NO: 32. In one embodiment, the anti-C5 antibody comprises a human IgG4 Fc fragment having an S108P mutation relative to SEQ ID NO: 32, or variant thereof. In one embodiment, the anti-C5 antibody mAb H2-6/L3-5 comprises a heavy chain comprising the amino acid sequence of SEQ ID NO:28; a light chain comprising the amino acid sequence of SEQ ID NO:31; and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody mAb H2-61L3-5 comprises a heavy chain comprising the amino acid sequence of SEQ ID NO:28; a light chain comprising the amino acid sequence of SEQ ID NO:31; and a human IgG4 Fc fragment having an S108P mutation, a M308L mutation, and a N314A mutation relative to SEQ ID NO: 32, comprising the amino acid sequence of SEQ ID NO: 61. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:3; VH-CDR2: SEQ ID NO:34; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:3; VH-CDR2: SEQ ID NO:34; VH-CDR3: SEQ ID NO:5; VL-CDR1: SEQ ID NO:8; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR1 comprising the amino acid sequence of SEQ ID NO:3 or a variant thereof comprising up to about 3 (such as about any of 1, 2, or 3) amino acid substitutions; and VL-CDR1: SEQ ID NO:8, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:3; and VL-CDR1: SEQ ID NO:8.

In some embodiments, the anti-C5 antibody or antigen-binding fragment thereof comprises: VH-CDR2 comprising the amino acid sequence of SEQ ID NO:34, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:34; and VL-CDR2: SEQ ID NO:9.

In some embodiments, the anti-C5 antibody or antigen-binding fragment thereof comprises: VH-CDR3 comprising the amino acid sequence of SEQ ID NO:5, or a variant thereof comprising up to about 3 (such as about any of 1, 2, or 3) amino acid substitutions; and VL-CDR3: SEQ ID NO:10, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:5; and VL-CDR3: SEQ ID NO:10.

In some embodiments, the anti-C5 antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:34, or a variant thereof comprising up to about 3 (such as about any of 1, 2, or 3) amino acid substitutions; VH-CDR3 comprising the amino acid sequence of SEQ ID NO:5, or a variant thereof comprising up to about 3 (such as about any of 1, 2, or 3) amino acid substitutions; VL-CDR1 comprising the amino acid sequence of SEQ ID NO:8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:34, or a variant thereof comprising up to about 3 (such as about any of 1, 2, or 3) amino acid substitutions; VH-CDR3 comprising the amino acid sequence of SEQ ID NO:5; VL-CDR1 comprising the amino acid sequence of SEQ ID NO:8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:3; VH-CDR2 comprising the amino acid sequence of SEQ ID NO:34; VH-CDR3 comprising the amino acid sequence of SEQ ID NO:5; VL-CDR1 comprising the amino acid sequence of SEQ ID NO:8; VL-CDR2 comprising the amino acid sequence of SEQ ID NO:9; and VL-CDR3 comprising the amino acid sequence of SEQ ID NO:10.

In some embodiments, the anti-C5 antibody or an antigen binding fragment thereof comprises a heavy chain comprising the amino acid sequence of SEQ ID NO:36, or a variant thereof. In other embodiments, the anti-C5 antibody comprises a light chain comprising the amino acid sequence of SEQ ID NO:7, or a variant thereof. In some embodiments, the monoclonal anti-C5 antibody comprises a heavy chain comprising the amino acid sequence of SEQ ID NO:36 and a light chain comprising the amino acid sequence of SEQ ID NO:7. In one embodiment, the anti-C5 antibody comprises an Fc fragment. In one embodiment, the anti-C5 antibody comprises a human IgG4 Fc fragment or variant thereof. In one embodiment, the anti-C5 antibody comprises a heavy chain comprising the amino acid sequence of SEQ ID NO:36; a light chain comprising the amino acid sequence of SEQ ID NO:7; and a human IgG4 Fc fragment comprising the amino acid sequence of SEQ ID NO: 32. In one embodiment, the anti-C5 antibody comprises a human IgG4 Fc fragment having an S108P mutation relative to SEQ ID NO: 32, or variant thereof. In one embodiment, the anti-C5 antibody comprises a heavy chain comprising the amino acid sequence of SEQ ID NO:36; a light chain comprising the amino acid sequence of SEQ ID NO:7; and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody comprises a heavy chain comprising the amino acid sequence of SEQ ID NO:36; a light chain comprising the amino acid sequence of SEQ ID NO:7; and a human IgG4 Fc fragment having an S108P mutation, a M308L mutation, and a N314A mutation relative to SEQ ID NO: 32, comprising the amino acid sequence of SEQ ID NO: 61. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:37; VH-CDR2: SEQ ID NO:38; VH-CDR3: SEQ ID NO:39; VL-CDR1: SEQ ID NO:23; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:37; VH-CDR2: SEQ ID NO:38; VH-CDR3: SEQ ID NO:39; VL-CDR1: SEQ ID NO:23; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR1 comprising the amino acid sequence of SEQ ID NO:37 or a variant thereof comprising up to about 3 (such as about any of 1, 2, or 3) amino acid substitutions; and VL-CDR1: SEQ ID NO:23, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:37; and VL-CDR1: SEQ ID NO:23.

In some embodiments, the anti-C5 antibody or antigen-binding fragment thereof comprises: VH-CDR2 comprising the amino acid sequence of SEQ ID NO:38, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:38; and VL-CDR2: SEQ ID NO:9.

In some embodiments, the anti-C5 antibody or antigen-binding fragment thereof comprises: VH-CDR3 comprising the amino acid sequence of SEQ ID NO:39, or a variant thereof comprising up to about 3 (such as about any of 1, 2, or 3) amino acid substitutions; and VL-CDR3: SEQ ID NO:10, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:39; and VL-CDR3: SEQ ID NO:10.

In some embodiments, the anti-C5 antibody or antigen-binding fragment thereof comprises: VH-CDR1 comprising the amino acid sequence of SEQ ID NO:37, or a variant thereof comprising up to about 3 (such as about any of 1, 2, or 3) amino acid substitutions; VH-CDR2 comprising the amino acid sequence of SEQ ID NO:38, or a variant thereof comprising up to about 3 (such as about any of 1, 2, or 3) amino acid substitutions; VH-CDR3 comprising the amino acid sequence of SEQ ID NO:39, or a variant thereof comprising up to about 3 (such as about any of 1, 2, or 3) amino acid substitutions; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:37, or a variant thereof comprising up to about 3 (such as about any of 1, 2, or 3) amino acid substitutions; VH-CDR2 comprising the amino acid sequence of SEQ ID NO:38, or a variant thereof comprising up to about 3 (such as about any of 1, 2, or 3) amino acid substitutions; VH-CDR3 comprising the amino acid sequence of SEQ ID NO:39; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:37; VH-CDR2 comprising the amino acid sequence of SEQ ID NO:38; VH-CDR3 comprising the amino acid sequence of SEQ ID NO:39; VL-CDR1 comprising the amino acid sequence of SEQ ID NO:23; VL-CDR2 comprising the amino acid sequence of SEQ ID NO:9; and VL-CDR3 comprising the amino acid sequence of SEQ ID NO:10.

In some embodiments, the anti-C5 antibody or an antigen binding fragment thereof comprises a heavy chain comprising the amino acid sequence of SEQ ID NO:41, or a variant thereof. In other embodiments, the anti-C5 antibody comprises a light chain comprising the amino acid sequence of SEQ ID NO:25, or a variant thereof. In another embodiment, the anti-C5 antibody is mAb H1-8/L1-9 variant IWW, or a variant thereof. In one embodiment, the monoclonal anti-C5 antibody mAb H1-8/L1-9 variant IWW comprises a heavy chain comprising the amino acid sequence of SEQ ID NO:41 and a light chain comprising the amino acid sequence of SEQ ID NO:25. In one embodiment, the anti-C5 antibody comprises an Fc fragment. In one embodiment, the anti-C5 antibody comprises a human IgG4 Fc fragment or variant thereof. In one embodiment, the anti-C5 antibody mAb H1-8/L1-9 variant IWW comprises a heavy chain comprising the amino acid sequence of SEQ ID NO:41; a light chain comprising the amino acid sequence of SEQ ID NO:25; and a human IgG4 Fc fragment comprising the amino acid sequence of SEQ ID NO: 32. In one embodiment, the anti-C5 antibody comprises a human IgG4 Fc fragment having an S108P mutation, or variant thereof. In one embodiment, the anti-C5 antibody mAb H1-8/L1-9 variant IWW comprises a heavy chain comprising the amino acid sequence of SEQ ID NO:41; a light chain comprising the amino acid sequence of SEQ ID NO:25; and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody mAb H1-8/L1-9 variant IWW comprises a heavy chain comprising the amino acid sequence of SEQ ID NO:41; a light chain comprising the amino acid sequence of SEQ ID NO:25; and a human IgG4 Fc fragment having an S108P mutation, a M308L mutation, and a N314A mutation relative to SEQ ID NO: 32, comprising the amino acid sequence of SEQ ID NO: 61. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:42; VH-CDR2: SEQ ID NO:43; VH-CDR3: SEQ ID NO:44; VL-CDR1: SEQ ID NO:23; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:42; VH-CDR2: SEQ ID NO:43; VH-CDR3: SEQ ID NO:44; VL-CDR1: SEQ ID NO:23; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR1 comprising the amino acid sequence of SEQ ID NO:42 or a variant thereof comprising up to about 3 (such as about any of 1, 2, or 3) amino acid substitutions; and VL-CDR1: SEQ ID NO:23, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:42; and VL-CDR1: SEQ ID NO:23.

In some embodiments, the anti-C5 antibody or antigen-binding fragment thereof comprises: VH-CDR2 comprising the amino acid sequence of SEQ ID NO:43, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:43; and VL-CDR2: SEQ ID NO:9.

In some embodiments, the anti-C5 antibody or antigen-binding fragment thereof comprises: VH-CDR3 comprising the amino acid sequence of SEQ ID NO:44, or a variant thereof comprising up to about 3 (such as about any of 1, 2, or 3) amino acid substitutions; and VL-CDR3: SEQ ID NO:10, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:44; and VL-CDR3: SEQ ID NO:10.

In some embodiments, the anti-C5 antibody or antigen-binding fragment thereof comprises: VH-CDR1 comprising the amino acid sequence of SEQ ID NO:42, or a variant thereof comprising up to about 3 (such as about any of 1, 2, or 3) amino acid substitutions; VH-CDR2 comprising the amino acid sequence of SEQ ID NO:43, or a variant thereof comprising up to about 3 (such as about any of 1, 2, or 3) amino acid substitutions; VH-CDR3 comprising the amino acid sequence of SEQ ID NO:44, or a variant thereof comprising up to about 3 (such as about any of 1, 2, or 3) amino acid substitutions; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:42, or a variant thereof comprising up to about 3 (such as about any of 1, 2, or 3) amino acid substitutions; VH-CDR2 comprising the amino acid sequence of SEQ ID NO:43, or a variant thereof comprising up to about 3 (such as about any of 1, 2, or 3) amino acid substitutions; VH-CDR3 comprising the amino acid sequence of SEQ ID NO:44; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:42; VH-CDR2 comprising the amino acid sequence of SEQ ID NO:43; VH-CDR3 comprising the amino acid sequence of SEQ ID NO:44; VL-CDR1 comprising the amino acid sequence of SEQ ID NO:23; VL-CDR2 comprising the amino acid sequence of SEQ ID NO:9; and VL-CDR3 comprising the amino acid sequence of SEQ ID NO:10.

In some embodiments, the anti-C5 antibody or an antigen binding fragment thereof comprises a heavy chain comprising the amino acid sequence of SEQ ID NO:46, or a variant thereof. In other embodiments, the anti-C5 antibody comprises a light chain comprising the amino acid sequence of SEQ ID NO:25, or a variant thereof. In another embodiment, the anti-C5 antibody is mAb H1-8/L1-9 variant IFW, or a variant thereof. In one embodiment, the monoclonal anti-C5 antibody mAb H1-8/L1-9 variant IFW comprises a heavy chain comprising the amino acid sequence of SEQ ID NO:46 and a light chain comprising the amino acid sequence of SEQ ID NO:25. In one embodiment, the anti-C5 antibody comprises an Fc fragment. In one embodiment, the anti-C5 antibody comprises a human IgG4 Fc fragment or variant thereof. In one embodiment, the anti-C5 antibody mAb H1-8/L1-9 variant IFW comprises a heavy chain comprising the amino acid sequence of SEQ ID NO:46; a light chain comprising the amino acid sequence of SEQ ID NO:25; and a human IgG4 Fc fragment comprising the amino acid sequence of SEQ ID NO: 32. In one embodiment, the anti-C5 antibody comprises a human IgG4 Fc fragment having an S108P mutation relative to SEQ ID NO: 32, or variant thereof. In one embodiment, the anti-C5 antibody mAb H1-8/L1-9 variant IFW comprises a heavy chain comprising the amino acid sequence of SEQ ID NO:46; a light chain comprising the amino acid sequence of SEQ ID NO:25; and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody mAb H1-8/L1-9 variant IFW comprises a heavy chain comprising the amino acid sequence of SEQ ID NO:46; a light chain comprising the amino acid sequence of SEQ ID NO:25; and a human IgG4 Fc fragment having an S108P mutation, a M308L mutation, and a N314A mutation relative to SEQ ID NO: 32, comprising the amino is acid sequence of SEQ ID NO: 61.

In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:47; VH-CDR2: SEQ ID NO:48; VH-CDR3: SEQ ID NO:49; VL-CDR1: SEQ ID NO:23; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:47; VH-CDR2: SEQ ID NO:48; VH-CDR3: SEQ ID NO:49; VL-CDR1: SEQ ID NO:23; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR1 comprising the amino acid sequence of SEQ ID NO:47 or a variant thereof comprising up to about 3 (such as about any of 1, 2, or 3) amino acid substitutions; and VL-CDR1: SEQ ID NO:23, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:47; and VL-CDR1: SEQ ID NO:23.

In some embodiments, the anti-C5 antibody or antigen-binding fragment thereof comprises: VH-CDR2 comprising the amino acid sequence of SEQ ID NO:48, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:48; and VL-CDR2: SEQ ID NO:9.

In some embodiments, the anti-C5 antibody or antigen-binding fragment thereof comprises: VH-CDR3 comprising the amino acid sequence of SEQ ID NO:49, or a variant thereof comprising up to about 3 (such as about any of 1, 2, or 3) amino acid substitutions; and VL-CDR3: SEQ ID NO:10, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:49; and VL-CDR3: SEQ ID NO:10.

In some embodiments, the anti-C5 antibody or antigen-binding fragment thereof comprises: VH-CDR1 comprising the amino acid sequence of SEQ ID NO:47, or a variant thereof comprising up to about 3 (such as about any of 1, 2, or 3) amino acid substitutions; VH-CDR2 comprising the amino acid sequence of SEQ ID NO:48, or a variant thereof comprising up to about 3 (such as about any of 1, 2, or 3) amino acid substitutions; VH-CDR3 comprising the amino acid sequence of SEQ ID NO:49, or a variant thereof comprising up to about 3 (such as about any of 1, 2, or 3) amino acid substitutions; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:47, or a variant thereof comprising up to about 3 (such as about any of 1, 2, or 3) amino acid substitutions; VH-CDR2 comprising the amino acid sequence of SEQ ID NO:48, or a variant thereof comprising up to about 3 (such as about any of 1, 2, or 3) amino acid substitutions; VH-CDR3 comprising the amino acid sequence of SEQ ID NO:49; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:47; VH-CDR2 comprising the amino acid sequence of SEQ ID NO:48; VH-CDR3 comprising the amino acid sequence of SEQ ID NO:49; VL-CDR1 comprising the amino acid sequence of SEQ ID NO:23; VL-CDR2 comprising the amino acid sequence of SEQ ID NO:9; and VL-CDR3 comprising the amino acid sequence of SEQ ID NO:10.

In some embodiments, the anti-C5 antibody or an antigen binding fragment thereof comprises a heavy chain comprising the amino acid sequence of SEQ ID NO:51, or a variant thereof. In other embodiments, the anti-C5 antibody comprises a light chain comprising the amino acid sequence of SEQ ID NO:25, or a variant thereof. In another embodiment, the anti-C5 antibody is mAb H1-8/L1-9 variant FME, or a variant thereof. In one embodiment, the monoclonal anti-C5 antibody mAb H1-8/L1-9 variant FME comprises a heavy chain comprising the amino acid sequence of SEQ ID NO:51 and a light chain comprising the amino acid sequence of SEQ ID NO:25. In one embodiment, the anti-C5 antibody comprises an Fc fragment. In one embodiment, the anti-C5 antibody comprises a human IgG4 Fc fragment or variant thereof. In one embodiment, the anti-C5 antibody mAb H1-8/L1-9 variant FME comprises a heavy chain comprising the amino acid sequence of SEQ ID NO:51; a light chain comprising the amino acid sequence of SEQ ID NO:25; and a human IgG4 Fc fragment comprising the amino acid sequence of SEQ ID NO: 32. In one embodiment, the anti-C5 antibody comprises a human IgG4 Fc fragment having an S108P mutation relative to SEQ ID NO: 32, or variant thereof. In one embodiment, the anti-C5 antibody mAb H1-8/L1-9 variant FME comprises a heavy chain comprising the amino acid sequence of SEQ ID NO:51; a light chain comprising the amino acid sequence of SEQ ID NO:25; and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody mAb H1-8/L1-9 variant FME comprises a heavy chain comprising the amino acid sequence of SEQ ID NO:51; a light chain comprising the amino acid sequence of SEQ ID NO:25; and a human IgG4 Fc fragment having an S108P mutation, a M308L mutation, and a N314A mutation relative to SEQ ID NO: 32, comprising the amino acid sequence of SEQ ID NO: 61. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:52; VH-CDR2: SEQ ID NO:53; VH-CDR3: SEQ ID NO:54; VL-CDR1: SEQ ID NO:23; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:52; VH-CDR2: SEQ ID NO:53; VH-CDR3: SEQ ID NO:54; VL-CDR1: SEQ ID NO:23; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR1 comprising the amino acid sequence of SEQ ID NO:52 or a variant thereof comprising up to about 3 (such as about any of 1, 2, or 3) amino acid substitutions; and VL-CDR1: SEQ ID NO:23, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:52; and VL-CDR1: SEQ ID NO:23.

In some embodiments, the anti-C5 antibody or antigen-binding fragment thereof comprises: VH-CDR2 comprising the amino acid sequence of SEQ ID NO:53, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:53; and VL-CDR2: SEQ ID NO:9.

In some embodiments, the anti-C5 antibody or antigen-binding fragment thereof comprises: VH-CDR3 comprising the amino acid sequence of SEQ ID NO:54, or a variant thereof comprising up to about 3 (such as about any of 1, 2, or 3) amino acid substitutions; and VL-CDR3: SEQ ID NO:10, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:54; and VL-CDR3: SEQ ID NO:10.

In some embodiments, the anti-C5 antibody or antigen-binding fragment thereof comprises: VH-CDR1 comprising the amino acid sequence of SEQ ID NO:52, or a variant thereof comprising up to about 3 (such as about any of 1, 2, or 3) amino acid substitutions; VH-CDR2 comprising the amino acid sequence of SEQ ID NO:53, or a variant thereof comprising up to about 3 (such as about any of 1, 2, or 3) amino acid substitutions; VH-CDR3 comprising the amino acid sequence of SEQ ID NO:54, or a variant thereof comprising up to about 3 (such as about any of 1, 2, or 3) amino acid substitutions; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:52, or a variant thereof comprising up to about 3 (such as about any of 1, 2, or 3) amino acid substitutions; VH-CDR2 comprising the amino acid sequence of SEQ ID NO:53, or a variant thereof comprising up to about 3 (such as about any of 1, 2, or 3) amino acid substitutions; VH-CDR3 comprising the amino acid sequence of SEQ ID NO:54; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:52; VH-CDR2 comprising the amino acid sequence of SEQ ID NO:53; VH-CDR3 comprising the amino acid sequence of SEQ ID NO:54; VL-CDR1 comprising the amino acid sequence of SEQ ID NO:23; VL-CDR2 comprising the amino acid sequence of SEQ ID NO:9; and VL-CDR3 comprising the amino acid sequence of SEQ ID NO:10.

In some embodiments, the anti-C5 antibody or an antigen binding fragment thereof comprises a heavy chain comprising the amino acid sequence of SEQ ID NO:56, or a variant thereof. In other embodiments, the anti-C5 antibody comprises a light chain comprising the amino acid sequence of SEQ ID NO:25, or a variant thereof. In another embodiment, the anti-C5 antibody is mAb H1-8/L1-9 variant FMW, or a variant thereof. In one embodiment, the monoclonal anti-C5 antibody mAb H1-8/L1-9 variant FMW comprises a heavy chain comprising the amino acid sequence of SEQ ID NO:56 and a light chain comprising the amino acid sequence of SEQ ID NO:25. In one embodiment, the anti-C5 antibody comprises an Fc fragment. In one embodiment, the anti-C5 antibody comprises a human IgG4 Fc fragment or variant thereof. In one embodiment, the anti-C5 antibody mAb H1-8/L1-9 variant FMW comprises a heavy chain comprising the amino acid sequence of SEQ ID NO:56; a light chain comprising the amino acid sequence of SEQ ID NO:25; and a human IgG4 Fc fragment comprising the amino acid sequence of SEQ ID NO: 32. In one embodiment, the anti-C5 antibody comprises a human IgG4 Fc fragment having an S108P mutation relative to SEQ ID NO: 32, or variant thereof. In one embodiment, the anti-C5 antibody mAb H1-8/L1-9 variant FMW comprises a heavy chain comprising the amino acid sequence of SEQ ID NO:56; a light chain comprising the amino acid sequence of SEQ ID NO:25: and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody mAb H1-8/L1-9 variant FMW comprises a heavy chain comprising the amino acid sequence of SEQ ID NO:56; a light chain comprising the amino acid sequence of SEQ ID NO:25; and a human IgG4 Fc fragment having an S108P mutation, a M308L mutation, and a N314A mutation relative to SEQ ID NO: 32, comprising the amino acid sequence of SEQ ID NO: 61. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:47; VH-CDR2: SEQ ID NO:57; VH-CDR3: SEQ ID NO:49; VL-CDR1: SEQ ID NO:23; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:47; VH-CDR2: SEQ ID NO:57; VH-CDR3: SEQ ID NO:49; VL-CDR1: SEQ ID NO:23; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR2 comprising the amino acid sequence of SEQ ID NO:57, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:57; and VL-CDR2: SEQ ID NO:9.

In some embodiments, the anti-C5 antibody or antigen-binding fragment thereof comprises: VH-CDR1 comprising the amino acid sequence of SEQ ID NO:47, or a variant thereof comprising up to about 3 (such as about any of 1, 2, or 3) amino acid substitutions; VH-CDR2 comprising the amino acid sequence of SEQ ID NO:57, or a variant thereof comprising up to about 3 (such as about any of 1, 2, or 3) amino acid substitutions; VH-CDR3 comprising the amino acid sequence of SEQ ID NO:49, or a variant thereof comprising up to about 3 (such as about any of 1, 2, or 3) amino acid substitutions; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:47, or a variant thereof comprising up to about 3 (such as about any of 1, 2, or 3) amino acid substitutions; VH-CDR2 comprising the amino acid sequence of SEQ ID NO:57, or a variant thereof comprising up to about 3 (such as about any of 1, 2, or 3) amino acid substitutions; VH-CDR3 comprising the amino acid sequence of SEQ ID NO:49; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:47; VH-CDR2 comprising the amino acid sequence of SEQ ID NO:57; VH-CDR3 comprising the amino acid sequence of SEQ ID NO:49; VL-CDR1 comprising the amino acid sequence of SEQ ID NO:23; VL-CDR2 comprising the amino acid sequence of SEQ ID NO:9; and VL-CDR3 comprising the amino acid sequence of SEQ ID NO:10.

In some embodiments, the anti-C5 antibody or an antigen binding fragment thereof comprises a heavy chain comprising the amino acid sequence of SEQ ID NO:59, or a variant thereof. In other embodiments, the anti-C5 antibody comprises a light chain comprising the amino acid sequence of SEQ ID NO:25, or a variant thereof. In another embodiment, the anti-C5 antibody is mAb H1-8/L1-9 variant FMEH, or a variant thereof. In one embodiment, the monoclonal anti-C5 antibody mAb H1-8L1-9 variant FMEH comprises a heavy chain comprising the amino acid sequence of SEQ ID NO:59 and a light chain comprising the amino acid sequence of SEQ ID NO:25. In one embodiment, the anti-C5 antibody comprises an Fc fragment. In one embodiment, the anti-C5 antibody comprises a human IgG4 Fc fragment or variant thereof. In one embodiment, the anti-C5 antibody mAb H1-8/L1-9 variant FMEH comprises a heavy chain comprising the amino acid sequence of SEQ ID NO:59; a light chain comprising the amino acid sequence of SEQ ID NO:25; and a human IgG4 Fc fragment comprising the amino acid sequence of SEQ ID NO: 32. In one embodiment, the anti-C5 antibody comprises a human IgG4 Fc fragment having an S108P mutation relative to SEQ ID NO: 32, or variant thereof. In one embodiment, the anti-C5 antibody mAb H1-8/L1-9 variant FMEH comprises a heavy chain comprising the amino acid sequence of SEQ ID NO:59; a light chain comprising the amino acid sequence of SEQ ID NO:25: and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody mAb H1-8/L1-9 variant FMEH comprises a heavy chain comprising the amino acid sequence of SEQ ID NO:59; a light chain comprising the amino acid sequence of SEQ ID NO:25; and a human IgG4 Fc fragment having an S108P mutation, a M308L mutation, and a N314A mutation relative to SEQ ID NO: 32, comprising the amino acid sequence of SEQ ID NO: 61. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:37; VH-CDR2: SEQ ID NO:62; VH-CDR3: SEQ ID NO:39; VL-CDR1: SEQ ID NO:23; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:37; VH-CDR2: SEQ ID NO:62; VH-CDR3: SEQ ID NO:39; VL-CDR1: SEQ ID NO:23; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR2 comprising the amino acid sequence of SEQ ID NO:62, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:62; and VL-CDR2: SEQ ID NO:9.

In some embodiments, the anti-C5 antibody or antigen-binding fragment thereof comprises: VH-CDR1 comprising the amino acid sequence of SEQ ID NO:37, or a variant thereof comprising up to about 3 (such as about any of 1, 2, or 3) amino acid substitutions; VH-CDR2 comprising the amino acid sequence of SEQ ID NO:62, or a variant thereof comprising up to about 3 (such as about any of 1, 2, or 3) amino acid substitutions; VH-CDR3 comprising the amino acid sequence of SEQ ID NO:39, or a variant thereof comprising up to about 3 (such as about any of 1, 2, or 3) amino acid substitutions; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:37, or a variant thereof comprising up to about 3 (such as about any of 1, 2, or 3) amino acid substitutions; VH-CDR2 comprising the amino acid sequence of SEQ ID NO:62, or a variant thereof comprising up to about 3 (such as about any of 1, 2, or 3) amino acid substitutions; VH-CDR3 comprising the amino acid sequence of SEQ ID NO:39; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:37; VH-CDR2 comprising the amino acid sequence of SEQ ID NO:62; VH-CDR3 comprising the amino acid sequence of SEQ ID NO:39; VL-CDR1 comprising the amino acid sequence of SEQ ID NO:23; VL-CDR2 comprising the amino acid sequence of SEQ ID NO:9; and VL-CDR3 comprising the amino acid sequence of SEQ ID NO:10.

In some embodiments, the anti-C5 antibody or an antigen binding fragment thereof comprises a heavy chain comprising the amino acid sequence of SEQ ID NO:64, or a variant thereof. In other embodiments, the anti-C5 antibody comprises a light chain comprising the amino acid sequence of SEQ ID NO:25, or a variant thereof. In another embodiment, the anti-C5 antibody is mAb H1-8/L1-9 variant IWWH, or a variant thereof. In one embodiment, the monoclonal anti-C5 antibody mAb H1-8/L1-9 variant IWWH comprises a heavy chain comprising the amino acid sequence of SEQ ID NO:64 and a light chain comprising the amino acid sequence of SEQ ID NO:25. In one embodiment, the anti-C5 antibody comprises an Fc fragment. In one embodiment, the anti-C5 antibody comprises a human IgG4 Fc fragment or variant thereof. In one embodiment, the anti-C5 antibody mAb H1-8/L1-9 variant IWWH comprises a heavy chain comprising the amino acid sequence of SEQ ID NO:64; a light chain comprising the amino acid sequence of SEQ ID NO:25; and a human IgG4 Fc fragment comprising the amino acid sequence of SEQ ID NO: 32. In one embodiment, the anti-C5 antibody comprises a human IgG4 Fc fragment having an S108P mutation relative to SEQ ID NO: 32, or variant thereof. In one embodiment, the anti-C5 antibody mAb H1-8/L1-9 variant IWWH comprises a heavy chain comprising the amino acid sequence of SEQ ID NO:64; a light chain comprising the amino acid sequence of SEQ ID NO:25; and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody mAb H1-8/L1-9 variant IWWH comprises a heavy chain comprising the amino acid sequence of SEQ ID NO:64; a light chain comprising the amino acid sequence of SEQ ID NO:25; and a human IgG4 Fc fragment having an S108P mutation, a M308L mutation, and a N314A mutation relative to SEQ ID NO: 32, comprising the amino acid sequence of SEQ ID NO: 61. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:42; VH-CDR2: SEQ ID NO:65; VH-CDR3: SEQ ID NO:44; VL-CDR1: SEQ ID NO:23; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:42; VH-CDR2: SEQ ID NO:65; VH-CDR3: SEQ ID NO:44; VL-CDR1: SEQ ID NO:23; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR2 comprising the amino acid sequence of SEQ ID NO:65, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:65; and VL-CDR2: SEQ ID NO:9.

In some embodiments, the anti-C5 antibody or antigen-binding fragment thereof comprises: VH-CDR1 comprising the amino acid sequence of SEQ ID NO:42, or a variant thereof comprising up to about 3 (such as about any of 1, 2, or 3) amino acid substitutions; VH-CDR2 comprising the amino acid sequence of SEQ ID NO:65, or a variant thereof comprising up to about 3 (such as about any of 1, 2, or 3) amino acid substitutions; VH-CDR3 comprising the amino acid sequence of SEQ ID NO:44, or a variant thereof comprising up to about 3 (such as about any of 1, 2, or 3) amino acid substitutions; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:42, or a variant thereof comprising up to about 3 (such as about any of 1, 2, or 3) amino acid substitutions; VH-CDR2 comprising the amino acid sequence of SEQ ID NO:65, or a variant thereof comprising up to about 3 (such as about any of 1, 2, or 3) amino acid substitutions; VH-CDR3 comprising the amino acid sequence of SEQ ID NO:44; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:42; VH-CDR2 comprising the amino acid sequence of SEQ ID NO:65; VH-CDR3 comprising the amino acid sequence of SEQ ID NO:44; VL-CDR1 comprising the amino acid sequence of SEQ ID NO:23; VL-CDR2 comprising the amino acid sequence of SEQ ID NO:9; and VL-CDR3 comprising the amino acid sequence of SEQ ID NO:10.

In some embodiments, the anti-C5 antibody or an antigen binding fragment thereof comprises a heavy chain comprising the amino acid sequence of SEQ ID NO:67, or a variant thereof. In other embodiments, the anti-C5 antibody comprises a light chain comprising the amino acid sequence of SEQ ID NO:25, or a variant thereof. In another embodiment, the anti-C5 antibody is mAb H1-8/L1-9 variant IFWH, or a variant thereof. In one embodiment, the monoclonal anti-C5 antibody mAb H1-8/L1-9 variant IFWH comprises a heavy chain comprising the amino acid sequence of SEQ ID NO:67 and a light chain comprising the amino acid sequence of SEQ ID NO:25. In one embodiment, the anti-C5 antibody comprises an Fc fragment. In one embodiment, the anti-C5 antibody comprises a human IgG4 Fc fragment or variant thereof. In one embodiment, the anti-C5 antibody mAb H1-8/L1-9 variant IFWH comprises a heavy chain comprising the amino acid sequence of SEQ ID NO:67; a light chain comprising the amino acid sequence of SEQ ID NO:25; and a human IgG4 Fc fragment comprising the amino acid sequence of SEQ ID NO: 32. In one embodiment, the anti-C5 antibody comprises a human IgG4 Fc fragment having an S108P mutation relative to SEQ ID NO: 32, or variant thereof. In one embodiment, the anti-C5 antibody mAb H1-8/L1-9 variant IFWH comprises a heavy chain comprising the amino acid sequence of SEQ ID NO:67; a light chain comprising the amino acid sequence of SEQ ID NO:25; and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody mAb H1-8/L1-9 variant IFWH comprises a heavy chain comprising the amino acid sequence of SEQ ID NO:67; a light chain comprising the amino acid sequence of SEQ ID NO:25; and a human IgG4 Fc fragment having an S108P mutation, a M308L mutation, and a N314A mutation relative to SEQ ID NO: 32, comprising the amino acid sequence of SEQ ID NO: 61. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:52; VH-CDR2: SEQ ID NO:68; VH-CDR3: SEQ ID NO:54; VL-CDR1: SEQ ID NO:23; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:52; VH-CDR2: SEQ ID NO:68; VH-CDR3: SEQ ID NO:54; VL-CDR1: SEQ ID NO:23; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR2 comprising the amino acid sequence of SEQ ID NO:68, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:68; and VL-CDR2: SEQ ID NO:9.

In some embodiments, the anti-C5 antibody or antigen-binding fragment thereof comprises: VH-CDR1 comprising the amino acid sequence of SEQ ID NO:52, or a variant thereof comprising up to about 3 (such as about any of 1, 2, or 3) amino acid substitutions; VH-CDR2 comprising the amino acid sequence of SEQ ID NO:68, or a variant thereof comprising up to about 3 (such as about any of 1, 2, or 3) amino acid substitutions; VH-CDR3 comprising the amino acid sequence of SEQ ID NO:54, or a variant thereof comprising up to about 3 (such as about any of 1, 2, or 3) amino acid substitutions; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:52, or a variant thereof comprising up to about 3 (such as about any of 1, 2, or 3) amino acid substitutions; VH-CDR2 comprising the amino acid sequence of SEQ ID NO:68, or a variant thereof comprising up to about 3 (such as about any of 1, 2, or 3) amino acid substitutions; VH-CDR3 comprising the amino acid sequence of SEQ ID NO:54; VL-CDR1 comprising the amino acid sequence of SEQ ID NO:23, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:52; VH-CDR2 comprising the amino acid sequence of SEQ ID NO:68; VH-CDR3 comprising the amino acid sequence of SEQ ID NO:54; VL-CDR1 comprising the amino acid sequence of SEQ ID NO:23; VL-CDR2 comprising the amino acid sequence of SEQ ID NO:9; and VL-CDR3 comprising the amino acid sequence of SEQ ID NO:10.

In some embodiments, the anti-C5 antibody or an antigen binding fragment thereof comprises a heavy chain comprising the amino acid sequence of SEQ ID NO:70, or a variant thereof. In other embodiments, the anti-C5 antibody comprises a light chain comprising the amino acid sequence of SEQ ID NO:25, or a variant thereof. In another embodiment, the anti-C5 antibody is mAb H1-8/L1-9 variant FMVH, or a variant thereof. In one embodiment, the monoclonal anti-C5 antibody mAb H1-8L1-9 variant FMWH comprises a heavy chain comprising the amino acid sequence of SEQ ID NO:70 and a light chain comprising the amino acid sequence of SEQ ID NO:25. In one embodiment, the anti-C5 antibody comprises an Fc fragment. In one embodiment, the anti-C5 antibody comprises a human IgG4 Fc fragment or variant thereof. In one embodiment, the anti-C5 antibody mAb H1-8/L1-9 variant FMWH comprises a heavy chain comprising the amino acid sequence of SEQ ID NO:70; a light chain comprising the amino acid sequence of SEQ ID NO:25; and a human IgG4 Fc fragment comprising the amino acid sequence of SEQ ID NO: 32. In one embodiment, the anti-C5 antibody comprises a human IgG4 Fc fragment having an S108P mutation relative to SEQ ID NO: 32, or variant thereof. In one embodiment, the anti-C5 antibody mAb H1-8/L1-9 variant FMWH comprises a heavy chain comprising the amino acid sequence of SEQ ID NO:70; a light chain comprising the amino acid sequence of SEQ ID NO:25; and a human IgG4 Fc fragment having an S108P mutation relative to SEQ ID NO: 32, comprising the amino acid sequence of SEQ ID NO: 33. In one embodiment, the anti-C5 antibody comprises a human IgG4 Fc fragment having an S108P mutation, a M308L mutation, and a N314A mutation relative to SEQ ID NO: 32, or variant thereof. In one embodiment, the anti-C5 antibody mAb H1-8/L1-9 variant FMWH comprises a heavy chain comprising the amino acid sequence of SEQ ID NO:70; a light chain comprising the amino acid sequence of SEQ ID NO:25; and a human IgG4 Fc fragment having an S108P mutation, a M308L mutation, and a N314A mutation relative to SEQ ID NO: 32, comprising the amino acid sequence of SEQ ID NO: 61. In some embodiments, the monoclonal anti-C5 antibody is humanized. In some embodiments the monoclonal anti-C5 antibody is a chimeric antibody.

In some embodiments, the anti-C5 antibody or antigen-binding fragment thereof comprises a substitution of proline at position #4 (i.e., P4) in VH CDR2, relative to SEQ ID NO:4. In various embodiments, the substitution at P4 is P4→F4 (i.e., P4F), P4→L4 (i.e., P4L), P4→M4 (i.e., P4M), P4→W4 (i.e., P4W), or P4→I4 (i.e., P4I)

In some embodiments, the anti-C5 antibody or antigen-binding fragment thereof comprises a substitution of threonine at position #9 (i.e., T9) in VH CDR2, relative to SEQ ID NO:4. In various embodiments, the substitution at T9 is T9→H9 (i.e., T9H), T9 is T9→F9 (i.e., T9F), T9→L9 (i.e., T9L), T9→M9 (i.e., T9M), T9→W9 (i.e., T9W), or T9→I9 (i.e., T9I).

In some embodiments, the anti-C5 antibody or antigen-binding fragment thereof comprises a substitution of proline at position #4 (i.e., P4) in VH CDR2, relative to SEQ ID NO:4; and a substitution of threonine at position #9 (i.e., T9) in VH CDR2, relative to SEQ ID NO:4. In various embodiments, the substitution at P4 is P4→F4 (i.e., P4F), P4→L4 (i.e., P4L), P4→M4 (i.e., P4M), P4→W4 (i.e., P4W), or P4→I4 (i.e., P4I); and the substitution at T9 is T9→H9 (i.e., T9H), T9 is T9→F9 (i.e., T9F), T9→L9 (i.e., T9L), T9→M9 (i.e., T9M), T9→W9 (i.e., T9W), or T9→I9 (i.e., T9I).

In some embodiments, the anti-C5 antibody or antigen-binding fragment thereof comprises a substitution of valine at position #16 (i.e., V16) in VH CDR3, relative to SEQ ID NO:5. In various embodiments, the substitution at V4 is V16→F16 (i.e., V16F), V16→E16 (i.e., V16E) or V16→W16 (i.e., V16W).

In some embodiments, the anti-C5 antibody or antigen-binding fragment thereof comprises a substitution of asparagine at position #8 (i.e., N8) in VH CDR1, relative to SEQ ID NO:3. In various embodiments, the substitution at N8 is N8→H8 (i.e., N8H), N8→W8 (i.e., N8W), N8→18 (i.e., N8I), N8→V8 (i.e., N8V), N8→Y8 (i.e., N8Y), or N8→F8 (i.e., N8F).

In some embodiments, the anti-C5 antibody or antigen-binding fragment thereof comprises a substitution of leucine at position #9 (i.e., L9) in VH CDR1, relative to SEQ ID NO:20. In various embodiments, the substitution at L9 is L9→W9 (i.e., L9W), L9→I9 (i.e., L9I), L9→V9 (i.e., L9V), L9→Y9 (i.e., L9Y), or L9→F9 (i.e., L9F).

In some embodiments, the anti-C5 antibody or antigen-binding fragment thereof comprises a substitution of two or more of the group consisting of proline 4 (i.e., P4) in VH CDR2, relative to SEQ ID NO:4, threonine 9 (i.e., T9) in VH CDR2, relative to SEQ ID NO:4, valine 16 (i.e., V16) in VH CDR3, relative to SEQ ID NO:5, and leucine 9 (i.e., L9) in VH CDR1, relative to SEQ ID NO:20. In various embodiments, the anti-C5 antibody or antigen-binding fragment thereof comprising a substitution at two or more of the group consisting of proline 4 (i.e., P4) in VH CDR2, relative to SEQ ID NO:4, threonine 9 (i.e., T9) in VH CDR2, relative to SEQ ID NO:4, valine 16 (i.e., V16) in VH CDR3, relative to SEQ ID NO:5, and leucine 9 (i.e., L9) in VH CDR1, relative to SEQ ID NO:20 comprises the two or more substitutions selected from the group consisting of L9I/P4M, L9I/P4W, L9I/P4F, L9F/P4M, L9F/P4W, L9F/P4F, L9I/P4M/V16W, L9I/P4W/V16W, L9I/P4F/V16W, L9F/P4M/V16W, L9F/P4W/V16W, L9F/P4F/V16W, L9I/P4M/V16E, L9I/P4W/V16E, L9I/P4F/V6E, L9F/P4M/V16E, L9F/P4W/V16E, L9F/P4F/V16E, L9I/P4M/T9H/V16W, L9I/P4W/T9H/V16W, L9I/P4F/T9H/V16W, L9F/P4M/T9H/V16W, L9F/P4W/T9H/V16W, L9F/P4F/T9H/V16W, L9I/P4M/T9H/V16E, L9I/P4W/T9H/V16E, L9I/P4F/T9H/V16E, L9F/P4M/T9H/V16E, L9F/P4W/T9H/V16E, and L9F/P4F/T9H/V16E.

In some embodiments the antibodies are chimeric antibodies. In some embodiments the anti-human C5 antibody may comprise human light chain and human heavy chain constant regions in combination with the variable region CDR sequences described in the specification above. One of skill in the art would be able to prepare and obtain a chimeric antibody using known techniques of swapping relevant domains of specific antibodies of interest. Such an antibody is easily prepared by grafting heterogeneous antibody domains, incorporating one or more CDR sequences described in this application. Using known recombinant technology, it is possible to obtain and prepare a recombinant antibody comprising heavy and light chain constant regions encoded by nucleic acid sequences of human heavy and light chain constant regions; and the heavy and light chain variable regions comprising CDRs encoded by nucleic acid sequences corresponding to the CDR sequences set forth in the disclosure. One of skill in the art can prepare an anti-human C5 antibody comprises one or more CDR sequences described in this disclosure, wherein portions of the light chain alone or portions of the heavy chain alone are replaced with regions from an antibody belonging to another species, such as, for example, human. A human anti-human-C5 antibody comprising variable regions having one or more CDR sequences selected from SEQ ID NOs: 3-5, 8-11, 14, 17, 20, 23, 26, 29, 34, 37-39, 42-44, 47-49, 52-54, 57, 62, 65, and 68 or a variant or variants thereof, in combination with murine or non-murine antibody structural elements outside the CDR regions can be prepared by routine methods known in the art. In some embodiments, the antibodies or antibody fragments are further humanized using known techniques in the art.

In some embodiments the anti-C5 antibody comprises an antibody having at least about 85% (such as at least about any of 85%, 86%, 87%, 88%, 89%, 90%, 91%, 92%, 93%, 94%, 95%, 96%, 97%, 98%, 99%, or 100%) amino acid identity with the CDR sequence described herein, listed in SEQ ID NOs 3-5, 8-11, 14, 17, 20, 23, 26, 29, 34, 37-39, 42-44, 47-49, 52-54, 57, 62, 65, and 68.

In one embodiment, the current disclosure encompasses an anti-C5 antibody having CDR sequences of at least about 85% (such as at least about any of 85%, 86%, 87%, 88%, 89%, 90%, 91%, 92%, 93%, 94%, 95%, 96%, 97%, 98%, 99%, or 100%) identity to the CDR sequences described above. In one embodiment, the antibody against human C5 has a heavy chain variable (vH) region and a light chain variable (vL) region, wherein the vH region has an amino acid sequence that is more than about 90% (such as more than about any of 90%, 91%, 92%, 93%, 94%, 95%, 96%, 97%, 98%, 99%, or 100%) identical to one selected from SEQ ID NOs 2, 19, 22, 28, 36, 41, 46, 51, 56, 59, 64, 67, and 70, and wherein the vL region has an amino acid sequence that is more than about 90% (such as more than about any of 90%, 91%, 92%, 93%, 94%, 95%, 96%, 97%, 98%, 99%, or 100%) identical to one selected from SEQ ID NOs 7, 13, 16, 17, 25, and 31.

In some embodiments the antibody or the antibody fragment is modified. In some embodiments the modifications include fusion of the antibody or the antigen-binding fragment thereof with portions of another protein, or a protein fragment. In some embodiments the antibody or the antibody fragment thereof of the invention is modified to increase the circulating half-life of the same in vivo. For example, the antibody of the fragment may be fused with an FcRn molecule, which is also known as neonatal Fc receptor to stabilize the antibody in vivo. (Nature Reviews Immunology 7:715-725). In some embodiments, the antibody or antigen-binding fragment thereof is conjugated (e.g., fused) to an effector molecule and/or another targeting moiety (such as an antibody or antibody fragment recognizing a different molecule, different antigen or a different epitope).

One of skill in the art would be able to prepare human-C5 binding single chain variable fragment (scFv), comprising at least one specific CDR sequence selected from SEQ ID NOs 3-5, 8-11, 14, 17, 20, 23, 26, 29, 34, 37-39, 42-44, 47-49, 52-54, 57, 62, 65, and 68 or a variant or variants thereof. An scFv may comprise heavy chain variable region sequences designated in SEQ ID NOs 3-5, 17, 20, 26, 34, 37-39, 42-44, 47-49, 52-54, 57, 62, 65, and 68, or a variant or variants thereof, and light chain variable regions designated in SEQ ID NOs 8-11, 14, 23, and 29, or a variant or variants thereof. CDR sequences incorporated within the scFv having amino acid sequence identity of at least about 85% 86%, 87%, 88%, 89%, 90%, 91%, 92%, 93%, 94%, 95%, 96%, 97%, 98%, or 99% to the CDR sequences described in the present disclosure are encompassed within the scope of the present disclosure.

In some embodiments, the isolated antibody binds to human C5, wherein the antibody binds to an epitope of human C5. In some embodiments, the human C5 antibody of the invention is one that binds to a specific epitope of human C5. In some embodiments, the epitope includes at least one amino acid in the α-chain of C5. In some embodiments, the epitope includes at least one amino acid in the β-chain of C5.

Screening Assays

The present invention has application in various screening assays, including, determining whether a candidate anti-C5 antibody can inhibit complement activity.

In some embodiments, the level of complement activity in the presence of the candidate anti-C5 antibody is compared with complement activity detected in a positive comparator control. The positive comparator control comprises complement activation in the absence of added test compound. In some embodiments, the candidate anti-C5 antibody is identified as an inhibitor of the complement when the complement activity in the presence of the candidate anti-C5 antibody is less than about 70% of the complement activity detected in a positive comparator control; this corresponds to greater than about 30% inhibition of complement activity in the presence of the test compound. In other embodiments, the candidate anti-C5 antibody is identified as an inhibitor of the complement when the complement activity in the presence of the candidate anti-C5 antibody is less than about 80% of the complement activity detected in a positive comparator control; this corresponds to greater than about 20% inhibition of complement activity in the presence of the test compound. In still other embodiments, the candidate anti-C5 antibody is identified as an inhibitor of the complement when the complement activity in the presence of the candidate anti-C5 antibody is less than about 90% of the complement activity detected in a positive comparator control; this corresponds to greater than about 10% inhibition of complement activity in the presence of the test compound. In some embodiments, the level of complement inhibition by the candidate anti-C5 antibody is compared with the level of inhibition detected in a negative comparator control.

A variety of immunoassay formats, including competitive and non-competitive immunoassay formats, antigen capture assays, two-antibody sandwich assays, and three-antibody sandwich assays are useful methods of the invention (Self et al., 1996, Curr. Opin. Biotechnol. 7:60-65). The invention should not be construed to be limited to any one type of known or heretofor unknown assay, provided that the assay is able to detect the inhibition of complement.

Enzyme-linked immunosorbent assays (ELISAs) are useful in the methods of the invention. An enzyme such as, but not limited to, horseradish peroxidase (HRP), alkaline phosphatase, beta-galactosidase or urease can be linked, for example, to an anti-C5 antibody or to a secondary antibody for use in a method of the invention. A horseradish-peroxidase detection system may be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which may be used with the chromogenic substrate p-nitrophenyl phosphate to yield a soluble product readily detectable at 405 nm. Similarly, a beta-galactosidase detection system may be used with the chromogenic substrate o-nitrophenyl-beta-D-galactopyranoside (ONPG) to yield a soluble product detectable at 410 nm. Alternatively, a urease detection system may be used with a substrate such as urea-bromocresol purple (Sigma Immunochemicals, St. Louis, Mo.). Useful enzyme-linked primary and secondary antibodies can be obtained from any number of commercial sources.

Chemiluminescent detection is also useful for detecting the inhibition of the terminal complement pathway. Chemiluminescent secondary antibodies may be obtained from any number of commercial sources.

Fluorescent detection is also useful for detecting the inhibition of the terminal complement. Useful fluorochromes include, but are not limited to, DAPI, fluorescein, Hoechst 33258, R-phycocyanin, B-phycoerythrin, R-phycoerythrin, rhodamine, Texas red and lissamine-Fluorescein- or rhodamine-labeled antibodies.

Radioimmunoassays (RIAs) are also useful in the methods of the invention. Such assays are well known in the art, and are described for example in Brophy et al. (1990, Biochem. Biophys. Res. Comm. 167:898-903) and Guechot et al. (1996, Clin. Chem. 42:558-563). Radioimmunoassays are performed, for example, using Iodine-125-labeled primary or secondary antibody (Harlow et al., supra, 1999).

A signal emitted from a detectable antibody is analyzed, for example, using a spectrophotometer to detect color from a chromogenic substrate; a radiation counter to detect radiation, such as a gamma counter for detection of Iodine-125; or a fluorometer to detect fluorescence in the presence of light of a certain wavelength. Where an enzyme-linked assay is used, quantitative analysis is performed using a spectrophotometer. It is understood that the assays of the invention can be performed manually or, if desired, can be automated and that the signal emitted from multiple samples can be detected simultaneously in many systems available commercially.

The methods of the invention also encompass the use of capillary electrophoresis based immunoassays (CEIA), which can be automated, if desired. Immunoassays also may be used in conjunction with laser-induced fluorescence as described, for example, in Schmalzing et al. (1997, Electrophoresis 18:2184-2193) and Bao (1997, J. Chromatogr. B. Biomed. Sci. 699:463-480). Liposome immunoassays, such as flow-injection liposome immunoassays and liposome immunosensors, may also be used according to the methods of the invention (Rongen et al., 1997, J. Immunol. Methods 204:105-133).

Quantitative western blotting may also be used to determine the level of terminal complement inhibition in the methods of the invention. Western blots are quantified using well known methods such as scanning densitometry (Parra et al., 1998, J. Vasc. Surg. 28:669-675).

Methods of Administration

The methods of the invention comprise administering a therapeutically effective amount of at least one anti-C5 antibody, or binding fragment thereof (such as any of the antibodies or fragments thereof described elsewhere herein), to an individual identified as having a complement-mediated disease or disorder. In one embodiment the individual is a mammal having a complement system. In one embodiment the individual is a human. In various embodiments, the at least one anti-C5 antibody, or binding fragment thereof, is administered locally, regionally, or systemically.

In various embodiments, the disease or disorder is at least selected from the group consisting of: macular degeneration (MD), age-related macular degeneration (AMD), ischemia reperfusion injury, arthritis, rheumatoid arthritis, asthma, allergic asthma, lupus, ulcerative colitis, stroke, post-surgery systemic inflammatory syndrome, asthma, allergic asthma, chronic obstructive pulmonary disease (COPD), paroxysmal nocturnal hemoglobinuria (PNH) syndrome, myasthenia gravis, neuromyelitis optica, (NMO), multiple sclerosis, delayed graft function, antibody-mediated rejection, atypical hemolytic uremic (aHUS) syndrome, central retinal vein occlusion (CRVO), central retinal artery occlusion (CRAO), epidermolysis bullosa, sepsis, organ transplantation, inflammation (including, but not limited to, inflammation associated with cardiopulmonary bypass surgery and kidney dialysis), C3 glomerulopathy, membranous nephropathy, IgA nephropathy, glomerulonephritis (including, but not limited to, anti-neutrophil cytoplasmic antibody (ANCA)-mediated glomerulonephritis, lupus nephritis, and combinations thereof), ANCA-mediated vasculitis, Shiga toxin induced HUS, and antiphospholipid antibody-induced pregnancy loss, or any combinations thereof. In some embodiments, the complement-mediated disease is C3 glomerulopathy. In some embodiments, the complement-mediated disease is macular degeneration, such as age-related macular degeneration. In one embodiment, administration of the anti-C5 antibody inhibits the generation of a C5a or C5b protein. In some embodiments, the compositions and methods of the invention are useful for treating subject, including subjects having PNH, who are not responsive to treatment with eculizumab. By way of non-limiting example, some subjects may have a mutation in the alpha chain of C5 that may render them resistant to treatment of eculizumab (see Genetic variants in C5 and poor response to eculizumab (Nishimura J, et al., N Engl J Med. 2014 Feb. 13; 370(7): 632-9).

The methods of the invention can comprise the administration of at least one anti-C5 antibody, or binding fragment thereof, but the present invention should in no way be construed to be limited to the anti-C5 antibodies described herein, but rather should be construed to encompass any anti-C5 antibody, both known and unknown, that diminish and reduce complement activation.

The method of the invention comprises administering a therapeutically effective amount of at least one anti-C5 antibody, or binding fragment thereof, to an individual wherein a composition of the present invention comprising at least one anti-C5 antibody, or binding fragment thereof, either alone or in combination with at least one other therapeutic agent. The invention can be used in combination with other treatment modalities, such as, for example anti-inflammatory therapies, and the like. Examples of anti-inflammatory therapies that can be used in combination with the methods of the invention include, for example, therapies that employ steroidal drugs, as well as therapies that employ non-steroidal drugs.

The method of the invention comprises administering a therapeutically effective amount of an anti-C5 antibody, or an antigen-binding fragment thereof, to a subject. In some embodiments, the invention encompasses a method of treatment of C5 related diseases involving dysregulation of the complement signaling by administering a therapeutically effective amount of an antibody of the invention, or a therapeutically effective amount of an antibody fragment thereof, such that a reduction of C5a or C5b or MAC formation is effected in the subject. In some embodiments the invention encompasses a method of treatment of C5 related diseases involving dysregulation of complement signaling by administering a therapeutically effective amount of an antibody or an antibody fragment. In some embodiments the invention encompasses a method of treatment of C5 related diseases involving dysregulation of complement signaling by administering to a subject an effective amount of an antibody, an antibody fragment, a polypeptide, a peptide, a conjugated peptide, such that the complement activation pathway activation is reduced in the subject. In some embodiments, the method of treatment encompasses administering to a subject a systemically effective dose of an antibody or an antibody fragment, whereby systemic reduction of C5a or C5b or MAC formation is effected in the subject.

The pharmaceutical compositions useful for practicing the invention may be administered to deliver a dose of at least about 1 ng/kg, at least about 5 ng/kg, at least about 10 ng/kg, at least about 25 ng/kg, at least about 50 ng/kg, at least about 100 ng/kg, at least about 500 ng/kg, at least about 1 μg/kg, at least about 5 μg/kg, at least about 10 μg/kg, at least about 25 μg/kg, at least about 50 μg/kg, at least about 100 μg/kg, at least about 500 μg/kg, at least about 1 mg/kg, at least about 5 mg/kg, at least about 10 mg/kg, at least about 25 mg/kg, at least about 50 mg/kg, at least about 100 mg/kg, at least about 200 mg/kg, at least about 300 mg/kg, at least about 400 mg/kg, and at least about 500 mg/kg of body weight of the subject. In one embodiment, the invention administers a dose which results in a concentration of the anti-C5 antibody of the present invention of at least about 1 pM, at least about 10 pM, at least about 100 pM, at least about 1 nM, at least about 10 nM, at least about 100 nM, at least about 1 μM, at least about 2 μM, at least about 3 μM, at least about 4 μM, at least about 5 μM, at least about 6 μM, at least about 7 μM, at least about 8 μM, at least about 9 μM and at least about 10 μM in an individual. In another embodiment, the invention envisions administration of a dose which results in a concentration of the anti-C5 antibody of the present invention between at least about 1 pM, at least about 10 pM, at least about 100 pM, at least about 1 nM, at least about 10 nM, at least about 100 nM, at least about 1 μM, at least about 2 μM, at least about 3 μM, at least about 4 μM, at least about 5 μM, at least about 6 μM, at least about 7 μM, at least about 8 μM, at least about 9 μM and at least about 10 μM in the plasma of an individual.

In some embodiments, the pharmaceutical compositions useful for practicing the invention may be administered to deliver a dose of no more than about 1 ng/kg, no more than about 5 ng/kg, no more than about 10 ng/kg, no more than about 25 ng/kg, no more than about 50 ng/kg, no more than about 100 ng/kg, no more than about 500 ng/kg, no more than about 1 μg/kg, no more than about 5 μg/kg, no more than about 10 μg/kg, no more than about 25 μg/kg, no more than about 50 μg/kg, no more than about 100 μg/kg, no more than about 500 μg/kg, no more than about 1 mg/kg, no more than about 5 mg/kg, no more than about 10 mg/kg, no more than about 25 mg/kg, no more than about 50 mg/kg, no more than about 100 mg/kg, no more than about 200 mg/kg, no more than about 300 mg/kg, no more than about 400 mg/kg, and no more than about 500 mg/kg of body weight of the subject. In one embodiment, the invention administers a dose which results in a concentration of the anti-C5 antibody of the present invention of no more than about 1 μM, no more than about 10 μM, no more than about 100 μM, no more than about 1 nM, no more than about 10 nM, no more than about 100 nM, no more than about 1 μM, no more than about 2 μM, no more than about 3 μM, no more than about 4 μM, no more than about 5 μM, no more than about 6 μM, no more than about 7 μM, no more than about 8 μM, no more than about 9 μM and no more than about 10 μM in an individual. In another embodiment, the invention envisions administration of a dose which results in a concentration of the anti-C5 antibody of the present invention between no more than about 1 μM, no more than about 10 μM, no more than about 100 μM, no more than about 1 nM, no more than about 10 nM, no more than about 100 nM, no more than about 1 μM, no more than about 2 μM, no more than about 3 μM, no more than about 4 μM, no more than about 5 μM, no more than about 6 μM, no more than about 7 μM, no more than about 8 µM, no more than about 9 µM and no more than about 10 µM in the plasma of an individual. Also contemplated are dosage ranges between any of the doses disclosed herein.

Typically, dosages which may be administered in a method of the invention to a subject, in some embodiments a human, range in amount from 0.5 µg to about 50 mg per kilogram of body weight of the subject. While the precise dosage administered will vary depending upon any number of factors, including but not limited to, the type of subject and type of disease state being treated, the age of the subject and the route of administration. In some embodiments, the dosage of the compound will vary from about 1 µg to about 10 mg per kilogram of body weight of the subject. In other embodiments, the dosage will vary from about 3 µg to about 1 mg per kilogram of body weight of the subject.

The antibody may be administered to a subject as frequently as several times daily, or it may be administered less frequently, such as once a day, twice a day, thrice a day, once a week, twice a week, thrice a week, once every two weeks, twice every two weeks, thrice every two weeks, once a month, twice a month, thrice a month, or even less frequently, such as once every several months or even once or a few times a year or less. The frequency of the dose will be readily apparent to the skilled artisan and will depend upon any number of factors, such as, but not limited to, the type and severity of the disease being treated, the type and age of the subject, etc. The formulations of the pharmaceutical compositions may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to subjects of all sorts. Modification of pharmaceutical compositions suitable for administration to humans in order to render the compositions suitable for administration to various subjects is well understood, and the ordinarily skilled veterinary pharmacologist can design and perform such modification with merely ordinary, if any, experimentation. Individuals to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intraocular, intravitreal, intramuscular, intradermal and intravenous routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. A unit dose is discrete amount of the pharmaceutical composition comprising a predetermined amount of the active ingredient. The amount of the active ingredient is generally equal to the dosage of the active ingredient which would be administered to an individual or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the individual treated and further depending upon the route by which the composition is to be administered. By way of example, the composition may comprise between 0.1% and 100% (w/w) active ingredient. In various embodiments, the composition comprises at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

Parenteral administration of a pharmaceutical composition includes any route of administration characterized by physical breaching of a tissue of an individual and administration of the pharmaceutical composition through the breach in the tissue. Parental administration can be local, regional or systemic. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, intraocular, intravitreal, subcutaneous, intraperitoneal, intramuscular, intradermal, intrasternal injection, and intratumoral.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and in some embodiments from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In some embodiments, such powders comprise particles wherein at least 98% of the particles by weight have a diameter greater than 0.5 nanometers and at least 95% of the particles by number have a diameter less than 7 nanometers. In some embodiments, at least 95% of the particles by weight have a diameter greater than 1 nanometer and at least 90% of the particles by number have a diameter less than 6 nanometers. In some embodiments, dry powder compositions include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in some embodiments having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. In some embodiments, the droplets provided by this route of administration have an average diameter in the range from about 0.1 to about 200 nanometers.

The formulations are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more additional ingredients.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more additional ingredients. Alternately, formulations suitable for buccal administration may comprise a powder or an aerosolized or atomized solution or suspension comprising the active ingredient. In some embodiments, such powdered, aerosolized, or aerosolized formulations, when dispersed, have an average particle or droplet size in the range from about 0.1 to about 200 nanometers, and may further comprise one or more additional ingredients.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Cells Producing Antibodies and Antigen Binding Fragments Thereof

In some embodiments, the invention is a cell or cell line (such as host cells) that produces at least one of the anti-C5 antibodies, or antigen binding fragments, described herein. In one embodiment, the cell or cell line is a genetically modified cell that produces at least one of the anti-C5 antibodies, or antigen binding fragments, described herein. In one embodiment, the cell or cell line is a hybridoma that produces at least one of the anti-C5 antibodies, or antigen binding fragments, described herein.

Hybrid cells (hybridomas) are generally produced from mass fusions between murine splenocytes, which are highly enriched for B-lymphocytes, and myeloma "fusion partner cells" (Alberts et al., Molecular Biology of the Cell (Garland Publishing, Inc. 1994); Harlow et al., Antibodies. A Laboratory Manual (Cold Spring Harbor Laboratory, Cold Spring Harbor, 1988). The cells in the fusion are subsequently distributed into pools that can be analyzed for the production of antibodies with the desired specificity. Pools that test positive can be further subdivided until single cell clones are identified that produce antibodies of the desired specificity. Antibodies produced by such clones are referred to as monoclonal antibodies.

Also provided are nucleic acids encoding any of the antibodies, or antibody fragments, disclosed herein, as well as vectors comprising the nucleic acids. Thus, the antibodies and fragments of the invention can be generated by expressing the nucleic acid in a cell or a cell line, such as the cell lines typically used for expression of recombinant or humanized immunoglobulins. Thus, the antibodies and fragments of the invention can also be generated by cloning the nucleic acids into one or more expression vectors, and transforming the vector into a cell line such as the cell lines typically used for expression of recombinant or humanized immunoglobulins.

The genes encoding the heavy and light chains of immunoglobulins, or fragments thereof, can be engineered according to methods, including but not limited to, the polymerase chain reaction (PCR), known in the art (see, e.g., Sambrook et al., Molecular Cloning: A Laboratory Manual, 2nd ed., Cold Spring Harbor, N.Y., 1989; Berger & Kimmel, Methods in Enzymology, Vol. 152: Guide to Molecular Cloning Techniques, Academic Press, Inc., San Diego, Calif., 1987; Co et al., 1992, J. Immunol. 148:1149). For example, genes encoding heavy and light chains, or fragments thereof, can be cloned from an antibody secreting cell's genomic DNA, or cDNA is produced by reverse transcription of the cell's RNA. Cloning is accomplished by conventional techniques including the use of PCR primers that hybridize to the sequences flanking or overlapping the genes, or segments of genes, to be cloned.

Nucleic acids encoding the antibody of the invention, or the heavy chain or light chain or fragments thereof, can be obtained and used in accordance with recombinant nucleic acid techniques for the production of the specific immunoglobulin, immunoglobulin chain, or a fragment or variant thereof, in a variety of host cells or in an in vitro translation system. For example, the antibody-encoding nucleic acids, or fragments thereof, can be placed into suitable prokaryotic or eukaryotic vectors, e.g., expression vectors, and introduced into a suitable host cell by an appropriate method, e.g., transformation, transfection, electroporation, infection, such that the nucleic acid is operably linked to one or more expression control elements, e.g., in the vector or integrated into the host cell genome.

In some embodiments, the heavy and light chains, or fragments thereof, can be assembled in two different expression vectors that can be used to co-transfect a recipient cell. In some embodiments, each vector can contain two or more selectable genes, one for selection in a bacterial system and one for selection in a eukaryotic system. These vectors allow for the production and amplification of the genes in a bacterial system, and subsequent co-transfection of eukaryotic cells and selection of the co-transfected cells. The selection procedure can be used to select for the expression of antibody nucleic acids introduced on two different DNA vectors into a eukaryotic cell.

Alternatively, the nucleic acids encoding the heavy and light chains, or fragments thereof, may be expressed from one vector. Although the light and heavy chains are coded for by separate genes, they can be joined, using recombinant methods. For example, the two polypeptides can be joined by a synthetic linker that enables them to be made as a single protein chain in which the $V_L$ and $V_H$ regions pair to form monovalent molecules (known as single chain Fv (scFv); see e.g., Bird et al., 1988, Science 242: 423-426; and Huston et al., 1988, Proc. Natl. Acad. Sci. USA 85:5879-5883).

The invention provides for an isolated nucleic acid molecule comprising a nucleic acid sequence encoding a heavy chain and/or a light chain, as well as fragments thereof. A nucleic acid molecule comprising sequences encoding both the light and heavy chain, or fragments thereof, can be engineered to contain a synthetic signal sequence for secretion of the antibody, or fragment, when produced in a cell. Furthermore, the nucleic acid molecule can contain specific DNA links which allow for the insertion of other antibody sequences and maintain the translational reading frame so to not alter the amino acids normally found in antibody sequences.

In accordance with the present invention, antibody-encoding nucleic acid sequences can be inserted into an appropriate expression vector. In various embodiments, the expression vector comprises the necessary elements for transcription and translation of the inserted antibody-encoding nucleic acid so as to generate recombinant DNA molecules that direct the expression of antibody sequences for the formation of an antibody, or a fragment thereof.

The antibody-encoding nucleic acids, or fragments thereof, can be subjected to various recombinant nucleic acid techniques known to those skilled in the art such as site-directed mutagenesis.

A variety of methods can be used to express nucleic acids in a cell. Nucleic acids can be cloned into a number of types of vectors. However, the present invention should not be construed to be limited to any particular vector. Instead, the present invention should be construed to encompass a wide variety of vectors which are readily available and/or known in the art. For example, the nucleic acid of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Viral vector technology is well known in the art and is described, for example, in Sambrook et al. (2012), and in Ausubel et al. (1999), and in other virology and molecular biology manuals. Viruses, which are useful as vectors include, but are not limited to, retroviruses, adenoviruses, adeno-associated viruses, herpes viruses, and lentiviruses. In some embodiments, a murine stem cell virus (MSCV) vector is used to express a desired nucleic acid. MSCV vectors have been demonstrated to efficiently express desired nucleic acids in cells. However, the invention should not be limited to only using a MSCV vector, rather any retroviral expression method is included in the invention. Other examples of viral vectors are those based upon Moloney Murine Leukemia Virus (MoMuLV) and HIV. In some embodiments, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193).

Additional regulatory elements, e.g., enhancers, can be used modulate the frequency of transcriptional initiation. A promoter may be one naturally associated with a gene or nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," e.g., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (U.S. Pat. Nos. 4,683,202, 5,928, 906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high-level expression of the introduced DNA segment, such as is advantageous in the large-scale production of recombinant proteins and fragments thereof.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue-specific promoter or cell-type specific promoter, which is a promoter that is active only in a desired tissue or cell. Tissue-specific promoters are well known in the art and include, but are not limited to, the HER-2 promoter and the PSA associated promoter sequences.

In order to assess the expression of the nucleic acids, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate nucleic acid and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing nucleic acids into a cell are known in the art. In the context of an expression vector, the vector can be readily introduced into a host cell, e.g., mammalian, bacterial, yeast or insect cell by any method in the art. For example, the expression vector can be transferred into a host cell by physical, chemical or biological means.

Physical methods for introducing a polynucleotide into a host cell include calcium phosphate precipitation, lipofection, particle bombardment, microinjection, electroporation, laserporation and the like. Methods for producing cells comprising vectors and/or exogenous nucleic acids are well-known in the art. See, for example, Sambrook et al. (2012) and Ausubel et al. (1999).

Biological methods for introducing a nucleic acid of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a nucleic acid into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (e.g., an artificial membrane vesicle). The preparation and use of such systems is well known in the art.

Regardless of the method used to introduce exogenous nucleic acids into a host cell or otherwise expose a cell to the nucleic acid of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Human C5 Expressing Non-Human Animals

The invention also includes a genetically modified non-human animal that expresses human C5. In some embodiments, the genetically modified non-human animal that expresses human C5 also expresses non-human animal C5. In some embodiments, the genetically modified non-human animal that expresses human C5 does not express non-human animal C5. In one embodiment, the invention is a genetically modified non-human animal that expresses human C5 from the non-human animal's endogenous regulatory elements, but does not express non-human animal C5. In some embodiments, the non-human animal is a mammal. In some embodiments, the non-human animal is a rodent. In some embodiments, the non-human animal is a rat or a mouse. In some embodiments, the mouse is an immunodeficient mouse. In some embodiments, the mouse is NOD/SCID mouse. In some embodiments, the mouse is FcRn/SCID mouse.

To create a genetically modified non-human animal, a nucleic acid encoding the human C5 protein can be incorporated into a recombinant expression vector in a form suitable for expression of the human C5 protein in a host cell. The term "in a form suitable for expression of the fusion protein in a host cell" is intended to mean that the recombinant expression vector includes one or more regulatory sequences operatively linked to the nucleic acid encoding the human C5 protein in a manner which allows for integration into the nonhuman animal genome to result in stable and permanent transcription of the nucleic acid into mRNA and translation of the mRNA into the human C5 protein. The term "regulatory sequence" is art-recognized and intended to include promoters, enhancers and other expression control elements (e.g., polyadenylation signals, PiggyBac and Sleeping Beauty transposon elements). Such regulatory sequences are known to those skilled in the art and are described in 1990, Goeddel, Gene Expression Technology: Methods in Enzymology 185, Academic Press, San Diego, Calif. and in Nakanishi H, Higuchi Y, Kawakami S, Yamashita F, Hashida M. Mol Ther. 2010 April; 18(4):707-14. doi: 10.1038/mt.2009.302. Epub 2010 Jan. 26; Hudecek M, Ivics Z. Curr Opin Genet Dev. 2018 Jun. 22; 52:100-108. doi: 10.1016/j.gde.2018.06.003. [Epub ahead of print] Review. It should be understood that the design of the expression vector may depend on such factors as the choice of the host cell and animals to be transfected and/or the amount of human C5 protein to be expressed.

A genetically modified non-human animal can be created, for example, by introducing a nucleic acid encoding the human C5 protein (typically linked to appropriate regulatory elements, such as a constitutive or tissue-specific enhancer) into oocyte, e.g., by microinjection, and allowing the oocyte to develop in a female founder mouse. Such animals can also be generated by introducing a nucleic acid encoding the human C5 protein (typically linked to appropriate regulatory elements, such as a constitutive or tissue-specific enhancer and/or PiggyBac and Sleeping Beauty transposon elements) into the animals through hydrodynamic injection via tail vein as described in Suda T, Liu D. Mol Ther. 2007 December; 15(12):2063-9. Epub 2007 Oct. 2. Review. Intronic sequences and polyadenylation signals can also be included in the transgene to increase the efficiency of expression of the transgene. Methods for generating genetically modified animals, such as mice, have become conventional in the art and are described, for example, in U.S. Pat. Nos. 4,736,866 and 4,870,009 and 1986, Hogan et al., A Laboratory Manual, Cold Spring Harbor, N.Y., Cold Spring Harbor Laboratory. A genetically modified founder animal can be used to breed additional subjects carrying the transgene if the transgene is introduced into oocytes. Genetically modified animals carrying a transgene encoding the C5 protein generated via oocyte injection of the invention can further be bred to other genetically modified animals carrying other transgenes, or to other knockout animals, e.g., a knockout mouse that does not express the murine C5 gene. Genetically modified animals carrying a transgene encoding the C5 protein generated via hydrodynamic tail vein injection can be readily produced using other gene knockout or transgenic mice, e.g. FcRn/SCID mice for experimental use. It will be understood that in addition to genetically modified animals, the system can be used to generate other human C5 expressing subjects.

In one embodiment, a genetically modified non-human animal that expresses human C5 from the non-human animal's regulatory elements is generated using a system that replaces the non-human animal's C5 exon sequences (or exon and intron sequences) with human C5 exon sequences (or exon and intron sequences), but leaves one, more, or all of the native non-human animal's regulatory elements (e.g., promoter, enhancers, flanking regions, introns, etc.) sequences unchanged. Although any suitable system can be used, one exemplary system capable of producing a genetically modified non-human animal in this way is the CRISPr/Cas9 system. The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III subtypes. Wild-type type II CRISPR/Cas systems utilize the RNA-mediated nuclease, Cas9 in complex with guide and activating RNA to recognize and cleave foreign nucleic acid. Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 protein is the Streptococcus pyogenes Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39): 15644-9; Sampson et al., Nature. 2013 May 9; 497(7448):254-7; and Jinek, et al., Science. 2012 Aug. 17; 337(6096):816-21

In one embodiment, the genetically modified non-human animal of the invention expresses human C5 from endogenous promoter. Examples of promoters useful in the invention include, but are not limited to, the native mouse promoter, DNA pol II promoter, PGK promoter, ubiquitin promoter, albumin promoter, globin promoter, ovalbumin promoter, SV40 early promoter, the Rous sarcoma virus (RSV) promoter, β-actin promoter, retroviral LTR, and lentiviral LTR. Promoter and enhancer expression systems useful in the invention also include inducible and/or tissue-specific expression systems.

In some embodiments, the genetically modified non-human animal of the invention that expresses human C5 is used for screening, testing, assessing, or evaluating anti-C5 antibodies. In some embodiments, the genetically modified non-human animal of the invention that expresses human C5 is used for screening, testing, assessing, or evaluating the characteristics, properties or activities of anti-C5 antibodies.

Kits

The invention also includes a kit comprising an anti-C5 antibody, or combinations thereof, of the invention and an instructional material which describes, for instance, administering the anti-C5 antibody, or combinations thereof, to an individual as a therapeutic treatment or a non-treatment use as described elsewhere herein. In an embodiment, this kit further comprises a (optionally sterile) pharmaceutically acceptable carrier suitable for dissolving or suspending the therapeutic composition, comprising an anti-C5 antibody, or combinations thereof, of the invention, for instance, prior to administering the antibody to an individual. Optionally, the kit comprises an applicator for administering the antibody.

Sequences humanized 2G1 VH-11801

```
cagcatatgatcagtgtcctctccaaagtccttgaacatagactctaaccatggactggaacc
                                                    M   D   W   T
tgggtctttctcttcctcctgtcagtaactgcaggtgtccactcccaggttcagctggtg
 W   V   F   L   F   L   L   S   V   T   A   G   V   H   S   Q   V   Q   L   V
cagtctggagctgaggtgaagaagcctggggcctcagtgaaggtctcctgcaaggcttct
 Q   S   G   A   E   V   K   K   P   G   A   S   V   K   V   S   C   K   A   S
ggatacacaatcacagactacaatttggactgggtgcgacaggcccctggacaagggctt
 G   Y   T   I   T   D   Y   N   L   D   W   V   R   Q   A   P   G   Q   G   L    CDR1 (SEQ ID NO: 3)
gagtggatgggagatattagtcctaactatggttatactatctacaaccagaaattcaag
 E   W   M   G   D   I   S   P   N   Y   G   Y   T   I   Y   N   Q   K   F   K    CDR2 (SEQ ID NO: 4)
gacagagtcaccatgaccacagacacatccacgagcacagcctacatggagctgaggagc
 D   R   V   T   M   T   T   D   T   S   T   S   T   A   Y   M   E   L   R   S
ctgagatctgacgacacggccgtgtattactgtgcgagaagggacattcgttactccggt
 L   R   S   D   D   T   A   V   Y   Y   C   A   R   R   D   I   R   Y   S   G    CDR3 (SEQ ID NO: 5)
Aattcctacaaatggtacttcgatgtctggggccaagggacaatggtcaccgtctcttca   (SEQ ID NO: 1)
 N   S   Y   K   W   Y   F   D   V   W   G   Q   G   T   M   V   T   V   S   S   (SEQ ID NO: 2)
```

Humanized 2G1 VL-1901

```
gtcagagccctggggaggaactgctcagttaggacccagagggaaccatggaagcccagct
                                                M   E   A   P   A
cagcttctcttcctcctgctactctggctcccagataccaccggagacatccagttgacc
 Q   L   F   L   L   L   W   L   P   D   T   T   G   D   I   Q   L   T
cagtctccatccttcctgtctgcatctgtaggagacagagtcaccatcacttgcaggaca
 Q   S   P   S   F   L   S   A   S   V   G   D   R   V   T   I   T   C   R   T    CDR1 (SEQ ID NO: 8)
agtaagagcataagcaaatatttagcctggtatcagcaaaaaccagggaaagcccctaag
 S   K   S   I   S   K   Y   L   A   W   Y   Q   Q   K   P   G   K   A   P   K
ctcctgatctattctggatccaccttgcaatctggggtcccatcaaggttcagcggcagt
 L   L   I   Y   S   G   S   T   L   Q   S   G   V   P   S   R   F   S   G   S    CDR2 (SEQ ID NO: 9)
ggatctgggacagaattcactctcacaatcagcagcctgcagcctgaagattttgcaact
 G   S   G   T   E   F   T   L   T   I   S   S   L   Q   P   E   D   F   A   T
tattactgtcaacaacataatgaatacccgtacacgtttggccaggggaccaagctggag
 Y   Y   C   Q   Q   H   N   E   Y   P   Y   T   F   G   Q   G   T   K   L   E    CDR3 (SEQ ID NO: 10)
Atcaaa    (SEQ ID NO: 6)
 I   K      (SEQ ID NO: 7)
```

-continued

Humanized 2G1 VL-1901 variant (Q->H mutation in CDR3)

```
gtcagagccctggggaggaactgctcagttaggacccagagggaaccatggaagcccagct
                                               M  E  A  P  A
cagcttctcttcctcctgctactctggctcccagataccaccggagacatccagttgacc
 Q  L  L  F  L  L  L  L  W  L  P  D  T  T  G  D  I  Q  L  T
cagtctccatcctcctgtctgcatctgtaggagacagagtcaccatcacttgcaggaca
 Q  S  P  S  F  L  S  A  S  V  G  D  R  V  T  I  T  C  R  T  CDR1(SEQ ID NO: 8)
agtaagagcataagcaaatatttagcctggtatcagcaaaaaccagggaaagcccctaag
 S  K  S  I  S  K  Y  L  A  W  Y  Q  Q  K  P  G  K  A  P  K
ctcctgatctattctggatccaccttgcaatctggggtcccatcaaggttcagcggcagt
 L  L  I  Y  S  G  S  T  L  Q  S  G  V  P  S  R  F  S  G  S  CDR2(SEQ ID NO: 9)
ggatctgggacagaattcactctcacaatcagcagcctgcagcctgaagattttgcaact
 G  S  G  T  E  F  T  L  T  I  S  S  L  Q  P  E  D  F  A  T
tattactgtcatcaacataatgaatacccgtacacgtttggccaggggaccaagctggag
 Y  Y  C  H  Q  H  N  E  Y  P  Y  T  F  G  Q  G  T  K  L  E  CDR3(SEQ ID NO: 11)
Atcaaa  (SEQ ID NO: 12)
 I  K   (SEQ ID NO: 13)
```

Humanized 2G1 VL-1901 variant (T->H mutation in CDR1)

```
gtcagagccctggggaggaactgctcagttaggacccagagggaaccatggaagcccagct
                                                M  E  A  P  A
cagcttctcttcctcctgctactctggctcccagataccaccggagacatccagttgacc
 Q  L  L  F  L  L  L  L  W  L  P  D  T  T  G  D  I  Q  L  T
cagtctccatcctcctgtctgcatctgtaggagacagagtcaccatcacttgcaggcat
 Q  S  P  S  F  L  S  A  S  V  G  D  R  V  T  I  T  C  R  H  CDR1(SEQ ID NO: 14)
agtaagagcataagcaaatatttagcctggtatcagcaaaaaccagggaaagcccctaag
 S  K  S  I  S  K  Y  L  A  W  Y  Q  Q  K  P  G  K  A  P  K
ctcctgatctattctggatccaccttgcaatctggggtcccatcaaggttcagcggcagt
 L  L  I  Y  S  G  S  T  L  Q  S  G  V  P  S  R  F  S  G  S  CDR2(SEQ ID NO: 9)
ggatctgggacagaattcactctcacaatcagcagcctgcagcctgaagattttgcaact
 G  S  G  T  E  F  T  L  T  I  S  S  L  Q  P  E  D  F  A  T
tattactgtcaacaacataatgaatacccgtacacgtttggccaggggaccaagctggag
 Y  Y  C  Q  Q  H  N  E  Y  P  Y  T  F  G  Q  G  T  K  L  E  CDR3(SEQ ID NO: 10)
Atcaaa  (SEQ ID NO: 15)
 I  K   (SEQ ID NO: 16)
``` humanized 2G1 VH-11801 variant (I->H mutation in CDR1)

```
cagcatatgatcagtgtcctctccaaagtccttgaacatagactctaaccatggactggacc
                                                 M  D  W  T
tgggtcttttctcttcctcctgtcagtaactgcaggtgtccactcccaggttcagctggtg
 W  V  F  L  F  L  L  S  V  T  A  G  V  H  S  Q  V  Q  L  V
cagtctggagctgaggtgaagaagcctggggcctcagtgaaggtctcctgcaaggcttct
 Q  S  G  A  E  V  K  K  P  G  A  S  V  K  V  S  C  K  A  S
ggatacacacatacagactacaatttggactgggtgcgacaggcccctggacaagggctt
 G  Y  T  H  T  D  Y  N  L  D  W  V  R  Q  A  P  G  Q  G  L  CDR1(SEQ ID NO: 17)
gagtggatgggagatattagtcctaactatggttatactatctacaaccagaaattcaag
 E  W  M  G  D  I  S  P  N  Y  G  Y  T  I  Y  N  Q  K  F  K  CDR2(SEQ ID NO: 4)
gacagagtcaccatgaccacagacacatccacgagcacagcctacatggagctgaggagc
 D  R  V  T  M  T  T  D  T  S  T  S  T  A  Y  M  E  L  R  S
ctgagatctgacgacacggccgtgtattactgtgcgagaagggacattcgttactccggt
 L  R  S  D  D  T  A  V  Y  Y  C  A  R  R  D  I  R  Y  S  G  CDR3(SEQ ID NO: 5)
Aattcctacaaatggtacttcgatgtctgggggccaagggacaatggtcaccgtctcttca  (SEQ ID NO: 18)
 N  S  Y  K  W  Y  F  D  V  W  G  Q  G  T  M  V  T  V  S  S  (SEQ ID NO: 19)
``` humanized 2G1 VH-11801 variant (N->H mutation in CDR1)

```
cagcatatgatcagtgtcctctccaaagtccttgaacatagactctaaccatggactggacc
                                                 M  D  W  T
tgggtcttttctcttcctcctgtcagtaactgcaggtgtccactcccaggttcagctggtg
 W  V  F  L  F  L  L  S  V  T  A  G  V  H  S  Q  V  Q  L  V
cagtctggagctgaggtgaagaagcctggggcctcagtgaaggtctcctgcaaggcttct
 Q  S  G  A  E  V  K  K  P  G  A  S  V  K  V  S  C  K  A  S
ggatacacaatcacagactaccatttggactgggtgcgacaggcccctggacaagggctt
 G  Y  T  I  T  D  Y  H  L  D  W  V  R  Q  A  P  G  Q  G  L  CDR1(SEQ ID NO: 20)
gagtggatgggagatattagtcctaactatggttatactatctacaaccagaaattcaag
 E  W  M  G  D  I  S  P  N  Y  G  Y  T  I  Y  N  Q  K  F  K  CDR2(SEQ ID NO: 4)
gacagagtcaccatgaccacagacacatccacgagcacagcctacatggagctgaggagc
 D  R  V  T  M  T  T  D  T  S  T  S  T  A  Y  M  E  L  R  S
ctgagatctgacgacacggccgtgtattactgtgcgagaagggacattcgttactccggt
 L  R  S  D  D  T  A  V  Y  Y  C  A  R  R  D  I  R  Y  S  G  CDR3(SEQ ID NO: 5)
Aattcctacaaatggtacttcgatgtctgggggccaagggacaatggtcaccgtctcttca  (SEQ ID NO: 21)
 N  S  Y  K  W  Y  F  D  V  W  G  Q  G  T  M  V  T  V  S  S  (SEQ ID NO: 22)
```

Humanized 2G1 VL-1901 variant (Y->H mutation in CDR1)

```
gtcagagccctggggaggaactgctcagttaggacccagagggaaccatggaagccccagct
                                              M  E  A  P  A
cagcttctcttcctcctgctactctggctcccagataccaccggagacatccagttgacc
 Q  L  L  F  L  L  L  W  L  P  D  T  T  G  D  I  Q  L  T
cagtctccatccttcctgtctgcatctgtaggagacagagtcaccatcacttgcaggaca
 Q  S  P  S  F  L  S  A  S  V  G  D  R  V  T  I  T  C  [R  T] CDR1(SEQ ID NO: 23)
agtaagagcataagcaaacatttagcctggtatcagcaaaaaccagggaaagcccctaag
[S  K  S  I  S  K  H  L  A] W  Y  Q  Q  K  P  G  K  A  P  K
ctcctgatctattctggatccaccttgcaatctggggtcccatcaaggttcagcggcagt
 L  L  I  Y [S  G  S  T  L  Q  S] G  V  P  S  R  F  S  G  S  CDR2(SEQ ID NO: 9)
ggatctgggacagaattcactctcacaatcagcagcctgcagcctgaagattttgcaact
 G  S  G  T  E  F  T  L  T  I  S  S  L  Q  P  E  D  F  A  T
tattactgtcaacaacataatgaatacccgtacacgtttggccaggggaccaagctggag
 Y  Y  C [Q  Q  H  N  E  Y  P  Y  T] F  G  Q  G  T  K  L  E  CDR3(SEQ ID NO: 10)
Atcaaa   (SEQ ID NO: 24)
 I  K    (SEQ ID NO: 25)
``` humanized 2G1 VH-11801 variant (Y->H mutation in CDR2)

```
cagcatatgatcagtgtcctctccaaagtccttgaacatagactctaaccatggactggacc
                                                M  D  W  T
tgggtctttctcttcctcctgtcagtaactgcaggtgtccactcccaggttcagctggtg
 W  V  F  L  F  L  L  S  V  T  A  G  V  H  S  Q  V  Q  L  V
cagtctggagctgaggtgaagaagcctggggcctcagtgaaggtctcctgcaaggcttct
 Q  S  G  A  E  V  K  K  P  G  A  S  V  K  V  S  C  K  A  S
ggatacacaatcacagactacaatttggactgggtgcgacaggcccctggacaagggctt
[G  Y  T  I  T  D  Y  N  L  D] W  V  R  Q  A  P  G  Q  G  L  CDR1(SEQ ID NO: 3)
gagtggatgggagatattagtcctaaccatggttatactatctacaaccagaaattcaag
 E  W  M  G [D  I  S  P  N  H  G  Y  T  I  Y  N  Q  K  F  K] CDR2(SEQ ID NO: 26)
gacagagtcaccatgaccacagacacatccacgagcacagcctacatggagctgaggagc
[D] R  V  T  M  T  T  D  T  S  T  S  T  A  Y  M  E  L  R  S
ctgagatctgacgacacggccgtgtattactgtgcgagaagggacattcgttactccggt
 L  R  S  D  D  T  A  V  Y  Y  C  A  R [R  D  I  R  Y  S  G  CDR3(SEQ ID NO: 5)
Aattcctacaaatggtacttcgatgtctgggggccaagggacaatggtcaccgtctcttca   (SEQ ID NO: 27)
[N  S  Y  K  W  Y  F  D  V] W  G  Q  G  T  M  V  T  V  S  S   (SEQ ID NO: 28)
```

Humanized 2G1 VL-1901 variant (E->H mutation in CDR3)

```
gtcagagccctggggaggaactgctcagttaggacccagagggaaccatggaagccccagct
                                              M  E  A  P  A
cagcttctcttcctcctgctactctggctcccagataccaccggagacatccagttgacc
 Q  L  L  F  L  L  L  W  L  P  D  T  T  G  D  I  Q  L  T
cagtctccatccttcctgtctgcatctgtaggagacagagtcaccatcacttgcaggaca
 Q  S  P  S  F  L  S  A  S  V  G  D  R  V  T  I  T  C  [R  T] CDR1(SEQ ID NO: 8)
agtaagagcataagcaaatatttagcctggtatcagcaaaaaccagggaaagcccctaag
[S  K  S  I  S  K  Y  L  A] W  Y  Q  Q  K  P  G  K  A  P  K
ctcctgatctattctggatccaccttgcaatctggggtcccatcaaggttcagcggcagt
 L  L  I  Y [S  G  S  T  L  Q  S] G  V  P  S  R  F  S  G  S  CDR2(SEQ ID NO: 9)
ggatctgggacagaattcactctcacaatcagcagcctgcagcctgaagattttgcaact
 G  S  G  T  E  F  T  L  T  I  S  S  L  Q  P  E  D  F  A  T
tattactgtcaacaacataatgaatacccgtacacgtttggccaggggaccaagctggag
 Y  Y  C [Q  Q  H  N  H  Y  P  Y  T] F  G  Q  G  T  K  L  E  CDR3(SEQ ID NO: 29)
Atcaaa   (SEQ ID NO: 30)
 I  K    (SEQ ID NO: 31)
``` humanized 2G1 VH-11801 variant (T->H mutation in CDR2)

```
cagcatatgatcagtgtcctctccaaagtccttgaacatagactctaaccat

Heavy chain sequence of mAb H1-8/L1-9 variant IWW (L->I mutation in CDR1, P->W mutation in CDR2, V->W mutation in CDR3)

IWW-VH

```
cagcatatgatcagtgtcctctccaaagtccttgaacatagactctaaccatggactggacc
                                                  M  D  W  T
tgggtctttctcttcctcctgtcagtaactgcaggtg

Heavy chain sequence of mAb H1-8/L1-9 variant FMW (L->F mutation in CDR1, P->M mutation in CDR2, V->W mutation in CDR3)

FMW-VH

```
cagcatatgatcagtgtcctctccaaagtccttgaacatagactctaaccatggactggacc
                                                    M  D  W  T
tgggtctttctcttcctcctgtcagtaactgcaggtgtccactcccaggttcagctggtg
 W  V  F  L  F  L  L  S  V  T  A  G  V  H  S  Q  V  Q  L  V
cagtctggagctgaggtgaagaagcctggggcctcagtgaaggtctcctgcaaggcttct
 Q  S  G  A  E  V  K  K  P  G  A  S  V  K  V  S  C  K  A  S
ggatacacaatcacagactaccatttcgactgggtgcgacaggcccctggacaagggctt      CDR1 (SEQ ID NO: 52)
 G  Y  T  I  T  D  Y  H  F  D  W  V  R  Q  A  P  G  Q  G  L
gagtggatgggagatattagtatgaactatggttatactatctacaaccagaaattcaag      CDR2 (SEQ ID NO: 53)
 E  W  M  G  D  I  S  M  N  Y  G  Y  T  I  Y  N  Q  K  F  K
gacagagtcaccatgaccacagacacatccacgagcacatacatggagctgaggagc
 D  R  V  T  M  T  T  D  T  S  T  S  T  A  Y  M  E  L  R  S
ctgagatctgacgacacggccgtgtattactgtgcgagaagggacattcgttactccggt      CDR3 (SEQ ID NO: 54)
 L  R  S  D  D  T  A  V  Y  Y  C  A  R  R  D  I  R  Y  S  G
aattcctacaaatggtacttcgattggtggggccaagggacaatggtcaccgtctcttca    (SEQ ID NO: 55)
 N  S  Y  K  W  Y  F  D  W  W  G  Q  G  T  M  V  T  V  S  S    (SEQ ID NO: 56)
```

Heavy chain sequence of mAb H1-8/L1-9 variant FMEH (L->F mutation in CDR1, P->W mutation and T->H mutations in CDR2, V->E mutation in CDR3)

FMEH-VH

```
cagcatatgatcagtgtcctctccaaagtccttgaacatagactctaaccatggactggacc
                                                    M  D  W  T
tgggtctttctcttcctcctgtcagtaactgcaggtgtccactcccaggttcagctggtg
 W  V  F  L  F  L  L  S  V  T  A  G  V  H  S  Q  V  Q  L  V
cagtctggagctgaggtgaagaagcctggggcctcagtgaaggtctcctgcaaggcttct
 Q  S  G  A  E  V  K  K  P  G  A  S  V  K  V  S  C  K  A  S
ggatacacaatcacagactaccatttcgactgggtgcgacaggcccctggacaagggctt      CDR1 (SEQ ID NO: 47)
 G  Y  T  I  T  D  Y  H  F  D  W  V  R  Q  A  P  G  Q  G  L
gagtggatgggagatattagtatgaactatggttatcatatctacaaccagaaattcaag     CDR2 (SEQ ID NO: 57)
 E  W  M  G  D  I  S  M  N  Y  G  Y  H  I  Y  N  Q  K  F  K
gacagagtcaccatgaccacagacacatccacgagcacatacatggagctgaggagc
 D  R  V  T  M  T  T  D  T  S  T  S  T  A  Y  M  E  L  R  S
ctgagatctgacgacacggccgtgtattactgtgcgagaagggacattcgttactccggt      CDR3 (SEQ ID NO: 49)
 L  R  S  D  D  T  A  V  Y  Y  C  A  R  R  D  I  R  Y  S  G
aattcctacaaatggtacttcgatgagtggggccaagggacaatggtcaccgtctcttca    (SEQ ID NO: 58)
 N  S  Y  K  W  Y  F  D  E  W  G  Q  G  T  M  V  T  V  S  S    (SEQ ID NO: 59)
```

Heavy chain sequence of mAb H1-8/L1-9 variant IWWH (L->I mutation in CDR1, P->W and T->H mutations in CDR2, V->W mutation in CDR3)

IWWH-VH

```
cagcatatgatcagtgtcctctccaaagtccttgaacatagactctaaccatggactggacc
                                                    M  D  W  T
tgggtctttctcttcctcctgtcagtaactgcaggtgtccactcccaggttcagctggtg
 W  V  F  L  F  L  L  S  V  T  A  G  V  H  S  Q  V  Q  L  V
cagtctggagctgaggtgaagaagcctggggcctcagtgaaggtctcctgcaaggcttct
 Q  S  G  A  E  V  K  K  P  G  A  S  V  K  V  S  C  K  A  S
ggatacacaatcacagactaccatatcgactgggtgcgacaggcccctggacaagggctt      CDR1 (SEQ ID NO: 37)
 G  Y  T  I  T  D  Y  H  I  D  W  V  R  Q  A  P  G  Q  G  L
gagtggatgggagatattagttggaactatggttatcatatctacaaccagaaattcaag     CDR2 (SEQ ID NO: 62)
 E  W  M  G  D  I  S  W  N  Y  G  Y  H  I  Y  N  Q  K  F  K
gacagagtcaccatgaccacagacacatccacgagcacagcctacatggagctgaggagc
 D  R  V  T  M  T  T  D  T  S  T  S  T  A  Y  M  E  L  R  S
ctgagatctgacgacacggccgtgtattactgtgcgagaagggacattcgttactccggt      CDR3 (SEQ ID NO: 39)
 L  R  S  D  D  T  A  V  Y  Y  C  A  R  R  D  I  R  Y  S  G
aattcctacaaatggtacttcgattggtggggccaagggacaatggtcaccgtctcttca    (SEQ ID NO: 63)
 N  S  Y  K  W  Y  F  D  W  W  G  Q  G  T  M  V  T  V  S  S    (SEQ ID NO: 64)
```

Heavy chain sequence of mAb H1-8/L1-9 variant IFWH (L->I mutation in CDR1, P->F and T->H mutations in CDR2, V->W mutation in CDR3)

IFWH-VH

```
cagcatatgatcagtgtcctctccaaagtccttgaacatagactctaaccatggactggacc
                                                  M  D  W  T
tgggtctttctcttcctcctgtcagtaactgcaggtgtccactcccaggttcagctggtg
 W  V  F  L  F  L  L  S  V  T  A  G  V  H  S  Q  V  Q  L  V
cagtctggagctgaggtgaagaagcctggggcctcagtgaaggtctcctgcaaggcttct
 Q  S  G  A  E  V  K  K  P  G  A  S  V  K  V  S  C  K  A  S
ggatacacaatcacagactaccatatcgactgggtgcgacaggcccctggacaagggctt
 G  Y  T  I  T  D  Y  H  I  D  W  V  R  Q  A  P  G  Q  G  L    CDR1 (SEQ ID NO: 42)
gagtggatgggagatattagtttcaactatggttatcatatctacaaccagaaattcaag
 E  W  M  G  D  I  S  F  N  Y  G  Y  H  I  Y  N  Q  K  F  K    CDR2 (SEQ ID NO: 65)
gacagagtcaccatgaccacagacacatccacgagcacagcctacatggagctgaggagc
 D  R  V  T  M  T  T  D  T  S  T  S  T  A  Y  M  E  L  R  S
ctgagatctgacgacacggccgtgtattactgtgcgagaagggacattcgttactccggt
 L  R  S  D  D  T  A  V  Y  Y  C  A  R  R  D  I  R  Y  S  G    CDR3 (SEQ ID NO: 44)
aattcctacaaatggtacttcgattggtggggccaagggacaatggtcaccgtctcttca      (SEQ ID NO: 66)
 N  S  Y  K  W  Y  F  D  W  W  G  Q  G  T  M  V  T  V  S  S      (SEQ ID NO: 67)
```

Heavy chain sequence of mAb H1-8/L1-9 variant FMWH (L->F mutation in CDR1, P->M and T->H mutations in CDR2, V->W mutation in CDR3)

FMWH-VH

```
cagcatatgatcagtgtcctctccaaagtccttgaacatagactctaaccatggactggacc
                                                   M  D  W  T
tgggtctttctcttcctcctgtcagtaactgcaggtgtccactcccaggttcagctggtg
 W  V  F  L  F  L  L  S  V  T  A  G  V  H  S  Q  V  Q  L  V
cagtctggagctgaggtgaagaagcctggggcctcagtgaaggtctcctgcaaggcttct
 Q  S  G  A  E  V  K  K  P  G  A  S  V  K  V  S  C  K  A  S
ggatacacaatcacagactaccatttcgactgggtgcgacaggcccctggacaagggctt
 G  Y  T  I  T  D  Y  H  F  D  W  V  R  Q  A  P  G  Q  G  L    CDR1 (SEQ ID NO: 52)
gagtggatgggagatattagtatgaactatggttatcatatctacaaccagaaattcaag
 E  W  M  G  D  I  S  M  N  Y  G  Y  H  I  Y  N  Q  K  F  K    CDR2 (SEQ ID NO: 68)
gacagagtcaccatgaccacagacacatccacgagcacagcctacatggagctgaggagc
 D  R  V  T  M  T  T  D  T  S  T  S  T  A  Y  M  E  L  R  S
ctgagatctgacgacacggccgtgtattactgtgcgagaagggacattcgttactccggt
 L  R  S  D  D  T  A  V  Y  Y  C  A  R  R  D  I  R  Y  S  G    CDR3 (SEQ ID NO: 54)
aattcctacaaatggtacttcgattggtggggccaagggacaatggtcaccgtctcttca      (SEQ ID NO: 69)
 N  S  Y  K  W  Y  F  D  W  W  G  Q  G  T  M  V  T  V  S  S      (SEQ ID NO: 70)
```

Amino acid sequence of human IgG4 Constant Heavy chain region

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125
```

```
Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro Gly Lys (SEQ ID NO: 32)
                325
```

Amino acid sequence of human IgG4 Constant Heavy chain region with S108P mutation (relative to SEQ ID NO: 32)

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125
```

```
Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Pro Gly Lys        (SEQ ID NO: 33)
                325
```

Sequences of human IgG4 Fc PLA domain mutation

```
gctagcaccaagggcccatcggtcttccccctggcgccctgctccaggagcacctccgag
 A   S   T   K   G   P   S   V   F   P   L   A   P   C   S   R   S   T   S   E
agcacagccgccctgggctgcctggtcaaggactacttccccgaaccggtgacggtgtcg
 S   T   A   A   L   G   C   L   V   K   D   Y   F   P   E   P   V   T   S   V
tggaactcaggcgccctgaccagcggcgtgcacaccttcccggctgtcctacagtcctca
 W   N   S   G   A   L   T   S   G   V   H   T   F   P   A   V   L   Q   S   S
ggactctactcccctcagcagcgtggtgaccgtgccctccagcagcttgggcacgaagacc
 G   L   Y   S   L   S   S   V   V   T   V   P   S   S   S   L   G   T   K   T
tacacctgcaacgtagatcacaagcccagcaacaccaaggtggacaagagagttgagtcc
 Y   T   C   N   V   D   H   K   P   S   N   T   K   V   D   K   R   V   E   S
aaatatggtcccccatgccca[cca]tgcccagcacctgagttcctggggggaccatcagtc
 K   Y   G   P   P   C   P  [P]  C   P   A   P   E   F   L   G   G   P   S   V
ttcctgttccccccaaaacccaaggacactctcatgatctcccggacccctgaggtcacg
 F   L   F   P   P   K   P   K   D   T   L   M   I   S   R   T   P   E   V   T
tgcgtggtggtggacgtgagccaggaagaccccgaggtccagttcaactggtacgtggat
 C   V   V   V   D   V   S   Q   E   D   P   E   V   Q   F   N   W   Y   V   D
ggcgtggaggtgcataatgccaagacaaagccgcgggaggagcagttcaacagcacgtac
 G   V   E   V   H   N   A   K   T   K   P   R   E   E   Q   F   N   S   T   Y
cgtgtggtcagcgtcctcaccgtcctgcaccaggactggctgaacggcaaggagtacaag
 R   V   V   S   V   L   T   V   L   H   Q   D   W   L   N   G   K   E   Y   K
tgcaaggtctccaacaaaggcctcccgtcctccatcgagaaaaccatctccaaagccaaa
 C   K   V   S   N   K   G   L   P   S   S   I   E   K   T   I   S   K   A   K
gggcagccccgagagccacaggtgtacaccctgccccccatcccaggaggagatgaccaag
 G   Q   P   R   E   P   Q   V   Y   T   L   P   P   S   Q   E   E   M   T   K
aaccaggtcagcctgacctgcctggtcaaaggcttctaccccagcgacatcgccgtggag
 N   Q   V   S   L   T   C   L   V   K   G   F   Y   P   S   D   I   A   V   E
tgggagagcaatgggcagccggagaacaactacaagaccacgcctcccgtgctggactcc
 W   E   S   N   G   Q   P   E   N   N   Y   K   T   T   P   P   V   L   D   S
gacggctccttcttcctctacagcaggctcaccgtggacaagagcaggtggcaggagggg
 D   G   S   P   F   L   Y   S   R   L   T   V   D   K   S   R   W   Q   E   G
aatgtcttctcatgctccgtg[ctg]catgaggctctgcag[gcc]cactacacacagaagagc
 N   V   F   S   C   S   V  [L]  H   E   A   L   H  [A]  H   Y   T   Q   K   S
Ctctccctgtctctgggtaaatga        (SEQ ID NO: 60)
 L   S   L   S   L   G   K   -   (SEQ ID NO: 61)
```

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore and are not to be construed as limiting in any way the remainder of the disclosure.

Example 1

Variants of humanized 2G1 (VH-11801 (SEQ ID NO:2) and VL-1901 (SEQ ID NO:7)) were generated (see FIG. 1), with the aim of developing variants with improved binding to C5 at pH 7.4 and reduced binding to C5 at pH 5.8.

The approach described herein is based on the understanding that a mAb's affinity and blocking efficacy measured in vitro does not necessarily correlate with its in vivo half-life, PK or PD. This is, at least in part, because for a soluble antigen that is present in high concentration in the blood, such as C5, forms an immune complex (i.e., mAb bound to antigen) that is targeted for removal from the body. Therefore, generally, high antibody concentrations in the blood are required to block activity of such soluble antigens in vivo.

The approach described herein is based on the understanding that in vivo efficacy of a therapeutic antibody can be enhanced by increasing antibody recycling or half-life (and therefore PK) and by accelerated antigen intracellular degradation by generating mAbs that possess "pH-dependent" binding properties. The desirable property in this regard is that the therapeutic mAb would bind well to the antigen (e.g., C5) at close to neutral pH (~pH 7.4) which is the pH of the blood. In this way, it effectively blocks the antigen (e.g., C5) activity. The immune complex is then taken up by cells where it moves to the endosome for proteolytic degradation. The pH of early endosome is acidic (~pH 6.0). So when a therapeutic mAb has poor binding to its antigen at acidic pH, the mAb will dissociate from the immune complex and can then be taken up by the neonatal Fc receptor (FcRn) and returned to the plasma. In this way, only the antigen (e.g., C5) is degraded through the endosome proteolytic pathway, whereas the recycling of the mAb through FcRn contributes to its extended persistence in the plasma.

Due to its propensity of protonation at acidic pH (H+), mAbs containing histidine residues in their CDRs may have weakened binding affinity upon protonation at acidic pH. The approach described herein made use of "histidine scanning" of all CDR residues (i.e., substitution of each CDR residue with histidine). Then Octet instrument (Pall ForteBio) was used to measure mAb and C5 dissociation at pH 7.4 and pH 5.8 to identify the histidine-substitution variants that had relatively faster dissociation at pH 5.8 and relatively slower dissociation at pH 7.4.

The parental humanized 2G1 mAb (VH-11801 (SEQ ID NO:2) and VL-1901 (SEQ ID NO:7)), appeared to have better affinity for C5 at pH 5.8 (see FIG. 7). Single-substitution variants having a histidine substitution at each residue in each of the six CDRs of mAb (VH-11801 (SEQ ID NO:2) and VL-1609 (SEQ ID NO:7)) were generated and evaluated for their pH-dependent binding property. For each variant, a VH and VL plasmid was constructed and then transiently transfected into HEK cells. mAb in the cell culture supernatant was tested for binding at pH 5.8 and pH 7.4.

Of these single-substitution variants, three (mAb L3-1, L1-2 and H1-4) exhibited some improvement in pH-dependent binding. The sequences of L3-1 are shown in FIG. 2 (SEQ ID NOs: 1-5, 8, 9, and 11-13). The sequences of L1-2 are shown in FIG. 3 (SEQ ID NOs: 1-5, 9, 10, and 14-16). The sequences of H1-4 are shown in FIG. 4 (SEQ ID NOs: 4, 5, 6-10, and 17-19).

In addition to generating the single-substitution variants, the single-substitution light chains and heavy chains were combined to generate double-substitution variants. Of these double-substitution variants, two (mAb H1-8/L1-9 and H2-6/L3-5) exhibited some improvement in pH-dependent binding. The sequences of H1-8/L1-9 are shown in FIG. 5 (SEQ ID NOs: 4, 5, 9, 10, and 20-25). The sequences of H2-6/L3-5 are shown in FIG. 6 (SEQ ID NOs: 3, 5, 8, 9, and 26-31).

Figure 13:
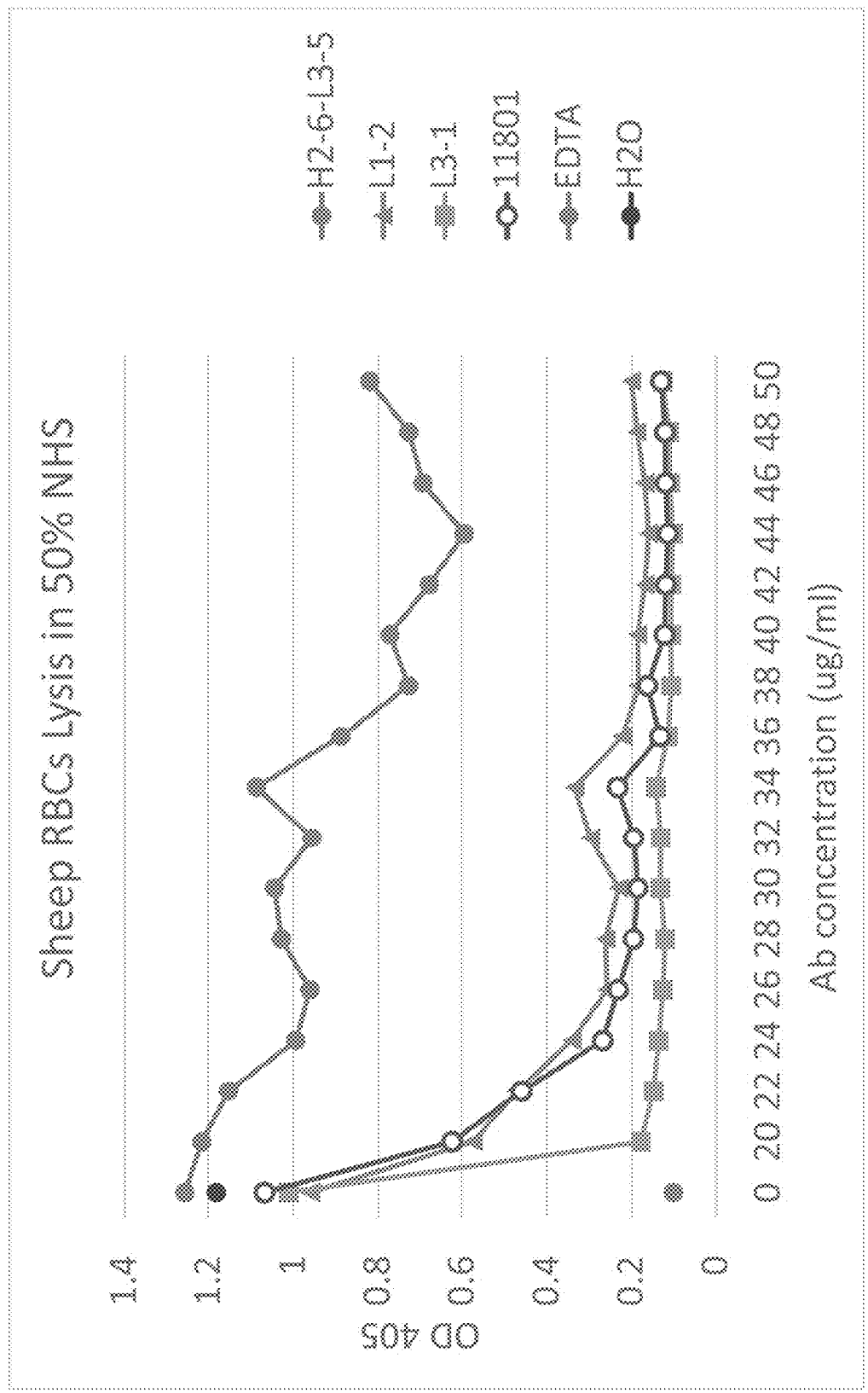
FIG. 13 depicts the results of a classical pathway complement-mediated sheep red blood cell lysis assay to assess the C5 inhibitory effect of the parental humanized mAb 11801 (VH-11801 (SEQ ID NO:2) and VL-1901 (SEQ ID NO:7)), and its variants mAb L1-2, mAb L3-1, and mAb H2-6/L3-5.
Figure 14:
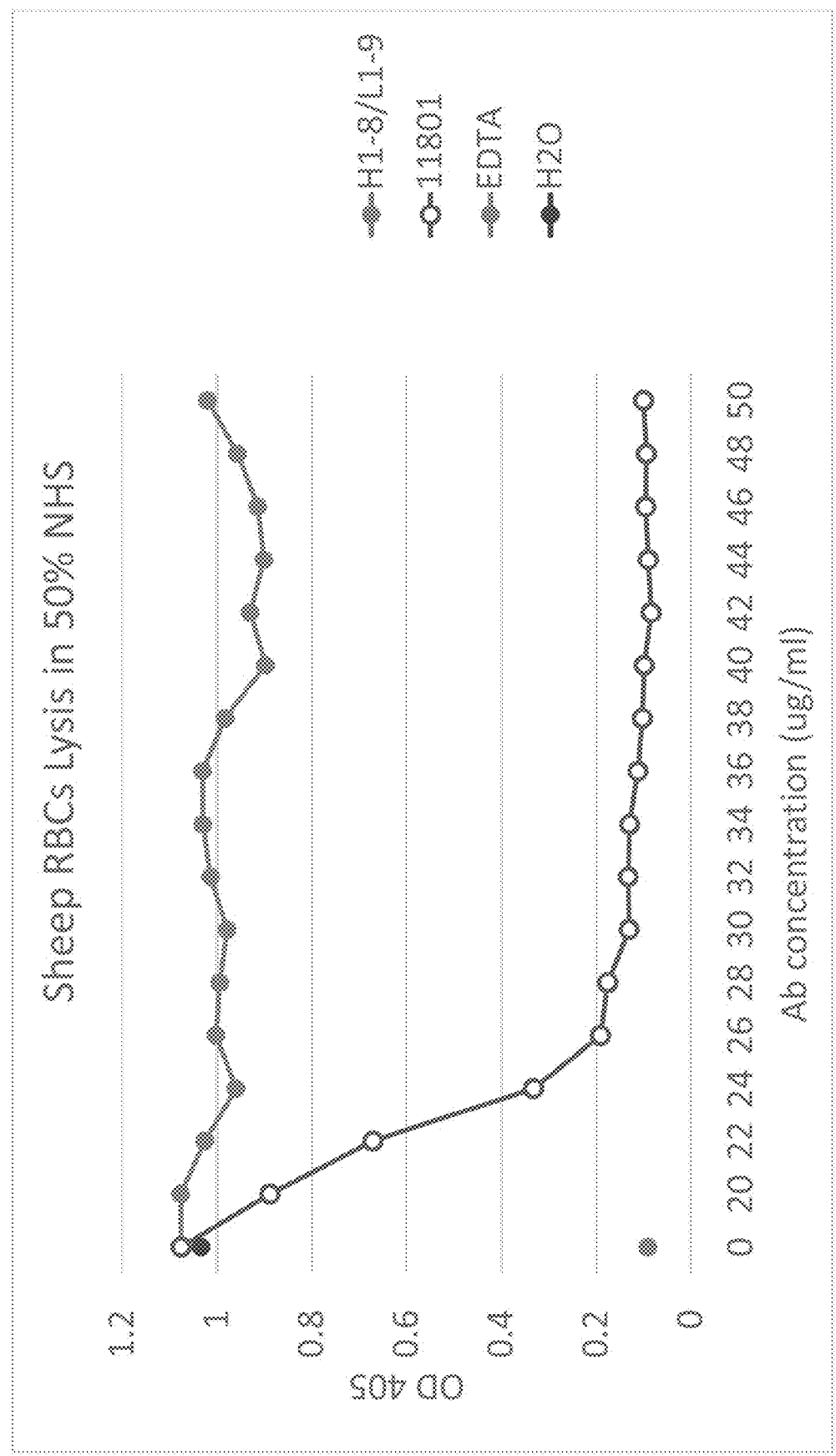
FIG. 14 depicts the results of a classical pathway complement-mediated sheep red blood cell lysis assay to assess the C5 inhibitory effect of the parental humanized mAb 11801 (VH-11801 (SEQ ID NO:2) and VL-1901 (SEQ ID NO:7)) and variant mAb H1-8/L1-9.
Figure 15:
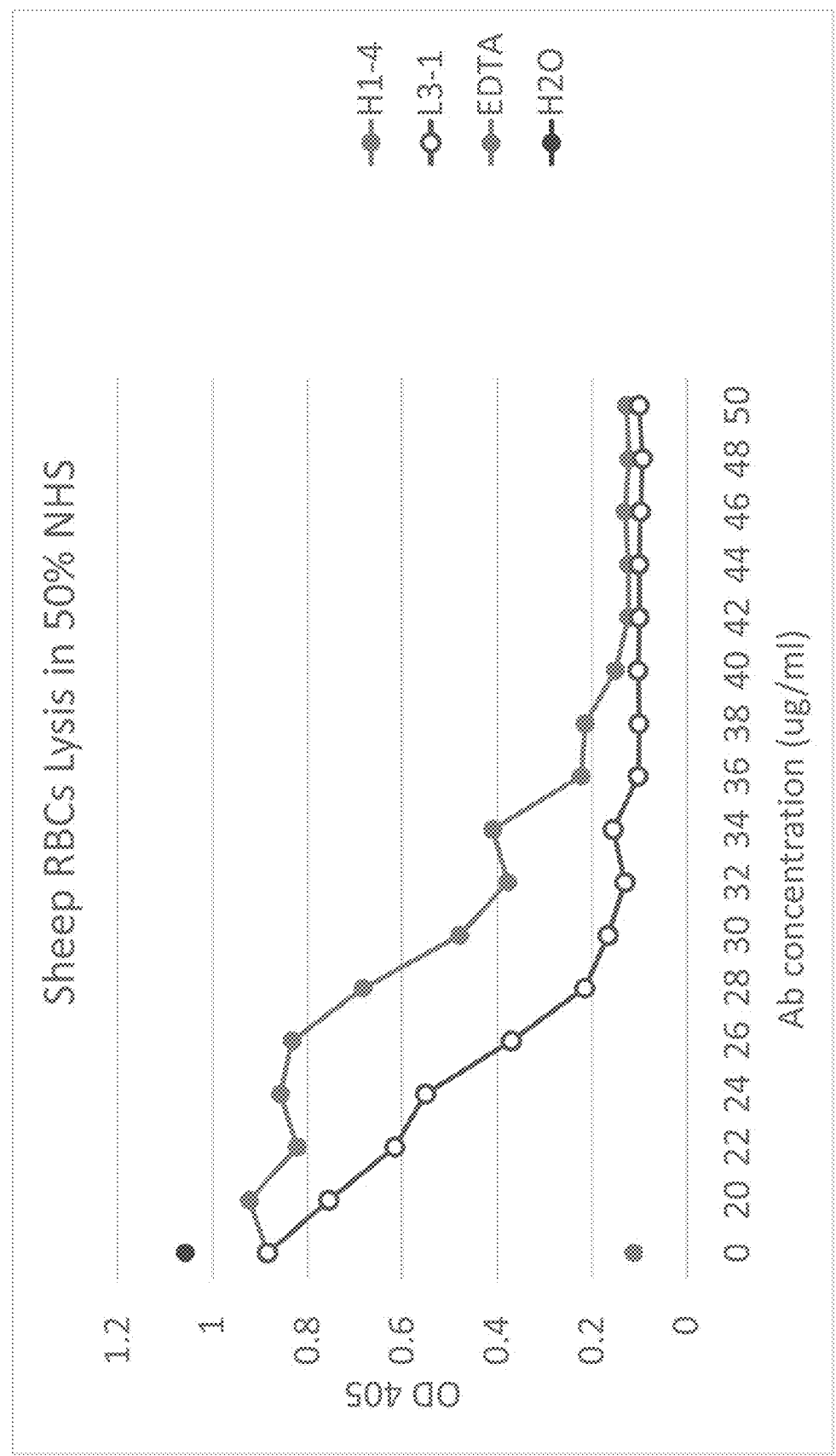
FIG. 15 depicts the results of a classical pathway complement-mediated sheep red blood cell lysis assay to assess the C5 inhibitory effect of the parental humanized mAb 11801 (VH-11801 (SEQ ID NO:2) and VL-1901 (SEQ ID NO:7)) and variant mAb H1-4 and mAb L3-1.

The Octet traces of C5 binding and dissociation of the parental humanized mAb 2G1 with VH-11801 SEQ ID NO:2 and VL-1901 SEQ ID NO:7, and the various single and double histidine mutants are shown in FIG. 7 through FIG. 12. Their relative activities in blocking C5 function is compared to the parent humanized 2G1 mAb (VH-11801/NL-1901) and are shown in FIG. 13 and FIG. 14, using a sheep red blood cell lysis assay. Except mAb L3-1 which showed equal or improved activity over the parental humanized 2G1 mAb, all other mutants showed reduced activity. In the case of the two double-substitution variants, their activity is greatly reduced with H1-8/L1-9 essentially lost all C5-blocking activity. This is not surprising because although we observed some desirable faster dissociation at pH 5.8 for mAb H1-8/L1-9 and H2-6/L3-5, their dissociation at pH 7.4 is also dramatically accelerated (which explains the loss of activity).

Even though the above histidine-substituted variants become less active in vitro, their in vivo half-life might be improved and therefore their PK/PD properties could be improved over the parent mAb due to reduced degradation due to pH-dependent binding.

Figure 16:
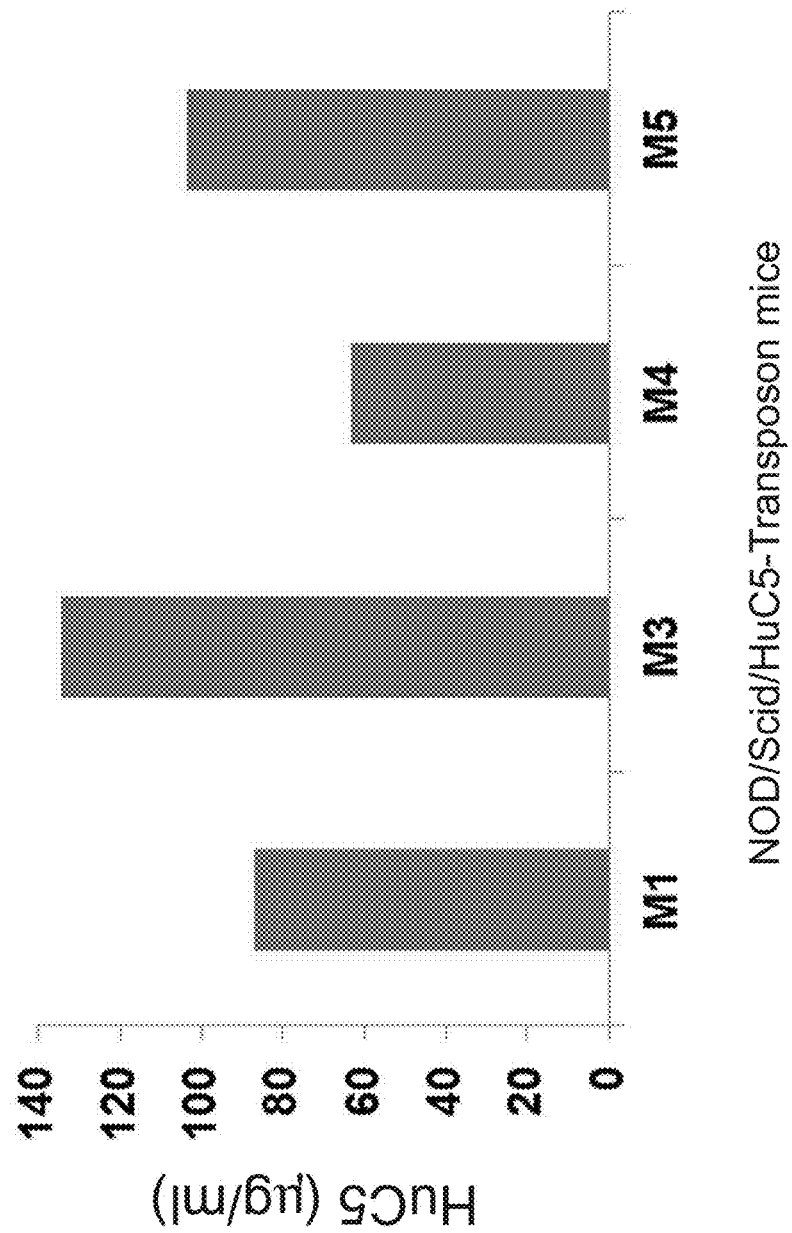
FIG. 16 depicts the results of an ELISA assay assessing the level of human C5 in the plasma of NOD/SCID mice genetically modified to express human C5. M1, M3, M4 and M5 designate 4 representative mice.

To test in vivo PK/PD, a C5 humanized mouse was developed by making NOD/SCID mice permanently expressing human C5 through hydrodynamic injection via tail vein of a human C5 cDNA containing the Sleeping Beauty transposon elements. NOD mice are naturally deficient in C5, so endogenous mouse C5 will not interfere with pharmacodynamics (PD) assay. The SCID genetic background ensures that the transgenically expressed human C5 will not elicit an immune response against human C5. The C5 humanized mouse was developed by hydrodynamic injection of human C5 plasmid containing the Sleeping Beauty transposon sequence elements for stable genomic integration. Representative data of high level human C5 expression in NOD/SCID mice are shown in FIG. 16. Typically, plasma concentrations of C5 ranging from 50 to 120 μg/mL were observed. This is comparable to C5 concentration in human plasma which is about 80 μg/mL.

Figure 17:
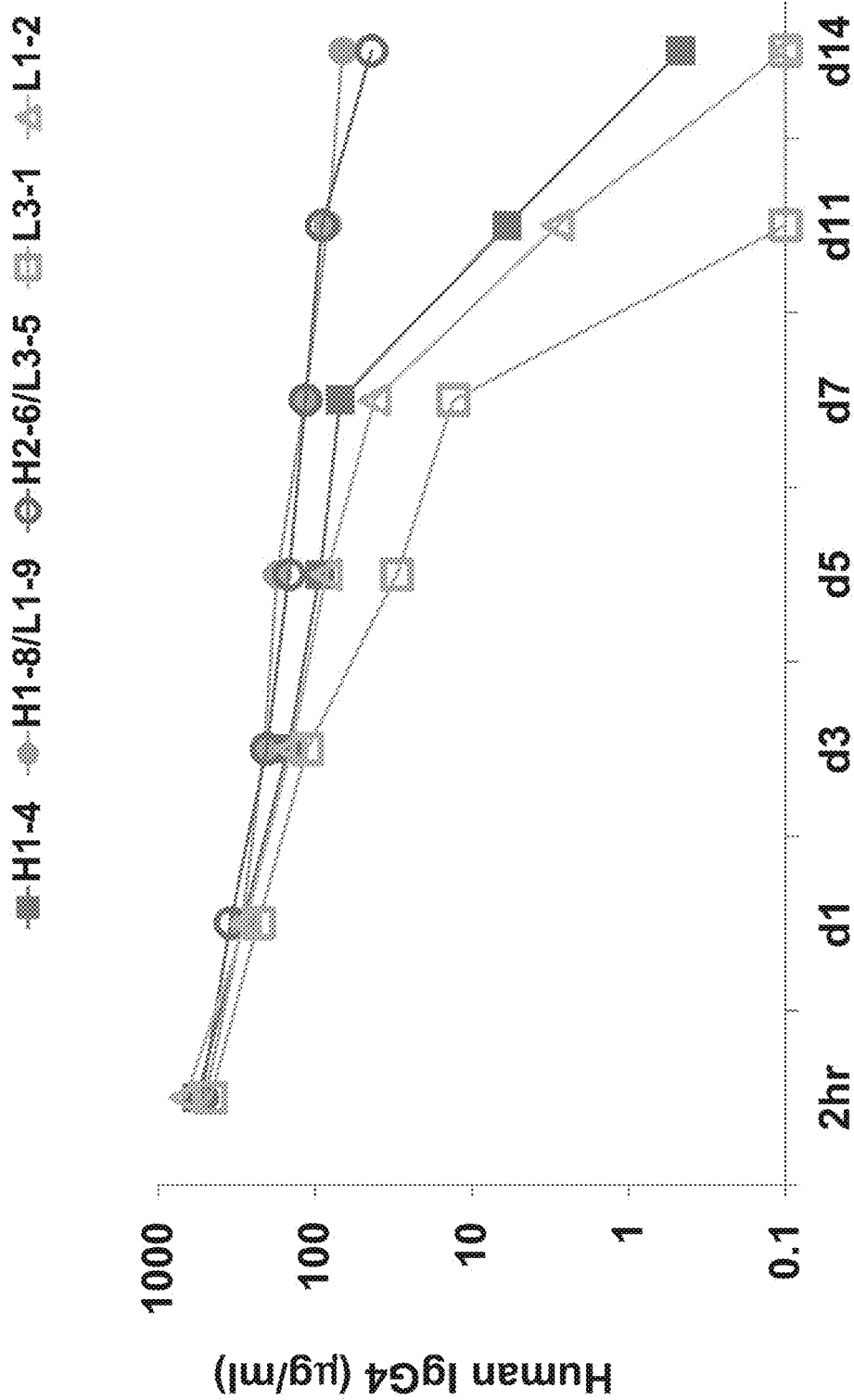
FIG. 17 depicts the results of an assay assessing the level of human IgG4 in the plasma of NOD/SCID mice genetically modified to express human C5 after injection with mAbs H1-4, H1-8/L1-9, H2-6/L3-5, L3-1 or L1-2.
Figure 18:
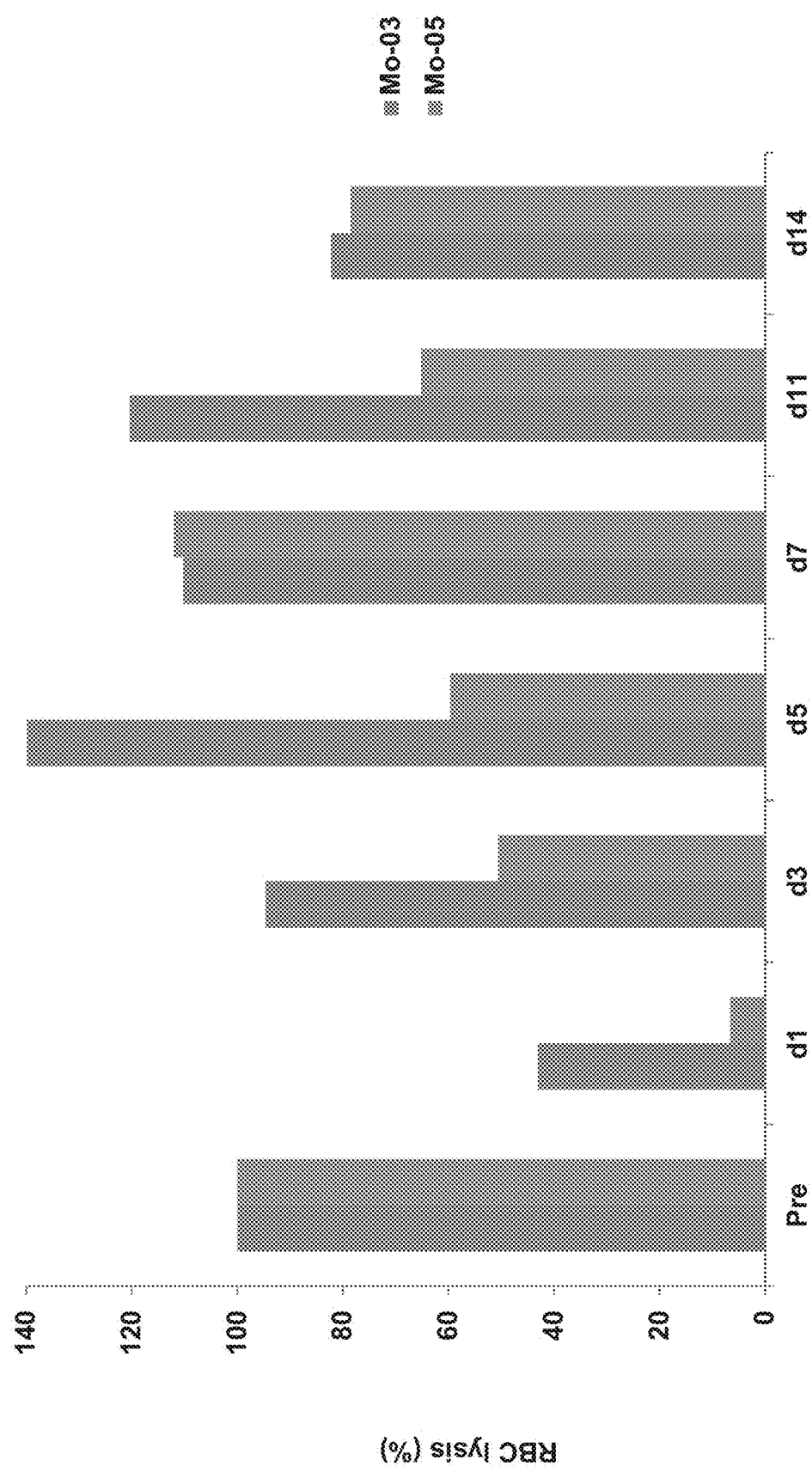
FIG. 18 depicts the results of a classical pathway complement-mediated chicken red blood cell assay assessing the pharmacodynamics of the parental humanized mAb 2G1 (VH-11801 (SEQ ID NO:2) and VL-1901 (SEQ ID NO:7)) in NOD/SCID mice genetically modified to express human C5.
Figure 19:
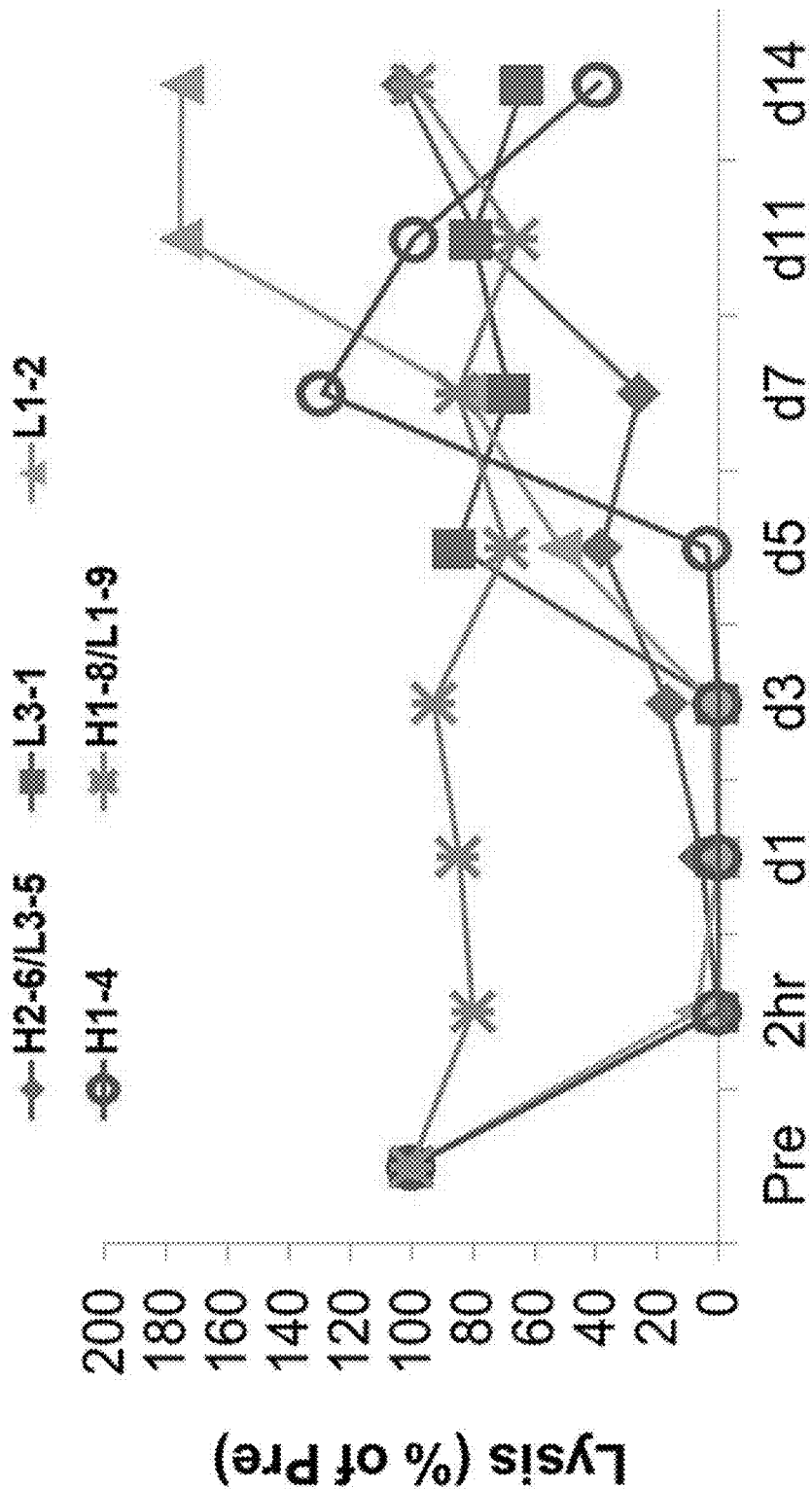
FIG. 19 depicts the results of a classical pathway complement-mediated chicken red blood cell assay assessing the pharmacodynamics of mAbs L3-1, L1-2, H1-4, H1-8/L1-9 and H2-6/L3-5 in NOD/SCID mice genetically modified to express human C5.
Figure 24:
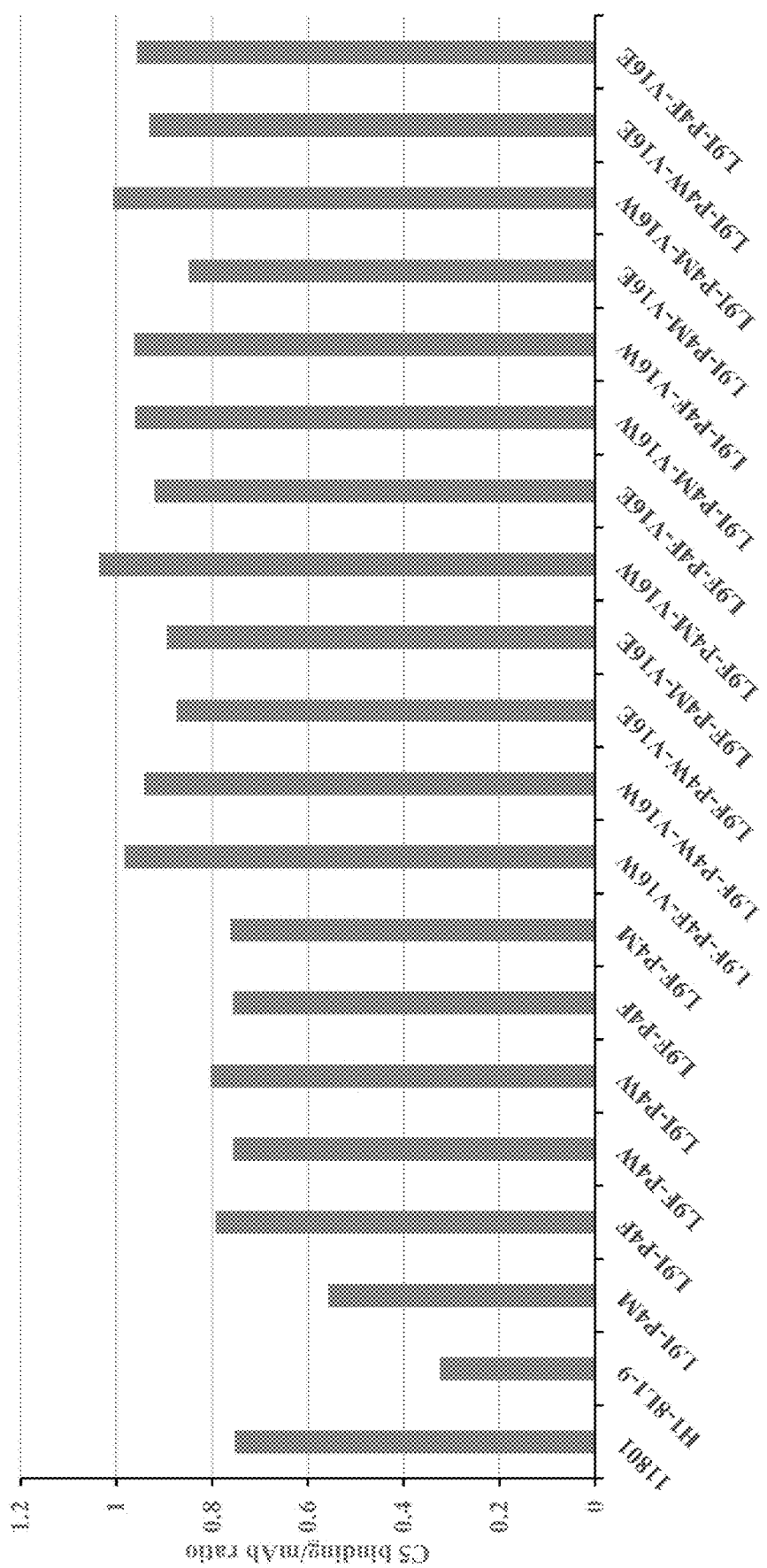
Figure 25:
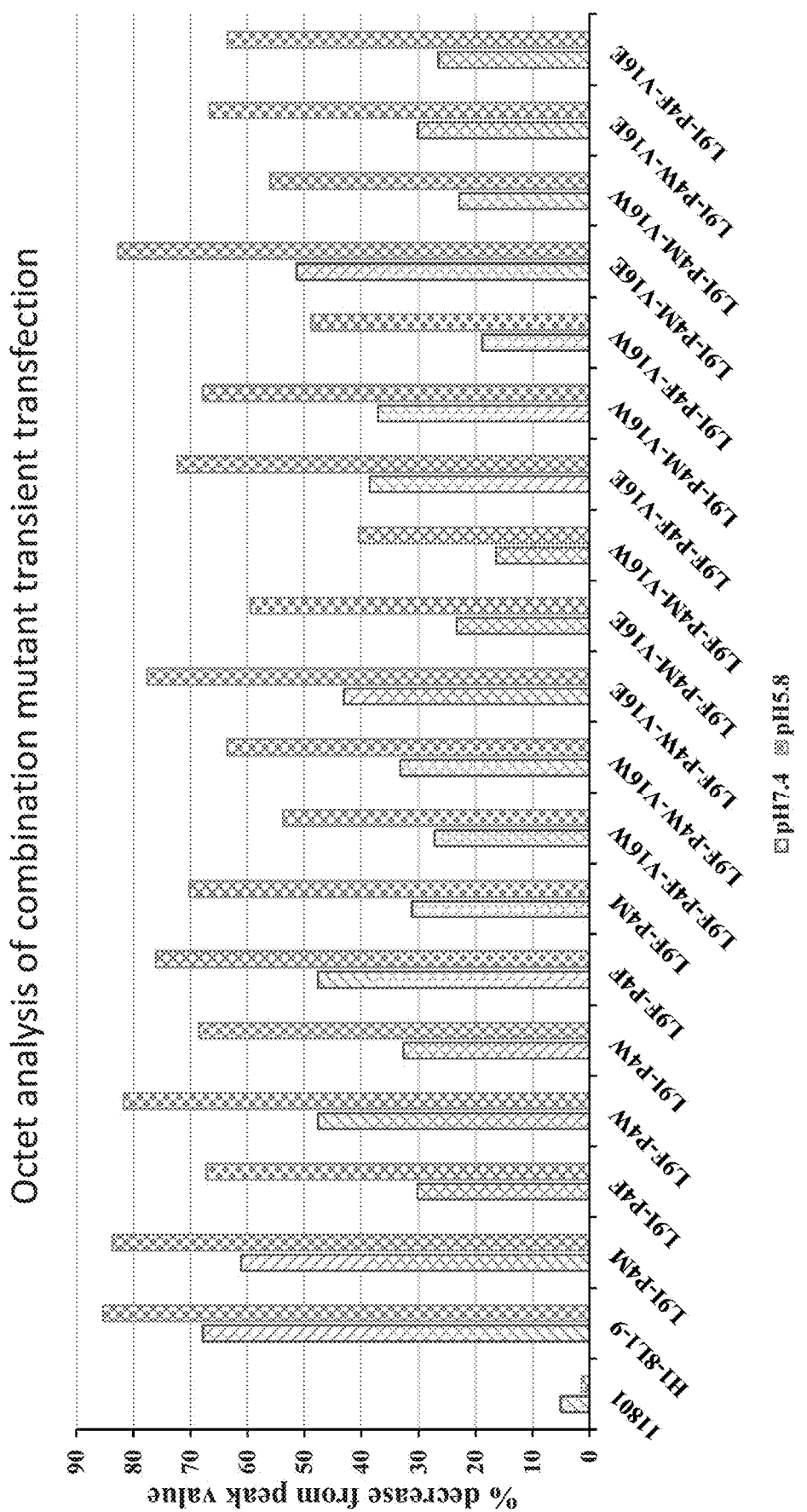
Figure 26:
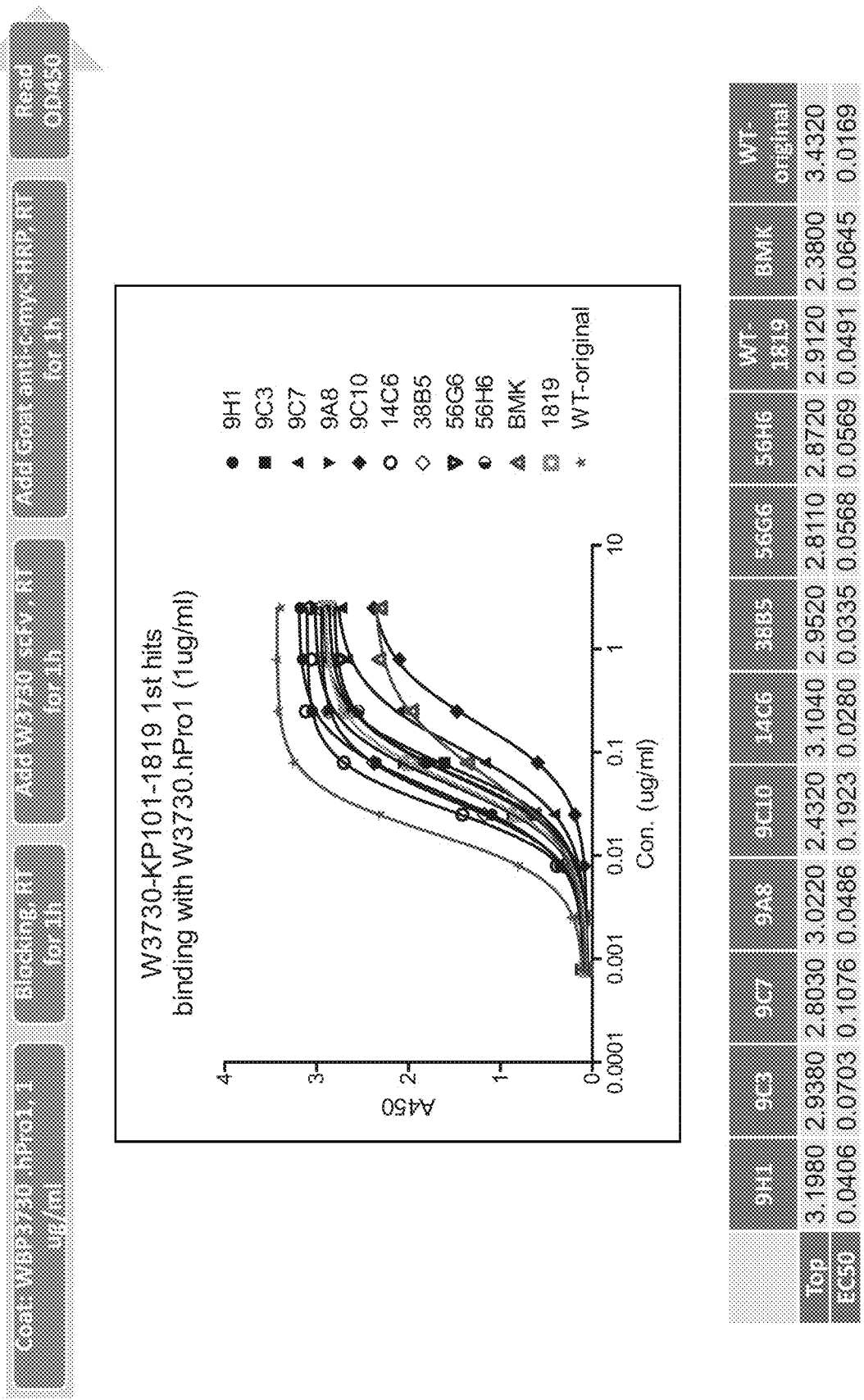
Figure 32:
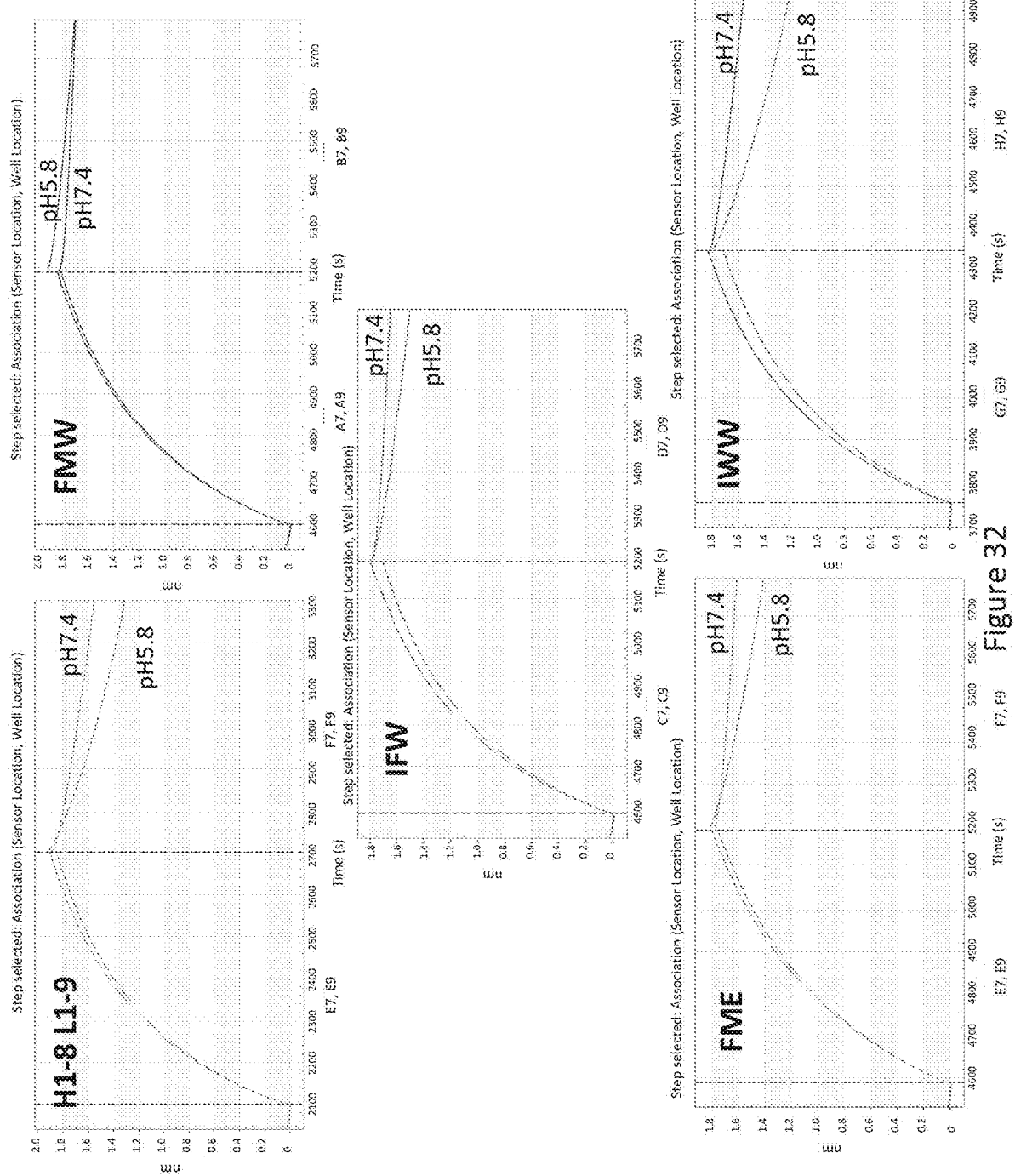
Figure 33:
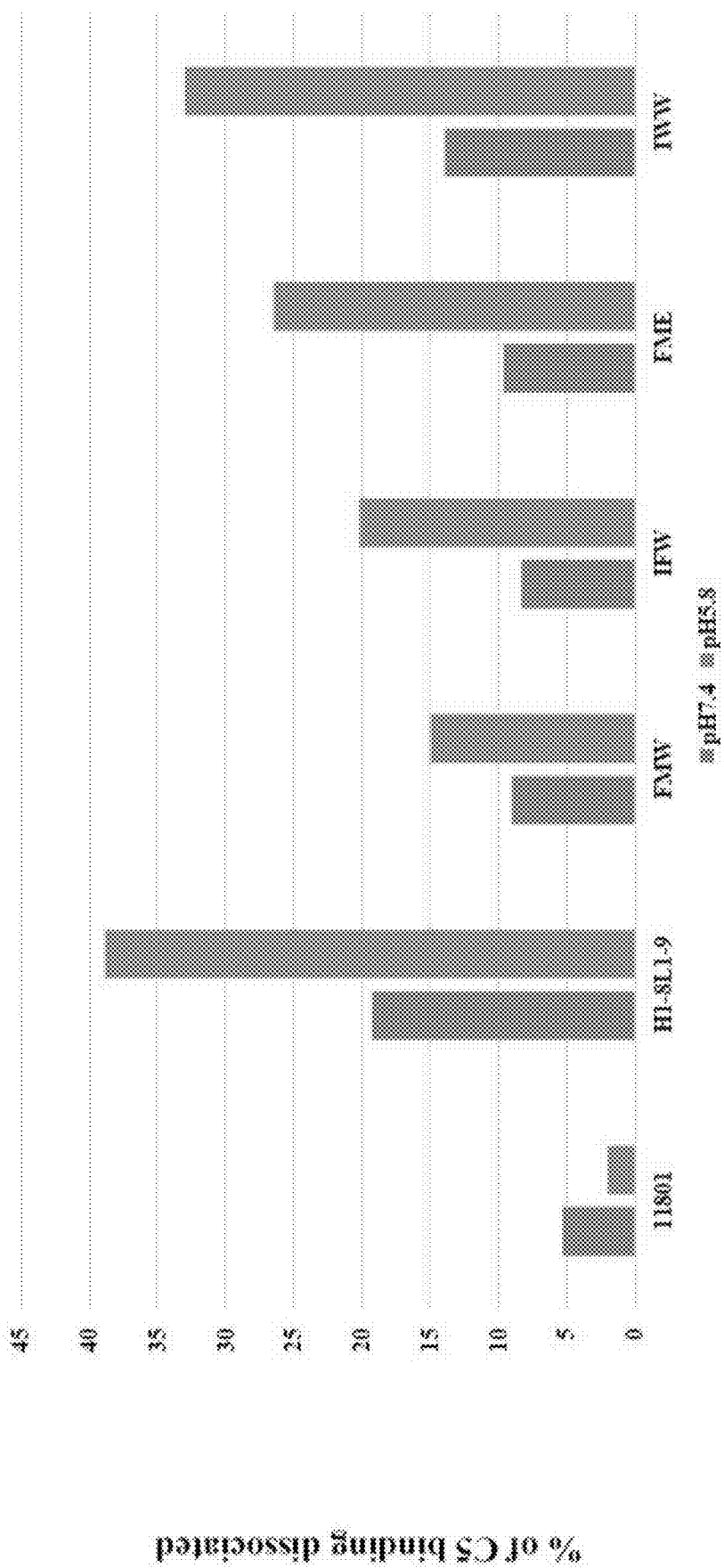
Figure 34:
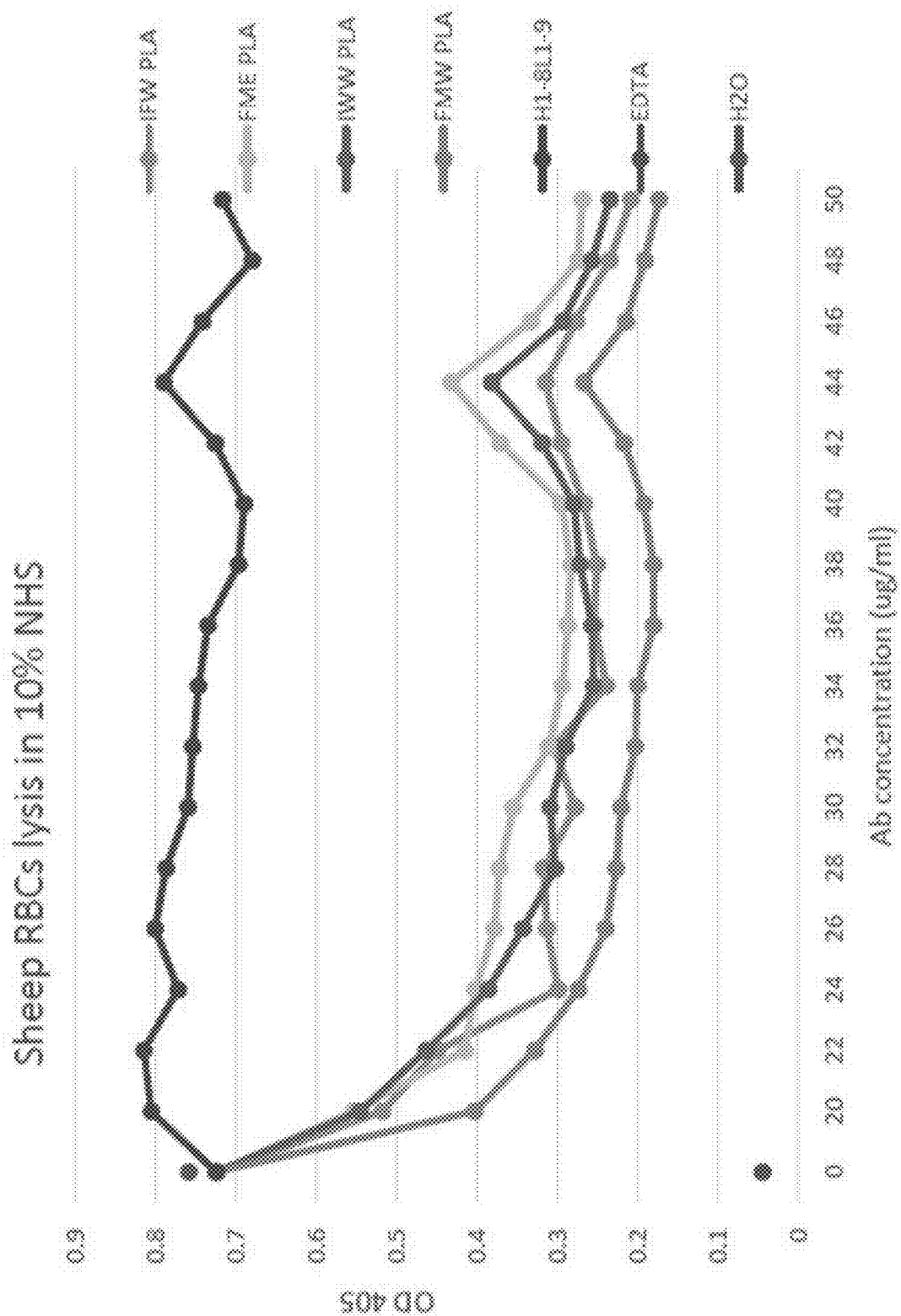
Figure 35:
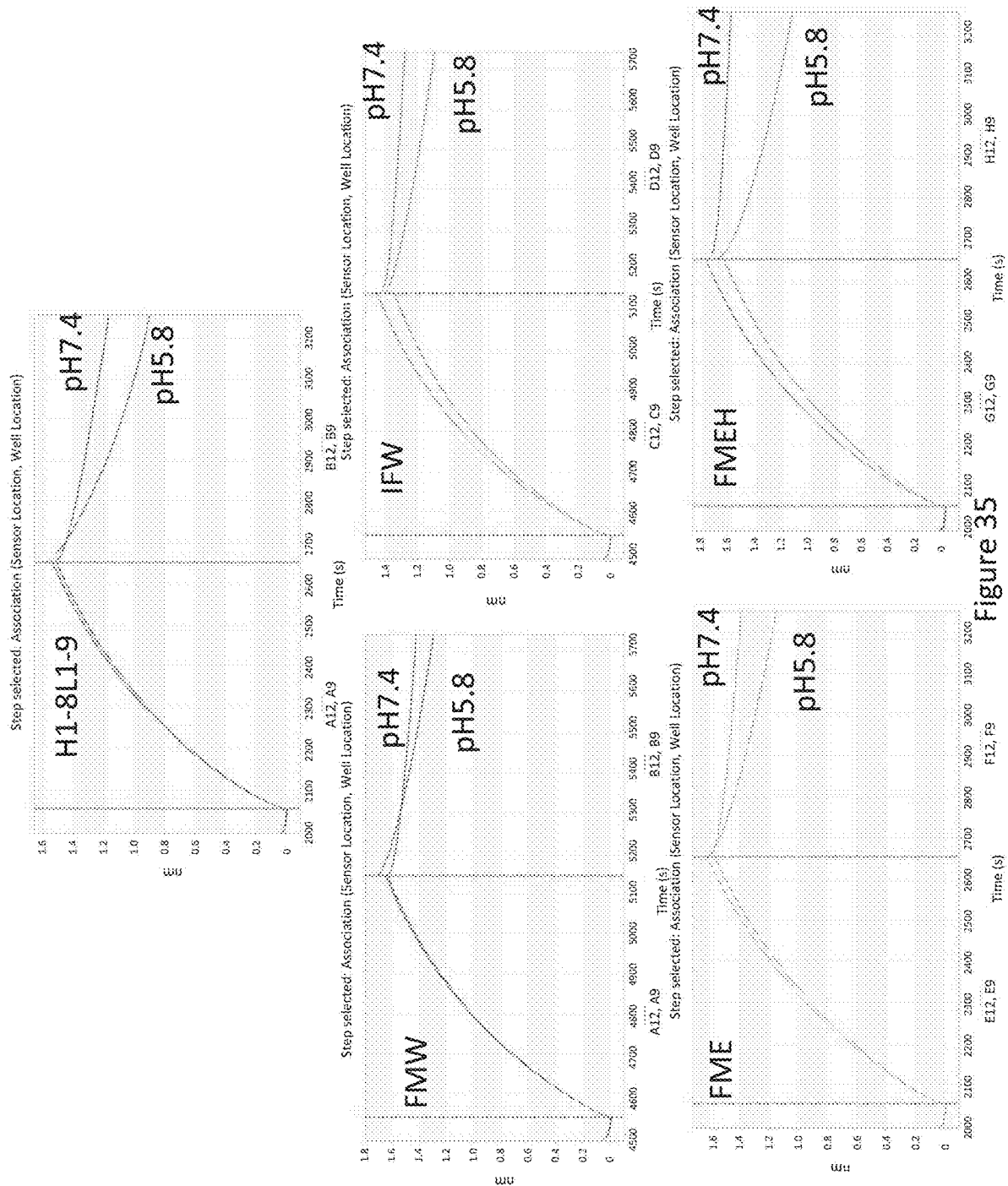
Figure 37:
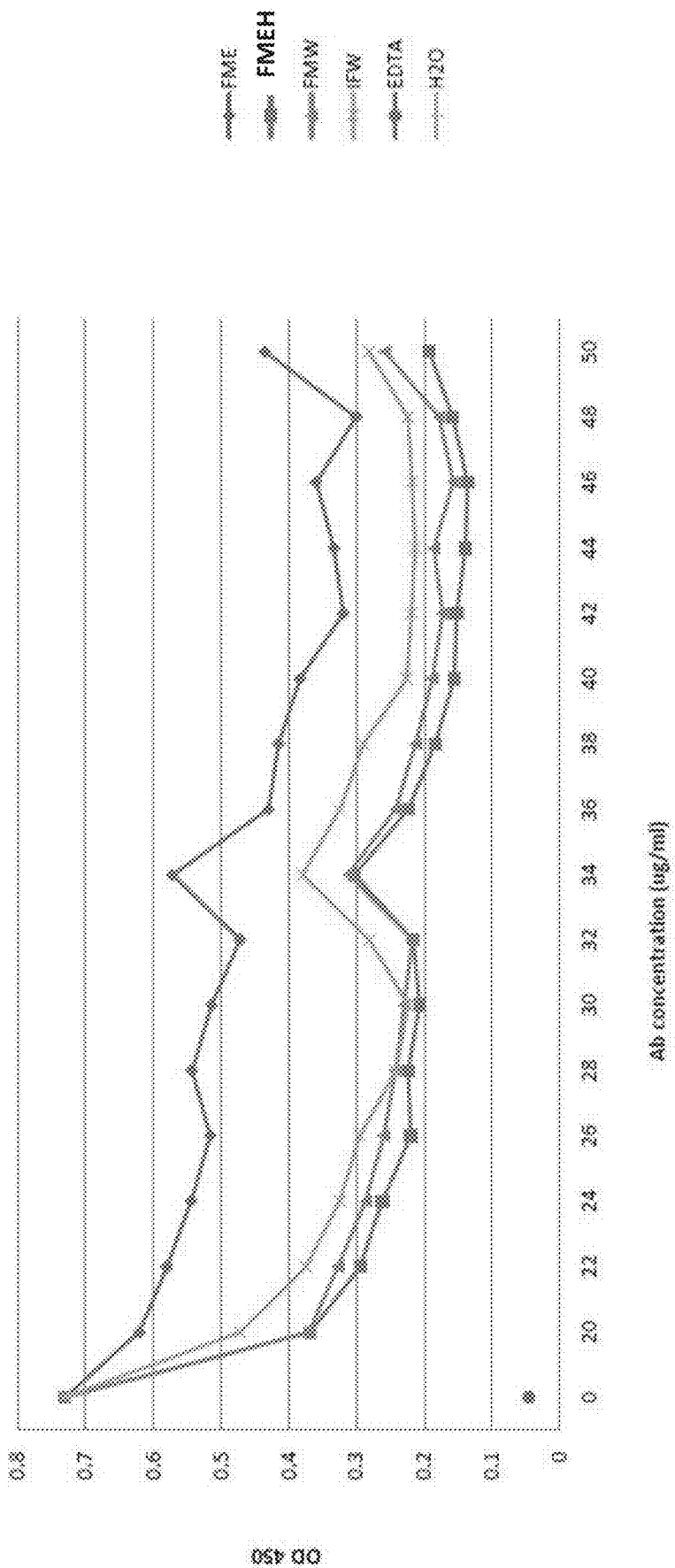
Figure 39:
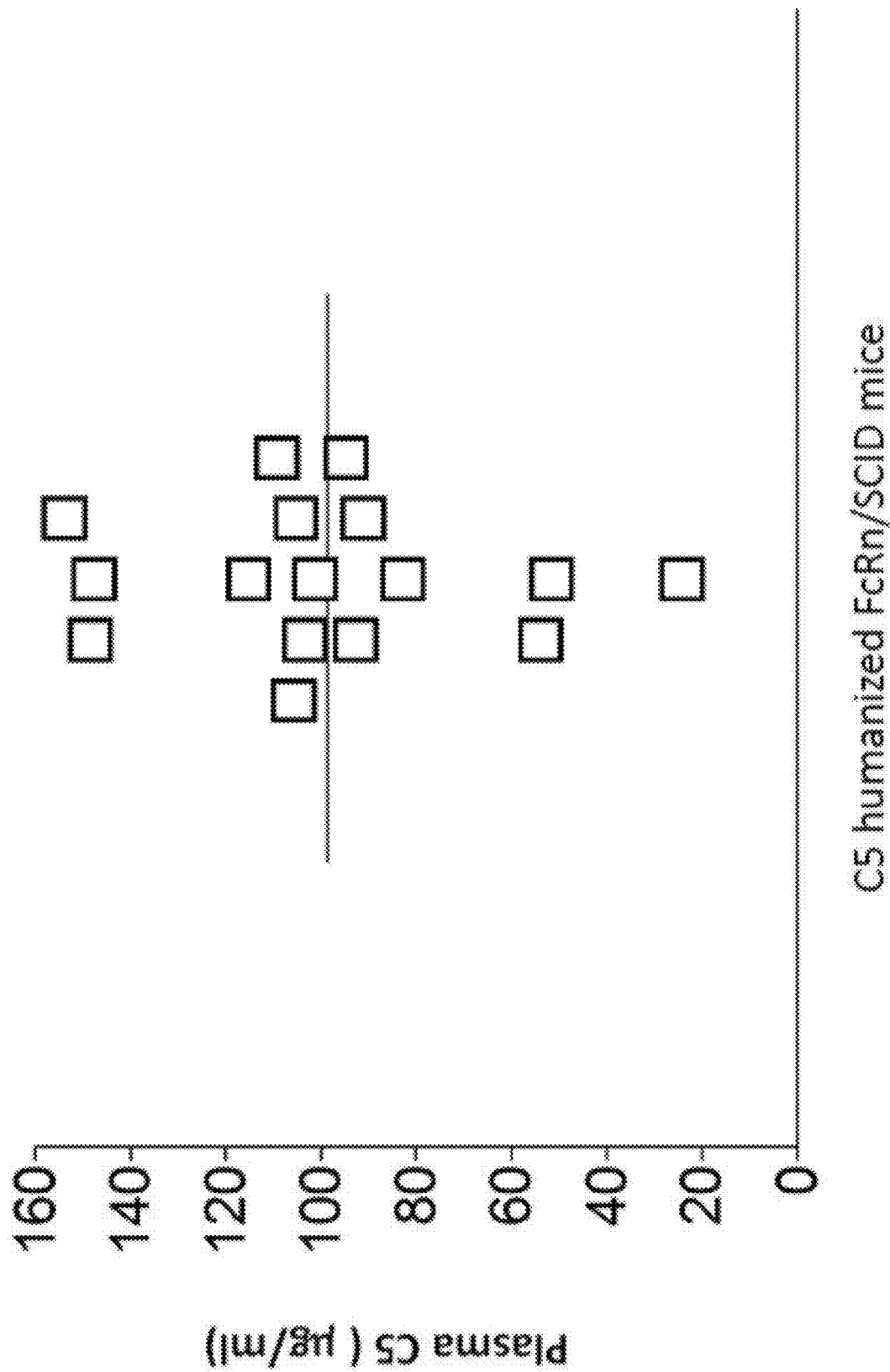

The five histidine-substitution variants (i.e., mAb L3-1, L1-2, H1-4, H1-8/L1-9 and H2-6/L3-5) were assessed for PK/PD. The two double-substitution variants (i.e., mAb H1-8/L1-9 and H2-6/L3-5) exhibited the greatest persistence. Of the three single-substitution variants, mAb H1-4 and L1-2 exhibited better persistence than mAb L3-1 (FIG. 17). Thus, although L3-1 had the best pH 7.4 affinity and in vitro blocking activity for human C5, it has the shortest half-life. Interestingly, except mAb H1-8/L1-9 which showed no blocking activity in vivo, all other variants have improved PD profile over the parent humanized 2G1 mAb (VH-11801, VL-1901) (see FIG. 18 and FIG. 19).

Figure 40:
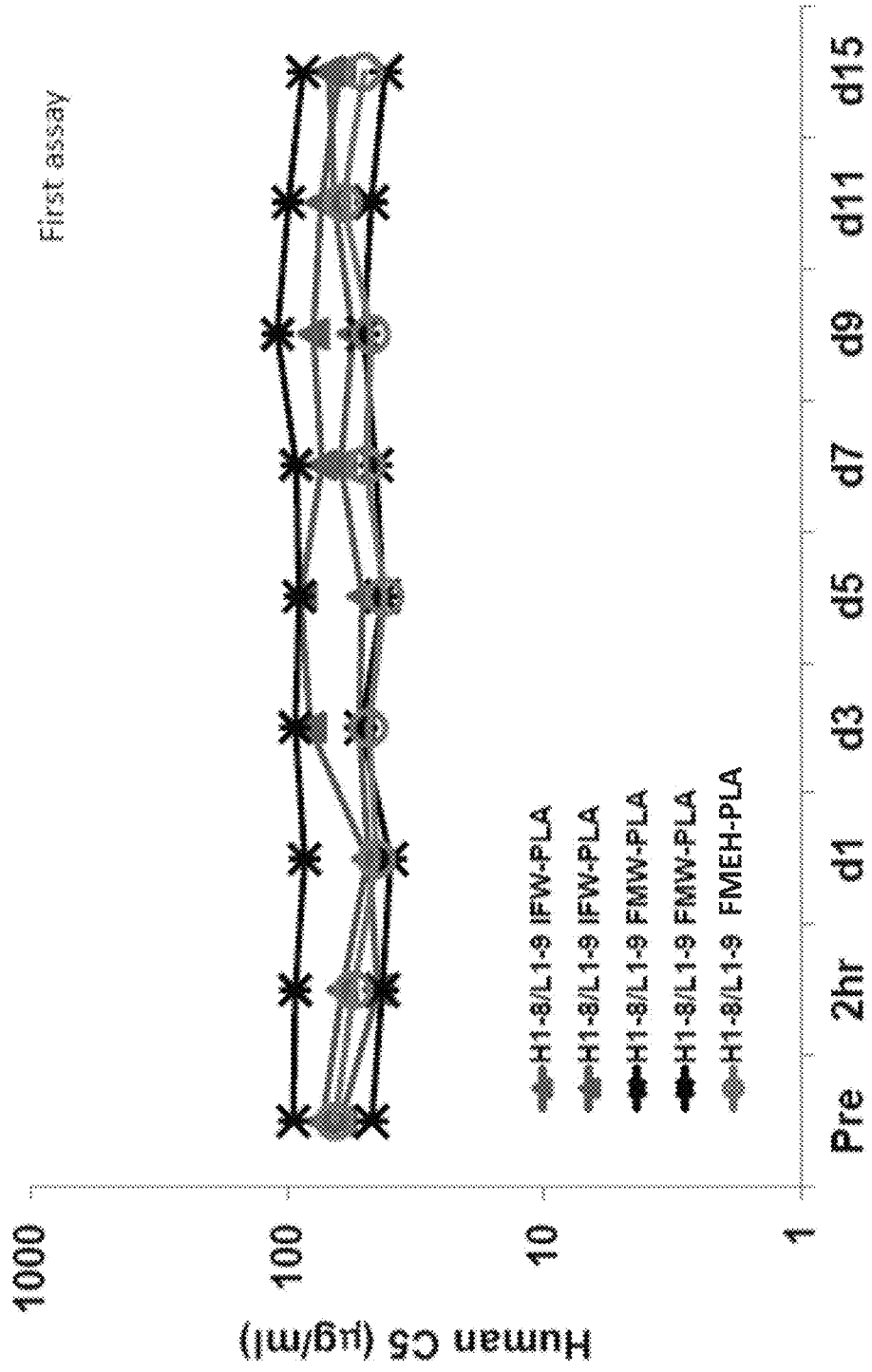
Figure 41:
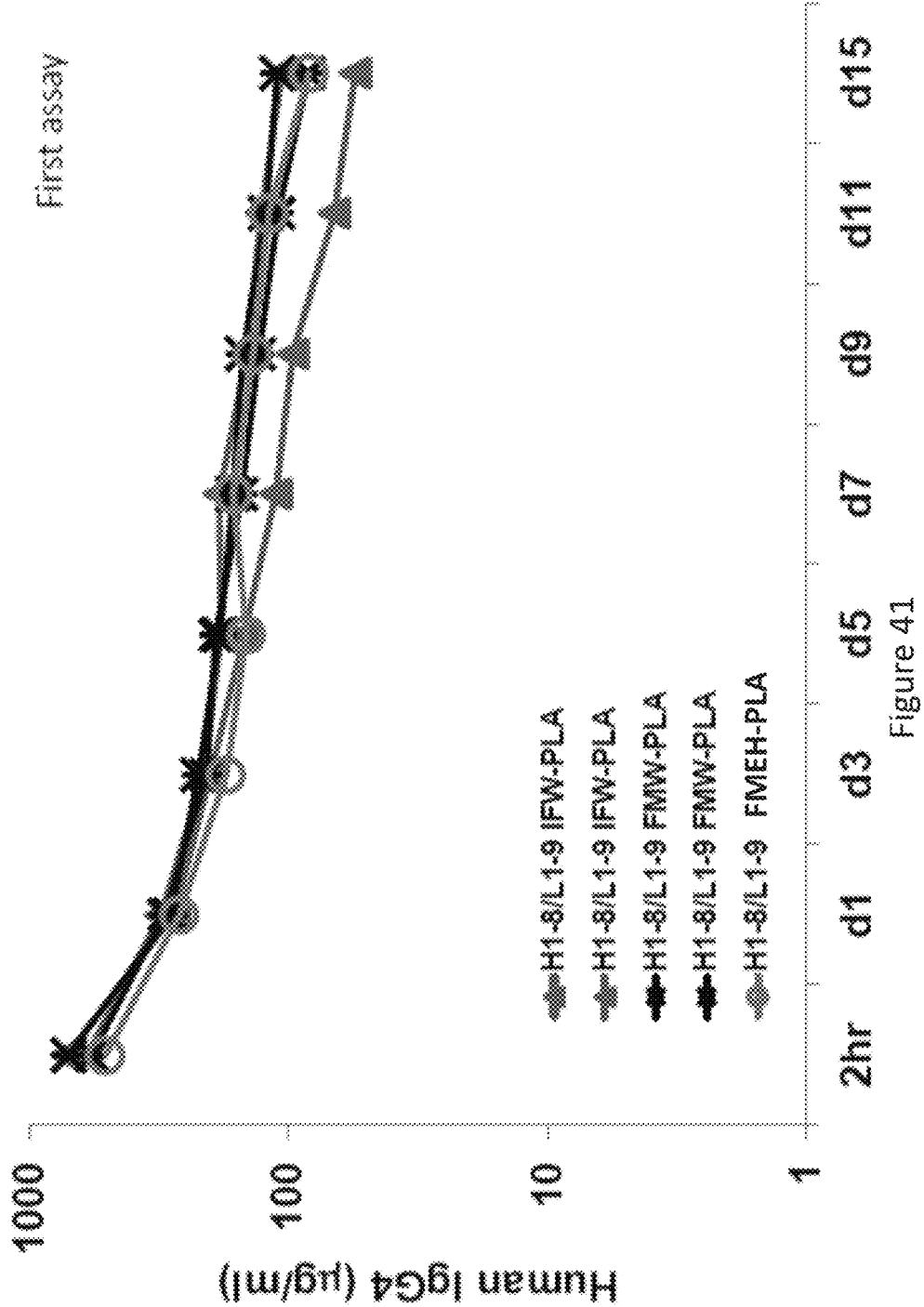
Figure 42:
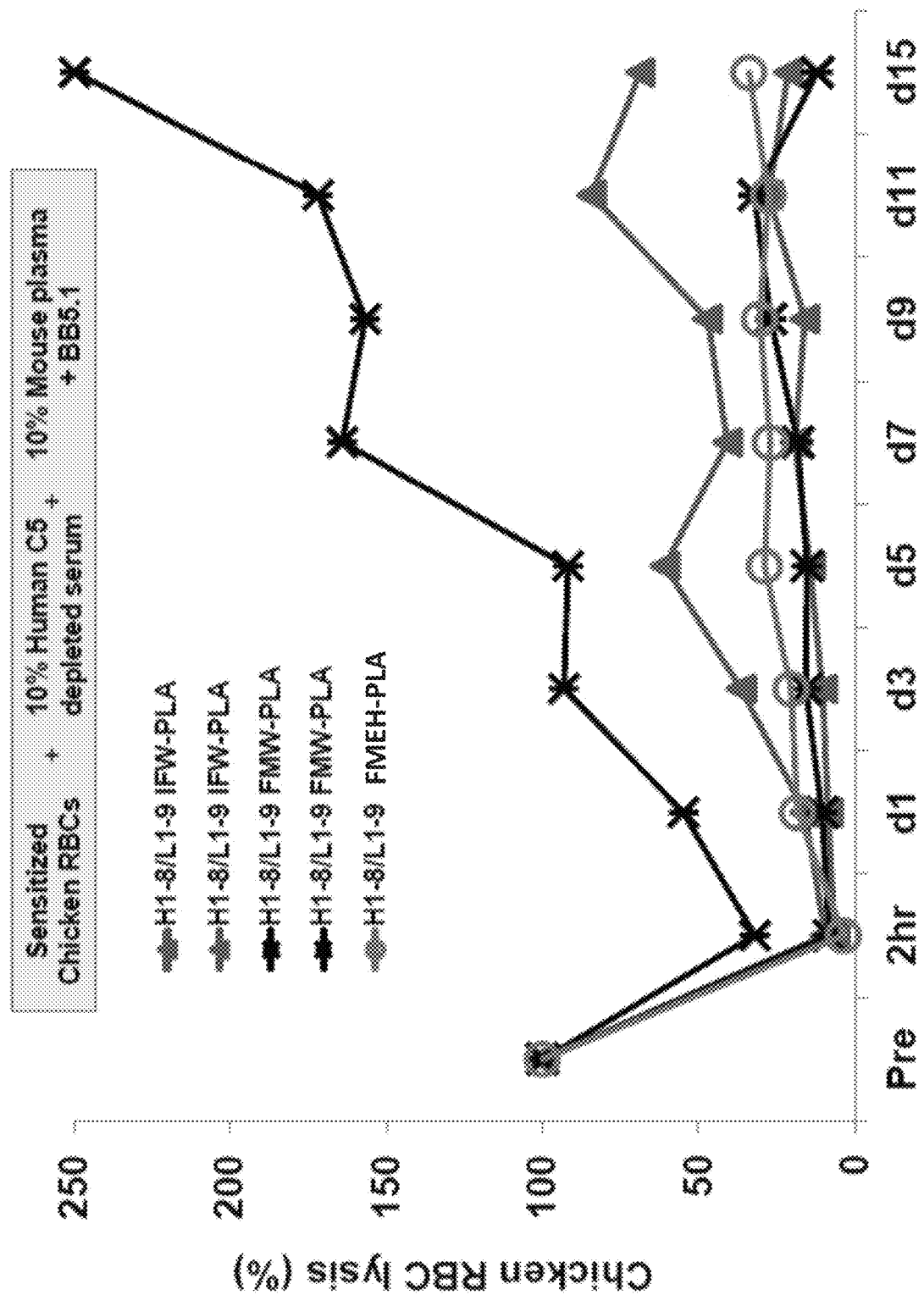
FIG. 42 depicts the results of a classical pathway complement-mediated chicken red blood cell assay assessing the pharmacodynamics of mAbs H1-8/L1-9 IFW-PLA, H1-8/L1-9 FMW-PLA, or H1-8/L1-9 FMEH-PLA in FcRn/SCID mice genetically modified to express human C5.
Figure 43:
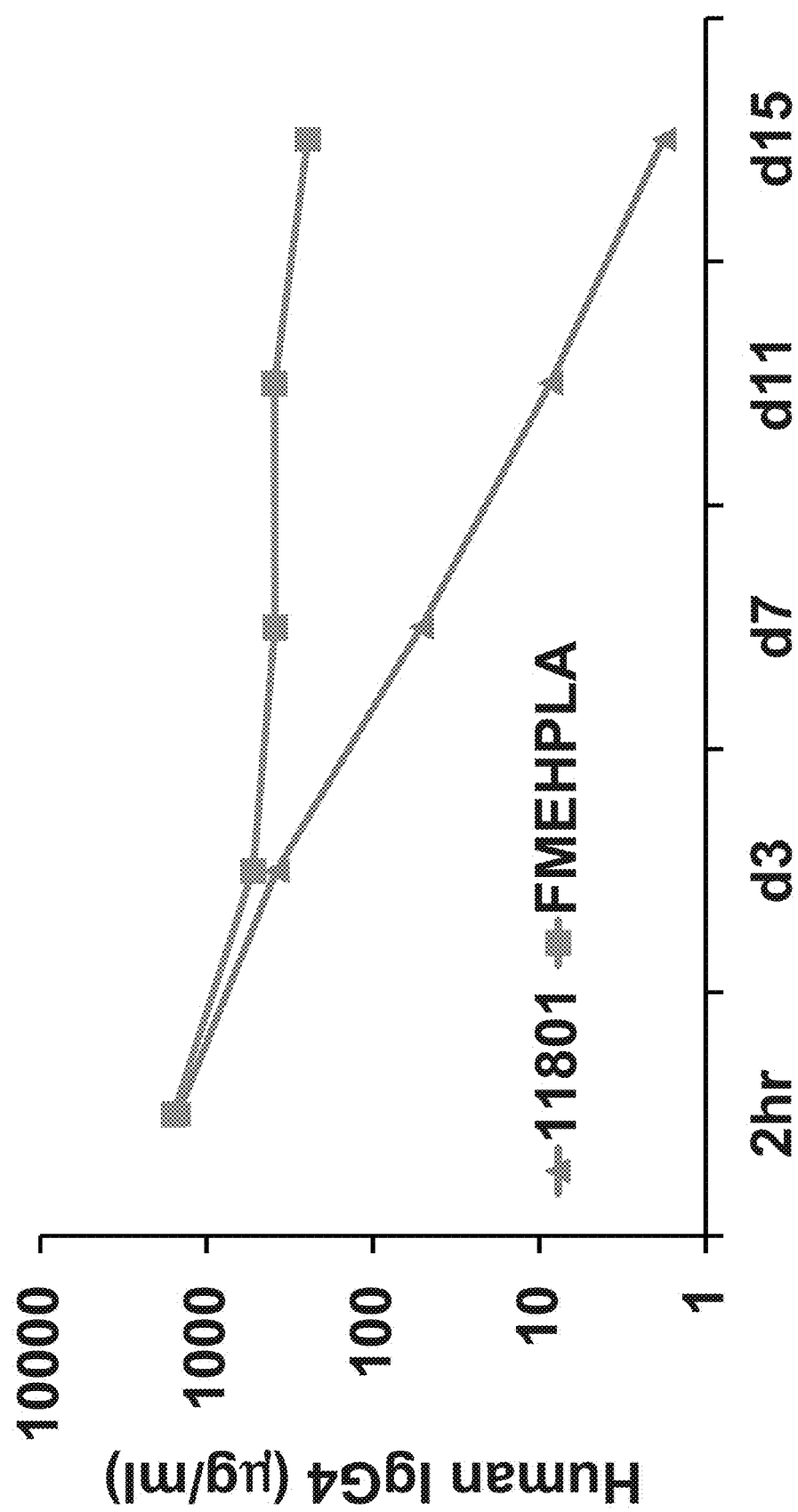
FIG. 43 depicts the results of an assay assessing the level of total hIgG4 in the plasma of FcRn/SCID mice genetically modified to express human C5 after injection with mAbs 11801 and FMEH-PLA.

Given that variant mAb H1-8/L1-9 exhibited the best pH-binding differential (i.e., antigen dissociation occurs much faster at pH 5.8 than pH 7.4 (see FIG. 12)), but lost much of its blocking activity (because antigen dissociation at pH 7.4 also increased), parsimonious mutagenesis was performed to randomly substitute each residue in the 6 CDRs of H1-8/L1-9 (while conserving the histidine substitutions of H1-8 and L1-9). Three "hot spots" were identified in VH that significantly improved pH 7.4 binding in ELISA plate assays of ScFV constructs. These residues were leucine at position #9 (i.e., L9) in VH CDR1, relative to SEQ ID NO:20, proline at position #4 (i.e., P4) in VH CDR2, relative to SEQ ID NO:4, and valine at position #16 (i.e., V16) in VH CDR3, relative to SEQ ID NO:5. The substitutions exhibiting the greatest improved binding were L9→W9 (i.e., L9W), L9→I9 (i.e., L9I), L9→V9 (i.e., L9V), L9→Y9 (i.e., L9Y), L9→F9 (i.e., L9F), P4→F4 (i.e., P4F), P4→L4 (i.e., P4L), P4→M4 (i.e., P4M), P4→W4 (i.e., P4W), P4→I4 (i.e., P4I), V16→F16 (i.e., V16F), V16→E16 (i.e., V16E) and V16→W16 (i.e., V16W) (see FIG. 20).

These 13 substitutions (i.e., L9→W9 (i.e., L9W), L9→19 (i.e., L9I), L9→V9 (i.e., L9V), L9→Y9 (i.e., L9Y), L9→F9 (i.e., L9F), P4→F4 (i.e., P4F), P4→L4 (i.e., P4L), P4→M4 (i.e., P4M), P4→W4 (i.e., P4W), P4→I4 (i.e., P4I), V16→F16 (i.e., V16F), V16→E16 (i.e., V16E) and V16→W16 (i.e., V16W)) were generated and evaluated for their pH-dependent binding property as IgG. For each variant, a VH and VL plasmid was constructed and then transiently transfected into Expi-CHO cells. mAb in the cell culture supernatant was tested for binding at pH 5.8 and pH 7.4. FIG. 21 and FIG. 22 summarize the C5 binding properties of these variants. FIG. 21 shows the ratio of C5 binding relative to mAb binding signals, and FIG. 22 shows the % decrease of binding signal from peak value in pH 7.4 and pH 5.8 after switching from association phase to dissociation phase. For any given mutant, a high ratio on FIG. 21 is preferred; and a lower % of dissociation at pH 7.4 (crosshatch bars) and higher % of dissociation at pH 5.8 (checkered bars) on FIG. 22 are preferred.

From this screen of the 13 mAb H1-8/L1-9 single histidine substitution variants, seven variants were selected for generating the 18 combination substitution variants listed on FIG. 23 (i.e., L9I/P4M, L9I/P4W, L9I/P4F, L9F/P4M, L9F/P4W, L9F/P4F, L9I/P4M/V16W, L9I/P4W/V16W, L9I/P4F/V16W, L9F/P4M/V16W, L9F/P4W/V16W, L9F/P4F/V16W, L9I/P4M/V16E, L9I/P4W/V16E, L9I/P4F/V16E, L9F/P4M/V16E, L9F/P4W/V16E, and L9F/P4F/V16E). These 18 combination substitution variants were generated and evaluated for their pH-dependent binding property. For each variant, a VH and VL plasmid was constructed and then transiently transfected into Expi-CHO cells. mAb in the cell culture supernatant was tested for binding at pH 5.8 and pH 7.4.

FIG. 24 and FIG. 25 summarize the C5 binding properties of these 18 combination substitution variants. FIG. 24 shows the ratio of C5 binding relative to mAb binding signals, and FIG. 25 shows the % decrease of binding signal from peak value in pH 7.4 and pH 5.8, respectively, after switching from association phase to dissociation phase. FIG. 25 shows the % decrease of binding signal from peak value in pH 7.4 and pH 5.8 after switching from association phase to dissociation phase. For any given mutant, a high ratio on FIG. 24 is preferred; and a lower % of dissociation at pH 7.4 (crosshatch bars) and higher % of dissociation at pH 5.8 (checkered bars) on FIG. 25 are preferred.

Example 2

Additional analysis and data mining of affinity maturation project were performed and identified T to His mutation at CDR2 position 9 as another promising random mutation to repair the pH 7.4 binding of V1-8/L1-9 (FIG. 26 through FIG. 28). Systemic changing of each residue in the CDRs of VH and VL to Histidine was also conducted and each mutant was tested for human C5 binding at pH 7.4 and pH 5.8. The purpose was to find mutants that show maximum pH-dependent binding differentials but retain C5 blocking activity. As such, a number of mutants, including a double mutant VH1-8/VL1-9, which carried a His mutation in CDR1 of VH amino acid 8 and in CDR1 of VL amino acid 9, were characterized and tested (FIG. 5, FIG. 30, and FIG. 31). The double mutant (referred to as "H1-8/L1-9"; FIG. 5) showed the most pH-dependent binding differential but lost most of its activity. Therefore, an affinity maturation process was used to identify a number of random mutants in the CDRs of H1-8/L1-9 that increased pH 7.4 binding (pH 7.4 binding correlates with C5 blocking activity) while still retaining pH 7.4 vs pH 5.8 differential binding.

Furthermore, a number of double and triple mutants to H1-8/L1-9 were generated by combining the top ranked single mutants. The pH 7.4 and pH 5.8 binding profiles of these double and triple mutants were tested by transient transfection cell culture supernatant and characterized. Based on the maximum pH 7.4 vs pH 5.8 binding differential and best pH 7.4 binding, IWW, IFW, FME and FMW were selected as the top 4 triple mutant clones of V1-8/L1-9. IWW, IFW, FME and FMW were expressed and the proteins were purified to confirm pH-dependent binding properties. C5 inhibiting activity in hemolytic assay was also tested (FIG. 29, FIG. 30, FIG. 32 through FIG. 34).

The above described triple mutants were further combined with the new His mutation (CDR2 of VH, position 9, T to H mutation) to produce 4 quadruple mutants (IWWH, IFWH, FMEH and FMWH; e.g., FIG. 31). These new mutants were tested for their pH-dependent binding properties and C5-inhibiting activities. Of them, the quadruple mutant FMEH was identified as an improved mutant over its triple mutant parent molecule FME (FIG. 35 through FIG. 37).

In addition to the C5 humanized mice on NOD/SCID mice, described in Example 1 and generated by hydrodynamic injection to test in vivo PK/PD of some of the engineered mutants of anti-C5 mAbs, C5 humanized mice on SCID/FcRn transgenic mice (human FcRn transgenic and mouse FcRn knockout) background was also generated. The latter strain enabled the testing of the combined effect of pH-dependent anti-C5 mAb mutants with further engineered Fc domain of IgG4 antibody construct (three mutations in Fc domain) (FIG. 38 and FIG. 39).

Using C5 humanized mice on SCID/FcRn transgenic background, PK/PD of the H1-8/L1-9 triple mutants IFW, FMW, and FMEH was also tested in IgG4 format with three residue mutations in Fc domain (PLA). The data showed significantly improved PK/PD activity over the original humanized anti-C5 mAb 11801 (from which H1-8/L1-9 was derived) (FIG. 40 through FIG. 42).

Example 3

Figure 44:
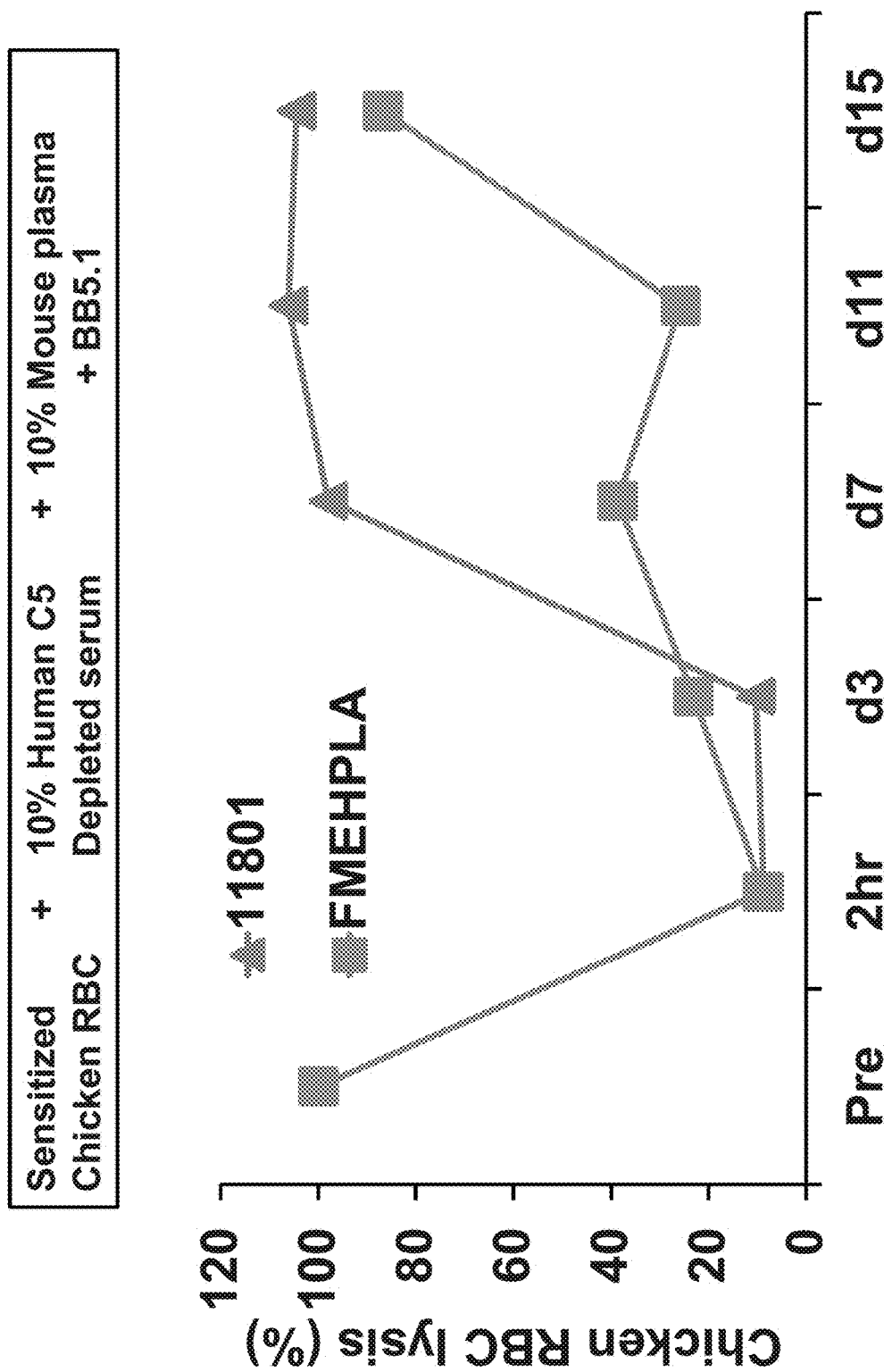
FIG. 44 depicts the results of a classical pathway complement-mediated chicken red blood cell assay assessing the pharmacodynamics of mAbs 11801 and FMEH-PLA in FcRn/SCID mice genetically modified to express human C5.
Figure 45:
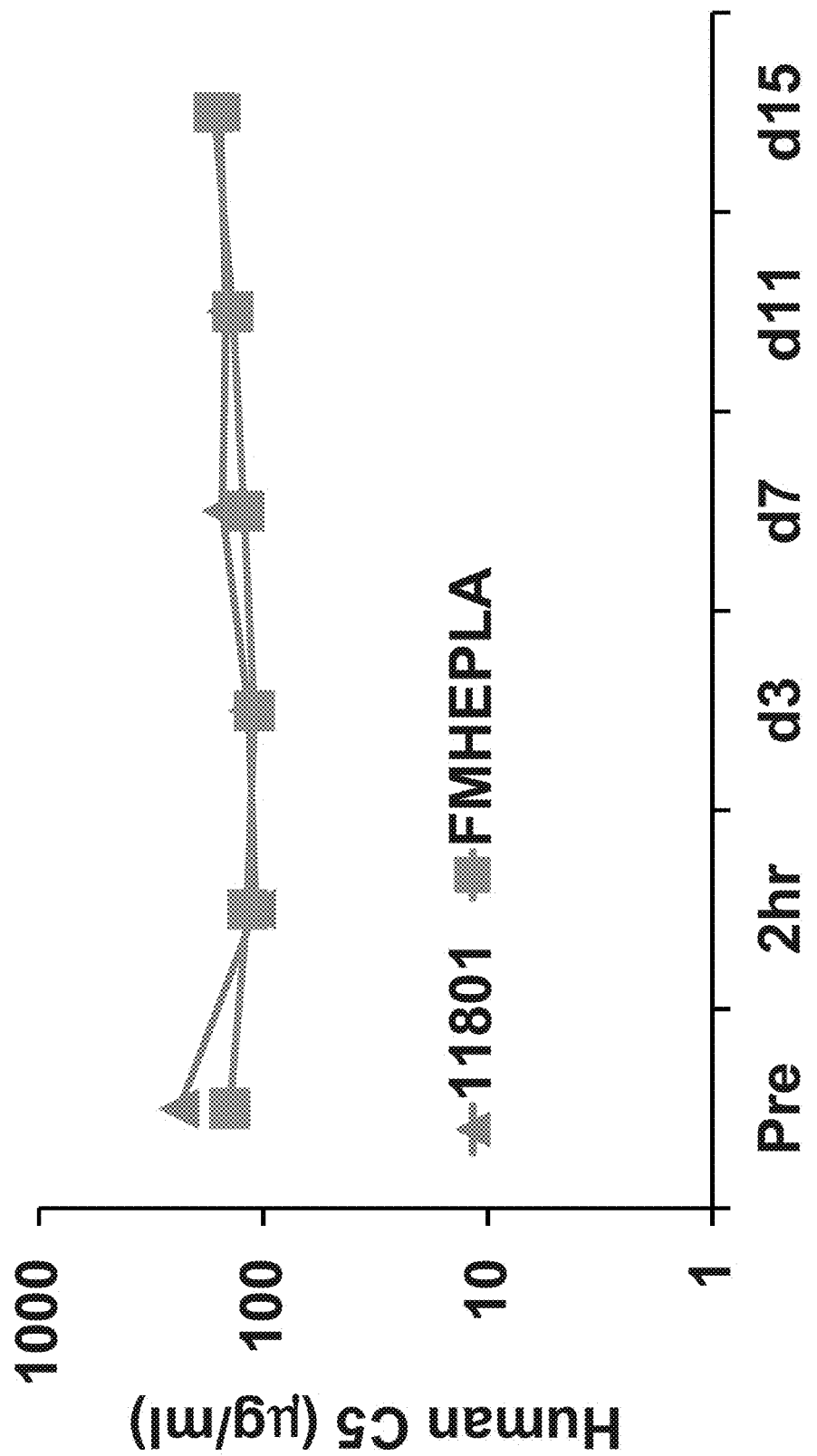
FIG. 45 depicts the results of an assay assessing the level of total C5 in the plasma of FcRn/SCID mice genetically modified to express human C5 after injection with mAbs 11801 and FMEH-PLA.

In vivo experiments were conducted to compare the PK, PD and C5 levels of the parent mAb 11801 and the engineered mAb H1-8/L1-9 FMEH-PLA. Experiments were conducted to assess the level of total hIgG4 in the plasma of FcRn/SCID mice that were genetically modified to express human C5 after injection of the mice with mAb11801 and mAb H1-8/L1-9 FMEH-PLA (FIG. 44). Further, an assay was conducted to assess the pharmacodynamics of mAb11801 and mAb H1-8/L1-9 FMEH-PLA in of FcRn/SCID mice that were genetically modified to express human C5, using the classical pathway complement-mediated chicken red blood cell assay. Further, an assay was conducted to examine the level of total C5 in the plasma of FcRn/SCID mice that were genetically modified to express human C5 after injection of the mice with mAb11801 and mAb H1-8/L1-9 FMEH-PLA (FIG. 45).

The materials and methods used in these Examples are now described.

Sandwich ELISA for Detection of Human C5 in Mice

Sandwich ELISA for detection of human C5 in NOD/SCID or FcRn/SCID mice expressing human C5 after hydrodynamic injection of human C5 cDNA plasmid: 96-well plates were coated with a anti-human C5 antibody (Quidel, A217) at a final concentration of 2 μg/mL in bicarbonate buffer at 37° C. for 1 hr. Following washes with PBS containing 0.05% Tween-20, the plates were incubated with diluted plasma samples in blocking solution at RT for 1 hr. After washing, the plates were incubated with biotinylated anti-human C5 mAb 9G6) in blocking solution at RT for 1 hr, washed again and incubated with avidin or streptavidin conjugated to horseradish peroxidase (BD pharmigen) in blocking solution at RT for 1 hr. After final washing, the plates were developed with HRP substrate for 3 min. The reaction was stopped with 2N H2SO4 and the plate was read at 450 nm in a micro plate reader. Sandwich ELISA for detection of human IgG4 in mice.

Sandwich ELISA for Detection of Human IgG4

Sandwich ELISA for detection of human IgG4 in mice treated with anti-human C5 IgG4 mAb: 96-well plates were coated with an anti-human kappa light chain antibody (Antibody Solutions, AS75-P) at a final concentration of 2 μg/mL in bicarbonate buffer at 37° C. for 1 hr. Following three washes with PBS containing 0.05% Tween-20, the plates were incubated with diluted plasma samples in blocking solution at RT for 1 hr. After washing, the plates were incubated with anti-human IgG4 HRP (1:2000 dilution, Invitrogen, A10654) in blocking solution at RT for 1 hr. After washing, the plates were developed with HRP substrate for 3 min. The reaction was stopped with 2N $H_2SO_4$ and the plate was read at 450 nm in a micro plate reader.

Sheep Red Blood Cell Lysis Test

Sheep RBCs ($1 \times 10^7$ cells per assay sample prepared in PBS, Complement Technology Inc) were incubated at 37° C. for 20 min with 50% normal human serum (NHS, from Complement Technology Inc) in gelatin veronal buffer (GVB2+, Sigma; total assay volume: 100 μL). Before addition to the sheep RBCs, NHS was pre-incubated with anti-C5 mAbs for 1 hr at 4° C. Lysis reaction was stopped by addition of ice-cold 40 mM EDTA in PBS. The incubation mixtures were centrifuged for 5 min at 1500 rpm and the supernatant was collected and measured for OD405 nm. Samples without NHS or with EDTA added were used as negative lysis controls, and a sample of sheep RBCs lysed completely with distilled water was used as a positive control (100% lysis) against which % lysis in other samples was normalized.

Chicken Red Blood Cell Lysis Assay

Chicken RBC (Rockland Immunochemicals Inc #R401-0050) were sensitized with anti-Chicken RBC antibody (Rockland Immunochemicals Inc #103-4139) (150 ug/mL) for 30 min and washed two times with GVB buffer. C5 humanized mouse lepirudin plasma pre-treated with mAb BB5.1 to block murine C5 activity and C5 depleted human serum (Quidel #A501) samples were diluted to 10% in GVB buffer (i.e., 5 mL to 50 mL final assay volume) and mixed with 5 mL of Antibody sensitized cRBC cells ul (5*10E8/mL) in final volume of 50 mL and incubated at 37° C. for 30 min. Reaction was stopped with 100 mL of cold 10 mM EDTA in PBS. Cells were centrifuged at 1500 rpm for 5 min at 4° C. Collected supernatant was measured OD at 405.

Human C5 Transposon Plasmid Construction

C5 cDNA from pCMV Sport6 sub cloned into pCAGGS vector at EcoRI site. At 5' site of the enhancer at Hinc II site SB IR/DR(L) transposon recognition sequence and at 3' site after rBG Stu I site SB IR/DR(R) recognition sequence was cloned by infusion cloning method. For hydrodynamic injection into NOD/SCD or FcRn/SCID (B6.Cg-Fcgrt$^{tm1Der}$ Prkdc$^{scid}$ Tg(FCGRT)32Dcr/DcrJ) mice, 2 μg of pCMV-T7-SB100 plasmid and 25 μg of hC5 in pCAGGS with transposon sites were injected by tail vain. Transfection efficiency was checked after day 1 by hC5 ELISA. Stable integration and permanent expression of human C5 was again checked by hC5 ELISA 2 weeks post injection.

Histidine Scanning

Histidine Scanning of humanized mAb 2G1 (VH-11801 and VL-1901):HEK cells in 24 well plates and transfected with 1 μg of VH and 2 μg of VL plasmid using 8 μL of X-TremeGene HP DNA Transfection Reagent (Roche #6366546001). Supt was collected 2 days post transfection and used for Octet assay. pH dependent dissociation of 11801 histidine mutants were analyzed by Biolayer interferometry on an Octet Red E instrument (ForteBio Inc.). Anti-human IgG Biosensors (ForteBio #18-5060). Antibody was captured onto sensors by dipping them into 200 μL of transfection supernatant for 600 sec. Later these biosensors were incubated with hC5 for 600 Sec fallowed by dissociated at pH 7.4 and pH 5.8.

Parsimonious Mutagenesis

To identify point amino acid substitution mutation that improves C5 binding at pH 7.4, all 6 complementary-determining regions (CDRs) of mAb H1-8/L1-9 was individually mutated to other 19 amino acids by a site-directed mutagenesis method. Oligonucleotides encoded designed mutation for each position are used to introduce mutations to the targeted CDR position by QuikChange® (Agilent) or Q5® Site-Directed Mutagenesis (NEB). To screen binding improved variant, 88 clones from each transfected reaction were picked and scFv secreted from the *E. coli* cell media is tested in a capture ELISA. In the capture ELISA, titrated amount of anti-Fd antibody is used to coat the wells to capture scFv from the bacteria supernatant. This was followed by incubation with biotinylated antigen. Binding signal is detected using HRP conjugated anti-Lc antibody followed by incubation with tetra-methyl-benzidine (TMB) substrate. The reaction is quenched with 0.2 M H2SO4, and the plates were read at 450 nm. Clones exhibiting an optical density (OD) 450 nm signal greater than the parental clone were picked. ScFv from regrown supernatant are re-assayed by ELISA (as above) in duplicate to confirm positive results.

The binding improved clones are further confirmed in a direct binding ELISA where antigen is coated in the ELISA wells, and calculated amount of scFv determined by a scFv quantitative ELISA is used. Clones that repeatedly exhibited greater than parental scFv binding were sequenced.

Measurement of pH Dependent Binding/Dissociation pH dependent binding of affinity matured H1-8L1-9 mutants: 2-3×10E6/mL ExpiCHO were seeded in to 24 well plates and transfected with 2 µg of VH and 4 µg of VL plasmid using 8 µL of X-TremeGene HP DNA Transfection Reagent (Roche #6366546001). Supt was collected 2 days post transfection and used for Octet assay. pH dependent dissociation of histidine mutants was analyzed by Biolayer interferometry on an Octet Red E instrument (ForteBio Inc.). Streptavidin Biosensors (ForteBio #18-5019) were coated with 3 µg/mL capture-select biotin anti human IgG 4 fab (Thermo fisher #7102902100) for 250-300 Sec and quenched with 2 mM Biocytin for 600 sec. These biosensors were incubated with 10 µg/mL hC5 (Complement tech #A320) for 600 Sec to saturate the non-specific binding of hC5 to biosensors. Antibody was captured onto sensors by dipping them into 200 µL of transfection supernatant for 600 sec. Later these biosensors were incubated with hC5 for 600 sec followed by Dissociated at pH 7.4 and pH 5.8.

Large-Scale Transfection

Large-scale ExpiCHO transfection protocol: For large-scale production of mAbs for in vivo study, ExpiCHO transfection system (Gibco #A29133) was used according to manufactures instructions using max-titer protocol. For 200 mL of Expi CHO medium 150 µg VH and 300 µg VL used for transfection.

In Vivo Pharmacokinetics (PK) and Pharmacodynamics (PD) Experiments

NOD/SCID or FcRn/SCID mice expressing human C5 by tail vein hydrodynamic injection of human C5 cDNA were screened and those that had human C5 expression at 75-100 µg/ml in blood were used for in PK/PD studies. Mice were injected with mAbs (human IgG4 format) intravenously at 40 mg/kg and Lepirudin anticoagulated blood samples were collected via retro-orbital route before mAb injection and various time points after injection. Plasma levels of human IgG and C5 in the collected samples were determined by ELISA and the pharmacodynamics of the injected mAbs was assessed by chicken red blood cell lysis test.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. An anti-human C5 antibody or antigen-binding fragment thereof that specifically binds human C5, wherein the anti-human C5 antibody or antigen-binding fragment thereof comprises:
   a) a VH-CDR1 comprising the amino acid sequence of SEQ ID NO: 47, a VH-CDR2 comprising the amino acid sequence of SEQ ID NO: 57, a VH-CDR3 comprising the amino acid sequence of SEQ ID NO: 49, a VL-CDR1 comprising the amino acid sequence of SEQ ID NO: 23, a VL-CDR2 comprising the amino acid sequence of SEQ ID NO: 9, and a VL-CDR3 comprising the amino acid sequence of SEQ ID NO: 10;
   b) a VH-CDR1 comprising the amino acid sequence of SEQ ID NO: 3, a VH-CDR2 comprising the amino acid sequence of SEQ ID NO: 4, a VH-CDR3 comprising the amino acid sequence of SEQ ID NO: 5, a VL-CDR1 comprising the amino acid sequence of SEQ ID NO: 8, a VL-CDR2 comprising the amino acid sequence of SEQ ID NO: 9, and a VL-CDR3 comprising the amino acid sequence of SEQ ID NO: 11;
   c) a VH-CDR1 comprising the amino acid sequence of SEQ ID NO: 3, a VH-CDR2 comprising the amino acid sequence of SEQ ID NO: 4, a VH-CDR3 comprising the amino acid sequence of SEQ ID NO: 5, a VL-CDR1 comprising the amino acid sequence of SEQ ID NO: 14, a VL-CDR2 comprising the amino acid sequence of SEQ ID NO: 9, and a VL-CDR3 comprising the amino acid sequence of SEQ ID NO: 10;
   d) a VH-CDR1 comprising the amino acid sequence of SEQ ID NO: 17, a VH-CDR2 comprising the amino acid sequence of SEQ ID NO: 4, a VH-CDR3 comprising the amino acid sequence of SEQ ID NO: 5, a VL-CDR1 comprising the amino acid sequence of SEQ ID NO: 8, a VL-CDR2 comprising the amino acid sequence of SEQ ID NO: 9, and a VL-CDR3 comprising the amino acid sequence of SEQ ID NO: 10;
   e) a VH-CDR1 comprising the amino acid sequence of SEQ ID NO: 20, a VH-CDR2 comprising the amino acid sequence of SEQ ID NO: 4, a VH-CDR3 comprising the amino acid sequence of SEQ ID NO: 5, a VL-CDR1 comprising the amino acid sequence of SEQ ID NO: 23, a VL-CDR2 comprising the amino acid sequence of SEQ ID NO: 9, and a VL-CDR3 comprising the amino acid sequence of SEQ ID NO: 10;
   f) a VH-CDR1 comprising the amino acid sequence of SEQ ID NO: 3, a VH-CDR2 comprising the amino acid sequence of SEQ ID NO: 26, a VH-CDR3 comprising the amino acid sequence of SEQ ID NO: 5, a VL-CDR1 comprising the amino acid sequence of SEQ ID NO: 8, a VL-CDR2 comprising the amino acid sequence of SEQ ID NO: 9, and a VL-CDR3 comprising the amino acid sequence of SEQ ID NO: 29;
   g) a VH-CDR1 comprising the amino acid sequence of SEQ ID NO: 3, a VH-CDR2 comprising the amino acid sequence of SEQ ID NO: 34, a VH-CDR3 comprising the amino acid sequence of SEQ ID NO: 5, a VL-CDR1 comprising the amino acid sequence of SEQ ID NO: 8, a VL-CDR2 comprising the amino acid sequence of SEQ ID NO: 9, and a VL-CDR3 comprising the amino acid sequence of SEQ ID NO: 10;
   h) a VH-CDR1 comprising the amino acid sequence of SEQ ID NO: 37, a VH-CDR2 comprising the amino acid sequence of SEQ ID NO: 38, a VH-CDR3 comprising the amino acid sequence of SEQ ID NO: 39, a VL-CDR1 comprising the amino acid sequence of SEQ ID NO: 23, a VL-CDR2 comprising the amino acid sequence of SEQ ID NO: 9, and a VL-CDR3 comprising the amino acid sequence of SEQ ID NO: 10;
   i) a VH-CDR1 comprising the amino acid sequence of SEQ ID NO: 42, a VH-CDR2 comprising the amino acid sequence of SEQ ID NO: 43, a VH-CDR3 comprising the amino acid sequence of SEQ ID NO: 44, a VL-CDR1 comprising the amino acid sequence of SEQ ID NO: 23, a VL-CDR2 comprising the amino acid sequence of SEQ ID NO: 9, and a VL-CDR3 comprising the amino acid sequence of SEQ ID NO: 10;
   j) a VH-CDR1 comprising the amino acid sequence of SEQ ID NO: 47, a VH-CDR2 comprising the amino acid sequence of SEQ ID NO: 48, a VH-CDR3 comprising the amino acid sequence of SEQ ID NO: 49, a VL-CDR1 comprising the amino acid sequence of SEQ ID NO: 23, a VL-CDR2 comprising the amino acid sequence of SEQ ID NO: 9, and a VL-CDR3 comprising the amino acid sequence of SEQ ID NO: 10;
   k) a VH-CDR1 comprising the amino acid sequence of SEQ ID NO: 52, a VH-CDR2 comprising the amino acid sequence of SEQ ID NO: 53, a VH-CDR3 comprising the amino acid sequence of SEQ ID NO: 54, a VL-CDR1 comprising the amino acid sequence of SEQ ID NO: 23, a VL-CDR2 comprising the amino acid sequence of SEQ ID NO: 9, and a VL-CDR3 comprising the amino acid sequence of SEQ ID NO: 10;
   l) a VH-CDR1 comprising the amino acid sequence of SEQ ID NO: 37, a VH-CDR2 comprising the amino acid sequence of SEQ ID NO: 62, a VH-CDR3 comprising the amino acid sequence of SEQ ID NO: 39, a VL-CDR1 comprising the amino acid sequence of SEQ ID NO: 23, a VL-CDR2 comprising the amino acid sequence of SEQ ID NO: 9, and a VL-CDR3 comprising the amino acid sequence of SEQ ID NO: 10;

m) a VH-CDR1 comprising the amino acid sequence of SEQ ID NO: 42, a VH-CDR2 comprising the amino acid sequence of SEQ ID NO: 65, a VH-CDR3 comprising the amino acid sequence of SEQ ID NO: 44, a VL-CDR1 comprising the amino acid sequence of SEQ ID NO: 23, a VL-CDR2 comprising the amino acid sequence of SEQ ID NO: 9, and a VL-CDR3 comprising the amino acid sequence of SEQ ID NO: 10; or n) a VH-CDR1 comprising the amino acid sequence of SEQ ID NO: 52, a VH-CDR2 comprising the amino acid sequence of SEQ ID NO: 68, a VH-CDR3 comprising the amino acid sequence of SEQ ID NO: 54, a VL-CDR1 comprising the amino acid sequence of SEQ ID NO: 23, a VL-CDR2 comprising the amino acid sequence of SEQ ID NO: 9, and a VL-CDR3 comprising the amino acid sequence of SEQ ID NO: 10.

2. The anti-human C5 antibody or antigen-binding fragment thereof of claim 1, wherein the anti-human C5 antibody or antigen-binding fragment thereof comprises:

a) a VH comprising the amino acid residues 20-144 of SEQ ID NO: 59, or a variant thereof comprising at least about 85% sequence identity to the amino acid residues 20-144 of SEQ ID NO: 59; and a VL comprising the amino acid residues 21-127 of SEQ ID NO: 25, or a variant thereof comprising at least about 85% sequence identity to the amino acid residues 21-127 of SEQ ID NO: 25;

b) a VH comprising the amino acid residues 20-144 of SEQ ID NO: 2, or a variant thereof comprising at least about 85% sequence identity to the amino acid residues 20-144 of SEQ ID NO: 2; and a VL comprising the amino acid residues 21-127 of SEQ ID NO: 13, or a variant thereof comprising at least about 85% identity to amino acid residues 21-127 of SEQ ID NO: 13;

c) a VH comprising the amino acid residues 20-144 of SEQ ID NO: 2, or a variant thereof comprising at least about 85% sequence identity to the amino acid residues 20-144 of SEQ ID NO: 2; and a VL comprising the amino acid residues 21-127 of SEQ ID NO: 16 or a variant thereof comprising at least about 85% identity to residues 21-127 of SEQ ID NO: 16;

d) a VH comprising the amino acid residues 20-144 of SEQ ID NO: 19, or a variant thereof comprising at least about 85% identity to amino acid residues 20-144 of SEQ ID NO: 19; and a VL comprising the amino acid residues 21-127 of SEQ ID NO: 7, or a variant thereof comprising at least about 85% identity to residues 21-127 of SEQ ID NO: 7;

e) a VH comprising the amino acid residues 20-144 of SEQ ID NO: 22, or a variant thereof comprising at least about 85% identity to amino acid residues 20-144 of SEQ ID NO: 22; and a VL comprising the amino acid residues 21-127 of SEQ ID NO: 25, or a variant thereof comprising at least about 85% identity to residues 21-127 of SEQ ID NO: 25;

f) a VH comprising the amino acid residues 20-144 of SEQ ID NO: 28, or a variant thereof comprising at least about 85% identity to amino acid residues 20-144 of SEQ ID NO: 28; and a VL comprising the amino acid residues 21-127 of SEQ ID NO: 31, or a variant thereof comprising at least about 85% identity to residues 21-127 of SEQ ID NO: 31;

g) a VH comprising the amino acid residues 20-144 of SEQ ID NO: 36, or a variant thereof comprising at least about 85% identity to amino acid residues 20-144 of SEQ ID NO: 36; and a VL comprising the amino acid residues 21-127 of SEQ ID NO: 7, or a variant thereof comprising at least about 85% identity to residues 21-127 of SEQ ID NO: 7;

h) a VH comprising the amino acid residues 20-144 of SEQ ID NO: 41, or a variant thereof comprising at least about 85% identity to amino acid residues 20-144 of SEQ ID NO: 41; and a VL comprising the amino acid residues 21-127 of SEQ ID NO: 25, or a variant thereof comprising at least about 85% identity to residues 21-127 of SEQ ID NO: 25;

i) a VH comprising the amino acid residues 20-144 of SEQ ID NO: 46, or a variant thereof comprising at least about 85% identity to amino acid residues 20-144 of SEQ ID NO: 46; and a VL comprising the amino acid residues 21-127 of SEQ ID NO: 25, or a variant thereof comprising at least about 85% identity to residues 21-127 of SEQ ID NO: 25;

j) a VH comprising the amino acid residues 20-144 of SEQ ID NO: 51, or a variant thereof comprising at least about 85% identity to amino acid residues 20-144 of SEQ ID NO: 51; and a VL comprising the amino acid residues 21-127 of SEQ ID NO: 25 or a variant thereof comprising at least about 85% identity to residues 21-127 of SEQ ID NO: 25;

k) a VH comprising the amino acid residues 20-144 of SEQ ID NO: 56, or a variant thereof comprising at least about 85% identity to amino acid residues 20-144 of SEQ ID NO: 56; and a VL comprising the amino acid residues 21-127 of SEQ ID NO: 25, or a variant thereof comprising at least about 85% identity to residues 21-127 of SEQ ID NO: 25;

l) a VH comprising the amino acid residues 20-144 of SEQ ID NO: 64, or a variant thereof comprising at least about 85% identity to amino acid residues 20-144 of SEQ ID NO: 64; and a VL comprising the amino acid residues 21-127 of SEQ ID NO: 25, or a variant thereof comprising at least about 85% identity to residues 21-127 of SEQ ID NO: 25;

m) a VH comprising the amino acid residues 20-144 of SEQ ID NO: 67, or a variant thereof comprising at least about 85% identity to amino acid residues 20-144 of SEQ ID NO: 67; and a VL comprising the amino acid residues 21-127 of SEQ ID NO: 25, or a variant thereof comprising at least about 85% identity to residues 21-127 of SEQ ID NO: 25; or n) a VH comprising the amino acid residues 20-144 of SEQ ID NO: 70, or a variant thereof comprising at least about 85% identity to amino acid residues 20-144 of SEQ ID NO: 70; and a VL comprising the amino acid residues 21-127 of SEQ ID NO: 25, or a variant thereof comprising at least about 85% identity to residues 21-127 of SEQ ID NO: 25.

3. The anti-human C5 antibody or antigen-binding fragment thereof of claim 2, wherein the anti-human C5 antibody or antigen-binding fragment thereof comprises:

a) a VH comprising the amino acid residues 20-144 of SEQ ID NO: 59, and a VL comprising the amino acid residues 21-127 of SEQ ID NO: 25;

b) a VH comprising the amino acid residues 20-144 of SEQ ID NO: 2, and a VL comprising the amino acid residues 21-127 of SEQ ID NO: 13;

c) a VH comprising the amino acid residues 20-144 of SEQ ID NO: 2, and a VL comprising the amino acid residues 21-127 of SEQ ID NO: 16;

d) a VH comprising the amino acid residues 20-144 of SEQ ID NO: 19, and a VL comprising the amino acid residues 21-127 of SEQ ID NO: 7;

e) a VH comprising the amino acid residues 20-144 of SEQ ID NO: 22, and a VL comprising the amino acid residues 21-127 of SEQ ID NO: 25;

f) a VH comprising the amino acid residues 20-144 of SEQ ID NO: 28, and a VL comprising the amino acid residues 21-127 of SEQ ID NO: 31;

g) a VH comprising the amino acid residues 20-144 of SEQ ID NO: 36, and a VL comprising the amino acid residues 21-127 of SEQ ID NO: 7;

h) a VH comprising the amino acid residues 20-144 of SEQ ID NO: 41, and a VL comprising the amino acid residues 21-127 of SEQ ID NO: 25;

i) a VH comprising the amino acid residues 20-144 of SEQ ID NO: 46, and a VL comprising the amino acid residues 21-127 of SEQ ID NO: 25;

j) a VH comprising the amino acid residues 20-144 of SEQ ID NO: 51, and a VL comprising the amino acid residues 21-127 of SEQ ID NO: 25;

k) a VH comprising the amino acid residues 20-144 of SEQ ID NO: 56, and a VL comprising the amino acid residues 21-127 of SEQ ID NO: 25;

l) a VH comprising the amino acid residues 20-144 of SEQ ID NO: 64, and a VL comprising the amino acid residues 21-127 of SEQ ID NO: 25;

m) a VH comprising the amino acid residues 20-144 of SEQ ID NO: 67, and a VL comprising the amino acid residues 21-127 of SEQ ID NO: 25; or n) a VH comprising the amino acid residues 20-144 of SEQ ID NO: 70, and a VL comprising the amino acid residues 21-127 of SEQ ID NO: 25.

4. The anti-human C5 antibody or antigen-binding fragment thereof of claim 1, wherein the anti-human C5 antibody or antigen-binding fragment thereof is a full-length antibody, a Fab, a Fab', a F(ab)2, a F(ab')2, an scFv, or a combination thereof.

5. The anti-human C5 antibody or antigen-binding fragment thereof of claim 1, wherein the anti-human C5 antibody is a full-length antibody.

6. The anti-human C5 antibody of claim 5, wherein the anti-human C5 full-length antibody comprises an Fc fragment derived from a human IgG4 Fc.

7. The anti-human C5 antibody of claim 5, wherein the anti-human C5 full-length antibody comprises:

a) a human IgG4 heavy chain constant domain comprising the amino acid sequence of SEQ ID NO: 32;

b) a human IgG4 heavy chain constant domain comprising the amino acid sequence of SEQ ID NO: 33;

c) a human IgG4 heavy chain constant domain having an S108P mutation, a M308L mutation, and a N314A mutation relative to SEQ ID NO: 32; or d) a human IgG4 heavy chain constant domain comprising the amino acid sequence of SEQ ID NO: 61.

8. A fusion protein comprising the anti-human C5 antibody or antigen-binding fragment thereof of claim 1 fused to an effector molecule, an FcRn molecule, or a targeting moiety.

9. An isolated nucleic acid encoding the anti-human C5 antibody or antigen-binding fragment thereof of claim 1.

10. A vector comprising the isolated nucleic acid of claim 9.

11. The vector of claim 10, which is a viral vector.

12. The vector of claim 11, wherein the viral vector is a retrovirus vector, an adenovirus vector, an adeno-associated virus vector, an herpes virus vector, a lentivirus vector, a murine stem cell virus vector, a moloney murine leukemia virus vector, or a human immunodeficiency virus vector.

13. A host cell comprising the isolated nucleic acid of claim 9.

14. A method of producing an anti-human C5 antibody or antigen-binding fragment thereof, comprising:

i) culturing the host cell of claim 13 under a condition suitable for the expression of the encoded anti-human C5 antibody or antigen-binding fragment thereof; and ii) recovering the expressed anti-human C5 antibody or antigen-binding fragment thereof from the cell culture.

15. A pharmaceutical composition comprising the anti-human C5 antibody or antigen-binding fragment thereof of claim 1, and a pharmaceutically acceptable carrier.

16. A method of treating a complement pathway-mediated disease or disorder in an individual, comprising administering to said individual the anti-human C5 antibody or antigen-binding fragment thereof of claim 1.

17. A method of treating a complement pathway-mediated disease or disorder in an individual, comprising administering to said individual the vector of claim 11.

18. A method of reducing the activity of a complement system of an individual, wherein the method comprises administering to the individual the anti-human C5 antibody or antigen-binding fragment thereof of claim 1.

19. The method of claim 16, wherein the individual is a human.

20. The method of claim 18, wherein the individual is a human.

* * * * *

SEQUENCE LISTING

```
<160> NUMBER OF SEQ ID NOS: 70

<210> SEQ ID NO 1
<211> LENGTH: 482
<212> TYPE: DNA
<213> ORGANISM: Artificial Sequence
<220> FEATURE:
<223> OTHER INFORMATION: Nucleotide sequence of humanized 2G1 VH-11801

<400> SEQUENCE: 1
cagcatatga tcagtgtcct ctccaaagtc cttgaacata gactctaacc atggactgga      60
cctgggtctt tctcttcctc ctgtcagtaa ctgcaggtgt ccactcccag gttcagctgg     120
tgcagtctgg agctgaggtg aagaagcctg gggcctcagt gaaggtctcc tgcaaggctt     180
ctggatacac aatcacagac tacaatttgg actgggtgcg acaggcccct ggacaagggc     240
ttgagtggat gggagatatt agtcctaact atggttatac tatctacaac cagaaattca     300
aggacagagt caccatgacc acagacacat ccacgagcac agcctacatg gagctgagga     360
gcctgagatc tgacgacacg gccgtgtatt actgtgcgag aagggacatt cgttactccg     420
gtaattccta caaatggtac ttcgatgtct ggggccaagg gacaatggtc accgtctctt     480
ca                                                                    482

<210> SEQ ID NO 2
<211> LENGTH: 144
<212> TYPE: PRT
<213> ORGANISM: Artificial Sequence
<220> FEATURE:
<223> OTHER INFORMATION: Amino acid sequence of humanized 2G1 VH-11801

<400> SEQUENCE: 2

Met Asp Trp Thr Trp Val Phe Leu Phe Leu Leu Ser Val Thr Ala Gly
 1               5                  10                  15
```

```
Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Ile
        35                  40                  45

Thr Asp Tyr Asn Leu Asp Trp Val Arg Gln Ala Pro Gly Gln Gly Leu
    50                  55                  60

Glu Trp Met Gly Asp Ile Ser Pro Asn Tyr Gly Tyr Thr Ile Tyr Asn
65                  70                  75                  80

Gln Lys Phe Lys Asp Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Arg Asp Ile Arg Tyr Ser Gly Asn Ser Tyr Lys
        115                 120                 125

Trp Tyr Phe Asp Val Trp Gly Gln Gly Thr Met Val Thr Val Ser Ser
    130                 135                 140

<210> SEQ ID NO 3
<211> LENGTH: 10
<212> TYPE: PRT
<213> ORGANISM: Artificial Sequence
<220> FEATURE:
<223> OTHER INFORMATION: Amino acid sequence of CDR1 of humanized 2G1
      VH-11801

<400> SEQUENCE: 3

Gly Tyr Thr Ile Thr Asp Tyr Asn Leu Asp
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Amino acid sequence of CDR2 of humanized 2G1
      VH-11801

<400> SEQUENCE: 4

Asp Ile Ser Pro Asn Tyr Gly Tyr Thr Ile Tyr Asn Gln Lys Phe Lys
1               5                   10                  15

Asp

<210> SEQ ID NO 5
<211> LENGTH: 16
<212> TYPE: PRT
<213> ORGANISM: Artificial Sequence
<220> FEATURE:
<223> OTHER INFORMATION: Amino acid sequence of CDR3 of humanized 2G1
      VH-11801

<400> SEQUENCE: 5

Arg Asp Ile Arg Tyr Ser Gly Asn Ser Tyr Lys Trp Tyr Phe Asp Val
1               5                   10                  15

<210> SEQ ID NO 6
<211> LENGTH: 428
<212> TYPE: DNA
<213> ORGANISM: Artificial Sequence
<220> FEATURE:
<223> OTHER INFORMATION: Nucleotide sequence of humanized 2G1 VL-1901
```

<400> SEQUENCE: 6

```
gtcagagccc tggggaggaa ctgctcagtt aggacccaga gggaaccatg gaagcccag      60
ctcagcttct cttcctcctg ctactctggc tcccagatac caccggagac atccagttga    120
cccagtctcc atccttcctg tctgcatctg taggagacag agtcaccatc acttgcagga    180
caagtaagag cataagcaaa tatttagcct ggtatcagca aaaaccaggg aaagccccta    240
agctcctgat ctattctgga tccaccttgc aatctggggt cccatcaagg ttcagcggca    300
gtggatctgg gacagaattc actctcacaa tcagcagcct gcagcctgaa gattttgcaa    360
cttattactg tcaacaacat aatgaatacc cgtacacgtt tggccagggg accaagctgg    420
agatcaaa                                                             428
```

<210> SEQ ID NO 7
<211> LENGTH: 127
<212> TYPE: PRT
<213> ORGANISM: Artificial Sequence
<220> FEATURE:
<223> OTHER INFORMATION: Amino acid sequence of humanized 2G1 VL-1901

<400> SEQUENCE: 7

```
Met Glu Ala Pro Ala Gln Leu Leu Phe Leu Leu Leu Leu Trp Leu Pro
1               5                   10                  15

Asp Thr Thr Gly Asp Ile Gln Leu Thr Gln Ser Pro Ser Phe Leu Ser
            20                  25                  30

Ala Ser Val Gly Asp Arg Val Thr Ile Thr Cys Arg Thr Ser Lys Ser
        35                  40                  45

Ile Ser Lys Tyr Leu Ala Trp Tyr Gln Gln Lys Pro Gly Lys Ala Pro
    50                  55                  60

Lys Leu Leu Ile Tyr Ser Gly Ser Thr Leu Gln Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Tyr Cys Gln Gln His Asn
            100                 105                 110

Glu Tyr Pro Tyr Thr Phe Gly Gln Gly Thr Lys Leu Glu Ile Lys
        115                 120                 125
```

<210> SEQ ID NO 8
<211> LENGTH: 11
<212> TYPE: PRT
<213> ORGANISM: Artificial Sequence
<220> FEATURE:
<223> OTHER INFORMATION: Amino acid sequence of CDR1 of humanized 2G1
    VL-1901

<400> SEQUENCE: 8

```
Arg Thr Ser Lys Ser Ile Ser Lys Tyr Leu Ala
1               5                   10
```

<210> SEQ ID NO 9
<211> LENGTH: 7
<212> TYPE: PRT
<213> ORGANISM: Artificial Sequence
<220> FEATURE:
<223> OTHER INFORMATION: Amino acid sequence of CDR2 of humanized 2G1

VL-1901

<400> SEQUENCE: 9

Ser Gly Ser Thr Leu Gln Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Amino acid sequencen of CDR3 of humanized 2G1
      VL-1901

<400> SEQUENCE: 10

Gln Gln His Asn Glu Tyr Pro Tyr Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Amino acid sequence of CDR3 of humanized 2G1
      VL-1901 variant (Q->H mutation in CDR3)

<400> SEQUENCE: 11

His Gln His Asn Glu Tyr Pro Tyr Thr
1               5

<210> SEQ ID NO 12
<211> LENGTH: 428
<212> TYPE: DNA
<213> ORGANISM: Artificial Sequence
<220> FEATURE:
<223> OTHER INFORMATION: Nucleotide sequence of humanized 2G1 VL-1901
      variant (Q->H mutation in CDR3)

<400> SEQUENCE: 12
gtcagagccc tggggaggaa ctgctcagtt aggacccaga gggaaccatg gaagccccag    60
ctcagcttct cttcctcctg ctactctggc tcccagatac caccggagac atccagttga   120
cccagtctcc atccttcctg tctgcatctg taggagacag agtcaccatc acttgcagga   180
caagtaagag cataagcaaa tatttagcct ggtatcagca aaaaccaggg aaagccccta   240
agctcctgat ctattctgga tccaccttgc aatctggggt cccatcaagg ttcagcggca   300
gtggatctgg gacagaattc actctcacaa tcagcagcct gcagcctgaa gattttgcaa   360
cttattactg tcatcaacat aatgaatacc cgtacacgtt tggccagggg accaagctgg   420
agatcaaa                                                            428

<210> SEQ ID NO 13
<211> LENGTH: 127
<212> TYPE: PRT
<213> ORGANISM: Artificial Sequence
<220> FEATURE:
<223> OTHER INFORMATION: Amino acid sequence of humanized 2G1 VL-1901
      variant (Q->H mutation in CDR3)

<400> SEQUENCE: 13

Met Glu Ala Pro Ala Gln Leu Leu Phe Leu Leu Leu Leu Trp Leu Pro
1               5                   10                  15

Asp Thr Thr Gly Asp Ile Gln Leu Thr Gln Ser Pro Ser Phe Leu Ser
            20                  25                  30

```
Ala Ser Val Gly Asp Arg Val Thr Ile Thr Cys Arg Thr Lys Ser
            35                  40                  45

Ile Ser Lys Tyr Leu Ala Trp Tyr Gln Gln Lys Pro Gly Lys Ala Pro
 50                  55                  60

Lys Leu Leu Ile Tyr Ser Gly Ser Thr Leu Gln Ser Gly Val Pro Ser
 65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Tyr Cys His Gln His Asn
            100                 105                 110

Glu Tyr Pro Tyr Thr Phe Gly Gln Gly Thr Lys Leu Glu Ile Lys
        115                 120                 125
```

<210> SEQ ID NO 14
<211> LENGTH: 11
<212> TYPE: PRT
<213> ORGANISM: Artificial Sequence
<220> FEATURE:
<223> OTHER INFORMATION: Amino acid sequence of CDR1 of humanized 2G1
      VL-1901 variant (T->H mutation in CDR1)

<400> SEQUENCE: 14

```
Arg His Ser Lys Ser Ile Ser Lys Tyr Leu Ala
 1               5                  10
```

<210> SEQ ID NO 15
<211> LENGTH: 428
<212> TYPE: DNA
<213> ORGANISM: Artificial Sequence
<220> FEATURE:
<223> OTHER INFORMATION: Nucleotide sequence of Humanized 2G1 VL-1901
      variant (T->H mutation in CDR1)

<400> SEQUENCE: 15

```
gtcagagccc tggggaggaa ctgctcagtt aggacccaga gggaaccatg gaagccccag      60
ctcagcttct cttcctcctg ctactctggc tcccagatac accggagaca tccagttga     120 cccagtctcc atccttcctg tctgcatctg taggagacag agtcaccatc acttgcaggc    180
atagtaagag cataagcaaa tatttagcct ggtatcagca aaaaccaggg aaagccccta    240
agctcctgat ctattctgga tccaccttgc aatctggggt cccatcaagg ttcagcggca    300
gtggatctgg gacagaattc actctcacaa tcagcagcct gcagcctgaa gattttgcaa    360
cttattactg tcaacaacat aatgaatacc cgtacacgtt tggccagggg accaagctgg    420
agatcaaa                                                             428
```

<210> SEQ ID NO 16
<211> LENGTH: 127
<212> TYPE: PRT
<213> ORGANISM: Artificial Sequence
<220> FEATURE:
<223> OTHER INFORMATION: Amino acid sequence of humanized 2G1 VL-1901
      variant (T->H mutation in CDR1)

<400> SEQUENCE: 16

```
Met Glu Ala Pro Ala Gln Leu Leu Phe Leu Leu Leu Leu Trp Leu Pro
 1               5                  10                  15

Asp Thr Thr Gly Asp Ile Gln Leu Thr Gln Ser Pro Ser Phe Leu Ser
                20                  25                  30

Ala Ser Val Gly Asp Arg Val Thr Ile Thr Cys Arg His Ser Lys Ser
            35                  40                  45
```

```
Ile Ser Lys Tyr Leu Ala Trp Tyr Gln Gln Lys Pro Gly Lys Ala Pro
    50                  55                  60

Lys Leu Leu Ile Tyr Ser Gly Ser Thr Leu Gln Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Tyr Cys Gln Gln His Asn
            100                 105                 110

Glu Tyr Pro Tyr Thr Phe Gly Gln Gly Thr Lys Leu Glu Ile Lys
        115                 120                 125
```

<210> SEQ ID NO 17
<211> LENGTH: 10
<212> TYPE: PRT
<213> ORGANISM: Artificial Sequence
<220> FEATURE:
<223> OTHER INFORMATION: Amino acid sequence of CDR1 of humanized 2G1
      VH-11801 variant (I->H mutation in CDR1)

<400> SEQUENCE: 17

```
Gly Tyr Thr His Thr Asp Tyr Asn Leu Asp
1               5                   10
```

<210> SEQ ID NO 18
<211> LENGTH: 482
<212> TYPE: DNA
<213> ORGANISM: Artificial Sequence
<220> FEATURE:
<223> OTHER INFORMATION: Nucleotide sequence of humanized 2G1 VH-11801
      variant (I->H mutation in CDR1)

<400> SEQUENCE: 18

```
cagcatatga tcagtgtcct ctccaaagtc cttgaacata gactctaacc atggactgga      60
cctgggtctt tctcttcctc ctgtcagtaa ctgcaggtgt ccactcccag gttcagctgg     120
tgcagtctgg agctgaggtg aagaagcctg ggcctcagt gaaggtctcc tgcaaggctt      180
ctggatacac acatacagac tacaatttgg actgggtgcg acaggcccct ggacaagggc     240
ttgagtggat gggagatatt agtcctaact atggttatac tatctacaac cagaaattca     300
aggacagagt caccatgacc acagacacat ccacgagcac agcctacatg agctgagga     360
gcctgagatc tgacgacacg gccgtgtatt actgtgcgag aagggacatt cgttactccg     420
gtaattccta caaatggtac ttcgatgtct ggggccaagg gacaatggtc accgtctctt     480
ca                                                                    482
```

<210> SEQ ID NO 19
<211> LENGTH: 144
<212> TYPE: PRT
<213> ORGANISM: Artificial Sequence
<220> FEATURE:
<223> OTHER INFORMATION: Amino acid sequence of humanized 2G1 VH-11801
      variant (I->H mutation in CDR1)

<400> SEQUENCE: 19

```
Met Asp Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr His
        35                  40                  45
```

```
Thr Asp Tyr Asn Leu Asp Trp Val Arg Gln Ala Pro Gly Gln Gly Leu
     50                  55                  60

Glu Trp Met Gly Asp Ile Ser Pro Asn Tyr Gly Tyr Thr Ile Tyr Asn
 65              70                  75                  80

Gln Lys Phe Lys Asp Arg Val Thr Met Thr Asp Thr Ser Thr Ser
                 85                  90                  95

Thr Ala Tyr Met Glu Leu Arg Ser Leu Arg Ser Asp Asp Thr Ala Val
             100                 105                 110

Tyr Tyr Cys Ala Arg Arg Asp Ile Arg Tyr Ser Gly Asn Ser Tyr Lys
             115                 120                 125

Trp Tyr Phe Asp Val Trp Gly Gln Gly Thr Met Val Thr Val Ser Ser
             130                 135                 140

<210> SEQ ID NO 20
<211> LENGTH: 10
<212> TYPE: PRT
<213> ORGANISM: Artificial Sequence
<220> FEATURE:
<223> OTHER INFORMATION: Amino acid sequence of CDR1 of humanized 2G1
      VH-11801 variant (N->H mutation in CDR1)

<400> SEQUENCE: 20

Gly Tyr Thr Ile Thr Asp Tyr His Leu Asp
 1               5                  10

<210> SEQ ID NO 21
<211> LENGTH: 482
<212> TYPE: DNA
<213> ORGANISM: Artificial Sequence
<220> FEATURE:
<223> OTHER INFORMATION: Nucleotide sequence of humanized 2G1 VH-11801
      variant (N->H mutation in CDR1)

<400> SEQUENCE: 21
cagcatatga tcagtgtcct ctccaaagtc cttgaacata gactctaacc atggactgga      60
cctgggtctt tctcttcctc ctgtcagtaa ctgcaggtgt ccactcccag gttcagctgg     120
tgcagtctgg agctgaggtg aagaagcctg ggcctcagt gaaggtctcc tgcaaggctt      180
ctggatacac aatcacagac taccatttgg actgggtgcg acaggcccct ggacaagggc     240
ttgagtggat gggagatatt agtcctaact atggttatac tatctacaac cagaaattca     300
aggacagagt caccatgacc acagacacat ccacgagcac agcctacatg gagctgagga     360
gcctgagatc tgacgacacg gccgtgtatt actgtgcgag aagggacatt cgttactccg     420
gtaattccta caaatggtac ttcgatgtct ggggccaagg gacaatggtc accgtctctt     480
ca                                                                   482

<210> SEQ ID NO 22
<211> LENGTH: 144
<212> TYPE: PRT
<213> ORGANISM: Artificial Sequence
<220> FEATURE:
<223> OTHER INFORMATION: Amino acid sequence of humanized 2G1 VH-11801
      variant (N->H mutation in CDR1)

<400> SEQUENCE: 22

Met Asp Trp Thr Trp Val Phe Leu Phe Leu Leu Ser Val Thr Ala Gly
 1               5                  10                  15

Val His Ser Gln Val Gln Leu Val Gln Ser Gly Ala Glu Val Lys Lys
             20                  25                  30
```

```
Pro Gly Ala Ser Val Lys Val Ser Cys Lys Ala Ser Gly Tyr Thr Ile
            35                  40                  45

Thr Asp Tyr His Leu Asp Trp Val Arg Gln Ala Pro Gly Gln Gly Leu
 50                  55                  60

Glu Trp Met Gly Asp Ile Ser Pro Asn Tyr Gly Tyr Thr Ile Tyr Asn
 65                  70                  75                  80

Gln Lys Phe Lys Asp Arg Val Thr Met Thr Thr Asp Thr Ser Thr Ser
                 85                  90                  95

Thr Ala Tyr Met Glu Leu Arg Ser Leu Arg Ser Asp Asp Thr Ala Val
                100                 105                 110

Tyr Tyr Cys Ala Arg Arg Asp Ile Arg Tyr Ser Gly Asn Ser Tyr Lys
            115                 120                 125

Trp Tyr Phe Asp Val Trp Gly Gln Gly Thr Met Val Thr Val Ser Ser
130                 135                 140
```

```
<210> SEQ ID NO 23
<211> LENGTH: 11
<212> TYPE: PRT
<213> ORGANISM: Artificial Sequence
<220> FEATURE:
<223> OTHER INFORMATION: Amino acid sequence of CDR1 of humanized 2G1
      VL-1901 variant (Y->H mutation in CDR1)

<400> SEQUENCE: 23

Arg Thr Ser Lys Ser Ile Ser Lys His Leu Ala
1               5                   10

<210> SEQ ID NO 24
<211> LENGTH: 428
<212> TYPE: DNA
<213> ORGANISM: Artificial Sequence
<220> FEATURE:
<223> OTHER INFORMATION: Nucleotide sequence of humanized 2G1 VL-1901
      variant (Y->H mutation in CDR1)

<400> SEQUENCE: 24
gtcagagccc tggggaggaa ctgctcagtt aggacccaga gggaaccatg gaagccccag      60
ctcagcttct cttcctcctg ctactctggc tcccagatac caccggagac atccagttga     120
cccagtctcc atccttcctg tctgcatctg taggagacag agtcaccatc acttgcagga     180
caagtaagag cataagcaaa catttagcct ggtatcagca aaaaccaggg aaagccccta     240
agctcctgat ctattctgga tccaccttgc aatctggggt cccatcaagg ttcagcggca     300
gtggatctgg gacagaattc actctcacaa tcagcagcct gcagcctgaa gattttgcaa     360
cttattactg tcaacaacat aatgaatacc cgtacacgtt tggccagggg accaagctgg     420
agatcaaa                                                              428

<210> SEQ ID NO 25
<211> LENGTH: 127
<212> TYPE: PRT
<213> ORGANISM: Artificial Sequence
<220> FEATURE:
<223> OTHER INFORMATION: Amino acid sequence of humanized 2G1 VL-1901
      variant (Y->H mutation in CDR1)

<400> SEQUENCE: 25

Met Glu Ala Pro Ala Gln Leu Leu Phe Leu Leu Leu Leu Trp Leu Pro
1               5                   10                  15

Asp Thr Thr Gly Asp Ile Gln Leu Thr Gln Ser Pro Ser Phe Leu Ser
            20                  25                  30
```

-continued

```
Ala Ser Val Gly Asp Arg Val Thr Ile Thr Cys Arg Thr Ser Lys Ser
        35                  40                  45

Ile Ser Lys His Leu Ala Trp Tyr Gln Gln Lys Pro Gly Lys Ala Pro
 50                  55                  60

Lys Leu Leu Ile Tyr Ser Gly Ser Thr Leu Gln Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Tyr Cys Gln Gln His Asn
            100                 105                 110

Glu Tyr Pro Tyr Thr Phe Gly Gln Gly Thr Lys Leu Glu Ile Lys
        115                 120                 125

<210> SEQ ID NO 26
<211> LENGTH: 17
<212> TYPE: PRT
<213> ORGANISM: Artificial Sequence
<220> FEATURE:
<223> OTHER INFORMATION: Amino acid sequence of CDR2 of humanized 2G1
      VH-11801 variant (Y->H mutation in CDR2)

<400> SEQUENCE: 26

Asp Ile Ser Pro Asn His Gly Tyr Thr Ile Tyr Asn Gln Lys Phe Lys
1               5                   10                  15

Asp

<210> SEQ ID NO 27
<211> LENGTH: 482
<212> TYPE: DNA
<213> ORGANISM: Artificial Sequence
<220> FEATURE:
<223> OTHER INFORMATION: Nucleotide sequence of humanized 2G1 VH-11801
      variant (Y->H mutation in CDR2)

<400> SEQUENCE: 27
cagcatatga tcagtgtcct ctccaaagtc cttgaacata gactctaacc atggactgga      60
cctgggtctt tctcttcctc ctgtcagtaa ctgcaggtgt ccactcccag gttcagctgg     120
tgcagtctgg agctgaggtg aagaagcctg gggcctcagt gaaggtctcc tgcaaggctt     180
ctggatacac aatcacagac tacaatttgg actgggtgcg acaggcccct ggacaagggc     240
ttgagtggat gggagatatt agtcctaacc atggttatac tatctacaac cagaaattca     300
aggacagagt caccatgacc acagacacat ccacgagcac agcctacatg gagctgagga     360
gcctgagatc tgacgacacg gccgtgtatt actgtgcgag aagggacatt cgttactccg     420
gtaattccta caaatggtac ttcgatgtct ggggccaagg acaatggtc accgtctctt      480 ca                                                                    482

<210> SEQ ID NO 28
<211> LENGTH: 144
<212> TYPE: PRT
<213> ORGANISM: Artificial Sequence
<220> FEATURE:
<223> OTHER INFORMATION: Amino acid sequence of humanized 2G1 VH-11801
      variant (Y->H mutation in CDR2)

<400> SEQUENCE: 28

Met Asp Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30
```

```
Pro Gly Ala Ser Val Lys Val Ser Cys Lys Ala Ser Gly Tyr Thr Ile
        35                  40                  45

Thr Asp Tyr Asn Leu Asp Trp Val Arg Gln Ala Pro Gly Gln Gly Leu
    50                  55                  60

Glu Trp Met Gly Asp Ile Ser Pro Asn His Gly Tyr Thr Ile Tyr Asn
65                  70                  75                  80

Gln Lys Phe Lys Asp Arg Val Thr Met Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Arg Asp Ile Arg Tyr Ser Gly Asn Ser Tyr Lys
                115                 120                 125

Trp Tyr Phe Asp Val Trp Gly Gln Gly Thr Met Val Thr Val Ser Ser
            130                 135                 140
```

<210> SEQ ID NO 29
<211> LENGTH: 9
<212> TYPE: PRT
<213> ORGANISM: Artificial Sequence
<220> FEATURE:
<223> OTHER INFORMATION: Amino acid sequence of CDR3 of humanized 2G1
      VL-1901 variant (E->H mutation in CDR3)

<400> SEQUENCE: 29

```
Gln Gln His Asn His Tyr Pro Tyr Thr
1               5
```

<210> SEQ ID NO 30
<211> LENGTH: 428
<212> TYPE: DNA
<213> ORGANISM: Artificial Sequence
<220> FEATURE:
<223> OTHER INFORMATION: Nucleotide sequence of humanized 2G1 VL-1901
      variant (E->H mutation in CDR3)

<400> SEQUENCE: 30

```
gtcagagccc tggggaggaa ctgctcagtt aggacccaga gggaaccatg gaagccccag     60
ctcagcttct cttcctcctg ctactctggc tcccagatac caccggagac atccagttga    120
cccagtctcc atccttcctg tctgcatctg taggagacag agtcaccatc acttgcagga    180
caagtaagag cataagcaaa tatttagcct ggtatcagca aaaaccaggg aaagccccta    240
agctcctgat ctattctgga tccaccttgc aatctggggt cccatcaagg ttcagcggca    300
gtggatctgg gacagaattc actctcacaa tcagcagcct gcagcctgaa gattttgcaa    360
cttattactg tcaacaacat aatcattacc cgtacacgtt tggccagggg accaagctgg    420
agatcaaa                                                             428
```

<210> SEQ ID NO 31
<211> LENGTH: 127
<212> TYPE: PRT
<213> ORGANISM: Artificial Sequence
<220> FEATURE:
<223> OTHER INFORMATION: Amino acid sequence of humanized 2G1 VL-1901
      variant (E->H mutation in CDR3)

<400> SEQUENCE: 31

```
Met Glu Ala Pro Ala Gln Leu Leu Phe Leu Leu Leu Leu Trp Leu Pro
1               5                   10                  15

Asp Thr Thr Gly Asp Ile Gln Leu Thr Gln Ser Pro Ser Phe Leu Ser
            20                  25                  30
```

Ala Ser Val Gly Asp Arg Val Thr Ile Thr Cys Arg Thr Ser Lys Ser
               35                  40                  45

Ile Ser Lys Tyr Leu Ala Trp Tyr Gln Gln Lys Pro Gly Lys Ala Pro
 50                  55                  60

Lys Leu Leu Ile Tyr Ser Gly Ser Thr Leu Gln Ser Gly Val Pro Ser
65                   70                  75                  80

Arg Phe Ser Gly Ser Gly Ser Gly Thr Glu Phe Thr Leu Thr Ile Ser
               85                  90                  95

Ser Leu Gln Pro Glu Asp Phe Ala Thr Tyr Tyr Cys Gln Gln His Asn
               100                 105                 110

His Tyr Pro Tyr Thr Phe Gly Gln Gly Thr Lys Leu Glu Ile Lys
               115                 120                 125

<210> SEQ ID NO 32
<211> LENGTH: 327
<212> TYPE: PRT
<213> ORGANISM: Artificial Sequence
<220> FEATURE:
<223> OTHER INFORMATION: Amino acid sequence of human IgG4 Constant
      Heavy chain region

<400> SEQUENCE: 32

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
               20                  25                  30

Phe Pro Glu Pro Val Thr Val Ser Trp Asn Ser Gly Ala Leu Thr Ser
               35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
65                   70                  75                  80

Tyr Thr Cys Asn Val Asp His Lys Pro Ser Asn Thr Lys Val Asp Lys
               85                  90                  95

Arg Val Glu Ser Lys Tyr Gly Pro Pro Cys Pro Ser Cys Pro Ala Pro
               100                 105                 110

Glu Phe Leu Gly Gly Pro Ser Val Phe Leu Phe Pro Pro Lys Pro Lys
               115                 120                 125

Asp Thr Leu Met Ile Ser Arg Thr Pro Glu Val Thr Cys Val Val Val
               130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
               165                 170                 175

Asn Ser Thr Tyr Arg Val Val Ser Val Leu Thr Val Leu His Gln Asp
               180                 185                 190

Trp Leu Asn Gly Lys Glu Tyr Lys Cys Lys Val Ser Asn Lys Gly Leu
               195                 200                 205

Pro Ser Ser Ile Glu Lys Thr Ile Ser Lys Ala Lys Gly Gln Pro Arg
               210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
               245                 250                 255

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305             310                 315                 320

Leu Ser Leu Ser Pro Gly Lys
                325

<210> SEQ ID NO 33
<211> LENGTH: 327
<212> TYPE: PRT
<213> ORGANISM: Artificial Sequence
<220> FEATURE:
<223> OTHER INFORMATION: Amino acid sequence of human IgG4 Constant
      Heavy chain region with S228P mutation

<400> SEQUENCE: 33

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 34
<211> LENGTH: 17
<212> TYPE: PRT
<213> ORGANISM: Artificial Sequence
<220> FEATURE:
<223> OTHER INFORMATION: Amino acid sequence of CDR2 of humanized 2G1
      VH-11801 variant (T->H mutation in CDR2)

<400> SEQUENCE: 34

Asp Ile Ser Pro Asn Tyr Gly Tyr His Ile Tyr Asn Gln Lys Phe Lys
1               5                   10                  15

Asp

<210> SEQ ID NO 35
<211> LENGTH: 482
<212> TYPE: DNA
<213> ORGANISM: Artificial Sequence
<220> FEATURE:
<223> OTHER INFORMATION: Nucleotide sequence of humanized 2G1 VH-11801
      variant (T->H mutation in CDR2)

<400> SEQUENCE: 35
cagcatatga tcagtgtcct ctccaaagtc cttgaacata gactctaacc atggactgga      60
cctgggtctt tctcttcctc ctgtcagtaa ctgcaggtgt ccactcccag gttcagctgg     120
tgcagtctgg agctgaggtg aagaagcctg gggcctcagt gaaggtctcc tgcaaggctt     180
ctggatacac aatcacagac tacaatttgg actgggtgcg acaggcccct ggacaagggc     240
ttgagtggat gggagatatt agtcctaact atggttatca tatctacaac cagaaattca     300
aggacagagt caccatgacc acagacacat ccacgagcac agcctacatg gagctgagga     360
gcctgagatc tgacgacacg gccgtgtatt actgtgcgag aagggacatt cgttactccg     420
gtaattccta caaatggtac ttcgatgtct ggggccaagg gacaatggtc accgtctctt     480
ca                                                                    482

<210> SEQ ID NO 36
<211> LENGTH: 144
<212> TYPE: PRT
<213> ORGANISM: Artificial Sequence
<220> FEATURE:
<223> OTHER INFORMATION: Amino acid sequence of humanized 2G1 VH-11801
      variant (T->H mutation in CDR2)

<400> SEQUENCE: 36

Met Asp Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Ile
        35                  40                  45

```
Thr Asp Tyr Asn Leu Asp Trp Val Arg Gln Ala Pro Gly Gln Gly Leu
        50                  55                  60

Glu Trp Met Gly Asp Ile Ser Pro Asn Tyr Gly Tyr His Ile Tyr Asn
 65                  70                  75                  80

Gln Lys Phe Lys Asp Arg Val Thr Met Thr Asp Thr Ser Thr Ser Thr
                 85                  90                  95

Thr Ala Tyr Met Glu Leu Arg Ser Leu Arg Ser Asp Asp Thr Ala Val
            100                 105                 110

Tyr Tyr Cys Ala Arg Arg Asp Ile Arg Tyr Ser Gly Asn Ser Tyr Lys
        115                 120                 125

Trp Tyr Phe Asp Val Trp Gly Gln Gly Thr Met Val Thr Val Ser Ser
        130                 135                 140

<210> SEQ ID NO 37
<211> LENGTH: 10
<212> TYPE: PRT
<213> ORGANISM: Artificial Sequence
<220> FEATURE:
<223> OTHER INFORMATION: Amino acid sequence of CDR1 of heavy chain
      sequence of mAb H1-8/L1-9 variant IWW (L->I mutation in CDR1, P->W
      mutation in CDR2, V->W mutation in CDR3)

<400> SEQUENCE: 37

Gly Tyr Thr Ile Thr Asp Tyr His Ile Asp
 1               5                  10

<210> SEQ ID NO 38
<211> LENGTH: 17
<212> TYPE: PRT
<213> ORGANISM: Artificial Sequence
<220> FEATURE:
<223> OTHER INFORMATION: Amino acid sequence of CDR2 of heavy chain
      sequence of mAb H1-8/L1-9 variant IWW (L->I mutation in CDR1, P->W
      mutation in CDR2, V->W mutation in CDR3)

<400> SEQUENCE: 38

Asp Ile Ser Trp Asn Tyr Gly Tyr Thr Ile Tyr Asn Gln Lys Phe Lys
 1               5                  10                  15

Asp

<210> SEQ ID NO 39
<211> LENGTH: 16
<212> TYPE: PRT
<213> ORGANISM: Artificial Sequence
<220> FEATURE:
<223> OTHER INFORMATION: Amino acid sequence of CDR3 of heavy chain
      sequence of mAb H1-8/L1-9 variant IWW (L->I mutation in CDR1, P->W
      mutation in CDR2, V->W mutation in CDR3)

<400> SEQUENCE: 39

Arg Asp Ile Arg Tyr Ser Gly Asn Ser Tyr Lys Trp Tyr Phe Asp Trp
 1               5                  10                  15

<210> SEQ ID NO 40
<211> LENGTH: 482
<212> TYPE: DNA
<213> ORGANISM: Artificial Sequence
<220> FEATURE:
<223> OTHER INFORMATION: Nucleotide sequence of heavy chain sequence of
      mAb H1-8/L1-9 variant IWW (L->I mutation in CDR1, P->W mutation in
      CDR2, V->W mutation in CDR3)
```

<400> SEQUENCE: 40

```
cagcatatga tcagtgtcct ctccaaagtc cttgaacata gactctaacc atggactgga      60
cctgggtctt tctcttcctc ctgtcagtaa ctgcaggtgt ccactcccag gttcagctgg     120
tgcagtctgg agctgaggtg aagaagcctg gggcctcagt gaaggtctcc tgcaaggctt     180
ctggatacac aatcacagac taccatatcg actgggtgcg acaggcccct ggacaagggc     240
ttgagtggat gggagatatt agttggaact atggttatac tatctacaac cagaaattca     300
aggacagagt caccatgacc acagacacat ccacgagcac agcctacatg gagctgagga     360
gcctgagatc tgacgacacg gccgtgtatt actgtgcgag aagggacatt cgttactccg     420
gtaattccta caaatggtac ttcgattggt ggggccaagg acaatggtc accgtctctt      480
ca                                                                    482
```

<210> SEQ ID NO 41
<211> LENGTH: 144
<212> TYPE: PRT
<213> ORGANISM: Artificial Sequence
<220> FEATURE:
<223> OTHER INFORMATION: Amino acid sequence of heavy chain sequence of
      mAb H1-8/L1-9 variant IWW (L->I mutation in CDR1, P->W mutation in
      CDR2, V->W mutation in CDR3)

<400> SEQUENCE: 41

```
Met Asp Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Ile
        35                  40                  45

Thr Asp Tyr His Ile Asp Trp Val Arg Gln Ala Pro Gly Gln Gly Leu
    50                  55                  60

Glu Trp Met Gly Asp Ile Ser Trp Asn Tyr Gly Tyr Thr Ile Tyr Asn
65                  70                  75                  80

Gln Lys Phe Lys Asp Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Arg Asp Ile Arg Tyr Ser Gly Asn Ser Tyr Lys
        115                 120                 125

Trp Tyr Phe Asp Trp Trp Gly Gln Gly Thr Met Val Thr Val Ser Ser
    130                 135                 140
```

<210> SEQ ID NO 42
<211> LENGTH: 10
<212> TYPE: PRT
<213> ORGANISM: Artificial Sequence
<220> FEATURE:
<223> OTHER INFORMATION: Amino acid sequence of CDR1 of heavy chain
      sequence of mAb H1-8/L1-9 variant IFW (L->I mutation in CDR1, P->F
      mutation in CDR2, V->W mutation in CDR3)

<400> SEQUENCE: 42

```
Gly Tyr Thr Ile Thr Asp Tyr His Ile Asp
1               5                   10
```

<210> SEQ ID NO 43
<211> LENGTH: 17
<212> TYPE: PRT

<213> ORGANISM: Artificial Sequence
<220> FEATURE:
<223> OTHER INFORMATION: Amino acid sequence of CDR2 of heavy chain
sequence of mAb H1-8/L1-9 variant IFW (L->I mutation in CDR1, P->F
mutation in CDR2, V->W mutation in CDR3)

<400> SEQUENCE: 43

Asp Ile Ser Phe Asn Tyr Gly Tyr Thr Ile Tyr Asn Gln Lys Phe Lys
1               5                   10                  15

Asp

<210> SEQ ID NO 44
<211> LENGTH: 16
<212> TYPE: PRT
<213> ORGANISM: Artificial Sequence
<220> FEATURE:
<223> OTHER INFORMATION: Amino acid sequence of CDR3 of heavy chain
sequence of mAb H1-8/L1-9 variant IFW (L->I mutation in CDR1, P->F
mutation in CDR2, V->W mutation in CDR3)

<400> SEQUENCE: 44

Arg Asp Ile Arg Tyr Ser Gly Asn Ser Tyr Lys Trp Tyr Phe Asp Trp
1               5                   10                  15

<210> SEQ ID NO 45
<211> LENGTH: 482
<212> TYPE: DNA
<213> ORGANISM: Artificial Sequence
<220> FEATURE:
<223> OTHER INFORMATION: Nucleotide sequence of heavy chain sequence of
mAb H1-8/L1-9 variant IFW (L->I mutation in CDR1, P->F mutation in
CDR2, V->W mutation in CDR3)

<400> SEQUENCE: 45
cagcatatga tcagtgtcct ctccaaagtc cttgaacata gactctaacc atggactgga      60
cctgggtctt tctcttcctc ctgtcagtaa ctgcaggtgt ccactcccag gttcagctgg     120
tgcagtctgg agctgaggtg aagaagcctg gggcctcagt gaaggtctcc tgcaaggctt     180
ctggatacac aatcacagac taccatatcg actgggtgcg acaggcccct ggacaagggc     240
ttgagtggat gggagatatt agtttcaact atggttatac tatctacaac cagaaattca     300
aggacagagt caccatgacc acagacacat ccacgagcac agcctacatg gagctgagga     360
gcctgagatc tgacgacacg gccgtgtatt actgtgcgag aagggacatt cgttactccg     420
gtaattccta caaatggtac ttcgattggt ggggccaagg gacaatggtc accgtctctt     480
ca                                                                    482

<210> SEQ ID NO 46
<211> LENGTH: 144
<212> TYPE: PRT
<213> ORGANISM: Artificial Sequence
<220> FEATURE:
<223> OTHER INFORMATION: Amino acid sequence of heavy chain sequence of
mAb H1-8/L1-9 variant IFW (L->I mutation in CDR1, P->F mutation in
CDR2, V->W mutation in CDR3)

<400> SEQUENCE: 46

Met Asp Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Ile
        35                  40                  45

```
Thr Asp Tyr His Ile Asp Trp Val Arg Gln Ala Pro Gly Gln Gly Leu
    50                  55                  60

Glu Trp Met Gly Asp Ile Ser Phe Asn Tyr Gly Tyr Thr Ile Tyr Asn
 65                  70                  75                  80

Gln Lys Phe Lys Asp Arg Val Thr Met Thr Thr Asp Thr Ser Thr Ser
                 85                  90                  95

Thr Ala Tyr Met Glu Leu Arg Ser Leu Arg Ser Asp Asp Thr Ala Val
            100                 105                 110

Tyr Tyr Cys Ala Arg Arg Asp Ile Arg Tyr Ser Gly Asn Ser Tyr Lys
        115                 120                 125

Trp Tyr Phe Asp Trp Trp Gly Gln Gly Thr Met Val Thr Val Ser Ser
    130                 135                 140

<210> SEQ ID NO 47
<211> LENGTH: 10
<212> TYPE: PRT
<213> ORGANISM: Artificial Sequence
<220> FEATURE:
<223> OTHER INFORMATION: Amino acid sequence of CDR1 of heavy chain
      sequence of mAb H1-8/L1-9 variant FME (L->F mutation in CDR1, P->M
      mutation in CDR2, V->E mutation in CDR3)

<400> SEQUENCE: 47

Gly Tyr Thr Ile Thr Asp Tyr His Phe Asp
1               5                   10

<210> SEQ ID NO 48
<211> LENGTH: 17
<212> TYPE: PRT
<213> ORGANISM: Artificial Sequence
<220> FEATURE:
<223> OTHER INFORMATION: Amino acid sequence of CDR2 of heavy chain
      sequence of mAb H1-8/L1-9 variant FME (L->F mutation in CDR1, P->M
      mutation in CDR2, V->E mutation in CDR3)

<400> SEQUENCE: 48

Asp Ile Ser Met Asn Tyr Gly Tyr Thr Ile Tyr Asn Gln Lys Phe Lys
1               5                   10                  15

Asp

<210> SEQ ID NO 49
<211> LENGTH: 16
<212> TYPE: PRT
<213> ORGANISM: Artificial Sequence
<220> FEATURE:
<223> OTHER INFORMATION: Amino acid sequence of CDR3 of heavy chain
      sequence of mAb H1-8/L1-9 variant FME (L->F mutation in CDR1, P->M
      mutation in CDR2, V->E mutation in CDR3)

<400> SEQUENCE: 49

Arg Asp Ile Arg Tyr Ser Gly Asn Ser Tyr Lys Trp Tyr Phe Asp Glu
1               5                   10                  15

<210> SEQ ID NO 50
<211> LENGTH: 482
<212> TYPE: DNA
<213> ORGANISM: Artificial Sequence
<220> FEATURE:
<223> OTHER INFORMATION: Nucleotide sequence of heavy chain sequence of
      mAb H1-8/L1-9 variant FME (L->F mutation in CDR1, P->M mutation in
      CDR2, V->E mutation in CDR3)
```

<400> SEQUENCE: 50

```
cagcatatga tcagtgtcct ctccaaagtc cttgaacata gactctaacc atggactgga      60
cctgggtctt tctcttcctc ctgtcagtaa ctgcaggtgt ccactcccag gttcagctgg     120
tgcagtctgg agctgaggtg aagaagcctg gggcctcagt gaaggtctcc tgcaaggctt     180
ctggatacac aatcacagac taccatttcg actgggtgcg acaggcccct ggacaagggc     240
ttgagtggat gggagatatt agtatgaact atggttatac tatctacaac cagaaattca     300
aggacagagt caccatgacc acagacacat ccacgagcac agcctacatg gagctgagga     360
gcctgagatc tgacgacacg gccgtgtatt actgtgcgag aagggacatt cgttactccg     420
gtaattccta caaatggtac ttcgatgagt ggggccaagg acaatggtc accgtctctt      480
ca                                                                    482
```

<210> SEQ ID NO 51
<211> LENGTH: 144
<212> TYPE: PRT
<213> ORGANISM: Artificial Sequence
<220> FEATURE:
<223> OTHER INFORMATION: Amino acid sequence of heavy chain sequence of
      mAb H1-8/L1-9 variant FME (L->F mutation in CDR1, P->M mutation in
      CDR2, V->E mutation in CDR3)

<400> SEQUENCE: 51

```
Met Asp Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Ile
        35                  40                  45

Thr Asp Tyr His Phe Asp Trp Val Arg Gln Ala Pro Gly Gln Gly Leu
    50                  55                  60

Glu Trp Met Gly Asp Ile Ser Met Asn Tyr Gly Tyr Thr Ile Tyr Asn
65                  70                  75                  80

Gln Lys Phe Lys Asp Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Arg Asp Ile Arg Tyr Ser Gly Asn Ser Tyr Lys
        115                 120                 125

Trp Tyr Phe Asp Glu Trp Gly Gln Gly Thr Met Val Thr Val Ser Ser
    130                 135                 140
```

<210> SEQ ID NO 52
<211> LENGTH: 10
<212> TYPE: PRT
<213> ORGANISM: Artificial Sequence
<220> FEATURE:
<223> OTHER INFORMATION: Amino acid sequence of CDR1 of heavy chain
      sequence of mAb H1-8/L1-9 variant FMW (L->F mutation in CDR1, P->M
      mutation in CDR2, V->W mutation in CDR3)

<400> SEQUENCE: 52

```
Gly Tyr Thr Ile Thr Asp Tyr His Phe Asp
1               5                   10
```

<210> SEQ ID NO 53
<211> LENGTH: 17
<212> TYPE: PRT

<213> ORGANISM: Artificial Sequence
<220> FEATURE:
<223> OTHER INFORMATION: Amino acid sequence of CDR2 of heavy chain
sequence of mAb H1-8/L1-9 variant FMW (L->F mutation in CDR1, P->M
mutation in CDR2, V->W mutation in CDR3)

<400> SEQUENCE: 53

Asp Ile Ser Met Asn Tyr Gly Tyr Thr Ile Tyr Asn Gln Lys Phe Lys
1               5                   10                  15
Asp

<210> SEQ ID NO 54
<211> LENGTH: 16
<212> TYPE: PRT
<213> ORGANISM: Artificial Sequence
<220> FEATURE:
<223> OTHER INFORMATION: Amino acid sequence of CDR3 of heavy chain
sequence of mAb H1-8/L1-9 variant FMW (L->F mutation in CDR1, P->M
mutation in CDR2, V->W mutation in CDR3)

<400> SEQUENCE: 54

Arg Asp Ile Arg Tyr Ser Gly Asn Ser Tyr Lys Trp Tyr Phe Asp Trp
1               5                   10                  15

<210> SEQ ID NO 55
<211> LENGTH: 482
<212> TYPE: DNA
<213> ORGANISM: Artificial Sequence
<220> FEATURE:
<223> OTHER INFORMATION: Nucleotide sequence of heavy chain sequence of
mAb H1-8/L1-9 variant FMW (L->F mutation in CDR1, P->M mutation in
CDR2, V->W mutation in CDR3)

<400> SEQUENCE: 55

```
cagcatatga tcagtgtcct ctccaaagtc cttgaacata gactctaacc atggactgga       60
cctgggtctt tctcttcctc ctgtcagtaa ctgcaggtgt ccactcccag gttcagctgg      120
tgcagtctgg agctgaggtg aagaagcctg gggcctcagt gaaggtctcc tgcaaggctt      180
ctggatacac aatcacagac taccatttcg actgggtgcg acaggcccct ggacaagggc      240
ttgagtggat gggagatatt agtatgaact atggttatac tatctacaac cagaaattca      300
aggacagagt caccatgacc acagacacat ccacgagcac agcctacatg gagctgagga      360
gcctgagatc tgacgacacg gccgtgtatt actgtgcgag aagggacatt cgttactccg      420
gtaattccta caaatggtac ttcgattggt ggggccaagg acaatggtc accgtctctt      480 ca                                                                     482
```

<210> SEQ ID NO 56
<211> LENGTH: 144
<212> TYPE: PRT
<213> ORGANISM: Artificial Sequence
<220> FEATURE:
<223> OTHER INFORMATION: Amino acid sequence of heavy chain sequence of
mAb H1-8/L1-9 variant FMW (L->F mutation in CDR1, P->M mutation in
CDR2, V->W mutation in CDR3)

<400> SEQUENCE: 56

Met Asp Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Ile
        35                  40                  45

```
Thr Asp Tyr His Phe Asp Trp Val Arg Gln Ala Pro Gly Gln Gly Leu
 50                  55                  60

Glu Trp Met Gly Asp Ile Ser Met Asn Tyr Gly Tyr Thr Ile Tyr Asn
 65                  70                  75                  80

Gln Lys Phe Lys Asp Arg Val Thr Met Thr Thr Asp Thr Ser Thr Ser
                 85                  90                  95

Thr Ala Tyr Met Glu Leu Arg Ser Leu Arg Ser Asp Asp Thr Ala Val
            100                 105                 110

Tyr Tyr Cys Ala Arg Arg Asp Ile Arg Tyr Ser Gly Asn Ser Tyr Lys
        115                 120                 125

Trp Tyr Phe Asp Trp Trp Gly Gln Gly Thr Met Val Thr Val Ser Ser
    130                 135                 140
```

<210> SEQ ID NO 57
<211> LENGTH: 17
<212> TYPE: PRT
<213> ORGANISM: Artificial Sequence
<220> FEATURE:
<223> OTHER INFORMATION: Amino acid sequence of CDR2 of heavy chain
      sequence of mAb H1-8/L1-9 variant FMEH (L->F mutation in CDR1,
      P->M and T->H mutations in CDR2, V->E mutation in CDR3)

<400> SEQUENCE: 57

```
Asp Ile Ser Met Asn Tyr Gly Tyr His Ile Tyr Asn Gln Lys Phe Lys
1               5                   10                  15

Asp
```

<210> SEQ ID NO 58
<211> LENGTH: 482
<212> TYPE: DNA
<213> ORGANISM: Artificial Sequence
<220> FEATURE:
<223> OTHER INFORMATION: Nucleotide sequence of heavy chain sequence of
      mAb H1-8/L1-9 variant FMEH (L->F mutation in CDR1, P->M and T->H
      mutations in CDR2, V->E mutation in CDR3)

<400> SEQUENCE: 58

```
cagcatatga tcagtgtcct ctccaaagtc cttgaacata gactctaacc atggactgga      60
cctgggtctt tctcttcctc ctgtcagtaa ctgcaggtgt ccactcccag gttcagctgg     120
tgcagtctgg agctgaggtg aagaagcctg gggcctcagt gaaggtctcc tgcaaggctt     180
ctggatacac aatcacagac taccatttcg actgggtgcg acaggcccct ggacaagggc     240
ttgagtggat gggagatatt agtatgaact atggttatca tatctacaac cagaaattca     300
aggacagagt caccatgacc acagacacat ccacgagcac agcctacatg gagctgagga     360
gcctgagatc tgacgacacg gccgtgtatt actgtgcgag aagggacatt cgttactccg     420
gtaattccta caaatggtac ttcgatgagt ggggccaagg acaatggtc accgtctctt       480 ca                                                                    482
```

<210> SEQ ID NO 59
<211> LENGTH: 144
<212> TYPE: PRT
<213> ORGANISM: Artificial Sequence
<220> FEATURE:
<223> OTHER INFORMATION: Amino acid sequence of heavy chain sequence of
      mAb H1-8/L1-9 variant FMEH (L->F mutation in CDR1, P->M and T->H
      mutations in CDR2, V->E mutation in CDR3)

<400> SEQUENCE: 59

```
Met Asp Trp Thr Trp Val Phe Leu Phe Leu Leu Ser Val Thr Ala Gly
1               5                   10                  15
```

```
Val His Ser Gln Val Gln Leu Val Gln Ser Gly Ala Glu Val Lys Lys
         20                  25                  30

Pro Gly Ala Ser Val Lys Val Ser Cys Lys Ala Ser Gly Tyr Thr Ile
             35                  40                  45

Thr Asp Tyr His Phe Asp Trp Val Arg Gln Ala Pro Gly Gln Gly Leu
 50                  55                  60

Glu Trp Met Gly Asp Ile Ser Met Asn Tyr Gly Tyr His Ile Tyr Asn
 65                  70                  75                  80

Gln Lys Phe Lys Asp Arg Val Thr Met Thr Thr Asp Thr Ser Thr Ser
                 85                  90                  95

Thr Ala Tyr Met Glu Leu Arg Ser Leu Arg Ser Asp Thr Ala Val
             100                 105                 110

Tyr Tyr Cys Ala Arg Arg Asp Ile Arg Tyr Ser Gly Asn Ser Tyr Lys
             115                 120                 125

Trp Tyr Phe Asp Glu Trp Gly Gln Gly Thr Met Val Thr Val Ser Ser
130                 135                 140
```

<210> SEQ ID NO 60
<211> LENGTH: 984
<212> TYPE: DNA
<213> ORGANISM: Artificial Sequence
<220> FEATURE:
<223> OTHER INFORMATION: Nucleotide sequence of human IgG4 Fc PLA domain mutation

<400> SEQUENCE: 60

```
gctagcacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accatgccca gcacctgagt tcctgggggg accatcagtc     360
ttcctgttcc cccaaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggctc accgtggaca agagcaggtg gcaggagggg     900
aatgtcttct catgctccgt gctgcatgag gctctgcacg cccactacac acagaagagc     960
ctctccctgt ctctgggtaa atga                                            984
```

<210> SEQ ID NO 61
<211> LENGTH: 327
<212> TYPE: PRT
<213> ORGANISM: Artificial Sequence
<220> FEATURE:
<223> OTHER INFORMATION: Amino acid sequence of human IgG4 Fc PLA domain mutation

```
<400> SEQUENCE: 61

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Leu His Glu Ala Leu His Ala His Tyr Thr Gln Lys Ser
305                 310                 315                 320

Leu Ser Leu Ser Leu Gly Lys
                325

<210> SEQ ID NO 62
<211> LENGTH: 17
<212> TYPE: PRT
<213> ORGANISM: Artificial Sequence
<220> FEATURE:
<223> OTHER INFORMATION: Amino acid sequence of CDR2 of heavy chain
      sequence of mAb H1-8/L1-9 variant IWWH (L->I mutation in CDR1,
      P->W and T

<400> SEQUENCE: 62

Asp Ile Ser Trp Asn Tyr Gly Tyr His Ile Tyr Asn Gln Lys Phe Lys
1               5                   10                  15

Asp

<210> SEQ ID NO 63
<211> LENGTH: 482
<212> TYPE: DNA
<213> ORGANISM: Artificial Sequence
<220> FEATURE:
<223> OTHER INFORMATION: Nucleotide sequence of heavy chain sequence of
      mAb H1-8/L1-9 variant IWWH (L->I mutation in CDR1, P->W and T->H
      mutations in CDR2, V->W mutation in CDR3)

<400> SEQUENCE: 63
cagcatatga tcagtgtcct ctccaaagtc cttgaacata gactctaacc atggactgga      60
cctgggtctt tctcttcctc ctgtcagtaa ctgcaggtgt ccactcccag gttcagctgg     120
tgcagtctgg agctgaggtg aagaagcctg gggcctcagt gaaggtctcc tgcaaggctt     180
ctggatacac aatcacagac taccatatcg actgggtgcg acaggcccct ggacaagggc     240
ttgagtggat gggagatatt agttggaact atggttatca tatctacaac cagaaattca     300
aggacagagt caccatgacc acagacacat ccacgagcac agcctacatg gagctgagga     360
gcctgagatc tgacgacacg gccgtgtatt actgtgcgag aagggacatt cgttactccg     420
gtaattccta caaatggtac ttcgattggt ggggccaagg acaatggtc accgtctctt      480 ca                                                                   482

<210> SEQ ID NO 64
<211> LENGTH: 144
<212> TYPE: PRT
<213> ORGANISM: Artificial Sequence
<220> FEATURE:
<223> OTHER INFORMATION: Amino acid sequence of heavy chain sequence of
      mAb H1-8/L1-9 variant IWWH (L->I mutation in CDR1, P->W and T->H
      mutations in CDR2, V->W mutation in CDR3)

<400> SEQUENCE: 64

Met Asp Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Ile
        35                  40                  45

Thr Asp Tyr His Ile Asp Trp Val Arg Gln Ala Pro Gly Gln Gly Leu
    50                  55                  60

Glu Trp Met Gly Asp Ile Ser Trp Asn Tyr Gly Tyr His Ile Tyr Asn
65                  70                  75                  80

Gln Lys Phe Lys Asp Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Arg Asp Ile Arg Tyr Ser Gly Asn Ser Tyr Lys
        115                 120                 125

Trp Tyr Phe Asp Trp Trp Gly Gln Gly Thr Met Val Thr Val Ser Ser
    130                 135                 140

<210> SEQ ID NO 65

<211> LENGTH: 17
<212> TYPE: PRT
<213> ORGANISM: Artificial Sequence
<220> FEATURE:
<223> OTHER INFORMATION: Amino acid sequence of CDR2 of heavy chain
sequence of mAb H1-8/L1-9 variant IFWH (L->I mutation in CDR1,
P->F and T->H mutations in CDR2, V->W mutation in CDR3)

<400> SEQUENCE: 65

Asp Ile Ser Phe Asn Tyr Gly Tyr His Ile Tyr Asn Gln Lys Phe Lys
1               5                   10                  15

Asp

<210> SEQ ID NO 66
<211> LENGTH: 482
<212> TYPE: DNA
<213> ORGANISM: Artificial Sequence
<220> FEATURE:
<223> OTHER INFORMATION: Nucleotide sequence of heavy chain sequence of
mAb H1-8/L1-9 variant IFWH (L->I mutation in CDR1, P->F and T->H
mutations in CDR2, V->W mutation in CDR3)

<400> SEQUENCE: 66

```
cagcatatga tcagtgtcct ctccaaagtc cttgaacata gactctaacc atggactgga      60
cctgggtctt tctcttcctc ctgtcagtaa ctgcaggtgt ccactcccag gttcagctgg     120
tgcagtctgg agctgaggtg aagaagcctg gggcctcagt gaaggtctcc tgcaaggctt     180
ctggatacac aatcacagac taccatatcg actgggtgcg acaggcccct ggacaagggc     240
ttgagtggat gggagatatt agtttcaact atggttatca tatctacaac cagaaattca     300
aggacagagt caccatgacc acagacacat ccacgagcac agcctacatg gagctgagga     360
gcctgagatc tgacgacacg gccgtgtatt actgtgcgag aagggacatt cgttactccg     420
gtaattccta caaatggtac ttcgattggt ggggccaagg acaatggtc accgtctctt      480 ca                                                                    482
```

<210> SEQ ID NO 67
<211> LENGTH: 144
<212> TYPE: PRT
<213> ORGANISM: Artificial Sequence
<220> FEATURE:
<223> OTHER INFORMATION: Amino acid sequence of heavy chain sequence of
mAb H1-8/L1-9 variant IFWH (L->I mutation in CDR1, P->F and T->H
mutations in CDR2, V->W mutation in CDR3)

<400> SEQUENCE: 67

Met Asp Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Ile
        35                  40                  45

Thr Asp Tyr His Ile Asp Trp Val Arg Gln Ala Pro Gly Gln Gly Leu
    50                  55                  60

Glu Trp Met Gly Asp Ile Ser Phe Asn Tyr Gly Tyr His Ile Tyr Asn
65                  70                  75                  80

Gln Lys Phe Lys Asp Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Arg Asp Ile Arg Tyr Ser Gly Asn Ser Tyr Lys
        115                 120                 125

Trp Tyr Phe Asp Trp Trp Gly Gln Gly Thr Met Val Thr Val Ser Ser
    130                 135                 140

<210> SEQ ID NO 68
<211> LENGTH: 17
<212> TYPE: PRT
<213> ORGANISM: Artificial Sequence
<220> FEATURE:
<223> OTHER INFORMATION: Amino acid sequence of CDR2 of heavy chain
      sequence of mAb H1-8/L1-9 variant FMWH (L->F mutation in CDR1,
      P->M and T->H mutations in CDR2, V->W mutation in CDR3)

<400> SEQUENCE: 68

Asp Ile Ser Met Asn Tyr Gly Tyr His Ile Tyr Asn Gln Lys Phe Lys
1               5                   10                  15

Asp

<210> SEQ ID NO 69
<211> LENGTH: 482
<212> TYPE: DNA
<213> ORGANISM: Artificial Sequence
<220> FEATURE:
<223> OTHER INFORMATION: Nucleotide sequence of heavy chain sequence of
      mAb H1-8/L1-9 variant FMWH (L->F mutation in CDR1, P->M and T->H
      mutations in CDR2, V->W mutation in CDR3)

<400> SEQUENCE: 69
cagcatatga tcagtgtcct ctccaaagtc cttgaacata gactctaacc atggactgga      60
cctgggtctt tctcttcctc ctgtcagtaa ctgcaggtgt ccactcccag gttcagctgg     120
tgcagtctgg agctgaggtg aagaagcctg ggcctcagt gaaggtctcc tgcaaggctt      180
ctggatacac aatcacagac taccatttcg actgggtgcg acaggcccct ggacaagggc     240
ttgagtggat gggagatatt agtatgaact atggttatca tatctacaac cagaaattca     300
aggacagagt caccatgacc acagacacat ccacgagcac agcctacatg gagctgagga     360
gcctgagatc tgacgacacg gccgtgtatt actgtgcgag aagggacatt cgttactccg     420
gtaattccta caaatggtac ttcgattggt ggggccaagg acaatggtc accgtctctt      480 ca                                                                    482

<210> SEQ ID NO 70
<211> LENGTH: 144
<212> TYPE: PRT
<213> ORGANISM: Artificial Sequence
<220> FEATURE:
<223> OTHER INFORMATION: Amino acid sequence of heavy chain sequence of
      mAb H1-8/L1-9 variant FMWH (L->F mutation in CDR1, P->M and T->H
      mutations in CDR2, V->W mutation in CDR3)

<400> SEQUENCE: 70

Met Asp Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Ile
        35                  40                  45

Thr Asp Tyr His Phe Asp Trp Val Arg Gln Ala Pro Gly Gln Gly Leu
    50                  55                  60

```
Glu Trp Met Gly Asp Ile Ser Met Asn Tyr Gly Tyr His Ile Tyr Asn
 65              70              75              80

Gln Lys Phe Lys Asp Arg Val Thr Met Thr Thr Asp Thr Ser Thr Ser
             85              90              95

Thr Ala Tyr Met Glu Leu Arg Ser Leu Arg Ser Asp Asp Thr Ala Val
            100             105             110

Tyr Tyr Cys Ala Arg Arg Asp Ile Arg Tyr Ser Gly Asn Ser Tyr Lys
        115             120             125

Trp Tyr Phe Asp Trp Trp Gly Gln Gly Thr Met Val Thr Val Ser Ser
        130             135             140
```